US009688761B2

(12) United States Patent
Adiwijaya et al.

(10) Patent No.: US 9,688,761 B2
(45) Date of Patent: *Jun. 27, 2017

(54) BIOMARKER PROFILES FOR PREDICTING OUTCOMES OF CANCER THERAPY WITH ERBB3 INHIBITORS AND/OR CHEMOTHERAPIES

(71) Applicant: Merrimack Pharmaceuticals, Inc., Cambridge, MA (US)

(72) Inventors: Bambang Adiwijaya, Belmont, MA (US); Akos Czibere, Medford, MA (US); William Kubasek, Belmont, MA (US); Gavin MacBeath, Wakefield, MA (US); Sharon Moulis, Manchester, NH (US); Rachel C. Nering, Stoneham, MA (US); Lin Nie, Needham, MA (US); Defne Yarar, Brookline, MA (US)

(73) Assignee: Merrimack Pharmaceuticals, Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/965,301

(22) Filed: Dec. 10, 2015

(65) Prior Publication Data

US 2016/0090418 A1 Mar. 31, 2016

Related U.S. Application Data

(63) Continuation of application No. PCT/US2014/072594, filed on Dec. 29, 2014.

(60) Provisional application No. 62/055,382, filed on Sep. 25, 2014, provisional application No. 62/027,042, filed on Jul. 21, 2014, provisional application No. 62/005,683, filed on May 30, 2014, provisional application No. 61/921,185, filed on Dec. 27, 2013.

(51) Int. Cl.
*C07K 16/28* (2006.01)
*G01N 33/574* (2006.01)
*C07K 16/30* (2006.01)
*C12Q 1/68* (2006.01)

(52) U.S. Cl.
CPC ...... *C07K 16/2863* (2013.01); *C07K 16/3015* (2013.01); *C07K 16/3023* (2013.01); *C07K 16/3069* (2013.01); *C12Q 1/6886* (2013.01); *G01N 33/574* (2013.01); *C07K 2317/34* (2013.01); *C07K 2317/565* (2013.01); *C12Q 2600/106* (2013.01); *C12Q 2600/112* (2013.01); *C12Q 2600/158* (2013.01); *G01N 2333/71* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,183,884 A | 2/1993 | Kraus et al. |
| 5,344,760 A | 9/1994 | Harvey et al. |
| 5,480,968 A | 1/1996 | Kraus et al. |
| 5,820,859 A | 10/1998 | Kraus et al. |
| 5,916,755 A | 6/1999 | Kraus et al. |
| 5,968,511 A | 10/1999 | Akita et al. |
| 6,331,415 B1 | 12/2001 | Cabilly et al. |
| 6,639,060 B1 | 10/2003 | Kraus et al. |
| 6,696,290 B2 | 2/2004 | Fitzpatrick et al. |
| 6,983,227 B1 | 1/2006 | Thalhammer-Reyero |
| 7,097,840 B2 | 8/2006 | Erickson et al. |
| 7,125,680 B2 | 10/2006 | Singer et al. |
| 7,285,649 B2 | 10/2007 | Akita et al. |
| 7,314,916 B2 | 1/2008 | Singer et al. |

(Continued)

FOREIGN PATENT DOCUMENTS

| | | |
|---|---|---|
| EP | 0896586 B1 | 2/1999 |
| EP | 1058562 B1 | 12/2000 |
| EP | 1187634 B1 | 3/2002 |
| EP | 1283053 A1 | 2/2003 |
| EP | 1351744 B1 | 10/2003 |

(Continued)

OTHER PUBLICATIONS

Breuleux (Cell. Mol. Life. Sci., 64:2358-2377, 2007).*
Tamimi et al. (Cancer Research, 53:5512-5516, 1993).*
Specht et al. (American Journal of Pathology, 158(2):419-429, 2001).*
Atlas et al. (Oncogene, 22: 3441-3451, 2003).*

(Continued)

*Primary Examiner* — Brad Duffy
*Assistant Examiner* — Nelson B Moseley, II
(74) *Attorney, Agent, or Firm* — Nelson Mullins Riley & Scarborough LLP; Jane E. Remillard, Esq.; Jill Gorny Sloper, Esq.

(57) ABSTRACT

Provided are methods for optimizing therapy of, treating a patient having, or selecting (identifying) patients who will benefit from treatment for, a cancer (e.g., a non-hematological cancer; e.g., a gynecological cancer). The methods comprise determining whether the patient will benefit from treatment with an ErbB3 inhibitor (e.g., an anti-ErbB3 antibody), with or without either a taxane or an aromatase inhibitor, or with a taxane or an aromatase inhibitor in the absence of an ErbB3 inhibitor, based on levels of particular biomarkers and combinations of biomarkers measured in a biological sample obtained from the patient. The methods further comprise optimizing the patient's therapy, selecting the patient for treatment, or treating the patient accordingly. In various aspects the biological samples are sections of a biopsy (e.g., a formalin fixed paraffin embedded biopsy). In other aspects the biomarkers are proteins and/or nucleic acids. In other aspects the biomarkers function in ErbB-mediated signal transduction.

24 Claims, 49 Drawing Sheets

(56) References Cited

U.S. PATENT DOCUMENTS

| | | |
|---|---|---|
| 7,390,632 B2 | 6/2008 | Maihle et al. |
| 7,589,180 B2 | 9/2009 | Old et al. |
| 7,638,302 B2 | 12/2009 | Maihle et al. |
| 7,638,303 B2 | 12/2009 | Maihle et al. |
| 7,705,130 B2 | 4/2010 | Rothe et al. |
| 7,846,440 B2 | 12/2010 | Schoeberl et al. |
| 7,923,221 B1 | 4/2011 | Cabilly et al. |
| 8,268,793 B2 | 9/2012 | Hedtjarn |
| 8,476,409 B2 | 7/2013 | Baum et al. |
| 8,481,687 B2 | 7/2013 | Vincent et al. |
| 8,623,592 B2 | 1/2014 | Schoeberl et al. |
| 8,691,225 B2 | 4/2014 | Schoeberl et al. |
| 8,877,687 B2 | 11/2014 | Song et al. |
| 8,895,001 B2 | 11/2014 | Moyo et al. |
| 8,927,694 B2 | 1/2015 | McDonagh et al. |
| 8,961,966 B2 | 2/2015 | Schoeberl et al. |
| 9,011,851 B2 | 4/2015 | Ullrich et al. |
| 9,101,760 B2 | 8/2015 | Hettmann et al. |
| 9,228,021 B2 | 1/2016 | Vincent et al. |
| 9,487,588 B2 | 11/2016 | Schoeberl |
| 2002/0001587 A1 | 1/2002 | Erickson et al. |
| 2002/0002276 A1 | 1/2002 | Fitzpatrick et al. |
| 2002/0119148 A1 | 8/2002 | Gerritsen et al. |
| 2002/0165193 A1 | 11/2002 | Greene et al. |
| 2003/0040605 A1 | 2/2003 | Siegel |
| 2003/0199020 A1 | 10/2003 | Fitzpatrick et al. |
| 2004/0052786 A1 | 3/2004 | Gerritsen et al. |
| 2004/0071696 A1 | 4/2004 | Adams et al. |
| 2004/0082510 A1 | 4/2004 | Ullrich et al. |
| 2004/0138417 A1 | 7/2004 | Fitzpatrick et al. |
| 2004/0197332 A1 | 10/2004 | Ullrich et al. |
| 2004/0229380 A1 | 11/2004 | Chan-Hui et al. |
| 2004/0248151 A1 | 12/2004 | Bacus et al. |
| 2004/0248196 A1 | 12/2004 | Adams et al. |
| 2005/0004018 A1 | 1/2005 | Jimeno et al. |
| 2005/0079184 A1 | 4/2005 | Hsing-Chang et al. |
| 2005/0187745 A1 | 8/2005 | Lurie et al. |
| 2005/0267720 A1 | 12/2005 | Hill et al. |
| 2006/0040363 A1 | 2/2006 | Kucherlapati et al. |
| 2006/0093603 A1 | 5/2006 | Gerritsen et al. |
| 2006/0127928 A1 | 6/2006 | Bacus et al. |
| 2006/0136139 A1 | 6/2006 | Elcock et al. |
| 2006/0167637 A1 | 7/2006 | Agur et al. |
| 2006/0177907 A1 | 8/2006 | Singer et al. |
| 2006/0204505 A1 | 9/2006 | Sliwkowski et al. |
| 2006/0210561 A1 | 9/2006 | Baughman et al. |
| 2007/0009972 A1 | 1/2007 | Chao et al. |
| 2007/0059785 A1 | 3/2007 | Bacus et al. |
| 2007/0081994 A1 | 4/2007 | Fitzpatrick et al. |
| 2007/0092513 A1 | 4/2007 | Gerritsen et al. |
| 2007/0122407 A1 | 5/2007 | Akita et al. |
| 2007/0134251 A1 | 6/2007 | Ashkenazi et al. |
| 2007/0134252 A1 | 6/2007 | Bacus et al. |
| 2007/0190583 A1 | 8/2007 | Spector et al. |
| 2007/0254295 A1 | 11/2007 | Harvey et al. |
| 2008/0026415 A1 | 1/2008 | Rimm et al. |
| 2008/0057064 A1 | 3/2008 | Zhou |
| 2008/0090233 A1 | 4/2008 | Garcia et al. |
| 2008/0112958 A1 | 5/2008 | Mass |
| 2008/0124334 A1 | 5/2008 | Akita et al. |
| 2008/0124345 A1 | 5/2008 | Rothe et al. |
| 2008/0172184 A1 | 7/2008 | Chaires et al. |
| 2008/0187948 A1 | 8/2008 | Chan-Hui et al. |
| 2008/0207615 A1 | 8/2008 | Bell et al. |
| 2008/0214584 A1 | 9/2008 | Ohta et al. |
| 2008/0254497 A1 | 10/2008 | Singh |
| 2008/0261270 A1 | 10/2008 | Maihle et al. |
| 2008/0274504 A1 | 11/2008 | Maihle et al. |
| 2008/0318894 A1 | 12/2008 | Hedtjarn |
| 2009/0061422 A1 | 3/2009 | Linke et al. |
| 2009/0181022 A1 | 7/2009 | Nielsen et al. |
| 2009/0246206 A1 | 10/2009 | Nielsen et al. |
| 2009/0291085 A1 | 11/2009 | Schoeberl et al. |
| 2010/0056761 A1 | 3/2010 | Schoeberl et al. |
| 2010/0158894 A1 | 6/2010 | Umemura et al. |
| 2010/0178651 A1 | 7/2010 | Hatzis et al. |
| 2010/0266584 A1 | 10/2010 | Schoeberl et al. |
| 2010/0310557 A1 | 12/2010 | Keyt et al. |
| 2011/0027291 A1 | 2/2011 | Schoeberl et al. |
| 2011/0033482 A1 | 2/2011 | Ullrich et al. |
| 2011/0123523 A1 | 5/2011 | Schoeberl et al. |
| 2011/0159513 A1 | 6/2011 | Schoeberl et al. |
| 2011/0171222 A1 | 7/2011 | Bossenmaier et al. |
| 2011/0229493 A1 | 9/2011 | Jackson et al. |
| 2011/0256154 A1 | 10/2011 | Vincent et al. |
| 2012/0015827 A1 | 1/2012 | Wirtz |
| 2012/0156130 A1 | 6/2012 | Hettmann et al. |
| 2012/0225870 A1 | 9/2012 | Janne et al. |
| 2012/0244163 A1 | 9/2012 | Schoeberl et al. |
| 2013/0034548 A1 | 2/2013 | Moyo et al. |
| 2013/0236459 A1 | 9/2013 | Baum et al. |
| 2013/0259867 A1 | 10/2013 | Amler et al. |
| 2014/0017264 A1 | 1/2014 | McDonagh et al. |
| 2014/0056898 A1 | 2/2014 | Zhang et al. |
| 2014/0079703 A1 | 3/2014 | Zhang et al. |
| 2014/0127238 A1 | 5/2014 | Schoeberl et al. |
| 2014/0134170 A1 | 5/2014 | Garcia et al. |
| 2014/0234317 A1 | 8/2014 | Onsum et al. |
| 2014/0234329 A1 | 8/2014 | Schoeberl et al. |
| 2014/0242597 A1 | 8/2014 | Vincent et al. |
| 2014/0248280 A1 | 9/2014 | Kubasek et al. |
| 2014/0271665 A1 | 9/2014 | Aftab et al. |
| 2014/0273006 A1 | 9/2014 | Singh et al. |
| 2015/0132292 A1 | 5/2015 | Moyo et al. |
| 2015/0147326 A1 | 5/2015 | Schneider et al. |
| 2015/0152508 A1 | 6/2015 | Schneider et al. |
| 2015/0231238 A1 | 8/2015 | Garcia et al. |
| 2016/0303232 A1 | 10/2016 | Adiwijaya et al. |

FOREIGN PATENT DOCUMENTS

| | | |
|---|---|---|
| EP | 1414494 B1 | 5/2004 |
| EP | 1728802 A2 | 12/2006 |
| EP | 1889631 A1 | 2/2008 |
| EP | 2067792 A2 | 6/2009 |
| EP | 2138511 A1 | 12/2009 |
| EP | 2751562 A1 | 7/2014 |
| EP | 2764364 A1 | 8/2014 |
| EP | 2788752 A1 | 10/2014 |
| JP | 2009500005 A | 1/2009 |
| WO | 97/35885 A1 | 10/1997 |
| WO | 98/02540 A1 | 1/1998 |
| WO | 99/54800 A2 | 10/1999 |
| WO | 99/60023 A1 | 11/1999 |
| WO | 00/78347 A1 | 12/2000 |
| WO | 02/18444 A2 | 3/2002 |
| WO | 02060470 A1 | 8/2002 |
| WO | 03012072 A2 | 2/2003 |
| WO | 03013602 A1 | 2/2003 |
| WO | 2004/003019 A3 | 1/2004 |
| WO | 2004/008099 A2 | 1/2004 |
| WO | 2004/053497 A2 | 6/2004 |
| WO | 2004/091384 A2 | 10/2004 |
| WO | 2005/017493 A2 | 2/2005 |
| WO | 2006/017538 A2 | 2/2006 |
| WO | 2006/020706 A2 | 2/2006 |
| WO | 2006/044748 A2 | 4/2006 |
| WO | 2006/063042 A2 | 6/2006 |
| WO | 2006/091209 A2 | 8/2006 |
| WO | 2007/015935 A2 | 2/2007 |
| WO | 2007/039705 A1 | 4/2007 |
| WO | 2007/041502 A2 | 4/2007 |
| WO | 2007/077028 A2 | 7/2007 |
| WO | 2007/115571 A2 | 10/2007 |
| WO | 2007/130677 A2 | 11/2007 |
| WO | 2008/032876 A1 | 3/2008 |
| WO | 2008/064884 A1 | 6/2008 |
| WO | 2008/100624 A2 | 8/2008 |
| WO | 2008/109440 A2 | 9/2008 |
| WO | 2009/027332 A1 | 3/2009 |
| WO | 2009/126920 A2 | 10/2009 |
| WO | 2009/156179 A1 | 12/2009 |
| WO | 2010/019952 A2 | 2/2010 |
| WO | 2010/059315 A1 | 5/2010 |

(56) References Cited

FOREIGN PATENT DOCUMENTS

| WO | 2010/127181 | A1 | 11/2010 | |
|---|---|---|---|---|
| WO | 2011/022727 | A2 | 2/2011 | |
| WO | 2011/044311 | A2 | 4/2011 | |
| WO | 2011/047180 | A1 | 4/2011 | |
| WO | 2011/112953 | A2 | 9/2011 | |
| WO | WO 2011/163466 | * | 12/2011 | ............ A61K 38/18 |
| WO | 2012/019952 | A1 | 2/2012 | |
| WO | 2012/125573 | A2 | 9/2012 | |
| WO | 2012/125864 | A2 | 9/2012 | |
| WO | 2012145507 | A2 | 10/2012 | |
| WO | 2012/154587 | A2 | 11/2012 | |
| WO | 2012/177440 | A1 | 12/2012 | |
| WO | 2013/023043 | A2 | 2/2013 | |
| WO | 2013/033623 | A1 | 3/2013 | |
| WO | 2013/052745 | A1 | 4/2013 | |
| WO | 2013/086031 | A1 | 6/2013 | |
| WO | 2013/152034 | A1 | 10/2013 | |
| WO | 2015/048793 | A2 | 4/2015 | |
| WO | 2015/100459 | A2 | 7/2015 | |
| WO | 2015/130554 | A2 | 9/2015 | |

OTHER PUBLICATIONS

Sequist, L.V. et al., "Targeting EGFR and ERBB3 in Lung Cancer Patients: Clinical Outcomes in a Phase 1 Trial of MM-121 in Comnation with Erlotinib," American Society of Clinical Oncology, 2012, Poster Presentation, 1 page.

Shintani, Satoru et al., "Expression of C-erbB Family Gene Products in Adenoid Cystic Carcinoma of Salivary Glands: An Immunohistochemical Study," Anticancer Research, vol. 15, pp. 2623-2626 (1995).

Shintani, Satoru et al., "Prognostic significance of ERRB3 overexpression in oral squamous cell carcinoma," Cancer Letters, vol. 95, pp. 79-83 (1995).

Simpson, BJB et al., "c-erbB-3 protein expression in ovarian tumours," British Journal of Cancer, vol. 71, pp. 758-762 (1995).

Singer, Elizabeth et al., "Identification of a Heregulin Binding Site in HER3 Extracellular Domain," The Journal of Biological Chemistry, vol. 276(47), pp. 44266-44274 (2001).

Skinner, Ann et al., "Transcriptional regulation of the c-erbB-3 gene in human breast carcinoma cell lines," Oncogene, vol. 8, pp. 3393-3401 (1993).

Slamon, Dennis J. et al., "Human Breast Cancer: Correlation of Relapse and Survival with Amplification of the HER-2/neu Oncogene," Science, vol. 235, pp. 177-182 (1987).

Slamon, Dennis J. et al., "Studies of the HER-2/neu Proto-oncogene in Human Breast and Ovarian Cancer," Science, vol. 244, pp. 707-712 (1989).

Sliwkowski, Mark X. et al., "Coexpression of erbB2 and erbB3 Proteins Reconstitutes a High Affinity Receptor for Heregulin," The Journal of Biological Chemistry, vol. 269(2), pp. 14661-14665 (1994).

Smith, B.L. et al., "The efficacy of Herceptin therapies is influenced by the expression of other erbB receptors, their ligands and the activation of downstream signalling proteins," British Journal of Cancer, vol. 91, pp. 1190-1194 (2004).

Smith-Gill, Sandra J. et al., "Contributions of Immunoglobulin Heavy and Light Chains to Antibody Specificity for Lysozyme and Two Haptens," The Journal of Immunology, vol. 139, pp. 4135-4144 (1987).

Soltoff, Stephen P. et al., "ErbB3 Is Involved in Activation of Phosphatidylinositol 3-Kinase by Epidermal Growth Factor," Molecular and Cellular Biology, vol. 14(6), pp. 3550-3558 (1994).

Song, Mi-Kyung et al., "Light Chain of Natural Antibody Plays a Dominant Role in Protein Antigen Binding," Biochemical and Biophysical Research Communications, vol. 268, pp. 390-394 (2000).

Sonne-Hansen, Katrine et al., "Breast cancer cells can switch between estrogen receptor alpha and ErbB signaling and combined treatment against both signaling pathways postpones development of resistance," Breast Cancer Res. Treat., vol. 121, pp. 601-613 (2010).

Surmacz, Eva, "Growth factor receptors as therapeutic targets: strategies to inhibit the insulin-like growth factor I receptor," Oncogene, vol. 22, pp. 6589-6597 (2003).

Thurber, Greg M. et al., "Antibody tumor penetration: Transport opposed by systemic and antigen-mediated clearance," Advanced Drug Delivery Reviews, vol. 60, pp. 1421-1434 (2008).

Tzahar, Eldad et al., "A Hierarchical Network of Interreceptor Interactions Determines Signal Transduction by Neu Differentiation Factor/Neuregulin and Epidermal Growth Factor," Molecular and Cellular Biology, vol. 16(10), pp. 5276-5287 (1996).

Tzahar, Eldad et al., "ErbB-3 and ErbB-4 Function as the Respective Low and High Affinity Receptors of All Neu Differentiation Factor/Heregulin Isoforms," The Journal of Biological Chemistry, vol. 269(40), pp. 25226-25233 (1994).

Ullrich, Axel et al., "Signal Transduction by Receptors with Tyrosine Kinase Activity," Cell, vol. 61, pp. 203-212 (1990).

Vaidya, Pradeep et al., "Overexpression of Different Members of the Type 1 Growth Factor Receptor Family and Their Association with Cell Proliferation in Periampullary Carcinoma," Journal of Pathology, vol. 178, pp. 140-145 (1996).

Vajdos, Felix F. et al., "Comprehensive Functional Maps of the Antigen-binding Site of an Anti-ErbB2 Antibody Obtained with Shotgun Scanning Mutagenesis," J. Mol. Biol., vol. 320, pp. 415-428 (2002).

Voskoglou-Nomikos, Theodora et al., "Clinical Predictive Value of the in Vitro Cell Line, Human Xenograft, and Mouse Allograft Preclinical Cancer Models," Clinical Cancer Research, vol. 9, pp. 4227-4239 (2003).

Wainstein, Mark A. et al., "CWR22: Androgen-dependent Xenograft Model Derived from a Primary Human Prostatic Carcinoma," Cancer Research, vol. 54, pp. 6049-6052 (1994).

Wainszelbaum, Marisa et al., "In vitro studies of MM-121/SAR 256212, an anti-ErbB-3 antibody, in combination with erlotinib; in EGFR-wild-type NSCLC," AARC Meeting 2013, Poster 5464, p. 1.

Wallasch, Christian et al., "Heregulin-dependent regulation of HER2/neu oncogenic signaling by heterodimerization with HER3," The EMBO Journal, vol. 14(17), pp. 4267-4275 (1995).

Ward, E. Sally et al., "Binding activities of a repertoire of single immunoglobulin variable domains secreted from *Escherichia coli*," Nature, vol. 341, pp. 544-546 (1989).

Wingens, Miriam et al., "Structural Analysis of an Epidermal Growth Factor/Transforming Growth Factor-a Chimera with Unique ErbB Binding Specificity," The Journal of Biological Chemistry, vol. 278(40), pp. 39114-39123 (2003).

Wu, Dianging et al., "Human Epidermal Growth Factor (EGF) Receptor Sequence Recognized by EGF Competitive Monoclonal Antibodies," The Journal of Biological Chemistry, vol. 264(29), pp. 17469-17475 (1989).

Wu, Herren et al., "Humanization of a Murine Monoclonal Antibody by Simultaneous Optimization of Framework and CDR Residues," J. Mol. Biol., vol. 294, pp. 151-162 (1999).

Yamamoto, Tadashi et al., "Similarity of protein encoded by the human c-erb-B-2 gene to epidermal growth factor receptor," Nature, vol. 319, pp. 230-234 (1986).

Ye, Dingwei et al., "Augmentation of a humanized Anti-HER2 mAb 4D6 induced growth inhibition by a human-mouse chimeric anti-EGF receptor mAb C225," Oncogene, vol. 18, pp. 731-738 (1999).

Zelada-Hedman, Moraima et al., "High Expression of the EGFR in Fibroadenomas Compared to Breast Carcinomas," Anticancer Research, vol. 14, pp. 1679-1688 (1994).

Zhang, Ke et al., "Transformation of NIH 3T3 Cells by HER3 or HER4 Receptors Requires the Presence of HER1 or HER2," The Journal of Biological Chemistry, vol. 271(7), pp. 3884-3890 (1996).

International Search Report and Written Opinion, PCT/US2014/072594, dated Jun. 29, 2015, 18 pages.

Invitation to Pay Additional Fees for Application No. PCT/US2008/002119, dated Oct. 7, 2008.

(56) References Cited

OTHER PUBLICATIONS

Irvin, W. et al., "What is triple-negative breast cancer?" European Journal of Cancer, vol. 44, pp. 2799-2805 (2008).

Issing, W.J. et al., "erbB-3, a third member of the erbB/epidermal growth factor receptor gene family: its expression in head and neck cancer cell lines," Eur. Arch. Otorhinolaryngol, vol. 250, pp. 392-395 (1993).

Jang, Y.-J. et al., "The structural basis for DNA binding by an anti-DNA autoantibody," Molecular Immunology, vol. 35, pp. 1207-1217 (1998).

Jeschke, Margit et al., "Targeted Inhibition of Tumor-cell Growth by Recombinant Heregulin-toxin Fusion Proteins," Int. J. Cancer, vol. 60, pp. 730-739 (1995).

Jiang, N., et al., "Combined Treatment with HER3 Antibody MM-121/SAR 256212 and EGFR Antibody Cetuximab for; Preclinical Models of Head and Neck Cancer," American Association for Cancer Research (AACR) Annual meeting,; 2013, Emory University Poster, 1 page.

Jo, Sangmee Ahn et al., "Neuregulins are concentrated at nerve-muscle synapses and activate ACh-receptor gene expression," Nature, vol. 373, pp. 158-161 (1995).

Jones, Jennifer T. et al., "Binding specificities and affinities of egf domains for ErbB receptors," FEBS Letters, vol. 447, pp. 227-231 (1999).

Karunagaran, Devarajan et al., "ErbB-2 is a common auxiliary subunit of NDF and EGF receptors: implications for breast cancer," The EMBO Journal, vol. 15(2), pp. 254-264 (1996).

Kasprzyk, Philip G. et al., "Therapy of an Animal Model of Human Gastric Cancer Using a Combination of Anti-erbB-2 Monoclonal Antibodies," Cancer Research, vol. 52, pp. 2771-2776 (1992).

Katoh, Masaru et al., "c-erbB3 Gene Encodes Secreted as Well as Transmembrane Receptor Tyrosine Kinase," Biochemical and Biophysical Research Communications, vol. 192(3), pp. 1189-1197 (1993).

Kim, Hong-Hee et al., "Epidermal Growth Factor-dependent Association of Phosphatidylinositol 3-Kinase with the erbB3 Gene Product," The Journal of Biological Chemistry, vol. 269(40), pp. 24747-24755 (1994).

Kim, Hong-Hee et al., "Signal transduction by epidermal growth factor and heregulin via the kinase-deficient ErbB3 protein," Biochem. J., vol. 334, pp. 189-195 (1998).

Kinugasa, Yumi et al., "Neuroglycan C, a novel member of the neuregulin family," Biochemical and Biophysical Research Communications, vol. 321, pp. 1045-1049 (2004).

Kita, Yoshiko A. et al., "NDF/heregulin stimulates the phosphorylation of Her3/erbB3," FEBS Letters, vol. 349, pp. 139-143 (1994).

Kita, Yoshiko et al., "Bioactive Synthetic Peptide of NDF/Heregulin," Biochemical and Biophysical Research Communicatnions, vol. 210(2), pp. 441-451 (1995).

Klapper, Leah N. et al., "A subclass of tumor-inhibitory monoclonal antibodies to ErbB-2/HER2 blocks crosstalk with growth factor receptors," Oncogene, vol. 14, pp. 2099-2109 (1997).

Kobayashi, Hiroyuki et al., "Tryptophan H33 plays an important role in pyrimidine (6-4) pyrimidone photoproduct binding by a high-affinity antibody," Protein Engineering, vol. 12(10), pp. 879-884 (1999).

Konecny, GE et al., "Activity of the dual kinase inhibitor lapatinib (GW572016) against HER-2-overexpressing and trastuzumab-treated breast cancer cells," Cancer Research, vol. 66, pp. 1630-1639 (2006).

Korabiowska, Monika et al., "Differential Expression of cerbB3 in Naevi and Malignant Melanomas," Anticancer Research, vol. 16, pp. 471-474 (1996).

Kraus, Matthias H. et al., "Demonstration of ligand-dependent signaling by the erbB-3 tyrosine kinase and its constitutive activation in human breast tumor cells," Proc. Natl. Acad. Sci. USA, vol. 90, pp. 290-2904 (1993).

Kraus, Matthias H. et al., "Isolation and characterization of ERBB3, a third member of the ERBB/epidermal growth factor receptor family: Evidence for overexpression in a dubset of human mammary tumors," Proc. Natl. Acad. Sci. USA, vol. 86, pp. 9193-9197 (1989).

Kraus, Matthias H. et al., "Overexpression of the EGF receptor-related proto-oncogene erbB-2 in human mammary tumor cell lines by different molecular mechanisms," The EMBO Journal, vol. 6(3), pp. 605-610 (1987).

Kumar, Sanjeev et al., "Molecular Cloning and Expression of the Fabs of Human Autoantibodies in *Escherichia coli*," The Journal of Biological Chemistry, vol. 275(45), pp. 35129-35136 (2000).

Lal, P. et al., "Correlation of HER-2 Status With Estrogen and Progesterone Receptors and Histologic Features in 3,655 Invasive Breast Carcinomas," American Journal of Clinical Pathology, vol. 123, pp. 541-546 (2005).

Lederman, Seth et al., "A Single Amino Acid Substitution in a Common African Allele of the CD4 Molecule Ablates Binding of the Monoclonal Antibody, OKT4," Molecular Immunology, vol. 28(11), pp. 1171-1181 (1991).

Lee, Hakjoo et al., "A Naturally Occurring Secreted Human ErbB3 Receptor Isoform Inhibits Heregulin-stimulated Activation of ErbB2, ErbB3, and ErbB4," Cancer Research, vol. 61, pp. 4467-4473 (2001).

Lee, Hakjoo et al., "Isolation and characterization of four alternate c-erbB3 transcripts expressed in ovarian caranoma-derived cell lines and normal human tissues," Oncogene, vol. 6, pp. 3243-3252 (1998).

Lee-Hoeflich, Si Tuen et al., "A Central Role for HER3 in HER2-Amplified Breast Cancer: Implications for Targeted Therapy," Cancer Res., vol. 68(14), pp. 5878-5887 (2008).

Lemoine, Nicholas R. et al., "The erbB-3 Gene in Human Pancreatic Cancer," Journal of Pathology, vol. 168, pp. 269-273 (1992).

Lenz, H.J., "Management and Preparedness for Infusion and Hypersensitivity Reactions," The Oncologist, vol. 12, pp. 601-609, (2007).

Levi, Allan D.O. et al., "The Influence of Heregulins on Human Schwann Cell Proliferation," The Journal of Neuroscience, vol. 15(2), pp. 1329-1340 (1995).

Lewis, Gail D. et al., "Growth Regulation of Human Breast and Ovarian Tumor Cells by Herebulin: Evidence for the Requirement of ErbB2 as a Critical Component in Mediating Heregulin Responsiveness," Cancer Research, vol. 56, pp. 1457-1465 (1996).

Li, Choh Hao et al., "Beta-Endorphin omission analogs: Dissociation of immunoreactivity from other biological activities," Proc. Natl. Acad. Sci. USA, vol. 77(6), pp. 3211-3214 (1980).

Li, Yu, et al., Expression and Activity of Carbonic Anhydrase IX is Associated With Metabolic Dysfunction in MDA-MB-231 Breast Cancer Cells, Cancer Investigation, 2009, vol. 27, pp. 613-623.

Little, M. et al., "Of mice and men: hybridoma and recombinant antibodies," Immunology Today, vol. 21(8), pp. 364-370 (2000).

Liu, B.et al., "Downregulation of erbB3 abrogates erbB2-mediated tamoxifen resistance in breast cancer cells," Int J Cancer, vol. 120, pp. 1874-1882 (2007).

Liu, Bolin et al., "Estrogenic Promotion of ErbB2 Tyrosine Kinase Activity in Mammary Tumor Cells Requires Activation of ErbB3 Signaling," Mol. Cancer Res., vol. 7(11), pp. 1882-1892 (2009).

Liu, J. et al., "A Phase 1 Study of the anti-ErbB3 antibody MM-121 in combination withweekly paclitaxel in patients with advanced gynecological and breast cancers," European Society for Medical Oncology Annual Congress, Vienna, Austria, Sep. 28 to Oct. 2, 2012, Poster Presentation, 1 page.

Liu, J. et al., "A Phase 2 Randomized Open Label Study of MM-121, a Fully Human Monoclonal Antibody Targeting ErbB3, in Combination with Weekly Paclitaxel, Versus Weekly Paclitaxel Alone, in Patients with Plantinum Resistant/Refractory Ovarian Cancers," American Society of Clinical Oncology, 2014, Poster Presentation, 1 page.

Lu, Dan et al., "Complete Inhibition of Vascular Endothelial Growth Factor (VEGF) Activities with a Bifunctional Diabody Directed against Both VEGF Kinase Receptors, fms-like Tyrosine Kinase Receptor and Kinase Insert Domain-containing Receptor," Cancer Research, vol. 61:7002-7008 (2001).

(56) References Cited

OTHER PUBLICATIONS

MacBeath, G. et al., A Meta-Analysis of Biomarkers in Three Randomized, Phase 2 Studies of MM-121, a Ligand-Blocking Anti-ErbB3 Antibody, in Patients with Ovarian, Lung and Breast Cancers, European Society for Medical Oncology (ESMO) Annual Meeting, 2014, Madrid Spain, Poster Presentation, 1 page.

MacCallum, Robert M. et al., "Antibody-antigen Interactions: Contact Analysis and Binding Site Topography," J. Mol. Biol., vol. 262, pp. 732-745 (1996).

Marchionni, Mark A. et al., "Glial growth factors are alternatively spliced erbB2 ligands expressed in the nervous system," Nature, vol. 362, pp. 312-318 (1993).

Markman, M. et al., "Phase II trial of weekly paclitaxel (80 mg/m2) in platinum and paclitaxel-resistant ovarian and primary peritoneal cancers: a gynecologic oncology group study," Gyncol. Oncol., vol. 101, pp. 436-440 (2006).

Marte, Barbara M. et al., "Neu Differentiation Factor/Heregulin Modulates Growth and Differentiation of HC11 Mammary Epithelial Cells," Molecular Endocrinology, vol. 9, pp. 14-23 (1995).

Masson, K. et al., "The ErbB3-targeting antibody MM-121 (seribantumab) abrogates heregulin-driven resistance to multiple chemotherapies in preclinical models," European Association for Cancer Research (EACR) AACR Poster, Merrimack Pharmaceuticals, 2015, 1 page.

McCall, Adrian M. et al., "Increasing the Affinity for Tumor Antigen Enhances Bispecific Antibody Cytotoxicity," The Journal of Immunology, vol. 166, pp. 6112-6117 (2001).

McDonagh, Charlotte F. et al., "Antitumor Activity of a Novel Bispecific Antibody That Targets the ErbB2/ErbB3 Oncogenic Unit and Inhibits Heregulin-Induced Activation of ErbB3," Mol. Cancer Ther., vol. 11(3), pp. 582-593 (2012).

Morrissey, Thomas K. et al., "Axon-induced mitogenesis of human Schwann cell involves heregulin and p185erbB2," Proc. Natl. Acad. Sci. USA, vol. 92, pp. 1431-1435 (1995).

Moscosco, Lisa M. et al., "Synapse-Associated Expression of an Acetylcholine Receptor-Inducing Protein, ARIA/Heregulin, and Its Putative Receptors, ErbB2 and ErbB3, in Developing Mammalian Muscle," Developmental Biology, vol. 172, pp. 158-169 (1995).

Musgrove, Elizabeth A. et al., "Biological determinants of endocrine resistance in breast cancer," Nature Reviews Cancer, vol. 9, pp. 631-643 (2009).

Myers, Russell B. et al., "Expression of p160erbB-3 and p185erbB-2 in Prostatic Intraepithelial Neoplasia and Prostatic Adenocarcinoma," Journal of the National Cancer Institute, vol. 86(15), pp. 1140-1145 (1994).

Naidu., R. et al.,"Expression of c-erbB3 protein in primary breast carcinomas," Br J Cancer 1998; vol. 78(10), pp. 1385-1390.

Nie, L et al., "High ErbB4/ErbB3 Ratio Attenuates Efficacy of Anti-ErbB3 Therapy," Abstract No. 677, European Association for Cancer Research (EACR) ErbB4 Poster, Merrimack Pharmaceuticals, 2015, 1 page.

Nie, Lin et al., "Efficacy of MM121 in ER+ and triple negative breast cancer studies," Proceedings of the American Association for Cancer Research, vol. 51, p. 436, Poster Presentation No. 1806 (2010).

Nielsen, Ulrik B. et al., "Targeting of Bivalent Anti-ErbB2 Diabody Antibody Fragments to Tumor Cells Is Independent of the Intrinsic Antibody Affinity," Cancer Research, vol. 60, pp. 6434-6440 (2000).

Notice of Opposition to a European Patent for Patent No. EP 2318548,7 pages, dated Jul. 21, 2014.

Oikawa, Tetsuro et al., "Frequent Expression of Genes for Receptor Tyrosine Kinases and Their Ligands in Human Pancreatic Cancer Cells," International Journal of Pancreatology, vol. 18(1), pp. 15-23 (1995).

Onsum, M. et al., "Prediction of xenograft response to MM-121, an anti-ErbB3 inhibitor, using computational modeling and measurements of five biomarkers," American Association for Cancer Research (AACR) Annual meeting, 2010, Monsum Biomarkers Poster, Abstract No. 3756, 1 page.

Orr-Urtreger, Avi et al., "Neural expression and chromosomal mapping of Neu differentiation factor to 8p12-p21," Proc. Natl. Acad. Sci. USA, vol. 90, pp. 1867-1871 (1993).

Peles, Elior et al., "Cell-type specific interaction of Neu differentiation factor (NDF/heregulin) with Neu/HER-2 suggests complex ligand-receptor relationships," The EMBO Journal, vol. 12(3), pp. 961-971 (1993).

Perez, E.,"Paclitaxel in breast cancer," The Oncologist, vol. 3(6), pp. 373-389 (1998).

Petrelli, F. et al., "Current data of targeted therapies for the treatment of triple-negative advanced breast cancer: empiricism or evidence-based?" Expert Opin. Investig. Drugs, vol. 18(10), pp. 1467-1477 (2009).

Pierce, Jacalyn H. et al., "Signal Transduction Through the EGF Receptor Transfected in IL-3-Dependent Hematopoietic Cells," Science, vol. 239, pp. 628-631 (1988).

Pinkas-Kramarski, Ronit et al., "Diversification of Neu differentiation factor and epidermal growth factor signaling by combinatorial receptor interactions," The EMBO Journal, vol. 15(10), pp. 2452-2467 (1996).

Pinkas-Kramarski, Ronit et al., "Neu Differentiation Factor/Neuregulin Isoforms Activate Distinct Receptor Combinations," The Journal of Biological Chemistry, vol. 271(32), pp. 19029-19032 (1996).

Pinkas-Kramarski, Ronit et al., "The oncogenic ErbB-2/ErbB-3 heterdimer is a surrogate receptor of the epidermal growth factor and betacellulin," Oncogene, vol. 16, pp. 1249-1258 (1998).

Plowman, Gregory D. et al., "Heregulin induces tyrosine phosphorylation of HER4/p180erbB4," Nature, vol. 366, pp. 473-475 (1993).

Plowman, Gregory D. et al., "Ligand-specific activation of HER4/p180erbB4, a fourth member of the epidermal growth factor receptor family," Proc. Natl. Acad. Sci. USA, vol. 90:1746-1750 (1993).

Plowman, Gregory D. et al., "Molecular cloning and expression of an additional epidermal growth factor receptor-related gene," Proc. Natl. Acad. Sci. USA, vol. 87, pp. 4905-4909 (1990).

Poller, D.N. et al., "Production and Characterization of a Polyclonal Antibody to the c-erbB-3 Protein: Examination of c-erbB-3 Protein Expression in Adenocarcinomas," Journal of Pathology, vol. 168, pp. 275-280 (1992).

Prat, A. et al., "The role of hormonal therapy in the management of hormonal-receptor-positive breast cancer with co-expression of HER2," Nature Clinical Practice Oncology vol. 5(9), pp. 531-542 (2008).

Presta, Leonard, "Antibody engineering for therapeutics," Current Opinion in Structural Biology, vol. 13, pp. 519-525 (2003).

Prigent, S.A. et al., "Expression of the c-erbB-3 protein in normal human adult and fetal tissues," Oncogene, vol. 7, pp. 1273-1278 (1992).

Prigent, Sally A. et al., "The Type 1 (EGFR-related) Family of Growth Factor Receptors and Their Ligands," Progress in Growth Factor Research, vol. 4, pp. 1-24 (1992).

Quinn, C.M. et al., "C-erbB-3 protein expression in human breast cancer: comparison with othe tumour variables and survival," Histopathology, vol. 25, pp. 247-252 (1994).

Rajkumar, T. et al., "A monoclonal antibody to the human c-erbB3 protein stimulates the anchorage-independent growth of breast cancer cell lines," Br. J. Cancer, vol. 70, pp. 459-465 (1994).

Rajkumar, T. et al., "Prevelance of c-erbB3 expression in squamous cell carcinomas of the cervix as determined by the monoclonal antibody RTJ2," International Journal of Oncology, vol. 6, pp. 105-109 (1995).

Rajkumar, T.et al., "Experssion of the C-erbB-3 Protein in Gastrointestinal Tract Tumours Determined by Monoclonal Antibody RTJ1," Journal of Pathology, vol. 170, pp. 271-278 (1993).

Rajkumar, Thangarajan et al., "The Type I growth factor receptors in human breast cancer," Breast Cancer Research and Treatment, vol. 29, pp. 3-9 (1994).

Ross, Jeffrey S. et al., "The HER-2/neu Oncogene in Breast Cancer: Prognostic Factor, Predictive Factor, and Target for Therapy," The Oncologist, vol. 3, pp. 237-252 (1998).

(56) References Cited

OTHER PUBLICATIONS

Rouzier, Roman et al., "Breast Cancer Molecular Subtypes Respond Differently to Preoperative Chemotherapy," Clin. Cancer Res., vol. 11, pp. 5678-5685 (2005).
Rudikoff, Stuart et al., "Single amino acid substitution altering antigen-binding specificity," Proc. Natl. Acad. Sci. USA, vol. 79, pp. 1979-1983 (1982).
Rudnick, Stephen I. et al., "Affinity and Avidity in Antibody-Based Tumor Targeting," Cancer Biotherapy and Radiopharmaceuticals, vol. 24(2), pp. 155-161 (2009).
Sabnis, G. et al., "Trastuzumab Reverses Letrozole Resistance and Amplifies the Sensitivity of Breast Cancer Cells to Estrogen," Cancer Research, vol. 69, pp. 1416-1428 (abstract) (2009).
Sadick, Michael D. et al., "Analysis of Heregulin-Induced ErbB2 Phosphorylation wtih a High-Throughput Kinase Receptor Activation Enzyme-Linked Immunosorbant Assay," Analytical Biochemistry, vol. 235, pp. 207-214 (1996).
Sak, M. et al., "Pertuzuman counteracts the inhibitory effect of ErbB2 on degradation of ErbB3," Carcinogenesis, vol. 34(9), pp. 2031-2038 (2013).
Salomon, David S. et al., "Epidermal growth factor-related peptides and their receptors in human malignancies," Critical Reviews in Oncology/Hematology, vol. 19, pp. 183-232 (1995).
Sanidas, E.E. et al., "Expression of the c-erbB-3 Gene Product in Gastric Cancer," Int. J. Cancer, vol. 54, pp. 935-940 (1993).
Schaefer, Karl-Ludwig et al., "Constitutive Activation of Neuregulin/ERBB3 Signaling Pathway in Clear Cell Sarcoma of Soft Tissue," Neoplasia, vol. 8(7), pp. 613-622 (2006).
Schaefer, Karl-Ludwig et al., "Expression Profiling of t(12;22) Positive Clear Cell Sarcoma of Soft Tissue Cell Lines Reveals Characteristic Up-Regulation of Potential New Marker Genes Including ERBB3," Cancer Research, vol. 64, pp. 3395-3405 (2004).
Schmidt, M. et al., "Targeted inhibition of tumour cell growth by a bispecific single-chain toxin containing an antibody domain and TGFa," British Journal of Cancer, vol. 74, pp. 853-862 (1996).
Schneider, Bryan P. et al., "Triple-Negative Breast Cancer: Risk Factors to Potential Targets," Clin. Cancer Res., vol. 14(24), pp. 8010-8018 (2008).
Schoeberl, Birgit et al., "An ErbB3 Antibody, MM-121, Is Active in Cancers with Ligand-Dependent Activation," Cancer Res., vol. 70(6), pp. 2485-2494 (2010).
Schoeberl, Birgit et al., "Computational modeling and simulation lead to the development of MM-121, a human monoclonal antibody ErbB3 antagonist," 99th AACR Annual Meeting, Abstract No. 1638, 2 pages (2008).
Schoeberl, Birgit et al., "MM-121: a human monoclonal antibody ErbB3 antagonist," 99th AACR Annual Meeting, Abstract No. 3974, 1 page (2008).
Semba, Kentaro et al., "A v-erbB-related protooncogene, c-erbB-2, is distinct from the c-erbB-1/epidermal growth factor-receptor gene and is amplified in a human salivary gland adenocarcinoma," Proc. Natl. Acad. Sci. USA, vol. 82, pp. 6497-6501 (1985).
Sequist, L.V. et al., "A Randomized Phase 2 Trial of MM-121, a Fully Human Monoclonal Antibody Targeting ErbB3, in Combination with Erlotinib, in EGFR Wild-type NSCLC Patients," American Society of Clinical Oncology, 2014, Poster Presentation, 1 page.
Aaronson, S.A. et al., "Growth factor-regulated pathways in epithelial cell proliferation," Am. Rev. Respir. Dis., vol. 142(6 pt. 2):S7-S10 (1990).
Adapt, "Probesets for Betacellulin," The Paterson Institute for Cancer Research, 2 pages (2013).
Adapt, "Probesets for ErbB1," The Paterson Institute for Cancer Research, 4 pages (2013).
Adapt, "Probesets for ErbB2," The Paterson Institute for Cancer Research, 3 pages (2013).
Adapt, "Probesets for ErbB3," The Paterson Institute for Cancer Research, 3 pages (2013).
Adapt, "Probesets for Neuregulin," The Paterson Institute for Cancer Research, 14 pages (2013).
Alberts, Bruce et al., Molecular Biology of the Cell, Third Edition, Garland Publishing, Inc., New York, pp. 897-899 (1994).
Alimandi, Maurizio et al., "Cooperative signaling of ErbB3 and ErbB2 in neoplastic transformation and human mammary carcinomas," Oncogene, vol. 10, pp. 813-1821 (1995).
Alimandi, Maurizio et al., "Epidermal growth factor and betacellulin mediate signal transduction through co-expressed ErbB2 adn ErbB3 receptors," The EMBO Journal, vol. 16(18), pp. 5608-5617 (1997).
ATCC, "AdrR," retrieved online at:www.atcc.org/ATCCAdvancedCatalogSearch/AllCollectionSearch/tabid/454/D-efault.aspx (2011).
Bae, S. et al., "HER3 status by immunohistochemistry is correlated with poor prognosis in hormone receptor-negative breast cancer patients," Breast Cancer Res. Treat, vol. 139, pp. 741-750 (2013).
Balint, Robert F. et al., "Antibody engineering by parsimonious mutagenesis," Gene, vol. 137, pp. 109-118 (1993).
Baselga, Jose et al., "Novel anticancer targets: revisiting ERBB2 and discovering ERBB3," Nature Reviews Cancer, vol. 9(7), pp. 463-475 (2009).
Baselga, Jose et al., "Phase II Trial of Pertuzumab and Trastuzumab in Patients With Human Epidermal Growth Factor Receptor 2-Positive Metastatic Breast Cancer That Progressed During Prior Trastuzumab Therapy," Journal of Clinical Oncology, vol. 28(7), pp. 1138-1144 (2010).
Becerril, Baltazar et al., "Toward Selection of Internalizing Antibodies from Phage Libraries," Biochemical and Biophysical Research Communications, vol. 255, pp. 386-393 (1999).
Beckman, Robert A. et al., "Antibody Constructs in Cancer Therapy, Protein Engineering Strategies to Improve Exposure in Solid Tumors," Cancer, vol. 109, pp. 170-179 (2007).
Beerli, Roger R. et al., "Neu Differentiation Factor Activation of ErbB-3 and ErbB-4 Is Cell Specific and Displays a Differential Requirement for ErbB-2," Molecular and Cellular Biology, vol. 15(12), pp. 6496-6505 (1995).
Bodey, Bela et al., "Immunophenotypically Varied Cell Subpopulations in Primary and Metastatic Human Melanomas. Monoclonal Antibodies for Diagnosis, Detection of Neoplastic Progression and Receptor Directed Immunotherapy," Anticancer Research, vol. 16, pp. 517-532 (1996).
Bortoletto, Nicola et al., "Optimizing anti-CD3 affinity for effective T cell targeting against tumor cells," Eur. J. Immunol., vol. 32, pp. 3102-3107 (2002).
Bostwick, David G., "c-erbB-2 Oncogene Expression in Prostatic Intraepithelial Neoplasia: Mounting Evidence for a Precursor Role," Journal of the National Cancer Institute, vol. 86(15), pp. 1108-1110 (1994).
Brand, et al., "Prospect for Anti-HER2 Receptor Therapy in Breast Cancer," Anticancer Res., vol. 26, pp. 463-470 (2006).
Brodie, Angela et al., "Adaptive changes result in activation of alternative signaling pathways and acquisition of resistance to aromatase inhibitors," Clin. Cancer Res., vol. 17(13), pp. 4208-4213 (2011).
Brorson, Kurt et al., "Mutational Analysis of Avidity and Fine Specificity of Anti-Levan Antibodies," The Journal of Immunology, vol. 163, pp. 6694-6701 (1999).
Brotherick, Ian et al., "A flow cytometric study of c-erbB-3 expression in breast cancer," Cancer Immunol. Immunother., vol. 41, pp. 280-286 (1995).
Brown, McKay et al., "Tolerance to Single, but Not Multiple, Amino Acid Replacements in Antibody VH CDR2," The Journal of Immunology, vol. 156, pp. 3285-3291 (1996).
Brummell, David A. et al., "Probing the Combining Site of an Anti-Carbohydrate Antibody by Saturation-Mutagenesis: Role of the Heavy-Chain CDR3 Residues," Biochemistry, vol. 32, pp. 1180-1187 (1993).
Burks, Elizabeth A. et al., "In vitro scanning saturation mutagenesis of an antibody binding pocket," Proc. Natl. Acad. Sci. USA, vol. 94, pp. 412-417 (1997).
Campbell, Marcia R. et al., "HER3 Comes of Age: New Insights into the Functions and Role in Signaling, Tumor Biology, and Cancer Therapy," Clin. Cancer Res., vol. 16(5), pp. 1373-1383 (2010).

(56) References Cited

OTHER PUBLICATIONS

Carraway, Kermit L. III et al., "A Neu Acquaintance for ErbB3 and ErbB4: A Role for the Receptor Heterodimerization in Growth Signaling," Cell, vol. 78, pp. 5-8 (1994).
Carraway, Kermit L. III et al., "Heregulin Stimulates Mitogenesis and Phosphatidylinositol 3-Kinase in Mouse Fibroblasts Transfected with erbB2/neu and erbB3," The Journal of Biological Chemistry, vol. 270(13), pp. 7111-7116 (1995).
Carraway, Kermit L. III et al., "The erbB3 Gene Product Is a Receptor for Heregulin," The Journal of Biological Chemistry, vol. 269(19), pp. 14303-14306 (1994).
Casset, Florence et al., "A peptide mimetic of an anti-CD4 monoclonal antibody by rational design," Biochemical and Biophysical Research Communications, vol. 307, pp. 198-205 (2003).
Cespedes, Maria Virtudes et al., "Mouse models in oncogenesis and cancer therapy," Clin. Transl. Oncol., vol. 8(5), pp. 318-329 (2006).
Chan, A. et al., "Therapeutic Antibodies for Autoimmunity and Inflamation," Nature Reviews Immunology, vol. 10, pp. 301-316 (2010).
Chen, Xiaomei et al., "An Immunological Approach Reveals Biological Differences between the Two NDF/Heregulin Receptors, ErbB-3 and ErbB-4," The Journal of Biological Chemistry, vol. 271(13), pp. 7620-7629 (1996).
Chen, Yvonne et al., "Selection and Analysis of an Optimized Anti-VEGF Antibody: Crystal Structure of an Affinity-matured Fab in Complex with Antigen," J. Mol. Biol., vol. 293, pp. 865-881 (1999).
Ciardiello, Fortunato et al., "Differential expression of epidermal growth factor-related proteins in human colorectal tumors," Proc. Natl. Acad. Sci. USA, vol. 88, pp. 7792-7796 (1991).
Cicenas, J. et al, "Phosphorylation of tyrosine 1248-ERBB2 measured by chemiluminescence-linked immunoassay is an independent predictor of poor prognosis in primary breast cancer patients," European J Cancer, vol. 42, pp. 636-645(2006).
Cleary, J.M., "A Phase 1 Study of MM-121 (a fully human monoclonal antibody targeting the epideral growth factor receptor family member ErbB3) in Combination with Cetuximab and Irinotecan in Patients with Advanced Cancers," American Society of Clinical Oncology, Poster Presentation, 1 page (2014).
Colman, P.M., "Effects of amino acid sequence changes on antibody-antigen interactions," Research in Immunology, vol. 145, pp. 33-36 (1994).
Curley, M et al., "MM-121/SAR256212, an anti-ErbB3 antibody, restores sensitivity to letrozole and delays the onset of resistance in an ER+ breast cancer model," Merrimack Pharmaceuticals & Sanofi, Apr. 1, 2013, Poster Presentation, pp. 1-22.
Curley, Michael "MM-121, an anti-ErbB3 antibody, inhibits PI3K/AKT signaling and viability in platinum-resistant ovarian cells; and in primary ascites derived from chemo-resistant ovarian cancer patients," European Organisation for Research and Treatment of Cancer (EORTC), 2012, Poster No. 108, page 1.
Davies, Jullian et al., "Affinity improvement of single antibody VH domains: residues in all three hypervariable regions affect antigen binding," Immunotechnology, vol. 2, pp. 169-179 (1996).
De Pascalis, Roberto et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169, pp. 3076-3084 (2002).
Denlinger, C.S. et al., "A phase 1/11 and pharmacologic study of MM-111 in patients with advanced, refractory HER2-positive (HER2+) cancers," J. Clin. Oncol., vol. 28(15s), 2010 ASCO Annual Meeting, Abstract No. TPS169, 4 pages (2010).
Dennis, Carina, "Off by a whisker," Nature, vol. 442, pp. 739-741 (2006).
Di Fiore, Pier Paolo et al., "Mechanisms involving an expanding erbB/EGF receptor family of tyrosine kinases in human neoplasia," Genes, Oncogenes, and Hormones, Robert B. Dickson, Ed., Kluwer Academic Publishers, pp. 139-160 (1992).
Dorvillius, Mylene et al., "Targeting of Human Breast Cancer by a Bispecific Antibody Directed against Two Tumour-Associated Antigens: ErbB-2 and Carcinoembryonic Antigen," Tumor Biol., vol. 23, pp. 337-347 (2002).
Drebin, Jeffrey A. et al., "Monoclonal antibodies reactive with distinct domains of the neu oncogene-encoded p185 molecule exert synergistic anti-tumor effects in vivo," Oncogene, vol. 2, pp. 273-277 (1988).
Dufner, Patrick et al., "Harnessing phage and ribosome display for antibody optimisation," Trends in Biotechnology, vol. 24(11), pp. 523-529 (2006).
U.S. Appl. No. 12/281,925, filed Sep. 5, 2008, Birgit Schoeberl.
U.S. Appl. No. 12/545,279, filed Aug. 21, 2009, Birgit Schoeberl.
U.S. Appl. No. 12/425,874, filed Apr. 17, 2009, Birgit Schoeberl.
U.S. Appl. No. 12/904,492, filed Oct. 14, 2010, Birgit Schoeberl.
U.S. Appl. No. 14/181,334, filed Feb. 14, 2014, Birgit Schoeberl.
U.S. Appl. No. 13/058,687, filed Feb. 11, 2011, Birgit Schoeberl.
U.S. Appl. No. 14/148,379, filed Jan. 6, 2014, Birgit Schoeberl.
U.S. Appl. No. 13/583,949, filed Sep. 11, 2012, Victor Moyo.
U.S. Appl. No. 14/518,900, filed Oct. 20, 2014, Victor Moyo.
U.S. Appl. No. 14/004,598, filed Nov. 20, 2013, Gabriela Garcia.
U.S. Appl. No. 12/281,925, Office Action dated Oct. 18, 2010.
U.S. Appl. No. 12/281,925, Office Action dated Sep. 13, 2010.
U.S. Appl. No. 12/281,925, Office Action dated Mar. 4, 2010.
U.S. Appl. No. 12/545,279, Office Action dated Nov. 20, 2013.
U.S. Appl. No. 12/545,279, Office Action dated Jun. 26, 2012.
U.S. Appl. No. 12/545,279, Office Action dated Sep. 9, 2011.
U.S. Appl. No. 12/545,279, Office Action dated May 20, 2011.
U.S. Appl. No. 12/545,279, Office Action dated Feb. 17, 2011.
U.S. Appl. No. 12/425,874, Office Action dated Apr. 14, 2010.
U.S. Appl. No. 12/904,492, Office Action dated Oct. 15, 2014.
U.S. Appl. No. 12/904,492, Office Action dated Jul. 24, 2014.
U.S. Appl. No. 12/904,492, Office Action dated Feb. 20, 2014.
U.S. Appl. No. 14/181,334, Office Action dated Oct. 27, 2015.
U.S. Appl. No. 14/181,334, Office Action dated Jun. 25, 2015.
U.S. Appl. No. 14/181,334, Office Action dated Mar. 6, 2015.
U.S. Appl. No. 13/058,687, Office Action dated Sep. 5, 2013.
U.S. Appl. No. 13/058,687, Office Action dated Jun. 27, 2013.
U.S. Appl. No. 13/058,687, Office Action dated Feb. 5, 2013.
U.S. Appl. No. 13/058,687, Office Action dated Nov. 7, 2012.
U.S. Appl. No. 14/148,379, Office Action dated Aug. 5, 2015.
U.S. Appl. No. 14/148,379, Office Action dated Jan. 7, 2015.
U.S. Appl. No. 14/148,379, Office Action dated Sep. 12, 2014.
U.S. Appl. No. 13/583,949, Office Action dated Jul. 23, 2014.
U.S. Appl. No. 13/583,949, Office Action dated Jan. 7, 2014.
U.S. Appl. No. 14/518,900, Office Action dated Oct. 16, 2015.
U.S. Appl. No. 14/004,598, Office Action dated Sep. 14, 2015.
U.S. Appl. No. 14/004,598, Office Action dated May 5, 2015.
Eccles, Suzanne A. et al., "Significance of the c-erbB Family of Receptor Tyrosine Kinases in Metastatic Cancer and Their Potential as Targets for Immunotherapy," Invasion Metastasis, vol. 14, pp. 337-348 (1995).
Engelman, Jeffrey A. et al., "MET Amplification Leads to Gefitinib Resistance in Lung Cancer by Activating ERBB3 Signaling," Science, vol. 316, pp. 1039-1043 (2007).
Erjala, Kaisa et al., "Signaling via ErbB2 and ErbB3 Associates with Resistance and Epidermal Growth Factor Receptor (EGFR) Amplification with Sensitivity to EGFR Inhibitor Gefitinib in Head and Neck Squamous Cell Carcinoma Cells," Clin. Cancer Res., vol. 12(13), pp. 4103-4111 (2006).
Esteva, Francisco J. et al., "Expression of erbB/HER Receptors, Heregulin and P38 in Primary Breast Cancer using Quantitative Immunohistochemistry," Pathology Oncology Research, vol. 7(3), pp. 171-177 (2001).
Ethier, Stephen P. et al., "erbB Family Receptor Expression and Growth Regulation in a Newly Isolated Human Breast Cancer Cell Line," Cancer Research, vol. 56, pp. 899-907 (1996).
Faksvåg, Dagny R. et al., "Expression of c-erbB-3 and c-erbB-4 Proteins in Papillary Thyroid Carcinomas," Cancer Research, vol. 56, pp. 1184-1188 (1996).

(56) References Cited

OTHER PUBLICATIONS

Fendly, Brian M. et al., "Characterization of Murine Monoclonal Antibodies Reactive to Either the Human Epidermal Growth Factor Receptor or HER2/neu Gene Product," Cancer Research, vol. 50, pp. 1550-1558 (1990).
Fiddes, Rodney J. et al., "Heregulin (HRG)-induced Mitogenic Signaling and Cytotoxic Activity of a HRG/PE40 Ligand Toxin in Human Breast Cancer Cells," Cell Growth & Differentiation, vol. 6, pp. 1567-1577 (1995).
Fitzpatrick, V. Danial et al., "Formation of a high affinity heregulin binding site using the soluble extracellular domains of ErbB2 with ErbB3 or ErbB4," FEBS Letters, vol. 431, pp. 102-106 (1998).
Foley, John et al., "EGFR Signaling in Breast Cancer: Bad to the Bone," Semin. Cell Dev. Biol., vol. 21(9), pp. 951-960 (2010).
Francois, Christine et al., "Antibodies directed at mouse IL-2-R a and b chains act in synergy to abolish T-cell proliferation in vitro and delayed type hypersensitivity reaction in vivo," Transpl. Int., vol. 9, pp. 46-50 (1996).
Friess, H. et al., "Pancreatic cancer: the potential clinical relevance of alterations in growth factors and their receptors," J. Mol. Med., vol. 74, pp. 35-42 (1996).
Friess, Helmut et al., "Enhanced erbB-3 Expression in Human Pancreatic Cancer Correlates with Tumor Progression," Clinical Cancer Research, vol. 1, pp. 1413-1420 (1995).
Frogne, Thomas et al., "Activation of ErbB3, EGFR and Erk is essential for growth of human breast cancer cell lines with acquired resistance to fulvestrant," Breast Cancer Res. Treat., vol. 114(2), pp. 263-275 (2009).
Fuchs, C.S., "Gastric Carcinoma," The New England Journal of Medicine, vol. 333(21), pp. 1426-1428 (1995).
Fujimori, Kenji et al., "A Modeling Analysis of Monoclonal Antibody Percolation Through Tumors: A Binding-Site Barrier," J. Nucl. Med., vol. 31, pp. 1191-1198 (1990).
Garnett, Daniel C. et al., "Heregulin-stimulated Signaling in Rat Pheochromocytoma Cells," The Journal of Biological chemistry, vol. 270(32), pp. 19022-19027 (1995).
Gasparini, G. et al., "Randomized phase II trial of weekly paclitaxelalone verus trastuzumab plus weekly paclitaxel as; first-line therapy of patients with Her-2 positive advanced breast cancer," Breast Cancer Res. Treat., vol. 101, pp. 355-365 (2007).
Gorgoulis, V. et al., "Molecular and immunohistochemical study of class I growth factor receptors in squamous cell lung carcinomas," Abstracts / Lung Cancer, vol. 14, p. 381 (1996).
Gown, AM, et al., "Current issues in ER and HER2 testing by IHC in breast cancer," Modern Pathol. vol. 21, pp. S8-S15 (2008).
Grasso, Adam W. et al., "ErbB kinases and NDF signaling in human prostate cancer cells," Oncogene, vol. 15, pp. 2705-2716 (1997).
Gullick, W.J., "The c-erbB3/HER3 Receptor in Human Cancer," Cancer Surveys, vol. 27, pp. 339-349 (1996).
Guy, Pamela M. et al., "Insect cell-expressed p180erbB3 possesses an impaired tyrosine kinase activity," Proc. Natl. Acad. Sci. USA, vol. 91, pp. 8132-8136 (1994).
Hamburger, Anne W. et al., "The Role of ErbB3 and its Binding Partners in Breast Cancer Progression and Resistance to Hormone and Tyrosine Kinase Directed Therapies," J. Mammary Gland Biol. Neoplasia, vol. 13(2), pp. 225-233 (2008).
Harms, Brian D. et al., "Application of computational modeling to guide the development of MM-111, a bispecific antibody targeting ErbB3 in ErbB2 overexpressing tumors," 2009 AACR Annual Meeting, Abstract No. 3298, 1 page (2009).
Harris, L.N et al., "Induction of sensitivity to doxorubicin and etoposide by transfection of MCF-7 breast cancer cells with heregulin beta-2," Clinical Cancer Research, 1998, vol. 4, pp. 1005-1012.
Harris, Lyndsay N. et al., "Molecular subtypes of breast cancer in relation to paclitaxel response and outcomes in women with metastatic disease: results from CALGB 9342," Breast Cancer Research, vol. 8(6):R66, 12 pages doi: 10.1186/bcr1622 (2006).
Heldin, Carl-Henrik, "Dimerization of Cell Surface Receptors in Signal Transduction," Cell, vol. 80, pp. 213-223 (1995).

Hellyer, Nathan J. et al., "Cloning of the rat ErbB3 cDNA and characterization of the recombinant protein," Gene, vol. 165, pp. 279-284 (1995).
Higgins, M. et al., "A Randomized, Double-Blind Phase II Trial of Exemestane+ MM-121, monoclonal antibody targeting ErbB3,or placebo in Postmenopausal Women with Locally Advanced or Metastatic ER+/PR+,Her2-negative Breast Cancer," American Society of Clinical Oncology, 2014, Poster Presentation, 1 page.
Hofmann, Francesco et al., "Blocking insulin-like growth factor-I receptor as a strategy for targeting cancer," DDT, vol. 10(15), pp. 1041-1047 (2005).
Holbro, Thomas et al., "The ErbB2/ErbB3 heterodimer functions as an oncogenic unit: ErbB2 requires ErbB3 to drive breast tumor cell proliferation," PNAS, vol. 100(15), pp. 8933-8938 (2003).
Holm, Patrik et al., "Functional mapping and single chain construction of the anti-cytokeratin 8 monoclonal antibody TS1," Molecular Immunology, vol. 44, pp. 1075-1084 (2007).
Holmes, F. et al., "A Randomized, Phase 2 Trial of Preoperative MM-121 with Paclitazel in triple Negative (TNBC) and Hormone Receptor (HR) Positive, HER2-negative Breast Cancer," San Antonio Breast Cancer Symposium—Dec. 9-13, 2014, Poster Presentation, 1 page.
Holmes, William E. et al., "Identification of Heregulin, a Specific Activator of p185erbB2," Science, vol. 256, pp. 1205-1210 (1992).
Holt, Lucy J. et al., "Domain antibodies: proteins for therapy," TRENDS in Biotechnology, vol. 21(11), pp. 484-490 (2003).
Horan, Thomas et al., "Binding of Neu Differentiation Factor with the Extracellular Domain of Her2 and Her3," The Journal of Biological Chemistry, vol. 270(40), pp. 24604-24608 (1995).
Hsieh, AC et al., "Targeting HER proteins in cancer therapy and the role of the non-target HER3," British Journal of Cancer, vol. 97, pp. 453-457 (2007).
Htun Van Der Horst, Edward et al., "Anti-HER-3 MAbs Inhibit HER-3-Mediated Signaling in Breast Cancer Cell Lines Resistant to Anti-HER-2 Antibodies," Int. J. Cancer, vol. 115, pp. 519-527 (2005).
Huhalov, Alexandra et al., "MM-111: A novel ErbB3 antagonist with potent antitumor activity in ErbB2 over-expressing malignancies," 2009 AACR Annual Meeting, Abstract No. 5472, 2 pages (2009).
Information Disclosure Submission concerning Agreement between Dyax Corporation and Merrimack Pharmaceuticals, Jun. 30, 2010.
International Preliminary Report on Patentability and Written Opinion for Application No. PCT/US2011/028129, 8 pages, dated Sep. 11, 2012.
International Preliminary Report on Patentability and Written Opinion for Application No. PCT/US2012/042164, 8 pages, dated Mar. 25, 2014.
International Preliminary Report on Patentability for Application No. PCT/US2008/002119, dated May 18, 2009.
International Preliminary Report on Patentability for Application No. PCT/US2009/054051, dated Feb. 15, 2011, 8 pages.
International Preliminary Report on Patentability for Application No. PCT/US2012/028792, 15 pages, dated Sep. 17, 2013.
International Search Report and Written Opinion for Application No. PCT/US2008/002119, dated Dec. 3, 2008.
International Search Report and Written Opinion for Application No. PCT/US2009/054051, dated May 4, 2010.
International Search Report and Written Opinion for Application No. PCT/US2011/028129, 12 pages, dated Oct. 13, 2011.
International Search Report and Written Opinion for Application No. PCT/US2012/028792, 22 pages, dated Nov. 7, 2012.
Denlinger, C.S. et al., "Phase 1 Dose escalation Study of MM-121, a Fully Human Monoclonal Antibody to ErbB3, in Patients with Advanced Solid Tumors," American Association for Cancer Research (AACR) Annual meeting, 2011, 1 page.
Neve et al, "A collection of breast cancer cell lines for the study of functionally distinct cancer subtypes," Cancer Cell, vol. 10(6):515-527 (2000).
Notice of Opposition, European Application No. EP11730112.7, dated Oct. 13, 2015, pp. 1-21.

(56) References Cited

OTHER PUBLICATIONS

Opponents Written Submission Summons to Attend Oral Proceedings,European Patent for Patent No. EP 2318548, 24 pages, dated Jan. 11, 2016.
Scartozzi, M. et al., "The Role of HER-3 Expression in the Predication of Clinical Outcome for Advanced Colorectal Cancer Patients Receiving Irinotecan and Cetuximab," The Oncologist, vol. 16, pp. 53-60 (2011).
Schoeberl, B. et al., "Therapeutically targeting ErbB3: A key node in ligand-induced activation of the ErbB receptor-PI3K axis," Science Signaling, American Association for the Advancement of Science, vol. 2 (77), pp. 1-14 (2009).
Siddiqui, S. et al., "Pre-analytic variables and phospho-specific antibodies: the Achilles heel of immunohistochemistry," Breast Cancer Research, vol. 12(113, pp. 1-2, (2010).
U.S. Appl. No. 14/181,334, Office Action dated Feb. 19, 2016.
Bes. C. et al., "Mapping the paratope of anti-CD4 recombinant Fab 13B8.2 by combining parallel peptide synthesis and site-directed mutagenesis," Journal of Biological Chemistry, vol. 278 (16,18):14265-14273 (2013).
Board, RE, et al., "Multiplexed assays for detection of mutations in PIK3CA," Clin. Chem., vol. 54(4):757-760 (2008).
Burenkova, O. et al., "In vivo effect of combination therapy: An anti ErbB3 antibody, MM121, plus selected cancer therapies," Proceedings of the American Association for Cancer Research, Annual Meeting, vol. 50, Apr. 2009 (Apr. 2009), 2 pages, Abstract 1243.
Fitzgerald, JB, et al.,"MM-141, an IGF-IR- and ErbB3-directed bispecific antibody, overcomes network adaptations that limit activity of IGF-IR inhibitors," Mol. Cancer. Ther., 13(2), 410-425 (2014).
Fontayne, A. et al., "Paratope and epitope mapping of the antithrombotic antibody 6B4 in complex with platelet glycoprotein 1b alpha," Journal of Biological Chemistry, vol. 282 (32):23517-23524 (2007).
Guddat, LW, et al., "Three-dimensional structure of human immunoglobulin with a hinge deletion," Proceedings of the National Academy of Sciences, National Academy of Sciences, US, vol. 90: 4271-4275 (1993).
Huse, et al., "Generation of a large combinatorial library of the immunoglobulin repertoire in phage lambda," Science 246: 1275-1281 (1989).
Janku, F., et al., "PIK3CA mutations in patients with advanced cancers treated with PI3K/AKT/mTOR axis inhibitors," Mol. Cancer Ther., 10(3): 558-565 (2011).
Kohler, et al., "Derivation of specific antibody-producing tissue culture and tumor lines by cell fusion," Eur. J. Immunol., vol. 6(7): 511-519 (1976).
Padlan, E.A., "X-Ray Crystallography of Antibodies," Advance Protein Chemistry, vol. 49:57-133 (1996).
Sequist, L. et al., "MM-121: A Human mAb to ErbB3," Santa Monica Lung Cancer Meeting, Preseantion 14 pages, 2014.
Arnedos, M. et al., "A Phase 1 Study of MM-121 in Combination with Multiple Anticancer Therapies in Patients with Advanced Solid Tumors," ASCO, 1 page (2013).
Aurisicchio, L. et al., "The promise of anti-ErbB3 monoclonals as new cancer therapeutics," Oncotarget, vol. 3(8):744-758 (2012).
Bazdar-Vinovrski, B. et al., "A Phase 1 biomarker-directed multi-arm study evaluating the co-administration of MM-151 with seribantumab (MM-121), istiratumab (MM-141), or trametinib in EGFR-driven cancers," ASCO, Abstract No. TPS11619 I pages (2016).
Biomarkers Definitions Working Group, "Biomarkers and surrogate endpoints: Preferred definitions and conceptual framework," Clinical Pharmacology and Therapeutics, vol. 69, No. 3, Mar. 2001, pp. 89-95.
Cho, "Contribution of oncoproteomics to cancer biomarker discovery," Molecular Cancer, vol. 6(25), 13 pages (2007).
Communication Pursuant to Article 94(3) EPC in European Patent Application No. 12775896 (EP2764364) dated Apr. 1, 2015 (5 pages).
Curley, MD et al., "Seribantumab, an Anti-ERBB3 Antibody, Delays the Onset of Resistance and Restores Sensitivity to Letrozole in an Estrogen Receptor-Positive Breast Cancer Model," Mol. Cancer Ther., vol. Pages (2015).
Engelman, et al. "The role of the ErbB family members in non-small cell lung cancers sensitive to epidermal growth factor receptor kinase inhibitors," Clinical Cancer Research, vol. 12, pp. 4372s-4376s (2006).
Finn, G. et al., "A Randomized Trial of Exemestane +/− Seribantumab (MM-121) in Postmenopausal Women With Locally Advanced or Metastatic ER/PR+ HER2- Breast Cancer: Final Analysis and Extended Subgroup Analysis," AACR Miami 1 page (2016).
Garner et al., "An antibody that locks HER3 in the inactive conformation inhibits tumor growth driven by; HER2 or neuregulin," Cancer Research, vol. 73,(19), pp. 6024-6035 (Aug. 2013).
Haddley, "MM-121," Human Anti-erbB-3 IgG2 MAb Oncolytic, Drugs of the Future, vol. 37(5):325-329 (2012).
International Preliminary Report on Patentability, PCT/US2014/072594, Jun. 28, 2016, 7 pages.
International Search Report and Written Opinion, International Application No. PCT/US2012/058871, mailed on Mar. 22, 2013 (11 pages).
International Search Report and Written Opinion, PCT/US2016/027933, dated Jun. 24, 2016, 15 pages.
International Search Report issued in corresponding application No. PCT/US2014/058437 mailed Apr. 13, 2015.
Kruser T J et al., "Mechanisms of Resistance to HER Family Targeting Antibodies," Exp. Cell Res, Apr. 15, 2010 (Apr. 15, 2010), Jan. 11, 2010 (Jan. 11, 2010)(ePub), vol. 316(7):1083-1100.
Masson, K. et al., "A network biology screen reveals ligand-receptor pathway connections and resistance mechanisms to RTK-directed therapies in cancer cells," AACR, Abstract 1199 1 page (2016).
Mathews, S. et al., "Identification of Heregulin (HRG) expression as a driver of a difficult-to-treat cancer phenotype and development of a companion diagnostic for the HRG-ErbB3 targeting drug seribantumab," AACR, Abstract No. A19, 1 page (2016).
Paul, Fundamental Immunology, 3rd Edition, 1993, 292-295.
Ritter, et al. "Human Breast Cancer Cells Selected for Resistance to Trastuzumab In vivo Overexpress; Epidermal Growth Factor Receptor and ErbB Ligands and Remain Dependent on the ErbB Receptor; Network" Clinical Cancer Research, vol.13, No. 16, Aug. 2007, pp. 4909-4919.
Sawyers, "The cancer biomarker problem," Nature, vol. 452, Apr. 2008, pp. 548-552.
Schoeberl et al., "An ErbB3 Antibody, MM-121, Is Active in Cancers with Ligand-Dependent Activation," including 18 pages of Supplemental Data.Cancer Res., 70(6):2485-2494 (2010).
Sequist, L.V. et al., "SHERLOC: A Phase 2 Study of Seribantumab (MM-121) in Combination with Docetaxel or Pemetrexed versus Docetaxel or Pemetrexed Alone in Patients with Heregulin Positive (HRG+), Locally Advanced or Metastatic Non-Small Cell Lung Cancer (NSCLC)," ASCO, Abstract No. TPS9110, 1 page, 2016.
Sergina, et al. "Escape from HER-family tyrosine kinase inhibitor therapy by the kinase-inactive HER3," vol. 445, Nature, 2007, pp. 437-441.
Sheng, Q. et al., "An activated ErbB3/NRG1 autocrine loop supports in vivo proliferation in overain cancer cells," Cancer Cell, vol. 17(3):298-310 (2010).
Sithanandam et al., "The ERBB3 receptor in cancer and cancer gene therapyERBB3 in cancer," Cancer Gene Therapy, Jul. 2008 (Jul. 2008), Apr. 11, 2008 (Apr. 11, 2008)(ePub), 15:413-448.
Wang, S. et al., "Therapeutic Targeting of ErbB3 with MM-121/Sar256212 enhances antitumor activity of paclitaxel against erbB2-overexpressing breast cancer," Breast Cancer Research, vol. 15(5): R101 (2013).
Wilson TR et al., "Neuregulin-1-Mediated Autocrine Signaling Underlies Sensitivity to HER2; Kinase Inhibitors in a Subset of Human Cancers," Cancer Cell, Aug. 16, 2011 (Aug. 16, 2011),; 20(2):158-172.

(56) References Cited

OTHER PUBLICATIONS

Yarar, D. et al., "Heregulin-ErbB3-driventumour growth persists in PI3 Kinase Mutant Cancer Cells," Mol. Cancer Ther., vol. 14(9):2072-2080 (2015).
Zhou BB et al., "Targeting ADAM-Mediated Ligand Cleavage to Inhibit HER3 and EGFR Pathways in Non-Small Cell Lung Cancer," Cancer Cell, Jul. 2006 (Jul. 2006), 10(1):39-50.
U.S. Appl. No. 15/274,989, filed Sep. 23, 2016, Birgit Schoeberl.
U.S. Appl. No. 14/967,158, filed Dec. 11, 2015, Gavin MacBeath.
U.S. Appl. No. 15/156,603, filed May 17, 2016, Bambang Adiwijaya.
U.S. Appl. No. 15/156,262, filed May 16, 2016, Bambang Adiwijaya.
U.S. Appl. No. 15/173,219, filed Jun. 3, 2016, Olga Burenkova.
U.S. Appl. No. 14/181,334, Office Action dated Jun. 22, 2016.
U.S. Appl. No. 14/148,379, Office Action dated Jun. 20, 2016.
U.S. Appl. No. 14/518,900, Office Action dated Aug. 9, 2016.
U.S. Appl. No. 14/518,900, Office Action dated Mar. 15, 2016.

\* cited by examiner

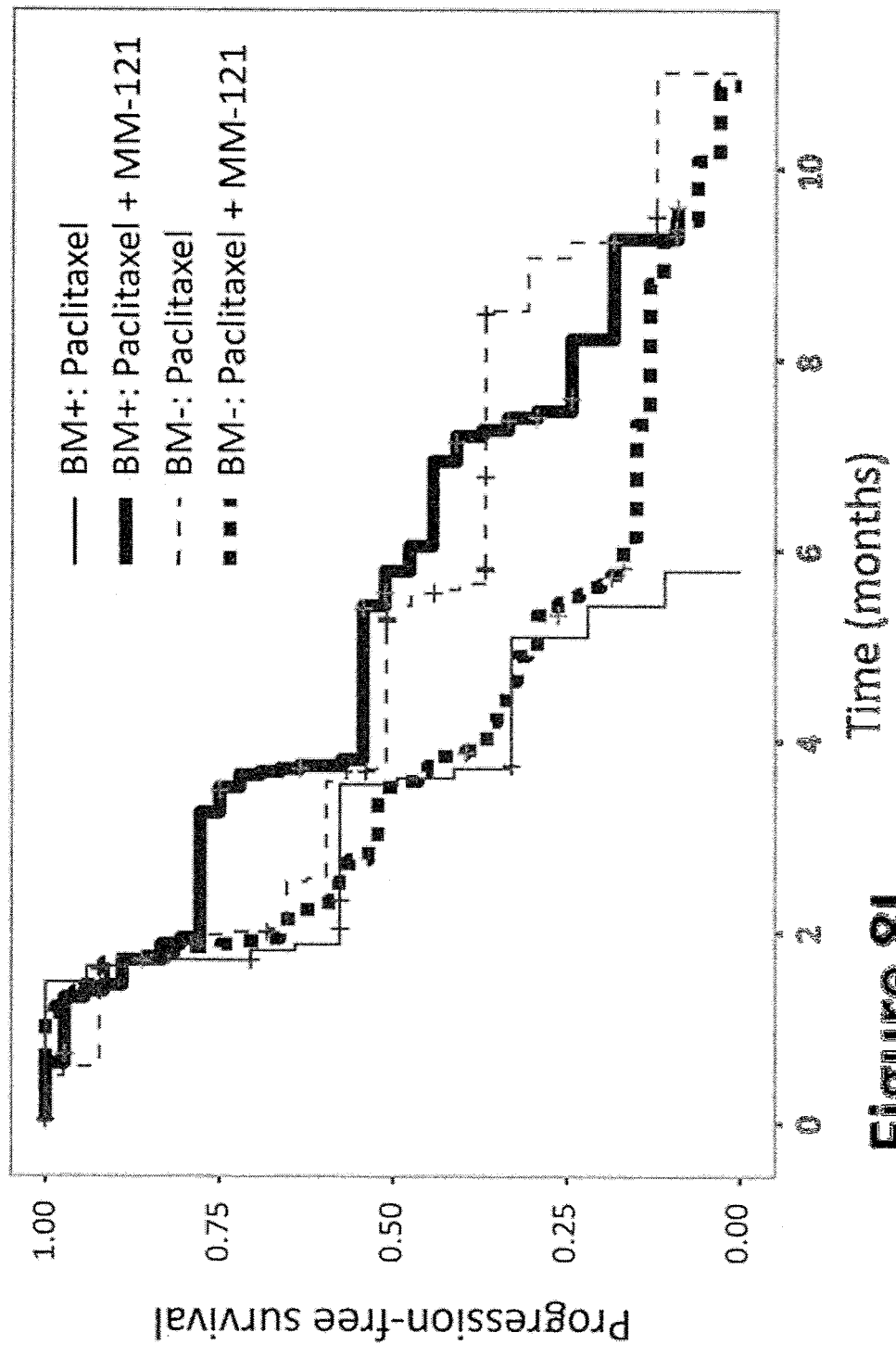

| study | group | N | N.BM+ | N.BM- | BM+ prev | HR | HR 95%CI | p | Median PFS BM- | Median PFS BM+ |
|---|---|---|---|---|---|---|---|---|---|---|
| 08 | HRG-ISH detectable & HER2<5.1 | 58 | 18 | 40 | 31% | 2.06 | 1.02-4.15 | 0.044 | 5.4 | 3.5 |
| 08 | HRG-ISH detectable | 55 | 31 | 24 | 56.40% | 1.2 | 0.61-2.34 | 0.597 | 3.6 | 3.7 |
| 08 | HRG RT-PCR archive -dCT > -5.00 | 38 | 18 | 20 | 47.40% | 1.23 | 0.59-2.56 | 0.575 | 3.7 | 3.7 |
| 08 | HRG RT-PCR archive -dCT > -14.83 | 38 | 35 | 3 | 92.10% | 1.36 | 0.32-5.79 | 0.677 | 5.8 | 3.7 |
| 08 | HRG RT-PCR archive -dCT > -12.73 | 38 | 29 | 9 | 76.30% | 0.88 | 0.37-2.1 | 0.779 | 3.7 | 3.7 |
| 08 | HRG RT-PCR archive -dCT > -9.75 | 38 | 27 | 11 | 71.10% | 1.03 | 0.47-2.29 | 0.934 | 3.7 | 3.7 |
| 08 | HRG RT-PCR archive -dCT > -7.4 | 38 | 25 | 13 | 65.80% | 1.09 | 0.51-2.36 | 0.819 | 3.7 | 3.6 |
| 08 | HRG RT-PCR archive -dCT > -5.96 | 38 | 19 | 19 | 50% | 1 | 0.48-2.09 | 0.992 | 3.6 | 3.7 |
| 08 | HRG RT-PCR archive -dCT > -4.91 | 38 | 18 | 20 | 47.40% | 1.23 | 0.59-2.56 | 0.575 | 3.7 | 3.7 |
| 08 | HRG RT-PCR archive -dCT > -3.78 | 38 | 13 | 25 | 34.20% | 2.8 | 1.25-6.29 | 0.012 | 3.7 | 2 |
| 08 | HRG RT-PCR archive -dCT > -2.73 | 38 | 9 | 29 | 23.70% | 2.16 | 0.92-5.05 | 0.076 | 3.7 | 2.8 |
| 08 | HRG RT-PCR archive -dCT > -0.75 | 38 | 5 | 33 | 13.20% | 1.51 | 0.52-4.41 | 0.449 | 3.7 | 3.5 |
| 08 | HER2 FL-IHC <5.1 | 61 | 32 | 29 | 52.50% | 1.92 | 1.02-3.63 | 0.043 | 5.4 | 3.5 |
| 08 | HER2 FL-IHC < 4.83 | 61 | 7 | 54 | 11.50% | 0.93 | 0.39-2.22 | 0.873 | 3.7 | 3.6 |
| 08 | HER2 FL-IHC < 4.9 | 61 | 10 | 51 | 16.40% | 1.12 | 0.52-2.43 | 0.769 | 3.7 | 3.5 |
| 08 | HER2 FL-IHC < 4.97 | 61 | 15 | 46 | 24.60% | 1.29 | 0.65-2.58 | 0.467 | 3.7 | 2.6 |
| 08 | HER2 FL-IHC < 5.03 | 61 | 22 | 39 | 36.10% | 1.56 | 0.84-2.9 | 0.162 | 5.1 | 3.5 |
| 08 | HER2 FL-IHC < 5.07 | 61 | 29 | 32 | 47.50% | 1.68 | 0.91-3.13 | 0.1 | 5.4 | 3.6 |
| 08 | HER2 FL-IHC < 5.13 | 61 | 37 | 24 | 60.70% | 1.51 | 0.8-2.82 | 0.201 | 5.4 | 3.5 |
| 08 | HER2 FL-IHC < 5.19 | 61 | 44 | 17 | 72.10% | 1.95 | 0.93-4.09 | 0.078 | 8.5 | 3.6 |
| 08 | HER2 FL-IHC < 5.26 | 61 | 47 | 14 | 77% | 2 | 0.92-4.34 | 0.081 | 8.5 | 3.6 |
| 08 | HER2 FL-IHC < 5.37 | 61 | 51 | 10 | 83.60% | 1.55 | 0.65-3.71 | 0.328 | 8.5 | 3.6 |
| 08 | HER3 Chr-IHC >=2 | 47 | 41 | 6 | 87.20% | 3.7 | 0.85-16.06 | 0.081 | 9.2 | 3.5 |
| 08 | HER3 Chr-IHC >=3 | 47 | 28 | 19 | 59.60% | 0.64 | 0.32-1.28 | 0.207 | 2 | 5.4 |
| 08 | HER4 Chr-IHC ==0 | 41 | 20 | 21 | 48.80% | 1.58 | 0.74-3.36 | 0.238 | 5.4 | 2 |

Fig. 13A

| | | | | | | | | |
|---|---|---|---|---|---|---|---|---|
| 101 | HRG-ISH detectable | 24 | 13 | 11 | 54.20% | 1.52 | 0.41-5.66 | 0.104 | 2.9 | 1.7 |
| 03 | HRG RT-PCR archive >-5 & HER2 FL-IHC archive <5.1 (imputed Herceptest 1+) | 25 | 8 | 17 | 32% | 1.14 | 0.41-3.16 | 0.196 | 1.9 | 2.7 |
| 03 | HRG RT-PCR archive -dCT > -5.00 | 25 | 10 | 15 | 40% | 1.29 | 0.42-3.97 | 0.188 | 3.5 | 1.9 |
| 03 | HRG RT-PCR archive -dCT > -13.83 | 25 | 23 | 2 | 92% | 0.45 | 0.09-2.1 | 0.15 | 2.2 | 1.9 |
| 03 | HRG RT-PCR archive -dCT > -12.43 | 25 | 21 | 4 | 84% | 1.17 | 0.31-4.44 | 0.2 | 2.3 | 1.9 |
| 03 | HRG RT-PCR archive -dCT > -8.86 | 25 | 19 | 6 | 76% | 0.72 | 0.25-2.09 | 0.183 | 1.7 | 3.5 |
| 03 | HRG RT-PCR archive -dCT > -7.4 | 25 | 16 | 9 | 64% | 0.81 | 0.31-2.09 | 0.195 | 1.7 | 2.7 |
| 03 | HRG RT-PCR archive -dCT > -6.62 | 25 | 16 | 9 | 64% | 0.81 | 0.31-2.09 | 0.195 | 1.7 | 2.7 |
| 03 | HRG RT-PCR archive -dCT > -5.26 | 25 | 12 | 13 | 48% | 0.75 | 0.28-2.01 | 0.186 | 1.9 | 2.7 |
| 03 | HRG RT-PCR archive -dCT > -3.77 | 25 | 8 | 17 | 32% | 1.14 | 0.37-3.52 | 0.198 | 3.5 | 1.9 |
| 03 | HRG RT-PCR archive -dCT > -2.59 | 25 | 4 | 21 | 16% | 0.97 | 0.28-3.32 | 0.206 | 1.9 | 2.7 |
| 03 | HRG RT-PCR archive -dCT > -1.19 | 25 | 2 | 23 | 8% | 0.38 | 0.06-2.26 | 0.125 | 1.9 | 3 |
| 03 | HER2 FL-IHC archive <5.1(imputed Herceptest 1+) | 56 | 46 | 10 | 82.10% | 2.2 | 0.84-5.72 | 0.301 | 5.4 | 2 |
| 03 | HER2 FL-IHC archive <5.1 | 35 | 25 | 10 | 71.40% | 1.62 | 0.59-4.46 | 0.283 | 5.4 | 3.7 |
| 03 | HER2 FL-IHC archive < 4.77 | 35 | 2 | 33 | 5.70% | 2.34 | 0.49-11.1 | 0.273 | 3.7 | 4.5 |
| 03 | HER2 FL-IHC archive < 4.84 | 35 | 6 | 29 | 17.10% | 2.31 | 0.79-6.75 | 0.193 | 4 | 2.8 |
| 03 | HER2 FL-IHC archive < 4.85 | 35 | 10 | 25 | 28.60% | 2.69 | 1.13-6.4 | 0.064 | 5.4 | 1.9 |
| 03 | HER2 FL-IHC archive < 4.9 | 35 | 14 | 21 | 40% | 2.07 | 0.92-4.65 | 0.111 | 5.5 | 1.9 |
| 03 | HER2 FL-IHC archive < 4.96 | 35 | 16 | 19 | 45.70% | 1.32 | 0.59-2.96 | 0.349 | 5.4 | 2.8 |
| 03 | HER2 FL-IHC archive < 4.99 | 35 | 20 | 15 | 57.10% | 1.56 | 0.63-3.86 | 0.284 | 5.5 | 2.8 |
| 03 | HER2 FL-IHC archive < 5.05 | 35 | 22 | 13 | 62.90% | 2.02 | 0.77-5.3 | 0.183 | 14.7 | 2.8 |
| 03 | HER2 FL-IHC archive < 5.15 | 35 | 25 | 10 | 71.40% | 1.62 | 0.59-4.46 | 0.283 | 5.4 | 3.7 |
| 03 | HER2 FL-IHC archive < 5.28 | 35 | 30 | 5 | 85.70% | 0.57 | 0.19-1.73 | 0.271 | 1.9 | 3.7 |

Fig. 13B and is 42,058 bytes in size.
BIOMARKER PROFILES FOR PREDICTING OUTCOMES OF CANCER THERAPY WITH ERBB3 INHIBITORS AND/OR CHEMOTHERAPIES

CROSS REFERENCE TO RELATED APPLICATIONS

This application is a continuation of International Application No. PCT/US2014/072594 filed Dec. 29, 2014, which claims priority to, and the benefit of, U.S. Application Nos. 61/921,185 filed Dec. 27, 2013; 62/005,683 filed May 30, 2014; 62/027,042 filed Jul. 21, 2014; and 62/055,382 filed Sep. 25, 2014. The contents of the aforementioned applications are hereby incorporated by reference in their entireties.

SEQUENCE LISTING

The instant application contains a Sequence Listing which has been submitted electronically in ASCII format and is hereby incorporated by reference in its entirety. Said ASCII copy, created on Jan. 5, 2015, is named MMJ-044PC_SL.txt and is 42,058 bytes in size.

BACKGROUND

Targeted therapies for the treatment of cancer include monoclonal antibodies that bind to antigens that are expressed on tumor cells. For example, cetuximab (Erbitux®) is a monoclonal antibody that targets the epidermal growth factor receptor (EGFR, also known as ErbB1 or HER1). While such monoclonal antibodies have been shown to be effective in some patients, the response rate for targeted therapies (and for untargeted chemotherapeutics) is never 100%. For example, only about 15-20% of patients whose tumors express EGFR respond to cetuximab monotherapy. Thus, expression by a tumor of an antigen that is targeted by a therapeutic monoclonal antibody does not necessarily predict responsiveness to treatment with the antibody.

In addition to EGFR, the ErbB/HER subfamily of polypeptide growth factor receptors include the neu oncogene product ErbB2 (HER2), and the more recently identified ErbB3 (HER3) and ErbB4 (HER4) proteins. Experiments in vitro have indicated that the protein tyrosine kinase activity of the ErbB3 protein is significantly attenuated relative to that of other ErbB/HER family members. Despite its deficient kinase activity, the ErbB3 protein has been shown to be phosphorylated in a variety of cellular contexts and to play an important role in ErbB signal transduction, e.g., in cancer cells. For example, ErbB3 is constitutively phosphorylated on tyrosine residues in a subset of human breast cancer cell lines that highly express this protein.

An explanation for the phosphorylation of ErbB3 and its oncogenic impact is that, in addition to forming various active homodimers, ErbBs are cell surface receptor proteins that form heterodimeric receptor complexes that mediate ligand-dependent (and in some cases ligand-independent) activation of multiple signal transduction pathways. ErbB3, upon binding to heregulin (HRG), its primary physiological ligand, heterodimerizes more efficiently with other ErbB family members than it does in the absence of ligand. It is the fully kinase-active ErbB hetero-partner of ErbB3 in such heterodimers that is believed to phosphorylate ErbB3, promoting high levels of (potentially oncogenic) signal transduction by the heterodimer. ErbB3-containing heterodimers (such as ErbB2/ErbB3) in tumor cells have been shown to be the most mitogenic and oncogenic ErbB receptor complexes. Accordingly, ErbB3 inhibitors, including anti-ErbB3 monoclonal antibodies, are in development for use in the treatment of various cancers.

The variable response rates of patients to monoclonal antibody therapies and chemotherapies indicates that methods are needed for accurately predicting which patients are likely to respond to therapeutic treatment with such targeted and untargeted agents so that the treatment can be administered to only those patients who are likely to receive benefits that outweigh the financial costs and potential deleterious effects of treatment (including the damage to the patient due to tumor growth over time during the administration of the ineffective treatments). Particular biomarkers or sets of biomarkers (e.g., gene products such as proteins or RNAs) in tumors may be found for which a particular concentration range for each biomarker (e.g., in the set) correlates with tumor responsiveness to a particular therapy.

Accordingly, considerable efforts are being made to discover and identify characteristic biomarkers whose levels are indicative of the probability of a particular individual tumor being responsive to particular therapies. The following disclosure provides novel biomarker criteria that allow for optimization of tumor therapy using ErbB3 inhibitors, chemotherapeutic agents (such as taxanes, anti-estrogens, topoisomerase inhibitors, and nucleoside analogs) or combinations thereof, and provides additional benefits.

SUMMARY

Provided herein are methods for a) optimizing therapy for, or b) selecting for ErbB3-targeted or other heregulin-inhibitory treatment and/or chemotherapeutic treatment or other heregulin-neutral treatment, or c) for treating; a patient having a cancer (e.g., a non-hematological cancer). These methods comprise determining whether the patient is likely to benefit from treatment with an ErbB3 inhibitor (i.e., an anti-ErbB3 antibody or another agent that inhibits the activation of ErbB3 by heregulin) or any other heregulin-inhibitory treatment with or without treatment with a heregulin-neutral treatment such as a taxane or estrogen inhibitor and whether or not the patient is likely to benefit from treatment with a chemotherapeutic agent without co-administration of an ErbB3 inhibitor. The determination is based on the measuring or scoring of levels of one or more of four particular biomarkers; ErbB2, ErbB3, ErbB4, and HRG. Each of the four particular biomarkers may be detected and measured as a protein, and may also or alternatively be detected and measured as an RNA (e.g., a gene transcript) that encodes the protein or specifically hybridizes with sequences encoding the protein. These levels are measured in at least one biological sample (biopsy) obtained from the patient. With regard to ErbB2 (HER2), certain cancer types typically express this marker at low levels and many rarely express ErbB2 at levels high enough to be scored as 2+ or 3+. As the frequency of cancers of these types that overexpress ErbB2 is low (e.g., less than 10%, or less than 5% of such cancers overexpress ErbB2, or in some cases less than 30% or less than 20%), it is possible in such cases to score levels of ErbB2 the practice of the disclosed methods by reference to cancer type (with cancer types that infrequently overexpress ErbB2 being scored as having fewer than 126,000 ErbB2 receptors per cell or as ErbB2 1+), rather than by measuring ErbB2 in a biological sample. Such cancer types may be defined in terms of the organ or tissue of origin as well as by the ethnicity of the patient.

Accordingly, in one aspect, the invention provides, a method of I) selecting therapy for a patient having a cancer, II) improving or optimizing therapeutic efficacy of treatment of a cancer in a patient, III) treating a cancer in a patient, or IV) ordering treatment of a cancer in a patient; the method comprising:

(a) obtaining one or more biomarker scores obtained from a biological sample from the patient, wherein the scored biomarker is one or more of ErbB2, ErbB3, ErbB4, or HRG, or any combination thereof; and (b) if the one or more scores meet a threshold, then
   1) selecting, and/or
   2) administering, and/or
   3) ordering the administration of,
   an effective amount of an ErbB3 inhibitor to the patient, and optionally thereby improving or optimizing therapeutic efficacy of treatment of the cancer in the patient, wherein the threshold is one or more of the following:
   (i) an immunohistochemistry (IHC) score for ErbB2 of less than 2+,
   (ii) fewer than 126,000 ErbB2 receptors per tumor cell;
   (iii) an ErbB3 IHC score of 2+ or higher;
   (iv) an ErbB4 IHC score of less than 1+;
   (v) a HRG RNA-ISH score of 1+ or higher;
   (vi) a HRG RT-PCR score of greater than or equal to −5;
   (vii) fewer than 126,000 ErbB2 receptors per tumor cell and a HRG RT-PCR score of greater than or equal to −5;
   (viii) an IHC score for ErbB2 of less than 2+ with a HRG RNA-ISH score of 1+ or higher;
   (ix) an IHC score for ErbB2 of less than 2+ with a HRG RNA-ISH score of 2+ or higher;
   (x) an IHC score for ErbB2 of less than 3+ with a HRG RNA-ISH score of 2+ or higher; or
   (xi) fewer than 200,000 ErbB2 receptors per tumor cell with a HRG RNA-ISH score of 2+ or higher.

In one variation of the above aspect, the scored biomarkers comprise ErbB3 and HRG or comprise ErbB3 and HRG and ErbB2, and the biological sample comprises tumor cells and the tumor cells comprise human phosphoinisitide-3-kinase catalytic subunit (PI3KCA)-encoding sequences comprising an activating mutation of PI3KCA and the one or more scores include (iii) and either a) either or both of (v) and (vi) or b) any one of (vii), (viii), (ix), (x), or (xi).

In an alternative embodiment, one or more scores for ErbB2, ErbB3, ErbB4, or HRG are measured in a patient biopsy of a cancer, and if the one or more scores indicate any one of the following conditions, a therapy for the patient is selected and/or ordered and/or administered that comprises ErbB3 inhibitor therapy and taxane therapy or ErbB3 inhibitor therapy and an anti-estrogen therapy:

a) ErbB2 low;
b) HRG positive;
c) ErbB2 low AND HRG positive;
d) ErbB3 medium/high;
e) ErbB2 low AND ErbB3 medium/high;
f) HRG positive AND ErbB3 medium/high;
g) ErbB2 low AND HRG positive AND ErbB3 medium/high;
h) ErbB4 negative;
i) ErbB2 low AND ErbB4 negative;
j) HRG positive AND ErbB4 negative;
k) ErbB2 low AND HRG positive AND ErbB4 negative;
l) ErbB3 medium/high AND ErbB4 negative;
m) ErbB2 low AND ErbB3 medium/high AND ErbB4 negative;
n) HRG positive AND ErbB3 medium/high AND ErbB4 negative; or
o) ErbB2 low AND HRG positive AND ErbB3 medium/high AND ErbB4 negative;

where, in a)-o) immediately above, ErbB2 low is defined as ErbB2≤(about) 126,000 receptors per cell; HRG positive is defined as HRG score ≥1; ErbB3 medium/high is defined as ErbB3 score ≥2; and ErbB4 negative is defined as ErbB4 score=0.

In another aspect, the invention provides, a method of I) selecting therapy for a patient having a cancer, II) optimizing therapeutic efficacy of treatment of cancer in a patient, III) treating cancer in a patient, or IV ordering the treatment of a cancer in a patient; the method comprising:

(a) obtaining one or more biomarker scores obtained from a biological sample from the patient, wherein the scored biomarker is one or more of ErbB2, ErbB3, ErbB4, or HRG, or any combination thereof; and (b) if the one or more scores meet a threshold, then administering to the patient (or ordering the administration to the patient of) an effective amount of an estrogen inhibitor (e.g., an aromatase inhibitor, e.g., exemestane), wherein the threshold is one or more of the following:
   (i) an immunohistochemistry (IHC) score for ErbB2 of less than 2+,
   (ii) fewer than 126,000 ErbB2 receptors per tumor cell;
   (iii) an ErbB3 IHC score of 2+ or higher;
   (iv) an ErbB4 IHC score of less than 1+;
   (v) a HRG RNA-ISH score of 1+ or higher;
   (vi) a HRG RT-PCR score of greater than or equal to −5;
   (vii) fewer than 126,000 ErbB2 receptors per tumor cell with a HRG RT-PCR score of greater than or equal to −5;
   (viii) an IHC score for ErbB2 of less than 2+ with a HRG RNA-ISH score of 1+ or higher;
   (ix) an IHC score for ErbB2 of less than 2+ with a HRG RNA-ISH score of 2+ or higher;
   (x) an IHC score for ErbB2 of less than 3+ with a HRG RNA-ISH score of 2+ or higher; or
   (xi) fewer than 200,000 ErbB2 receptors per tumor cell with a HRG RNA-ISH score of 2+ or higher.

In one variation of the above aspect, the scored biomarkers comprise ErbB3 and HRG or comprise ErbB3 and HRG and ErbB2, and the biological sample comprises tumor cells and the tumor cells comprise human phosphoinisitide-3-kinase catalytic subunit (PI3KCA)-encoding sequences comprising an activating mutation of PI3KCA and the one or more scores include (iii) and either a) either or both of (v) and (vi) or b) any one of (vii), (viii), (ix), (x), or (xi).

The estrogen inhibitor may be an estrogen receptor blocker such as tamoxifen, a selective estrogen receptor modulator such as raloxifene or an aromatase inhibitor such as exemestane.

For use in the described methods, exemplary assays include immunohistochemistry assays, immunofluorescence assays, and in situ hybridization assays, such as those provided below.

An exemplary assay by which a HRG score can be determined is an RNA-in situ hybridization (RNA-ISH) assay. In one embodiment, the RNA-ISH is read out via a chromogenic signal as set forth below. In a particular embodiment, the probes used to detect HRG by RNA-ISH hybridize specifically to a nucleic acid that comprises nucleotides 442-2977 of the nucleotide sequence set forth in GenBank accession number NM-013956 (SEQ ID NO:42).

In certain embodiments the probes hybridize specifically to RNAs encoding each of the HRG isoforms α, β1, β1b, β1c, β1d, β2, β2b, β3, β3b, γ, γ2, γ3, ndf43, ndf43b, and GGF2.

In another embodiment, the HRG score is determined by RT-PCR using probes specific for HRG.

In the case of ErbB2, ErbB3, and ErbB4, the score can be determined using an immunohistochemistry (IHC) assay. In one embodiment, the IHC assay is a read out quantitatively via a chromogenic signal (qIHC). In other embodiments, the IHC assay is an immunofluorescence assay.

ErbB3 inhibitors for use in the methods described herein include antibodies, nucleic acids (such an RNA that inhibits the expression of ErbB3 or of heregulin), or proteins (e.g., an anti-heregulin antibody, a soluble form of the ErbB3 receptor that inhibits signaling by trapping ErbB3 ligands) or small molecules (e.g., a sheddase protease inhibitor that blocks the cleavage of active heregulin from its larger precursor protein). In each of the foregoing methods, the ErbB3 inhibitor may be formulated with a pharmaceutically acceptable carrier.

In a particular embodiment, the ErbB3 inhibitor is an anti-ErbB3 antibody. An exemplary anti-ErbB3 antibody is MM-121 (SAR256212), comprising $V_H$ and $V_L$ sequences as shown in SEQ ID NOs: 1 and 2, respectively. Another exemplary anti-ErbB3 antibody is an antibody comprising in amino-terminal to carboxy-terminal order, $V_H$ CDR1, 2 and 3 sequences as shown in SEQ ID NOs: 3-5, respectively, and $V_L$ CDR1, 2 and 3 sequences as shown in SEQ ID NOs: 6-8, respectively. In other embodiments, the anti-ErbB3 antibody is Ab #3 (comprising $V_H$ and $V_L$ sequences as shown in SEQ ID NOs: 9 and 10, respectively), Ab #14 (comprising $V_H$ and $V_L$ sequences as shown in SEQ ID NOs: 17 and 18, respectively), Ab #17 (comprising $V_H$ and $V_L$ sequences as shown in SEQ ID NOs: 25 and 26, respectively) or Ab #19 (comprising $V_H$ and $V_L$ sequences as shown in SEQ ID NOs: 33 and 34, respectively). In still other embodiments, the anti-ErbB3 antibody is mAb 1B4C3, mAb 2D1D12, AMG-888, humanized mAb 8B8, AV-203, MM-141 or MEHD7945A. In another embodiment, administration of the anti-ErbB3 antibody inhibits growth or invasiveness or metastasis of the tumor.

The methods provided herein can be used to determine whether: I) a cancer in a patient is likely to respond to treatment with ErbB3 inhibitors, II) to select treatment for a cancer in a patient, III) to order treatment for a cancer in a patient, or IV to treat a cancer in a patient. In one embodiment, the cancer is a non-hematological cancer (e.g., a solid tumor). In a particular embodiment, the cancer is an ovarian cancer. In another embodiment, the cancer is a platinum resistant ovarian cancer. In another embodiment, the cancer is a breast cancer. In a further embodiment, the cancer is either or both of ER+ and PR+. In yet a further embodiment, the cancer is either or both of ER+ and PR+ and is a HER2 negative breast cancer. In an additional embodiment the cancer is a lung cancer, e.g. a non-small cell lung cancer (NSCLC).

Any suitable tumor biopsy sample can be used in the methods described herein. In one embodiment, the sample is a microtome section of a biopsy (e.g., which was formalin fixed and paraffin embedded prior to microtome sectioning). In another embodiment the biopsy is a blood draw comprising circulating tumor cells. In a further embodiment, the biopsy is obtained within 30, 60, or 90 days prior to treating the patient.

In another aspect, the treatment methods provided herein further comprise administering to the patient at least one additional anti-cancer agent that is not an ErbB3 inhibitor. In one embodiment, the at least one additional anti-cancer agent comprises at least one chemotherapeutic drug, such as a drug(s) selected from the group consisting of platinum-based chemotherapy drugs, taxanes, tyrosine kinase inhibitors, and combinations thereof.

In another aspect, the treatment further comprises administering paclitaxel in combination with the ErbB3 inhibitor. In a particular embodiment, the method comprises at least one cycle, wherein the cycle is a period of 4 weeks, wherein for each cycle the anti-ErbB3 antibody is administered every other week at a dose of 20 mg/kg (except for the first cycle, in which the initial administration of antibody may be at 40 mg/kg) and paclitaxel is administered once per week at a dose of 80 mg/m$^2$.

In another aspect, the treatment further comprises administering exemestane in combination with the ErbB3 inhibitor. In a particular embodiment, the ErbB3 inhibitor is an anti-ErbB3 antibody that is administered at an initial loading dose of 40 mg/kg and a weekly dose of 20 mg/kg thereafter together with daily administration of 25 mg of exemestane (e.g., in the form of a single tablet).

BRIEF DESCRIPTION OF THE DRAWINGS

In the figure descriptions below, indications such as "left," "right," "top," or "bottom" refer to the orientation of the figure that agrees with the orientation of the text annotation.

FIG. 5A is a graph showing the number of patients that scored positive for any one or more of six biomarkers out of the 220 patients in the safety population. For each assay type (y-axis), the numbers of patients (x-axis) in the control arm and the number of patients who received MM-121 therapy are indicated. FIG. 5B shows the ranking of biomarkers by biomarker-treatment interactions. The x-axis shows biomarkers and variables and the y-axis shows P-values. A horizontal line has been drawn at a P-value of 0.4 as an indicator of very high predictive value—this is an arbitrary cutoff—in this context P-values of greater than 0.4 may still correspond to highly predictive outcomes.

FIG. 6A shows the relationship between local HR and ErbB2 levels. The speckled dots in this figure are observed HRs, whereas the thick solid line provides a smoothed rendering (Smoothed HR) of these data accounting for noise in the ErbB2 measurements. The thinner solid lines above and below the dots represent the 95% Confidence Interval (CI). The dashed line shows the cumulative percentage of patients by ErbB2 level. FIG. 6B is three adjacent graphs showing the relationships between local HRs (treatment vs. control) and biomarker levels for HRG, ErbB4, and ErbB3 as indicated by the headers. The solid dots indicate local HR per the Y axis labeling on the left, whereas the speckled dots show the prevalence, i.e., percentage of patients with the given biomarker value, per the Y axis labeling on the right. X axis labeling is discrete for each biomarker. The black dashes above and/or below each solid dot represent the 95% CI of the HR estimates. FIG. 6C shows local HR (Y-axis) as a function of HRG levels (X axis) for RT-PCR of archived tissue (FFPE) from ovarian cancers. FIG. 6D shows local HR (Y-axis) as a function of HRG levels (X axis) for RT-PCR of samples from archived tissue (FFPE) from breast cancers.

FIGS. 7A-7F show bivariate HR scans for six pairwise biomarker comparisons set forth in Example 1: Headings indicate biomarker pairs. Cumulative HR scans were performed by selecting a subpopulation of patients based on their status regarding the $2^{nd}$ biomarker of each indicated pair, and then plotting cumulative HR across the prevalence levels of the first biomarker of each pair. The dashed lines represent patients with a score above zero for the biomarker; the thickest solid lines represent patients with a $2^{nd}$ biomarker score of 1 or higher (i.e. detectable levels of the $2^{nd}$ biomarker), and the thinnest solid lines represent patients with a $2^{nd}$ biomarker score of greater than or equal to 2. FIG. 7G shows local HR as a function of ErbB2 levels for all subjects ("Unselected") and for subjects with a HRG score of 1+ or greater ("HRG+"). Dots and dashes indicate individual data points, heavy and light continuous lines indicate smoothed data plots.

FIGS. 8A to 8I illustrate responses of biomarker profile positive and negative subpopulations from the clinical trial described in Example 5. Data collected at 60 weeks are summarized in FIGS. 8A-8F, whereas data collected at about 16 months is summarized in FIGS. 8G-8I. For each of the six plots in FIGS. 8A-8E, the treatment arm (paclitaxel+MM-121) is a solid line and the control arm (paclitaxel without MM-121) is a dashed line. FIG. 8A shows a Kaplan-Meier progression-free survival (PFS) plot for the overall (unselected) safety population. FIGS. 8B-8E are Kaplan-Meier plots for the pairwise biomarker combination ErbB2 low (ErbB2<2+) and HRG positive (HRG≥1 "HRG+"). Data for patients positive for this biomarker profile (BM+) are shown in FIG. 8B and FIG. 8D, and data for patients negative for this biomarker profile (BM−) are shown in FIG. 8C and FIG. 8E. FIG. 8B and FIG. 8C are progression free survival (PFS) plots, while FIG. 8D and FIG. 8E are overall survival (OS) plots. FIG. 8F sets forth best response rates in the treatment and control arms for the same biomarker profile positive and negative subpopulations. Percentages of Progressive Disease (PD), Stable Disease (SD), and Partial Response (PR) outcomes are shown. FIG. 8G: PFS for entire study population (unstratified). FIG. 8H: OS for entire study population (unstratified). FIG. 8I: PFS for entire study population (stratified). The data set forth in FIG. 8I demonstrate (inter alia) that of the patients treated with paclitaxel alone, BM− patients (light dashed line, in this case, heregulin−) achieved much longer PFS than did BM+ patients (light solid line, in this case, heregulin+), indicating that heregulin is a predictive biomarker for this standard of care therapy.

FIG. 9A—Median CK+ cells, all patients; FIG. 9B—Median CK+ cells, HRG+ patients; FIG. 9C—Top 10% of CK+ cells, all patients; FIG. 9D—Top 10% of CK+ cells, HRG+ patients. These results demonstrate that patients with tumors with detectable HRG levels and low HER2 levels (of log 10 5.1 or less, or 5.2 or less, or 5.3 or less) are more likely to benefit from MM-121 therapy than are patients with tumors exhibiting the same HER2 levels but that have not been further selected for having detectable levels of HRG.

FIGS. 10A and 10B summarize data collected at about 60 weeks, whereas FIGS. 10C-10E summarize data collected at between 4 and 20 months. FIG. 10A: Progression-free survival (PFS) for subpopulation with biomarker profile negative tumors (NOT log 10 ErbB2≤5.1 and detectable HRG). These results show that there was little if any benefit from adding MM-121 to control (exemestane) therapy in the biomarker negative patient population. FIG. 10B: PFS for subpopulation with biomarker profile positive (log 10 ErbB2≤5.1 and detectable HRG) tumors. These results show that there was a dramatic benefit from adding MM-121 to exemestane therapy in the biomarker positive population, as all control (exemestane alone) treated patients exhibited disease progression within 20 weeks, while over half of the MM-121 plus exemestane treated patients had not exhibited disease progression at this time point, and over 35% still had not progressed within 60 weeks. FIG. 10C: PFS for entire study population (unstratified). FIG. 10D: OS for entire unstratified study population. FIG. 10E: PFS for entire study population (stratified), with BM+ patients treated with erlotinib alone, BM+ patients treated with MM-121+erlotinib, BM− patients treated with erlotinib alone, and BM− patients treated with MM-121+erlotinib. The data set forth in FIG. 10E demonstrate (inter alia) that of the patients treated with exemestane alone, BM− patients (light dashed line, in this case, heregulin−) achieved much longer PFS than did BM+ patients (light solid line, in this case, heregulin+), indicating that heregulin is a predictive biomarker for this standard of care therapy.

FIGS. 12A and 12B show data from all patients treated with MM-121+erlotinib and erlotinib alone, showing that in the unselected overall population there is not a significant difference in PFS (FIG. 12A) and overall survival (FIG. 12B) between the two groups. FIG. 12C shows data sorted between biomarker positive (BM+) patients (in this case, heregulin+) and biomarker negative (BM−) patients (in this case, heregulin−). Shown are BM+ patients treated with erlotinib alone, BM+ patients treated with MM-121+erlotinib, BM− patients treated with erlotinib alone, and BM− patients treated with MM-121+erlotinib. In contrast to the PFS data for the overall population in FIG. 12A, FIG. 12C shows that BM+ patients treated with MM-121+erlotinib had a longer PFS than BM+ patients treated with erlotinib alone. The data set forth in FIG. 12C demonstrate (inter alia) that of the patients treated with erlotinib alone, BM− patients (light dashed line, in this case, heregulin−) achieved much longer PFS than did BM+ patients (light solid line, in this case, heregulin+), indicating that heregulin is a predictive biomarker for this standard of care therapy.

FIGS. 13A and 13B is a spreadsheet showing data for various groupings of patients in the studies set forth above. The left-hand column "study" indicates which of these three studies as follows: 08=Example 5, 101=Example 6, and 03=Example 8. Column "N" indicates number of patients in the group: "N.BM+" indicates number of BM+ patients in the group; "N.BM−" indicates number of BM− patients in the group; "BM+prev" indicates the percentage of BM+ patients in the group; "HR" indicates hazard ratio; "HR 95% CI" indicates the 95 percent confidence interval for the hazard ratio; "P" indicates the P value for the hazard ratio; "Median PFS BM−" indicates the median progression free survival for BM− patients in the group; and "Median PFS BM+" indicates the median progression free survival for BM+ patients in the group.

FIG. 15C shows re-expression of ErbB3 into control and PI3K-H1047R cells, and FIG. 15D shows HRG-stimulated growth in H1047R mutant cells transduced with empty ErbB3-reexpression vector (EV-NEG) and H1047R mutant cells transduced with ErbB3 (E30X). Cells were treated with serum-free medium alone (SFM), SFM+HRG, or SFM+HRG+MM-121.

DETAILED DESCRIPTION

Figure 1:
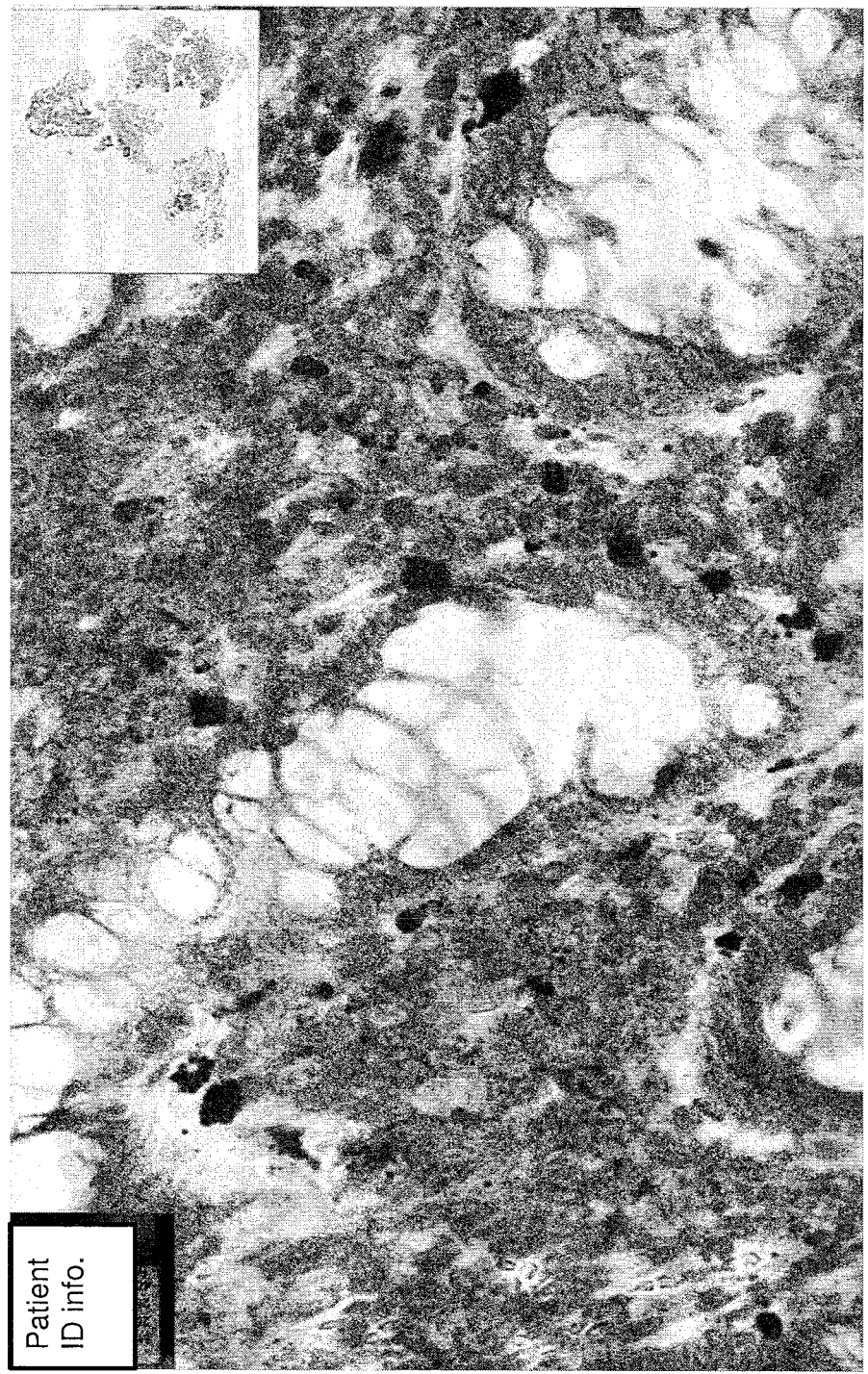
FIG. 1 shows an exemplary heregulin (HRG) RNA staining pattern in a micrograph of an ovarian cancer biopsy. Inset on upper right shows a low magnification image of the same biopsy sample.

Provided herein are methods for selecting and/or optimizing therapy for patients having cancer (e.g., non-hematological cancers) by determining whether the patient will benefit from treatment with an ErbB3 inhibitor (e.g., an antibody, such as MM-121), based on particular biomarker scores obtained from a biological sample of the patient (i.e., ErbB2, ErbB3, ErbB4, HRG, or any combination thereof). Also provided are methods of treating patients having cancer based on particular biomarker scores obtained from a biological sample of the patient (i.e., ErbB2, ErbB3, ErbB4, HRG, or any combination thereof).

Definitions

"ErbB3" and "HER3" both refer to human ErbB3 protein, as described in U.S. Pat. No. 5,480,968.

"ErbB3 inhibitor" indicates a therapeutic agent that inhibits, downmodulates, suppresses or downregulates activity or expression of ErbB3, e.g., an agent that does one or more of the following: reduces cellular ErbB3 levels, reduces ligand binding to ErbB3, and reduces ErbB3-mediated intracellular signal transduction. The term is intended to include small molecule kinase inhibitors, antibodies, interfering RNAs (shRNA, siRNA), soluble receptors, and the like. An exemplary ErbB3 inhibitor is an anti-ErbB3 antibody.

An "anti-ErbB3 antibody" is an antibody that immunospecifically binds to the ectodomain of ErbB3 and an "anti-ErbB2 antibody" is an antibody that immunospecifically binds to the ectodomain of ErbB2. The antibody may be an isolated antibody. Exemplary anti-ErbB3 antibodies inhibit ligand mediated phosphorylation of ErbB3 by HRG, and some (such as MM-121) also inhibit phosphorylation of ErbB3 mediated by one or more of the EGF-like ligands EGF, TGFα, betacellulin, heparin-binding epidermal growth factor, biregulin, epigen, epiregulin, and amphiregulin.

An "antibody," is a protein consisting of one or more polypeptides comprising binding domains substantially encoded by immunoglobulin genes or fragments of immunoglobulin genes, wherein the protein immunospecifically binds to an antigen. One type of naturally occurring immunoglobulin structural unit (e.g., an IgG) comprises a tetramer that is composed of two identical pairs of polypeptide chains, each pair having one "light" (about 25 kD) and one "heavy" chain (about 50-70 kD). "$V_L$" and "$V_H$" refer to the variable regions of these light and heavy chains respectively. "Antibodies" include intact proteins as well as antigen-binding fragments, which may be produced by digestion of intact proteins, e.g., with various peptidases, or may be synthesized de novo either chemically or using recombinant DNA expression technology. Such fragments include, for example, $F(ab)_2$ dimers and Fab monomers, and single chain antibodies. Single chain antibodies exist, generally due to genetic engineering, as a single polypeptide chain, e.g., single chain Fv antibodies (scFv) in which a $V_H$ fragment and a $V_L$ fragment are joined together (directly or through a peptide linker) to form a continuous polypeptide that retains immunospecific binding activity.

"Immunospecific" or "immunospecifically" refer to binding via domains substantially encoded by the variable region(s) of immunoglobulin genes or fragments of immunoglobulin genes to one or more epitopes of a protein of interest, but which do not specifically bind to unrelated molecules in a sample containing a mixed population of antigenic molecules. Typically, an antibody binds immunospecifically to a cognate antigen with a $K_D$ with a value of no greater than 100 nM, or preferably no greater than 50 nM, (a higher $K_D$ value indicates weaker binding) as measured e.g., by a surface plasmon resonance assay or a cell binding assay.

The term "platinum-based agent" refers to an organoplatinum compound, including for example carboplatin, cisplatin, oxaliplatin and nedaplatin.

Aromatase inhibitors are a class of drugs that inhibit the production of estrogen by blocking the activity of aromatase, an enzyme required for estrogen biosynthesis. As gynecological (e.g., breast and ovarian) cancers often require estrogen to grow, aromatase inhibitors can inhibit growth of such tumors.

The terms "suppress", "suppression", "inhibit" and "inhibition" as used herein, refer to any statistically significant decrease in biological activity (e.g., tumor cell growth), including full blocking of the activity. For example, "inhibition" can refer to a decrease of about 10%, 20%, 30%, 40%, 50%, 60%, 70%, 80%, 90%, or 100% in biological activity.

The term "patient" indicates a human subject receiving either prophylactic or therapeutic treatment.

The terms "treat," "treating," and "treatment," as used herein, refer to therapeutic or preventative (prophylactic) measures such as those described herein. The methods of "treatment" employ administration to a patient of an ErbB3 inhibitor as provided herein, for example, a patient having cancer, in order to prevent, cure, delay, reduce the severity of, or ameliorate one or more symptoms of the cancer, or in order to prolong the survival of a patient beyond that expected in the absence of such treatment.

The term "effective amount," as used herein, refers to that amount of an agent, such as an anti-ErbB3 antibody, which is sufficient to product a therapeutic benefit when administered to a patient.

The terms "anti-cancer agent" and "antineoplastic agent" refer to drugs used to treat malignancies, such as cancerous growths.

The term "obtaining" as used in reference to biomarker scores herein and in the claims, indicates the procurement of one or more biomarker scores, whether directly or indirectly. Biomarkers may be directly measured and scored by laboratory personnel. The biomarker scores measured by the laboratory personnel may be made available to at least one other party (e.g., a healthcare provider) as data (e.g., in written or electronic format). In such embodiments, a second party "obtains" the scores by consulting the data, e.g., by reading the data or hearing them read.

The term "and/or", as used herein, means either or both.

"CI" indicates confidence interval.

"CV" indicates coefficient of variation.

"dH$_2$O" indicates distilled water.

"FFPE" indicates formalin fixation and paraffin embedding (or formalin fixed and paraffin embedded).

"Fl-IHC" indicates fluorescence-based quantitative immunohistochemistry.

"HCT" refers to the HercepTest® assay, which is a commercially available (DAKO) semi-quantitative immunohistochemical assay for determination of HER2 protein (c-erbB-2 oncoprotein) expression levels.

"HR" indicates hazard ratio—see, e.g., Spruance, et al., "Hazard Ratio in Clinical Trials". *Antimicrob Agents Chemother* (2010) 48 (8):2787-2792.

"HRG" or "HRG1" indicates any and all isotypes of heregulin (neuregulin-1, "NRG"), a set of naturally occurring ligands of ErbB3.

"PCR" indicates polymerase chain reaction in any experimental embodiment of the method first set forth in Mullis, 1987, U.S. Pat. No. 4,683,202).

"qIHC" indicates chromogenic quantitative immunohistochemistry.

"qPCR indicates quantitative fluorogenic RT-PCR.

"RMSE" indicates root mean square error.

"RT-PCR" indicates reverse transcription followed by PCR of the resulting reverse transcripts.

Various aspects and embodiments are described in further detail in the following subsections.

Biomarkers

The methods described herein involve one or more particular biomarkers, levels of which are measured in a biological sample from the patient.

Scores for any single one of the biomarkers ErbB2, ErbB3, ErbB4 and HRG can be used in the methods provided herein.

Additionally, scores for each of any combination of the biomarkers described herein can be used. In one embodiment, the scores of at least two biomarkers are used (e.g., HRG and ErbB2; HRG and ErbB3; HRG and ErbB4; ErbB2 and ErbB3; ErbB2 and ErbB4; or ErbB3 and ErbB4). In other embodiments, the scores of at least three biomarkers are used.

As described above in the Summary, in embodiments in which a plurality of scores are used, levels of ErbB2 may be determined by reference to cancer type rather than by measuring ErbB2 in a biological sample. In particular, in accordance with this aspect, cancers other than breast cancer, bladder cancer, sarcoma, endometrial cancer, esophageal cancer, gastric cancer, gastro-esophageal junction cancer, ovarian cancer, lung cancer, colorectal cancer, pancreatic cancer, testicular germ cell cancer, gastric cancer, and multiple myeloma are scored as having fewer than 126,000 ErbB2 receptors per cell or as ErbB2 1+. In one embodiment, non-small cell lung cancers (NSCLCs) are also so scored.

Mutational Status

The biological sample may comprise tumor cells that are characterized by DNA sequencing, or other methods well known in the art (such as hybridization assays) as comprising at least one activating mutation in the catalytic subunit of human phosphoinisitide-3-kinase (PI3KCA). Such PI3KCA activating mutations include Exon 9 mutations and Exon 20 mutations. Exemplary activating Exon 9 mutations include E545K, E542K, and Q546R. Other exemplary mutations in Exon 9 include E545G, E545K/D549H Q546K, and P539R. Exemplary activating Exon 20 mutations include H1047R and G1049R. Other exemplary mutations in Exon 20 include H1047L, M1043V and M1043I.

Biological Samples

The expression of one or more biomarkers may be determined in a biological sample (biopsy) obtained from a subject. Such a sample is typically further processed after it is obtained from the subject. Biopsy samples suitable for detecting and quantitating the biomarkers described herein may be fresh, frozen, or fixed. Suitable samples are preferably sectioned. Alternatively, samples may be solubilized and/or homogenized and subsequently analyzed.

In one embodiment, a freshly obtained biopsy sample embedded in a cryoprotectant such as OCT® or Cryomatrix® and frozen using, for example, liquid nitrogen or difluorodichloromethane. The frozen sample is serially sectioned in a cryostat. In another embodiment, samples are fixed and embedded prior to sectioning. For example, a tissue sample may be fixed in, for example, formalin, gluteraldehyde, ethanol or methanol, serially dehydrated (e.g., using alcohol and or xylenes) and embedded in, for example, paraffin.

In one embodiment, the sample is a microtome section of a biopsy (e.g., FFPE prior to microtome sectioning). In another embodiment, the biopsy was obtained within 30, 60, or 90 days prior to treating the patient.

Detecting and Scoring Biomarkers

Nucleic Acid Assays

In various embodiments, expression of the biomarker is detected at the nucleic acid level. For example, the biomarker score for HRG can be assessed based on HRG RNA levels. In one embodiment, RNA is detected using an RNA-ISH assay as discussed in further detail below.

Another, method for determining the level of RNA in a sample involves the process of nucleic acid amplification from homogenized tissue, e.g., by RT-PCR (reverse transcribing the RNA and then, amplifying the resulting cDNA employing PCR or any other nucleic acid amplification method, followed by the detection of the amplified molecules.

In particular aspects, RNA expression is assessed by quantitative fluorogenic RT-PCR (qPCR) e.g., by using the TaqMan™ System. Such methods typically utilize pairs of oligonucleotide primers that are specific for the nucleic acid of interest. Further details of such assays are provided below in the Examples.

1. Assay Specificity

Figure 3:
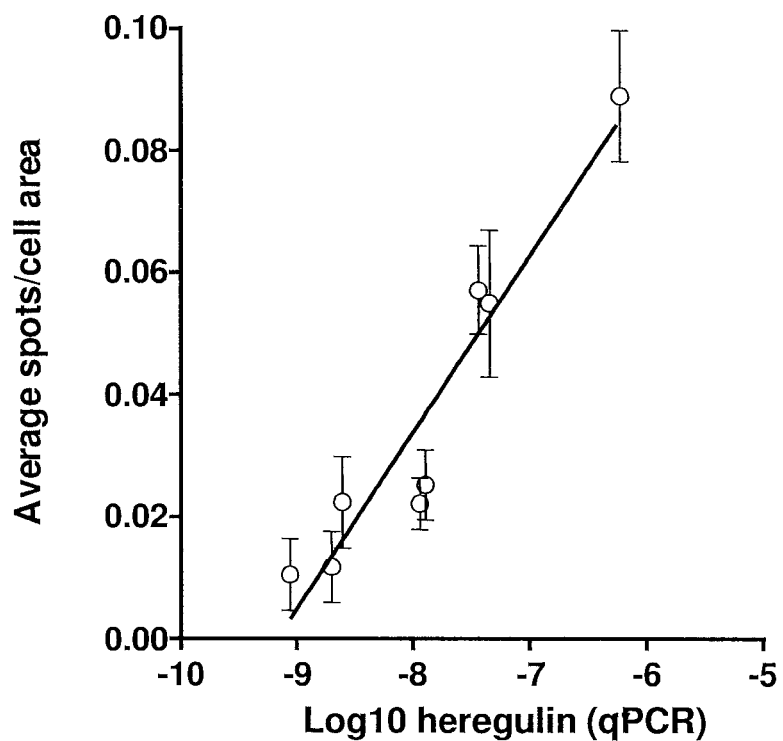
FIG. 3 shows the comparison of HRG RNA levels in four control cell lines measured by (Y axis) RNA-ISH scoring of average spots per cell area and (X-axis) qPCR.

In one approach, quantitative image analysis was used with the RNA-ISH assay to count individual dots in cells, which generally correspond to individual transcripts. A quantitative comparison of HRG RNA levels in four control cell lines measured by RNA-ISH and qPCR showed an $R^2$ of 0.91 (FIG. 3), wherein $R^2$ is the coefficient of correlation for linear regression of spots/cell area vs. Log 10 qPCR.

2. Limits of Detection

RNAscope® assays are designed to detect individual RNA transcripts (each dot generally represents one transcript). Thus, the lower limit of detection is 0 HRG RNA transcripts (0-1 dots per cell), corresponding to a pathologist score of 0. The upper limit of detection occurs when single dots in a cell become indistinguishable from each other. This corresponds to a pathologist score of 4+.

3. Reproducibility and Error Measures

Assay reproducibility can be assessed using the reference TMA of cell line plugs (reproducibility testing on human tumor tissue is ongoing) and software-aided quantification of number of spots per cell. Twenty-five reference TMAs are stained on different days, performed either manually or on a VENTANA autostainer, by two different operators. Both versions of the assay showed <20% CV as detailed in Table 1.

TABLE 1

Observed Variance of HRG RNA-ISH Assay across 25 Independent Experiments.

| Platform | Readout | N | Mean of spots/cell | RMSE | RMSE CV |
|---|---|---|---|---|---|
| Manual | HRG | 381 | 5.4289 | 0.9523 | 18% |
| VENTANA autostainer | HRG | 66 | 7.6307 | 1.0970 | 14% |

Protein Assays

Expression of the biomarker also can be detected at the protein level. Accordingly, the score for ErbB2, ErbB3, and or ErbB4 can be assessed based on detected levels of protein. In a particular embodiment, expression of protein levels is measured using immunohistochemistry (IHC) Immunohistochemistry is a technique for detecting proteins in cells of a tissue section by using antibodies that specifically bind to the proteins. Exemplary IHC assays, such as Fl-IHC and qIHC are described in further detail below.

Exemplary IHC assays, such as Fl-IHC and qIHC are described in further detail below in the Examples.

ErbB3 Inhibitors

Methods provided herein can be used to predict efficacy of therapeutic treatment using any suitable ErbB3 inhibitor or combination of inhibitors.

In one embodiment, the ErbB3 inhibitor is an anti-ErbB3 antibody, e.g., a monoclonal antibody. An exemplary anti-ErbB3 monoclonal antibody is SAR256212 (MM-121), described further in WO 2008/100624 and U.S. Pat. No. 7,846,440 (Ab #6), and having $V_H$ and $V_L$ sequences as shown in SEQ ID NOs: 1 and 2, respectively. Alternately, the anti-ErbB3 monoclonal antibody is an antibody that competes with MM-121 for binding to ErbB3. In another embodiment, the anti-ErbB3 antibody is an antibody comprising the $V_H$ and $V_L$ CDR sequences of MM-121 in the same relative order as they are present in MM-121, and which are shown in SEQ ID NOs: 3-5 ($V_H$ CDR1, 2, 3) and 6-8 ($V_L$ CDR1, 2, 3), respectively. MM-121 administration may be intravenous at exactly or about 6 mg/kg or 12 mg/kg weekly, or 12 mg/kg or 24 mg/kg biweekly. Additional dosing regimens are described below. Other examples of anti-ErbB3 antibodies include Ab #3, Ab #14, Ab #17 and Ab #19, also described further in WO 2008/100624 and U.S. Pat. No. 7,846,440, and having $V_H$ and $V_L$ sequences as shown in SEQ ID NOs: 9 and 10, 17 and 18, 25 and 26, and 33 and 34, respectively. In another embodiment, the anti-ErbB3 antibody is an antibody comprising the $V_H$ and $V_L$ CDR sequences of Ab #3 (shown in SEQ ID NOs: 11-13 and 14-18, respectively) or antibody comprising the $V_H$ and $V_L$ CDR sequences of Ab #14 (shown in SEQ ID NOs: 19-21 and 22-24, respectively) or an antibody comprising the $V_H$ and $V_L$ CDR sequences of Ab #17 (shown in SEQ ID NOs: 27-29 and 30-32, respectively) or an antibody comprising the $V_H$ and $V_L$ CDR sequences of Ab #19 (shown in SEQ ID NOs: 35-37 and 38-40, respectively), each of said CDRs being present in the same relative order as they are present in the corresponding Ab # antibody.

Alternately, the anti-ErbB3 antibody is a monoclonal antibody or antigen binding portion thereof which binds an epitope of human ErbB3 comprising residues 92-104 of SEQ ID NO:41 and is characterized by inhibition of proliferation of a cancer cell expressing ErbB3. The cancer cell may be a MALME-3M cell, an AdrR cell, or an ACHN cell and the proliferation may be reduced by at least 10% relative to control. In an additional embodiment this isolated monoclonal antibody or antigen binding portion thereof binds an epitope comprising residues 92-104 and 129 of SEQ ID NO:41.

Other examples of useful anti-ErbB3 antibodies include the antibodies 1B4C3 and 2D1D12 (U3 Pharma AG), both of which are described in US Patent Application Publication No. 20040197332 by Ullrich et al., and monoclonal antibodies (including humanized versions thereof), such as AMG-888 (U3 Pharma AG and Amgen), 8B8 (Genentech) as described in U.S. Pat. No. 5,968,511, AV-203 (Aveo Oncology), MEHD7945A (Genentech/Roche), and MM-141 (Merrimack Pharmaceuticals) as described in U.S. Pat. No. 8,476,409.

In yet another embodiment, the anti-ErbB3 antibody can comprise a mixture, or cocktail, of two or more anti-ErbB3 antibodies, each of which binds to a different epitope on ErbB3. In one embodiment, the mixture, or cocktail, comprises three anti-ErbB3 antibodies, each of which binds to a different epitope on ErbB3.

In another embodiment, the ErbB3 inhibitor comprises a nucleic acid molecule, such as an RNA molecule, that inhibits the expression or activity of ErbB3. RNA antagonists of ErbB3 have been described in the art (see e.g., US Patent Application Publication No. 20080318894). Moreover, interfering RNAs specific for ErbB3, such as shRNAs or siRNAs that specifically inhibits the expression and/or activity of ErbB3, have been described in the art.

In yet another embodiment, the ErbB3 inhibitor comprises a soluble form of ErbB3 that inhibits signaling through the ErbB3 pathway. Such soluble ErbB3 molecules have been described in the art (see e.g., U.S. Pat. No. 7,390,632, U.S. Patent Application Publication No. 20080274504 and U.S. Patent Application Publication No. 20080261270, each by Maihle et al., and U.S. Patent Application Publication No. 20080057064 by Zhou).

The ErbB3 inhibitor can be administered to the patient by any route suitable for the effective delivery of the inhibitor to the patient. For example, many small molecule inhibitors are suitable for oral administration. Antibodies and other biologic agents typically are administered parenterally, e.g., intravenously, intraperitoneally, subcutaneously or intramuscularly. Various routes of administration, dosages and pharmaceutical formulations suitable for use in the methods provided herein are described in further detail below.

Pharmaceutical Compositions:

Prior to administration, ErbB3 inhibitors can be formulated with a pharmaceutical carrier (i.e., into a pharmaceutical composition). In one embodiment, the ErbB3 inhibitor in the composition is an anti-ErbB3 antibody, e.g., MM-121 (SAR256212) or an antibody comprising the $V_H$ and $V_L$ CDRs of MM-121 positioned in the antibody in the same relative order as they are present in MM-121 so as to provide immunospecific binding of ErbB3. Additional non-limiting exemplary anti-ErbB3 antibodies and other forms of ErbB3 inhibitors are described in detail above.

MM-121 for intravenous infusion (e.g., over the course of one hour) is supplied as a clear liquid solution in sterile, single-use vials containing 10.1 ml of MM-121 at a concentration of 25 mg/ml in an aqueous solution of 20 mM histidine, 150 mM sodium chloride, pH 6.5, which should be stored at 2-8° C.

Pharmaceutical compositions comprising an ErbB3 inhibitor can be administered alone or in combination therapy. For example, the combination therapy can include a composition provided herein comprising an ErbB3 inhibitor and at least one or more additional therapeutic agents, such as one or more chemotherapeutic agents known in the art, discussed in further detail in Subsection IV below. Pharmaceutical compositions can also be administered in conjunction with radiation therapy and/or surgery.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation.

Exemplary dosage ranges for administration of an antibody include: 10-1000 mg (antibody)/kg (body weight of the patient), 10-800 mg/kg, 10-600 mg/kg, 10-400 mg/kg, 10-200 mg/kg, 30-1000 mg/kg, 30-800 mg/kg, 30-600 mg/kg, 30-400 mg/kg, 30-200 mg/kg, 50-1000 mg/kg, 50-800 mg/kg, 50-600 mg/kg, 50-400 mg/kg, 50-200 mg/kg, 100-1000 mg/kg, 100-900 mg/kg, 100-800 mg/kg, 100-700 mg/kg, 100-600 mg/kg, 100-500 mg/kg, 100-400 mg/kg, 100-300 mg/kg and 100-200 mg/kg. Exemplary dosage schedules include once every three days, once every five days, once every seven days (i.e., once a week), once every 10 days, once every 14 days (i.e., once every two weeks), once every 21 days (i.e., once every three weeks), once every 28 days (i.e., once every four weeks) and once a month.

Estrogen Inhibitors

The estrogen inhibitor may be an estrogen receptor blocker such as tamoxifen, a selective estrogen receptor modulator such as raloxifene or an aromatase inhibitor such as anastrozole, letrozole, exemestane, vorozole, formestane, or fadrozole. Each of the preceding estrogen inhibitors is in current clinical use and may be administered in accordance with the manufacturer's instructions.

Taxanes/Taxoids

Taxanes (used interchangeably herein with (and broadly incorporating the meaning of) the term "taxoids") are diterpene derivatives, including natural products obtained from plants of the genus *Taxus* (yews), and include paclitaxel (Taxol®), docetaxel (Taxotere), cabazitaxel (Jevtana®), and Abraxane® (a formulation of paclitaxel bound to albumin) Each of the preceding taxanes is in current clinical use and may be administered in accordance with the manufacturer's instructions. Other taxanes in development include, EndoTAG®-1, a formulation of paclitaxel encapsulated in positively charged lipid-based complexes being developed by MediGene; and Tesetaxel®, an orally bioavailable semi-synthetic taxane derivative being developed by Genta Inc.

Combination Therapy

In certain embodiments, the methods and uses provided herein for treating a patient with cancer can comprise administration of an ErbB3 inhibitor and at least one additional anti-cancer agent that is not an ErbB3 inhibitor.

In one embodiment, the at least one additional anti-cancer agent comprises at least one chemotherapeutic drug. Non-limiting examples of such chemotherapeutic drugs include taxanes; estrogen inhibitors; platinum-based chemotherapy drugs (e.g., cisplatin, carboplatin); and tyrosine kinase inhibitors; e.g., imatinib (Gleevec®), sunitinib (Sutent®), dasatinib and (Sprycel®).

In another aspect, the at least one additional anti-cancer agent is paclitaxel. In a particular embodiment, the method comprises at least one cycle, wherein the cycle is a period of 4 weeks, wherein for each cycle the anti-ErbB3 antibody is administered every other week at a dose of 20 mg/kg and paclitaxel is administered once per week at a dose of 80 mg/m².

Paclitaxel injection USP is a clear colorless to slightly yellow viscous solution. It is supplied as a nonaqueous solution intended for dilution with a suitable parenteral fluid prior to intravenous infusion. Paclitaxel is available in 30 mg (5 mL), 100 mg (16.7 mL), and 300 mg (50 mL) multidose vials. Each mL of sterile nonpyrogenic solution contains 6 mg Paclitaxel, 527 mg of polyoxyl 35 castor oil, NF1 and 49.7% (v/v) dehydrated alcohol, USP.

Paclitaxel has the following structural formula:

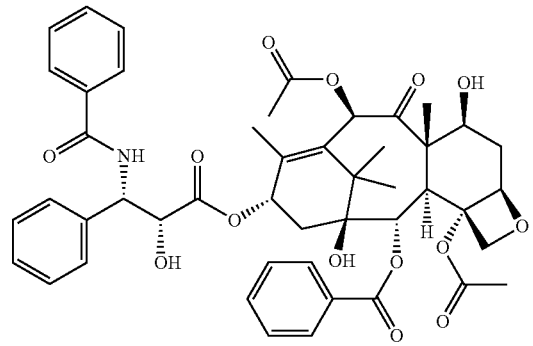 [SMILES: CC(=O)O[C@H]1C(=O)[C@@]2(C)[C@H]([C@H](OC(=O)c3ccccc3)[C@]3(O)C[C@H](OC(=O)[C@H](O)[C@@H](NC(=O)c4ccccc4)c4ccccc4)C(C)=C1C3(C)C)[C@]1(OC(C)=O)CO[C@@H]1C[C@@H]2O]

Paclitaxel is a white to off-white crystalline powder with the molecular formula C47H51NO14 and a molecular weight of 853.9. It is highly lipophilic, insoluble in water, and melts at around 216° C. to 217° C.

In another embodiment, the at least one additional anticancer agent is exemestane.

Exemestane is marketed by Pfizer as Aromasin® Aromasin tablets for oral administration. These tablets each contain 25 mg of exemestane, an irreversible, steroidal aromatase inactivator chemically described as 6-methylenandrosta-1,4-diene-3,17-dione. Its molecular formula is $C_{20}H_{24}O_2$ and its structural formula is:

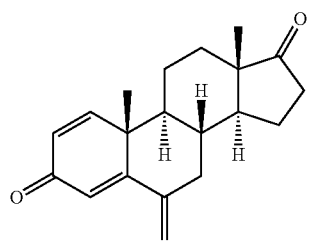

Exemestane is a white to slightly yellow crystalline powder with a molecular weight of 296.41. It is freely soluble in N, N-dimethylformamide, soluble in methanol, and practically insoluble in water. Each Aromasin® Aromasin tablet contains the following inactive ingredients: mannitol, crospovidone, polysorbate 80, hypromellose, colloidal silicon dioxide, microcrystalline cellulose, sodium starch glycolate, magnesium stearate, simethicone, polyethylene glycol 6000, sucrose, magnesium carbonate, titanium dioxide, methylparaben, and polyvinyl alcohol.

In another embodiment, the anti-ErbB3 antibody is administered at an initial loading dose of 40 mg/kg and a weekly dose of 20 mg/kg thereafter and one tablet (25 mg) of exemestane is administered daily.

As used herein, combined administration (coadministration, combination therapy) includes simultaneous administration of the compounds in the same or different dosage form, or separate administration of the compounds (e.g., sequential administration). For example, the ErbB3 inhibitor can be administered in combination with the exemestane or with paclitaxel, wherein both the ErbB3 inhibitor and the exemestane or the paclitaxel are formulated for separate administration and are administered concurrently or sequentially in either order. Such concurrent or sequential administration preferably results in both the compounds (e.g., an ErbB3 inhibitor and exemestane or an ErbB3 inhibitor and paclitaxel) being simultaneously present in treated patients.

Patient Populations

Provided herein are effective methods for treating cancer in a human patient and for selecting patients to be so treated. In one embodiment, the human patient suffers from a cancer selected from the group consisting of non-small cell lung cancer (NSCLC), renal cell carcinoma (RCC), melanoma (e.g., cutaneous or intraocular malignant melanoma), colorectal cancer, serous ovarian carcinoma, liver cancer, bone cancer, pancreatic cancer, skin cancer, cancer of the head or neck, breast cancer, lung cancer, uterine cancer, colon cancer, rectal cancer, cancer of the anal region, esophageal cancer, gastric cancer, gastro-esophageal junction cancer, testicular cancer, uterine cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, cancer of the bladder, cancer of the kidney or ureter, carcinoma of the renal pelvis, neoplasm of the central nervous system (CNS), spinal axis tumor, glioma, pituitary adenoma, Kaposi's sarcoma, epidermoid cancer, squamous cell cancer, and mesothelioma. The disclosed methods are also applicable to treatment of metastatic cancers. In a particular embodiment, the cancer is ovarian cancer. In another particular embodiment, the cancer is breast cancer. The breast cancer may be either or both of ER+ and PR+ breast cancer ("ER+ and/or PR+"). The breast cancer may be HER2 negative. The breast cancer may be either or both of 1) ER+ and/or PR+ and 2) HER2 negative. Methods for testing ER and PR status are used as a matter of clinical routine in the treatment of gynecological tumors. Such methods may be carried out in accordance with the well-established guidelines of Hammond, M E et al., "American Society of Clinical Oncology/College of American Pathologists Guideline Recommendations for Immunological Testing of Estrogen and Progesterone Receptors in Breast Cancer" *Arch Pathol Lab Med.* 2010; 134:E1-E16. HER2 status may be determined using HCT, with a score of 3+ being considered HER2 positive and a score of 2+ or 1+ or 0 being considered HER2 negative.

In one embodiment, a human patient for treatment using the subject methods and compositions has evidence of recurrent or persistent disease following primary chemotherapy.

In another embodiment, a human patient for treatment using the subject methods and compositions has had at least one prior platinum based chemotherapy regimen for management of primary or recurrent disease.

In another embodiment, the patient has a cancer that is platinum-resistant or refractory. In one example, the platinum-resistant cancer is ovarian cancer.

In another embodiment, a human patient for treatment using the subject methods and compositions has evidence of recurrent or persistent disease following a) primary treatment, e.g., with an anti-estrogen therapy or b) an adjuvant treatment with a non-steroidal aromatase inhibitor and/or tamoxifen.

In another embodiment, the cancer undergoing treatment is advanced. In one aspect, the term "advanced" cancer denotes a cancer above Stage II. In another, "advanced" refers to a stage of disease where chemotherapy is typically recommended, which is any one of the following: 1. in the setting of recurrent disease: any stage or grade; 2. stage IC or higher, any grade; 3. stage IA or IB, grade 2 or 3; or 4. in the setting of incomplete surgery or suspected residual disease after surgery (where further surgery can not be performed): any stage or grade.

Outcomes

The efficacy of the treatment methods provided herein can be assessed using any suitable means. In one embodiment, the treatment produces at least one therapeutic effect selected from the group consisting of reduction in growth rate of tumor, reduction in size of tumor, reduction in number of metastatic lesions over time, increase in duration of progression-free survival, and increase in overall response rate.

With respect to target lesions, responses to therapy may include:

Complete Response (CR): Disappearance of all target lesions. Any pathological lymph nodes (whether target or non-target) must have reduction in short axis to <10 mm;

Partial Response (PR): At least a 30% decrease in the sum of the diameters of target lesions, taking as reference the baseline sum diameters;

Progressive Disease (PD): At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm (Note: the appearance of one or more new lesions is also considered progression); and Stable Disease (SD): Neither sufficient shrinkage to qualify for PR, nor sufficient increase to qualify for PD, taking as reference the smallest sum diameters while on study. (Note: a change of 20% or less that does not increase the sum of the diameters by 5 mm or more is coded as stable disease). To be assigned a status of stable disease, measurements must have met the stable disease criteria at least once after study entry at a minimum interval of 6 weeks.

With respect to non-target lesions, responses to therapy may include:

Complete Response (CR): Disappearance of all non-target lesions and normalization of tumor marker level. All lymph nodes must be non-pathological in size (<10 mm short axis). If tumor markers are initially above the upper normal limit, they must normalize for a patient to be considered in complete clinical response;

Non-CR/Non-PD: Persistence of one or more non-target lesion(s) and/or maintenance of tumor marker level above the normal limits; and Progressive Disease (PD): Appearance of one or more new lesions and/or unequivocal progression of existing non-target lesions. Unequivocal progression should not normally trump target lesion status. It must be representative of overall disease status change, not a single lesion increase.

In exemplary outcomes, patients treated according to the methods disclosed herein may experience improvement in at least one sign of a cancer, such as platinum resistant/refractory advanced ovarian cancer.

In one embodiment, the patient so treated exhibits CR, PR, or SD.

In another embodiment, the patient so treated experiences tumor shrinkage and/or decrease in growth rate, i.e., suppression of tumor growth. In yet another embodiment, one or more of the following can occur: the number of cancer cells is reduced; tumor size is reduced; cancer cell infiltration into peripheral organs is inhibited, retarded, slowed, or stopped; tumor metastasis is slowed or inhibited; tumor growth is inhibited; recurrence of tumor is prevented or delayed; or one or more of the symptoms associated with cancer is relieved to some extent.

In other embodiments, such improvement is measured by a reduction in the quantity and/or size of measurable tumor lesions. Measurable lesions are defined as those that can be accurately measured in at least one dimension (longest diameter is to be recorded) as >10 mm by either or both of CT scan (CT scan slice thickness no greater than 5 mm) and caliper measurement via clinical exam, or as >20 mm by chest X-ray. The size of non-target lesions, e.g., pathological lymph nodes, can also be measured for improvement. In one embodiment, lesions can be measured on chest x-rays or CT or MRI outputs.

In other embodiments, cytology or histology can be used to evaluate responsiveness to a therapy. The cytological confirmation of the neoplastic origin of any effusion that appears or worsens during treatment when the measurable tumor has met criteria for response or stable disease can be considered to differentiate between response or stable disease (an effusion may be a side effect of the treatment) and progressive disease.

The following examples are merely illustrative and should not be construed as limiting the scope of this disclosure in any way as many variations and equivalents will become apparent to those skilled in the art upon reading the present disclosure.

All patents, patent applications and publications cited herein are incorporated herein by reference in their entireties.

EXAMPLES

Example 1

Chromogenic RNA-In Situ Hybridization Assay (RNA-ISH)

HRG RNA was detected using a chromogenic RNA-In Situ Hybridization Assay (RNA-ISH). A chromogenic RNA-ISH assay may be used to stain an FFPE tissue section for an RNA of interest. For each RNA-ISH assay, a scoring system was applied by a certified pathologist. The system scores levels as the discrete variables 0, 1+, 2+, 3+, or 4+.

Heregulin (HRG) is an ErbB3 ligand that activates ErbB3, thereby initiating intracellular signaling in tumor cells. This may occur in an autocrine fashion, in which the HRG produced by a cell activates the same cell, or it may occur in a paracrine fashion, in which HRG produced by one cell (e.g., a stromal cell in a tumor) activates neighboring cells (e.g., tumor cells). Accordingly, it is be desirable to measure HRG expression in both tumor cells and stromal cells in the same biopsy. This can be achieved by visualizing HRG transcripts (e.g., in FFPE patient samples) using RNA in situ hybridization (RNA-ISH) and scoring patient samples based on the observed hybridization levels.

FIG. 1 shows an example of HRG RNA staining in an ovarian cancer biopsy section. The staining pattern is strikingly non-uniform, with a small subset of cells expressing high levels of HRG transcripts (dark blotches) and the majority of cells not expressing detectable levels of transcripts.

1. Overview of the Assay

FFPE tumor samples are scored for HRG RNA levels using the following variant of an Advanced Cell Diagnostics® ("ACD" Hayward, Calif.) RNAscope® assay. In this assay, cells are permeabilized and incubated with a set of oligonucleotide "Z" probes (see, e.g., U.S. Pat. No. 7,709,198) specific for HRG. Using "Z" probes, as well as using multiple sets of probes per transcript, increases the specificity of the assay over standard ISH methods. One HRG probe set that can be used in this assay is ACD Part Number 311181. Another HRG probe set prepared by ACD (and used in RNAscope® assays to generate the data presented below and in the Figures) includes 62 probes (31 pairs), each 25 bases in length, that target a 1919 base long region of the HRG transcript comprising nucleotides 442-2977 of SEQ ID NO:42 and that together detect 15 separate HRG isoforms α, β1, β1b, β1c, β1d, β2, β2b, β3, β3b, γ, γ2, γ3, ndf43, ndf43b, and GGF2. Following Z probe incubation, a pre-amplifier is added that can only hybridize to a pair of adjacent Z probes bound to the target transcript. This minimizes amplification of non-specific binding. Several sequential amplification steps are then performed based on sequence-specific hybridization to the pre-amplifier, followed by enzyme-mediated chromogenic detection that enables semi-quantitative measurement of HRG RNA levels in the tumor tissue.

Step 1: FFPE tissue sections are deparaffinized and pretreated to block endogenous phosphatases and peroxidases and to unmask RNA binding sites. Step 2: Target-specific double Z probes are applied, which specifically hybridize to the target RNA at adjacent sequences. Step 3: Targets are detected by sequential applications of a preamplifier oligonucleotide, amplifier oligonucleotides, a final HRP-conjugated oligonucleotide, and DAB. Step 4: Slides are visualized using a light microscope and scored by a pathologist.

To score the assay, a reference tissue microarray (TMA) of four cell lines is stained alongside the tumor sample. These cell lines express different levels of HRG, ranging from low to high. A pathologist then assigns the patient sample a score based on a visual comparison with the reference TMA.

2. Sample Preparation and Staining

Patient sample preparation and pathologist review procedures are similar to qIHC assays. Upon biopsy or surgical resection, patient tumor samples are immediately placed in fixative (10% neutral buffered formalin) typically for 20-24 hours at room temperature. Samples are then transferred to 70% ethanol and embedded in paraffin as per standard hospital procedures. Before the assay is performed, 4-μm sections of the sample are prepared and mounted on positively charged 75×25 mm glass slides. These are baked for improved tissue adhesion (10-30 min at 65° C.), dipped in paraffin for tissue preservation, and stored at room temperature under nitrogen. One of the sections is used for routine H&E staining, which a pathologist reviews for tumor content, quality, and clinical diagnosis. The pathologist differentiates areas of tumor, stroma, and necrosis. Following this review, an adjacent or nearby tissue section (within 20 μm of the H&E section) is used for the assay.

Pretreat solutions, target probes, and wash buffers for RNAscope® assays are obtained from ACD. The assay can be run manually, or using a VENTANA autostainer (Discovery XT). For the manual assay, 40° C. incubations are performed in a metal slide tray inside a HybEZ oven (ACD). For the automated assay, incubation temperatures are controlled by the autostainer. ACD software is used to run the RNAscope® assays on the VENTANA autostainer.

To begin the assay, samples are deparaffinized by baking at 65° C. for 30 min, followed by sequential immersion in xylenes (2×20 min) and 100% ethanol (2×3 min). After air-drying, tissues are covered with Pretreat1 solution, which blocks endogenous enzymes (phosphatases and peroxidases which would produce background with chromogenic detection reagents), incubated for 10 min at room temperature, then rinsed twice by immersion in $dH_2O$. Slides are then incubated in boiling Pretreat2 solution for 15 min, which unmasks binding sites, and transferred immediately to containers of $dH_2O$.

After washing by immersion in $dH_2O$ (2×2 min), tissue is covered with Pretreat3 solution and incubated in a HybEZ oven at 40° C. for 30 min Pretreat3 solution contains a protease, which strips the RNA transcripts of protein and exposes them to the target probes. After washing the slides 2×2 min in $dH_2O$, the tissues are covered with the 15 isoform-detecting HRG RNAscope® probes described above. Serial tissue sections are incubated with positive control probes (protein phosphatase 1B (PP1B) ACD Part Number 313901), negative control probes (bacterial gene DapB-ACD Part Number 310043), or HRG probes for 2 h at 40° C. Slides are washed (2×2 min) with 1×RNAscope® wash buffer before incubating with Amp1 reagent Amp1 incubation conditions (30 min, 40° C.) favor binding only to pairs of adjacent probes bound to RNA transcripts. Slides are washed by immersion in RNAscope® wash buffer before incubating with subsequent amplification reagents.

For signal amplification, each of the sequentially applied reagents binds to the preceding reagent and amplifies the signal present at the previous step Amplification steps may include Amp2 (15 min, 40° C.), Amp3 (30 min, 40° C.), Amp4 (15 min, 40° C.), Amp5 (30 min, room temperature), and Amp6 (15 min, room temperature). The final reagent, Amp6, can be conjugated to horseradish peroxidase (HRP). To visualize the transcripts, the slides are then incubated with the ACD staining reagent, which contains diaminobenzidine (DAB), for 10 min at room temperature. Chromogen development is stopped by rinsing with $dH_2O$. Nuclei are then counterstained with hematoxylin, which is blued with dilute ammonium chloride. Stained slides are immersed in 80% ethanol (2×5 min), 100% ethanol (2×5 min), and xylenes (2×5 min) before coverslipping with Cytoseal non-aqueous mounting medium (Thermo Scientific, 8312-4).

3. Generation of Biomarker Values

The biomarker values to be generated are a composite of pathologist scores. To score the assay, a TMA comprising plugs of four different cell lines is included in each staining run. Cell line plugs are prepared prior to generating a TMA. Cultured cells grown to a sub-confluent density are harvested by trypsinization, rinsed in PBS, and fixed for 16-24 hr at 4° C. before rinsing in PBS and resuspending in 70% ethanol. Cells are then centrifuged for 1-2 minutes at approximately 12,000 rpm to produce a dense cell pellet, which is then coated with low-melting point agarose. The agarose pellets are stored in 70% ethanol at 4° C., and embedded in paraffin before constructing the TMA.

Figure 2:
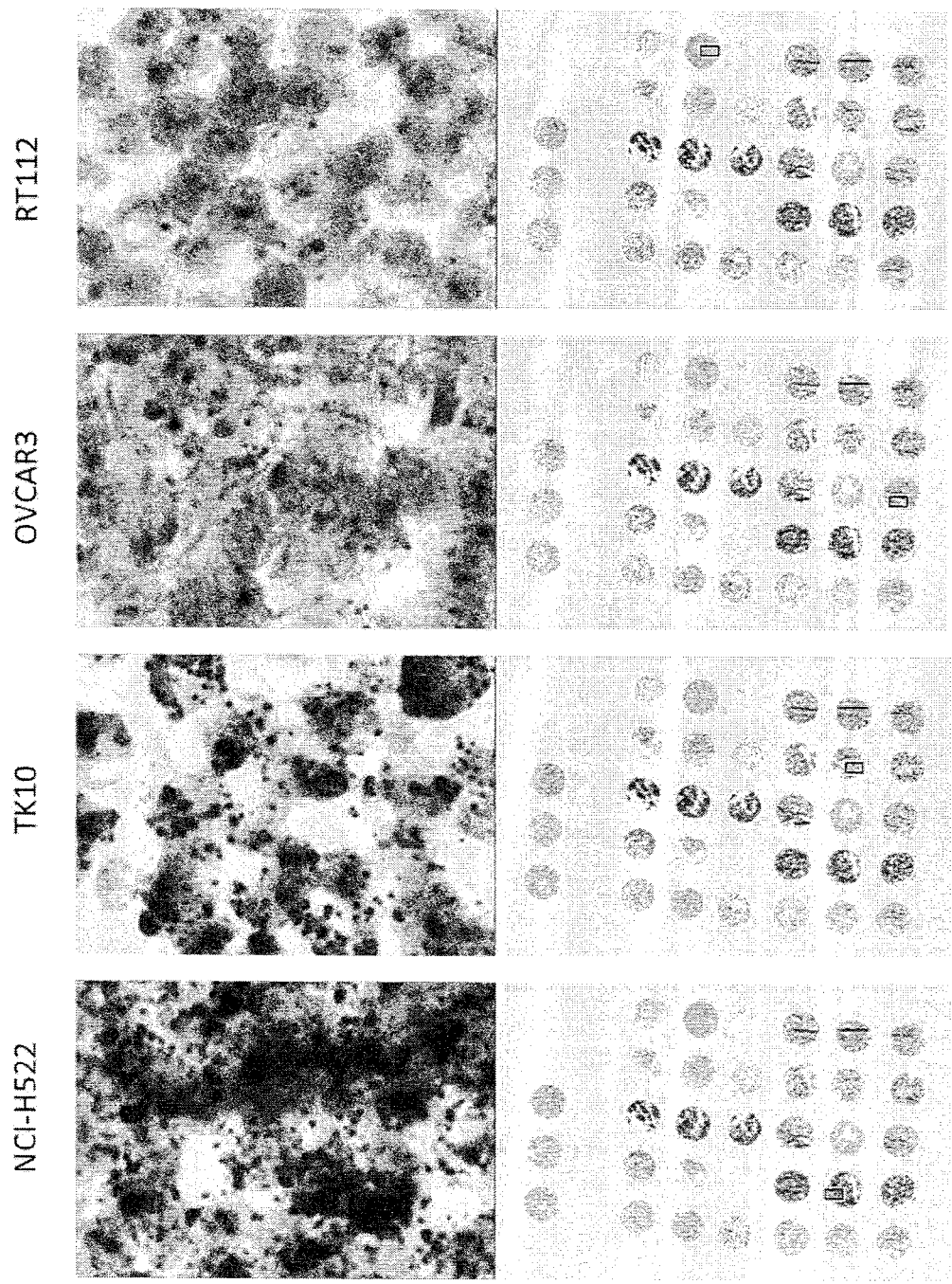
FIG. 2 shows reference tissue microarray (TMA) analysis using the HRG RNA-ISH assay. The four upper panes show representative high magnification images for each cell line TMA (cell line indicated by heading). Lower panes show TMAs, with the three cell plugs along the top of each lower pane being internal reference plugs for sample orientation. Rectangles drawn over individual plugs indicate the locations of the corresponding high magnification images in the panels above each array.

The arrays are constructed, e.g., using a Manual Tissue Arrayer (MTA-1, Beecher Instruments), with which a 0.6 mm punch is used to take a portion of the cell pellet and plug it into an empty recipient paraffin block. The pathologist uses the images of the TMA to provide a score ranging from 0 (undetectable) to 4 (high). As shown in FIG. 2, RT112 (RT-112, CLS Cell Lines Service GmbH, Eppelheim, Germany) is assigned a score of 1, OVCAR3 (ATCC® HTB-161™) a score of 2, TK10 (TK.10 cells, NCI, Bethesda, Md.) a score of 3, and NCI-522 (ATCC® CRL5810™) a score of 4. The pathologist provides two scores for the top two populations of tumor cells, and one score for the top population of stromal cells (when available), along with the percentage of cells in each population. So, for example, a patient sample may have 20% tumor with a score of 3, 40% tumor with a score of 2, and 60% stroma with a score of 2. Scores are provided for the target probe (HRG), as well as the positive control probe (PP1B) and the negative control probe (DapB).

Example 2

Fluorescence-Based Quantitative IHC (Fl-IHC) Assay for ErbB2

Figure 4:
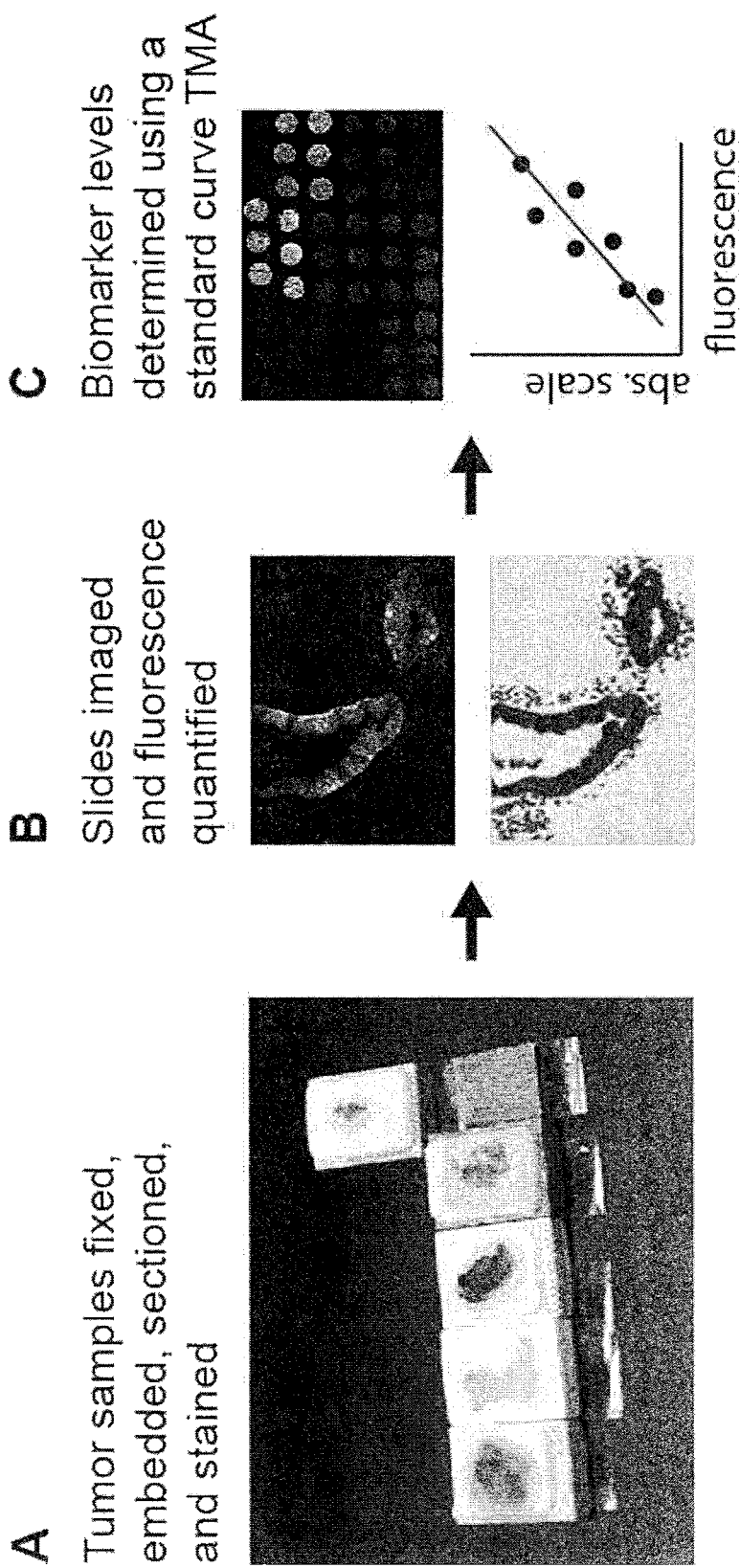
FIG. 4 is a schematic exemplification of the steps of a qIHC assay.

Fl-IHC can be used to measure ErbB2 protein levels in tumor cells in FFPE tissue. Fl-IHC is an imaging-based assay and provides a measure of the number of protein molecules per tumor cell in each sample. This assay, schematized in FIG. 4, is quantitative and yields a continuous variable.

Either surgically resected tumor tissue or core needle biopsies are collected from patients, fixed in formalin for 24 h, and embedded in paraffin blocks using standard procedures. FFPE blocks are sectioned (4 μm thickness), mounted on glass slides, and co-stained for DNA, cytokeratin, and the ErbB2 receptor. Final detection of these markers is based on fluorescence. The slides are imaged using an Aperio® ScanScope® FL set at 20× magnification and analyzed using quantitative digital image analysis. The automated image analysis algorithm applies a regular grid across the tissue region where each square tile is approximately the size of a single cell. Each tile is classified as either cytokeratin positive (CK+) or negative (CK−) using a fixed threshold for the CK staining (see details below). The fluorescence measurements of the CK+ tiles are then converted to an absolute scale (receptors per cell) using a standard curve generated from a tissue microarray (TMA), stained and imaged at the same time as the patient sample, that is composed of cell lines with known ErbB2 protein levels.

1. Sample Preparation and Staining

Following surgical resection or core needle biopsy, patient tumor samples are placed immediately in fixative (10% Neutral Buffered Formalin) for 20-24 hours at room temperature. Samples are then transferred to 70% ethanol and subsequently embedded in paraffin as per standard hospital procedures. Before the assay is performed, 4-μm sections of the sample are prepared and mounted on positively charged 75×25 mm glass slides. These are baked for improved tissue adhesion (10-30 min at 65° C.), and dipped in xylenes to preserve antigens (2-5 min at room temperature). Sections to be used for the assay are dipped in paraffin to preserve them until the assay is ready to be performed. One section is used for routine H&E staining, which a pathologist reviews for tumor content, quality, and clinical diagnosis. The pathologist differentiates areas of tumor, stroma, and necrosis. Following this review, an adjacent or nearby tissue section (within 20 μm of the H&E section) is used for the assay.

Prior to staining, the sample is deparaffinized by baking for 30 min at 65° C., followed by sequential immersion in xylenes (2×20 min), 100% ethanol (2×2-5 min), 80% ethanol (2×2-5 min) and re-hydrated by immersion in water. Heat induced antigen retrieval in Tris-EDTA buffer, pH 9 (Fisher TA-250-PM4X) is performed in a PT Module (Thermo Scientific) set to 102° C. for 25 min, with the no-boil setting enabled. Subsequent steps are performed on a Dako Autostainer, with all incubations at room temperature. Slides are pre-rinsed with 1×TBS-T (Fisher, TA-999-TT) before blocking for endogenous peroxidases (10 min incubation in Peroxidazed 1 (BioCare Medical, PX968M)). The autostainer rinses each slide with 13 mL TBS-T twice before blowing air for several seconds to displace it immediately before addition of the next reagent. Nonspecific protein binding is blocked with Background Sniper (10 min, BioCare Medical, BS966M). Slides are rinsed twice in TBS-T. Primary antibodies for ErbB2 and pan-cytokeratin (CK) are applied to the slides together diluted in DaVinci™ Green diluent (BioCare Medical, PD900M) for 1 h. The primary antibody for ErbB2 is a rabbit-derived monoclonal antibody from Fisher Scientific (catalog # RM-9103-S) applied at a dilution of 1:300. The primary antibody for CK is a mouse-derived monoclonal antibody anti Hu IgG1 Kappa from DAKO (catalog # M351501) applied at a dilution of 1:50. Slides are rinsed twice in TBS-T. The detection antibody cocktail consists of Alexa Fluor® 555-GAM IgG (H+L) (Invitrogen®, A-21422) diluted 1:200 into DAKO Envision+® anti-rabbit HRP labeled polymer (K400311, supplied ready to use). Following a 30-min incubation with detection antibodies, slides are rinsed twice in TBS-T before visualization of the ErbB2 signal by 10 min incubation with Perkin-Elmer® CY5-Tyramide (SAT705A, used as per manufacturer's instructions with reconstituted Tyramide diluted 1:50 into supplied diluent). The slides are rinsed twice in TBS-T. Slides are removed from the autostainer and coverslips applied over mounting medium. DAPI nuclear stain is included in the Prolong Gold mounting medium (Invitrogen®, P36935). After allowing the mounting medium to set (in the dark at room temperature overnight), slides are imaged using an Aperio® fluorescence scanning microscope (Aperio® ScanScope® FL).

2. Generation of Biomarker Values

The biomarker values to be generated are the receptor-per-cell expressions of target receptors in the cytokeratin-positive cells. The images of the fluorescently stained biopsies are analyzed using Definiens-Developer image analysis software (Definiens, Inc., Carlsbad, Calif.). The algorithm measures the mean fluorescent intensity of regularly sampled square tiles overlaid on the tissue region of the image. Each tile is approximately the size of a single cell. Regular grid sampling of the image removes the complexity and uncertainty of accurate single-cell segmentation of the image while preserving the ability to measure spatial intensity variations. The tiles are classified as either cytokeratin positive (CK+) or negative (CK−) using a fixed cytokeratin threshold computed as the intersect of two normal distributions fit to combined normalized quantile distributions (sampled every 5%) across all patient biopsies within the current MM-121 clinical trials. The biomarker and cytokeratin fluorescence for each tile is normalized for each biopsy using a standard curve generated with a cell-line based tissue microarray (TMA). A biomarker quantile analysis of all CK+ tiles are reported for each biopsy and the most predictive quantile level is determined empirically for each trial.

3. Reproducibility and Error Measures

Assay reproducibility can be determined by staining and analyzing about 40 independent sections of replicate TMAs containing plugs from 12 cell lines in triplicate over the course of >12 months. The RMSE and CV of the measured fluorescence values for all repeated cell lines across all TMAs were measured for the ErbB2 assay. In parallel, two similar assays, one for EGFR and one for ErbB3, were also assessed. The reproducibility and error measurements for all three assays are provided in Table 2.

TABLE 2

Reproducibility and Error Measurements of Fluorescence Values of qIHC Assays for EGFR, ErbB2, and ErbB3 Using TMAs of Cell Line Plugs.

| Receptor | N | Mean Fluorescence ($\log_{10}$) | RMSE | CV |
| --- | --- | --- | --- | --- |
| EGFR | 1232 | 4.0919 | 0.1058 | 2.6% |
| HER2 | 1222 | 3.4500 | 0.1485 | 4.3% |
| HER3 | 1183 | 3.9745 | 0.0891 | 2.2% |

4. Dynamic Range and Limits of Detection

The limits of detection and dynamic range of the qIHC assay can be defined by the lower and upper bounds of the microscope camera sensor and by the lower and upper expression levels of receptors in the cell lines used on the standard curve TMA. The upper bound of the 16-bit camera used in the Aperio® ScanScope® FL microscope is 65,535 intensity units ($2^{16}-1$). The lower bounds were determined empirically by measuring the background fluorescence of ~41 slides containing biopsy tissue from three independent staining batches. The average lower bounds and dynamic ranges were computed for DNA (DAPI), cytokeratin (Cy3) and biomarker (Cy5) channels (Table 3). As above, this calculation was performed for three separate assays for each of EGFR, ErbB2, and ErbB3.

TABLE 3

Dynamic Range of Measurements in the DNA, Cytokeratin, and Biomarker channels and Target expressions in cell lines of control curve TMA

| Channel | Ab Stain | N | Dynamic range of the fluorescence values | | | | Dynamic range of target expressions in the cell lines of TMA ($\log_{10}$ receptors per cell) | |
|---|---|---|---|---|---|---|---|---|
| | | | Upper Bound | Lower Bound | Lower 95% | Upper 95% | Upper Bound | Lower Bound |
| DNA (DAPI) | EGFR | 41 | 65535 | 619.80 | 544.75 | 705.18 | | |
| DNA (DAPI) | ErbB3 | 41 | 65535 | 1346.48 | 1183.59 | 1531.79 | | |
| DNA (DAPI) | HER2 | 42 | 65535 | 2149.81 | 1892.34 | 2442.31 | | |
| Cytokeratin (Cy3) | EGFR | 41 | 65535 | 317.04 | 274.35 | 366.44 | | |
| Cytokeratin (Cy3) | ErbB3 | 41 | 65535 | 379.19 | 328.10 | 438.23 | | |
| Cytokeratin (Cy3) | HER2 | 42 | 65535 | 396.93 | 344.03 | 457.93 | | |
| Biomarker (Cy5) | EGFR | 41 | 65535 | 364.75 | 314.85 | 422.57 | 5.651 | 1.968 |
| Biomarker (Cy5) | ErbB3 | 41 | 65535 | 247.46 | 213.60 | 286.68 | 4.688 | 3.729 |
| Biomarker (Cy5) | HER2 | 42 | 65535 | 302.96 | 261.94 | 350.35 | 6.143 | 3.491 |

The lower and upper expression levels of ErbB receptors included on the TMAs define the dynamic range of the standard curve. Any value inside the range can be interpolated whereas values outside require extrapolation. The reference values were measured using quantitative flow cytometry (Table 4).

TABLE 4

Lower and Upper Receptor Expression Levels for Cell Lines Used on the Standard Curve TMA. Units are receptors per cell with cell line name in parenthesis.

| Value | EGFR | HER2 | ErbB3 |
|---|---|---|---|
| Low | 93 (CHOK-1) | 3,100 (CHOK-1) | 5,360 (IGROV-1) |
| High | 448,000 (ACHN) | 1,390,000 (BT474-M3) | 48,700 (MDA-MB-453) |

Example 3

ErbB2, ErbB3 and ErbB4 Chromogenic Quantitative IHC (qIHC)

qIHC can be used to detect protein levels of ErbB2, ErbB3 and ErbB4. qIHC uses a standard brown-stain technology to indicate protein levels in FFPE tissue sections. For each qIHC assay used in this study, the TMA-based scoring system described above was applied by a certified pathologist. As described, this system yields scores based on staining intensity (0, 1, 2, 3, 4). In the clinical assay results described herein, the same pathologist scored all patient samples for a given assay. Table 5 lists the materials used in these studies.

TABLE 5

Materials Chart:

| Incubation Time/Step | Reagent Name | Vendor Catalog # | Dilution Factor |
|---|---|---|---|
| N/A | DI Water | in house N/A | N/A |
| N/A | Tris Buffered Saline and Tween 20 (20×) | FISHER SCIENTIFIC TA-999-TT | 1:20 |
| N/A | ErbB2: PT Module Buffer 4, Tris EDTA, pH 9 | FISHER SCIENTIFIC TA-250-PM4X | 1:300 |
| | ErbB3: PT Module Buffer 4, Tris EDTA, pH 9 | FISHER SCIENTIFIC TA-250-PM4X | 1:100 |
| | ErbB4: PT Module Buffer 1, Citrate, pH 6 | FISHER SCIENTIFIC TA-250-PM1X | |

TABLE 5-continued

Materials Chart:

| Incubation Time/Step | Reagent Name | Vendor Catalog # | Dilution Factor |
|---|---|---|---|
| 10 min | Peroxidazed ® 1 | BIOCARE MEDICAL PX968 H, M | RTU |
| 10 min | Background Sniper | BIOCARE MEDICAL BS966 H, M | RTU |
| 60 min | DA VINCI GREEN | BIOCARE MEDICAL PD900 H, M | RTU |
|  | ErbB2: Cytokeratin (Mono Ms Anti-Hu IgG1 Kappa) | DAKO M351501 | ErbB2: 1:50 |
|  | ErbB3: Her3/ErbB3 (D22C5) Rabbit mAb | CELL SIGNALING TECHNOLOGY 12708BC | 1:100 |
|  | ErbB4: HER-4/c-erbB-4 (Rabbit Polyclonal Antibody) | FISHER SCIENTIFIC RB-9045-P1 | 1:200 |
| 30 min | ErbB2: Alexa Fluor ® 555 GAM IgG (H + L) | INVITROGEN A-21422 | 1:200 |
|  | ErbB2-4: ENVISION+ Anti-Rabbit HRP Labeled Polymer | DAKO K400311 | RTU |
| 10 min | ErbB2: Cyanide 5 Tyramide Reagent | PERKIN ELMER SAT705A | 1:50 |
|  | ErbB3/4: Liquid DAB+ Substrate Chromogen System | DAKO K3468 |  |
| 6 min | Automation Hematoxylin | DAKO S3301 | RTU |
| N/A | CYTOSEAL XYL | FISHER SCIENTIFIC 8312-4 | RTU |
| N/A | Rectangular cover glass (sized to tissue) | Various N/A | N/A |

*1 drop DAB+ per mL of substrate solution.

Additional details for the materials are as follows:
ErbB2: Her-2/c-erB-2/neu, Rabbit monoclonal antibody (Fisher Scientific, Cat. # RM-9103-S) and Cytokeratin (Mono Mouse Anti-Hu IgG1 Kappa) (Dako, Cat. # M351501)
ErbB3: HER-3/ErbB-3 Rabbit monoclonal antibody (RB mAb) (Cell Signaling Technology, catalog #12708BC)
ErbB4: HER-4/c-erbB-4 Rabbit polyclonal antibody (RB pAb) (FISHER SCIENTIFIC, catalog # RB-9045-P1)
ENVISION+System-HRP Labelled Polymer Anti-Rabbit (DAKO, catalog # K4003)
Liquid DAB+Substrate Chromogen System (DAB Chromogen and Substrate Buffer solutions in separate containers) (DAKO, catalog # K3468)
Automation Hematoxylin Histological Staining Reagent (DAKO, catalog # S3301)
Tris Buffered Saline and Tween 20 (20×; TBS-T) (FISHER SCIENTIFIC, catalog # TA-999-TT)
ErbB2/3: PT Module Buffer 4, Tris EDTA, pH9 (FISHER SCIENTIFIC, catalog # TA-250-PM4X)
ErbB4: PT Module Buffer 1, Citrate, pH 6 (FISHER SCIENTIFIC, catalog # TA-250-PM1X)
PEROXIDAZED 1 (BIOCARE MEDICAL, catalog # PX968 H, M)
BACKGROUND SNIPER (BIOCARE MEDICAL, catalog # BS966 H, M)
DA VINCI GREEN Diluent (BIOCARE MEDICAL, catalog # PD900 H, M)
FLEX 100 Alcohol Solution (FISHER SCIENTIFIC, catalog #8101)
FLEX 80 Alcohol Solution (FISHER SCIENTIFIC, catalog #8301R)
Xylene (SIGMA, catalog #534056)
ErbB3/4: CYTOSEAL XYL (FISHER SCIENTIFIC, catalog #8312-4)
ErbB2: Cyanine 5 Tyramide (Perkin Elmer, Cat. # SAT705A)
ErbB2: :PROLONG GOLD Antifade Reagent with DAPI ((Invitrogen, Cat. # P36935)
Glass coverslips (VWR No. 1)

The assays were performed according to the following methods.

1. Deparaffinize/hydrate slides
   1.1. If necessary, use a razor blade to scrape paraffin wax off of the back of the slides. Scrape the wax off of the front around the tissue region if it is visible. If the tissue is not clearly visible under the wax, do not scrape any wax from the front.
   1.2. Incubate slides for 30-50 min at 65° C. in a metal slide rack (or equivalent) in the oven to melt wax covering tissues.
   1.3. Transfer slides to a Tissue-Tek (or equivalent) slide rack Immerse slides in the following solutions with occasional gentle agitation:
       xylene, twice for 20-30 min each
       100% ethanol, twice for 2-5 minutes
       80% ethanol, twice for 2-5 minutes
       Distilled water for 2-5 minutes
   1.4. Apply programmed DAKO slide labels to the front frosted end of the slides and place them on the DAKO slide rack(s).

2. Antigen retrieval (AR):
   2.1. Perform AR in the PT module using
      ErbB2/3: PT module buffer 4 (Tris EDTA at pH 9±0.05)
      ErbB4: PT module buffer 1 (Citrate at pH 6±0.05)
      using the following settings:
         Incubation time: 25 minutes
         Incubation temperature: 102° C.
         No-boil function: Enabled
   2.2. Once the program has run and the solution cooled down to 65° C. remove the slide rack(s) from the PT module and place in the DAKO buffer wash basin(s) containing 1×TB S-T for 3-5 minutes.
3. Reagent Preparation: This should be done when slides are in the PT module.
   3.1. In DAKOLINK program, select all slides to be stained from the "Pending" tab and click "Reagents" button at the bottom of the screen. This will generate a list and volumes needed per reagent (this assumes two 150 μL drop zones for a total of 300 μL per slide). Print this list.
   3.2. Select the appropriate number and size of DAKO user fillable bottles.
   3.3. Scan the barcode of each bottle and plug the volume required of that particular reagent into the "usable quantity" box. This will then factor in the dead volume of that particular size bottle into your "Fill quantity" or total volume.
   3.4. Calculate the individual amounts of reagents needed for your assay.
      Endogenous peroxidase block (Peroxidazed 1), protein block (Background Sniper), secondary antibody (ENVISION+System-HRP Labelled Polymer Anti-Rabbit) and automation hematoxylin are ready to use reagents and may be filled right away.
      Primary antibody will be diluted in blocking diluent at the desired dilution factor.
      Liquid DAB+Substrate Chromogen working reagent: add 1 drop (or 20 μL) of the DAB Chromogen per mL of Substrate Buffer.
4. Autostainer run preparation: Once all reagents are made and AR process is complete, place the reagent bottles into the DAKO AutostainerLink 48.
   4.1. Fill the 10 L buffer carboy with 1×TBS-T (add more if required)
   4.2. Fill the 10 L water carboy with DI water
   4.3. Remove all the rack(s) from the wash basin(s) and place on the autostainer.
   4.4. Click on the "Instruments" tab in the DAKOLink software and click "Start" button.
5. Automated staining: The following is the summary of the DAKO AutostainerLink48 chromogenic staining protocol. Note: The autostainer calculates the appropriate rinse step after each critical incubation step therefore the rinse incubation time is arbitrary.
6. Remove the mounting medium from freezer and allow it to come to room temperature.
7. Once the staining is complete, transfers Dako slide racks(s) from the autostainer to the Dako wash basin(s) fill with 1×TBS-T.
8. Mount each slides with 55-75 μL of room temperature ProLong Gold Antifade reagent with DAPI.
9. Allow mounting medium to set on a level surface in a dark, dry place.

TABLE 6

Summary of ErbB2 protocol

| Category | Reagent | Incubation (min) | Volume (μL) |
|---|---|---|---|
| Rinse | Buffer | 1 | |
| Endogenous enzyme block | BioCare Medical Peroxidazed 1 | 10 | 150 |
| Rinse | Buffer | 1 | |
| Rinse | Buffer | 1 | |
| Protein Block | BioCare Medical Background Sniper | 10 | 150 |
| Rinse | Buffer | 1 | |
| Rinse | Buffer | 1 | |
| Primary antibody | Neomarkers Rabbit Anti-C-ErbB2 (SP3) | 60 | 150 |
| Rinse | Buffer | 1 | |
| Rinse | Buffer | 1 | |
| Secondary Reagent | DAKO EnVision Anti-Rabbit + A555GAM | 30 | 150 |
| Rinse | Buffer | 1 | |
| Rinse | Buffer | 1 | |
| Substrate-chromogen | Perkin Elmer Cyanine 5 Tyramide Reagent | 10 | 150 |
| Rinse | Buffer | 1 | |
| Rinse | Buffer | 1 | |

TABLE 7

Summary of ErbB3/4 protocol:

| Category | Reagent | Incubation (min) | Volume (μL) (per drop zone) |
|---|---|---|---|
| Rinse | Buffer | 1 | |
| Endogenous enzyme block | BIOCARE MEDICAL PEROXIDAZED 1 | 10 | 150 |
| Rinse | Buffer | 1 | |
| Rinse | Buffer | 1 | |
| Protein Block | BIOCARE MEDICAL BACKGROUND SNIPER | 10 | 150 |
| Rinse | Buffer | 1 | |
| Rinse | Buffer | 1 | |
| Primary antibody (in DA VINCI GREEN) | ErbB3: RB mAb to ErbB3 ErbB4: RB pAb to ErbB4 | 60 | 150 |
| Rinse | Buffer | 1 | |
| Rinse | Buffer | 1 | |
| Labeled polymer | DAKO ENVISION anti-rabbit HRP | 30 | 150 |
| Rinse | Buffer | 1 | |
| Rinse | Buffer | 1 | |
| Rinse | Buffer | 1 | |
| Substrate-chromogen | Substrate working solution (mix) | 10 | 300 |
| Rinse | DI water | 1 | |
| Rinse | DI water | 1 | |
| Counterstain | DAKO Hematoxylin S3301 | 6 | 300 |
| Rinse | DI water | 1 | |
| Rinse | DI water | 1 | |
| Rinse | DI water | 1 | |

ErbB3/4:

Once the staining is complete, perform the following for dehydration step:

Incubate slides in 80% ethanol twice, each for 2 minutes.

Incubate slides in 100% ethanol twice, each for 2 minutes.

Incubate slides in xylene twice, each for 5 minutes.

Mount each slide with 1-2 drops of CYTOSEAL XYL and a coverslip.

Example 4

RT-PCR Assays

Quantitative RT-PCR (real-time polymerase chain reaction) assays were developed to measure ErbB receptors and ligand transcript levels in FFPE patient samples. Assays were carried out by AltheaDX® using the TaqMan® Low Density Array (TLDA) format. Each SOP referred to in this example is an AltheaDX® SOP.

Overview of RT-PCR Assay:

A section from a FFPE patient specimen is macrodissected and RNA is extracted from a tumor-containing region. Target and reference gene transcripts are reverse transcribed into cDNA and pre-amplified by gene-specific PCR. The products of this pre-amplification step are then transferred into TaqMan® Low Density Array TLDA plate format (Wechser et al, 2004) and each target is quantified by qPCR. To normalize for different RNA amount across biopsies, three reference genes were also measured (GUSB, B2M, HPRT1). TaqMan® Gene Expression Assays consist of a pair of unlabeled PCR primers and a TaqMan® probe with a FAM™ (56-FAM) dye label on the 5' end and a non-fluorescent quencher (3BHQ_1) on the 3' end. RNA from samples of interest is reverse transcribed into cDNA and pre-amplified by PCR. The product of this amplification step then serves as the template for real-time PCR.

Selection of Primers and Probes:

The gene information for both target and endogenous reference (control) genes are provided in Table 8 below. Forward and reverse PCR primers are selected by sequence alignment and BLAST sequence homology searches throughout the entire human genome. The assay primers and probes are listed in Table 9 below. The forward and reverse primers for HRG1 are designed to hybridize within a single exon because the consensus region of all HRG1 isoforms exists in a single exon. As a result, the HRG1 assay can detect both mRNA and genomic DNA. All other forward and reverse primers are designed in separate exons to insure specific detection of mRNA and not genomic DNA. For mRNA-specific HRG1 analysis, all samples are tested by an independent run of the HRG1 assay without reverse transcription to confirm absence of genomic DNA contamination.

The melting temperature (Tm) of the primers was designed to be around 60° C., and the (Tm) for the TaqMan® hydrolysis probes is designed to be 5 to 7° C. higher. The size range of the target amplicon was designed to be between 80 and 100 bp (an appropriate size for FFPE samples). All synthetic oligonucleotides were purchased from Integrated DNA Technologies, Inc.

Total RNA Extraction and Qualification:

Total RNA extraction from samples is conducted per SOP 914023 "Extraction of RNA from Tissue & Cells Using Qiagen RNeasy® Mini Kit," and total RNA extraction from FFPE tissue is conducted per SOP 914017 "RNA Extraction from Formalin Fixed Paraffin Embedded Tissue (FFPE) using EPICENTRE MasterPure® RNA Kit." Isolated total RNA is quantified per SOP 914052 "Determining Nucleic Acid Concentration Using the NanoDrop 1000 Spectrophotometer." Assessment of sample RNA quality is performed per SOP 914049 "Assessment of RNA Using the Agilent® 2100 Bioanalyzer with RNA 6000 Nano & Pico LabChip® Kits."

Genomic DNA contamination in RNA samples is determined by singleplex Taqman® RT-PCR using the HRG1 primer/probe set without reverse-transcriptase. If human genomic DNA is detected in sample RNA with Ct<35, additional DNase I treatment is conducted per SOP 914010, "DNase I Treatment of RNA," and RNA is then re-purified per SOP 914009 "Nucleic Acid Extraction Using Phenolic Reagents."

cDNA Synthesis and Multiplex Pre-Amplification:

Extracted and qualified RNAs are converted to cDNA and pre-amplified per SOP 914039 "One Step Reverse Transcriptase Polymerase Chain Reaction" with a minor modification. Total 25 μL reactions containing various amount of RNA, 1×QIAGEN RT-PCR buffer, 2 μM of all forward and reverse primers mixture, 0.4 mM of dNTP, 1× enzyme mix, and 0.4 units/μL of RNase inhibitor in 96-well plates are placed on a ThermoCycler (ABI 9700) pre-heated at 50° C. After a 30-minute incubation, reactions are heated to 95° C. for 15 minutes to inactivate the reverse transcriptase and activate the Hot-start Taq polymerase. The synthesized cDNAs are amplified by 14 cycles of 94° C. for 30 sec, 55° C. for 30 sec, and 72° C. for 30 sec. The reactions are kept at 4° C. until they are needed for the next process.

TaqMan® Real-Time PCR Assay on TLDA Card:

TLDA (TaqMan® Low Density Array) cards are custom manufactured by Applied Biosystems (ABI). Each lane consists of 12 quadruplicate assays including two repeats of HRG1B1 and HER3. The GAPDH assay is a TLDA manufacturing control that is excluded from further analysis.

The 25 μl of pre-amplified reactions are mixed with 25 μL of dH2O and 50 μL of 2× Universal qPCR master mix (ABI). A total of 100 μL of mixture is loaded into each TLDA lane reservoir. The TLDA card is then placed into a swing bucket rotor, and centrifuged twice for 1 minute at 1200 RPM. After sealing the card, the reservoirs are removed with scissors. The trimmed TLDA card is placed into the real-time PCR instrument (ViiA7®, ABI), and run at: 50° C. for 2 minutes, 94° C. for 10 minutes, followed by 40 cycles of 94° C. for 30 sec and 57° C. for 60 sec. Data collection and analysis is performed using ViiA7® software and DataAssist® v2.0 from ABI.

TABLE 8

List of Target and Reference Genes for RT-PCR Assays

| Category | Gene name | Gene symbols | Genotype covered |
|---|---|---|---|
| Target | Epidermal growth factor receptor 3 | HER3, ErbB3 | HER3 (NM_001982) |
| Target | Heregulin 1 | HRG1 | HRG1-α<br>HRG1-β1<br>HRG1-β2<br>HRG1-β3<br>HRG1-γ |
| Target | Heregulin 1-β1 | HRG1β1 | HRG1-β1 |
| Target | Epidermal growth factor receptor 1 | HER1, ErbB1, EGFR | |
| Target | Epidermal growth factor receptor 2 | HER2 | |
| Target | β-cellulin | BTC | |
| Reference (control) | Glucoronidase-β | GUSB | GUSb (NM_000181) |
| Reference (control) | β-2-microglobulin | B2M, β2M | B2M (NM_004048) |
| Reference (control) | Hypothantin-guanine phosphoribosyltranferase 1 | HPRT1 | HPRT1 (NM_000194) |

Total RNA Extraction and Qualification:

Total RNA extraction from samples was conducted as described in AltheaDx SOP 914023. Extraction of RNA from Tissue & Cells Using Qiagen® Qiagen RNeasy® Mini Kit, and total RNA extraction from FFPE tissue was conducted as described in SOP 914017 RNA Extraction from Formalin Fixed Paraffin Embedded Tissue (FFPE) using EPICENTRE MasterPure™ RNA Kit. Isolated total RNA was quantified using a NanoDrop® (ND-1000) spectrophotometer as described in SOP 914052 Determining Nucleic Acid Concentration Using the NanoDrop 1000 Spectrophotometer. Assessment of sample RNA quality was performed using Agilent 2100 Bioanalyzer with RNA 6000 Nano and Pico LabChip kit according to SOP 914049 (Assessment of RNA Using the Agilent 2100 Bioanalyzer with RNA 6000 Nano & Pico LabChip Kits).

Genomic DNA contamination in RNA samples was determined by singleplex TaqMan real-time PCR using the HRG1 primer/probe (below) set without reverse-transcriptase. If human genomic DNA was detected in sample RNA with Ct<35, additional DNase I treatment would be conducted according to SOP 914010, DNase I Treatment of RNA, then RNA would be re-purified with phenolic reagents according to SOP 914009 (Nucleic Acid Extraction Using Phenolic Reagents). Probes for RT-PCR are set forth below in Table 9, in which the third probe of each sequential group of 3 probes (indicated by a name ending in "P" or "P" followed by one or two digits) has a 5' terminal 56-FAM fluor and a 3' terminal 3BHQ_1 fluor attached thereto.

TABLE 9

List of primers and probes for RT-PCR assay.

| Oligo Name | Sequence | SEQ ID NO: | # of nucleotides | Tm ° C. |
|---|---|---|---|---|
| HER1-F3 | CTATGTGCAGAGGAATTATGATCTTTC | 43 | 27 | 61.7 |
| HER1-R11 | GCTAAGGCATAGGAATTTTCGTAG | 44 | 24 | 61.2 |
| HER1-P10 | TGCAGGTTTTCCAAAGGAATTCGCTC | 45 | 26 | 67.4 |
| HER2-F11 | GGAAACCTGGAACTCACCTAC | 46 | 21 | 61.7 |
| HER2-R13 | CCTGCCTCACTTGGTTGTGA | 47 | 20 | 63.0 |
| HER2-P10 | ACCAATGCCAGCCTGTCCTTCC | 48 | 22 | 68.4 |
| HER3-F5 | GCAACTCTCAGGCAGTGTG | 49 | 19 | 62.4 |
| HER3-R5 | TGGTATTGGTTCTCAGCATCG | 50 | 21 | 61.9 |
| HER3-AP3 | CGGTCACACTCAGGCCATTCAGA | 51 | 23 | 67.6 |
| HRG1-F1 | CTTGTAAAATGTGCGGAGAAGGA | 52 | 23 | 62.8 |
| HRG1-R1 | ATCTCGAGGGGTTTGAAAGGTCT | 53 | 23 | 64.1 |
| HRG1-P | TGTGAATGGAGGGGAGTGCTTCATGG | 54 | 26 | 69.3 |
| HRG1B1 F4 | GTGCAAGTGCCCAAATGAGTTTAC | 55 | 24 | 64.4 |
| HRG1B1 R5 | CTCCATAAATTCAATCCCAAGATGC | 56 | 25 | 62.1 |
| HRG1B1 ASP | TGGCCATTACGTAGTTTTGGCAGCGA | 57 | 26 | 69.8 |
| BTC-F3b | TGGGAATTCCACCAGAAGTC | 58 | 20 | 61.3 |
| BTC-R1b | GCCTTTCCGCTTTGATTGT | 59 | 19 | 60.9 |
| BTC-P2 | ACTGTGCAGCTACCACCACACCAATC | 60 | 26 | 69.7 |
| GUSB-F4 | AGGAATTTTGCCGATTTCATGACTG | 61 | 24 | 62.7 |
| GUSB-R5 | GTCTCTGCCGAGTGAAGATC | 62 | 20 | 61.3 |
| GUSB-P | CACCGACGAGAGTGCTGGGG | 63 | 20 | 67.9 |
| B2M-F1 | TGACTTTGTCACAGCCCAAGATA | 64 | 23 | 63.7 |
| B2M-R1 | AATCCAAATGCGGCATCTTC | 65 | 20 | 61.2 |
| B2M-P1 | TGATGCTGCTTACATGTCTCGATCCCA | 66 | 27 | 68.7 |
| HPRT-F1 | CCTTGGTCAGGCAGTATAATCC | 67 | 22 | 61.9 |
| HPRT-R1 | TCTGGCTTATATCCAACACTTCG | 68 | 23 | 61.9 |
| HPRT-SP1 | AAGCTTGCTGGTGAAAAGGACCC | 69 | 23 | 67.0 |

Example 5

Clinical Trial—Ovarian Cancer

A clinical trial was performed that was designed to allow, inter alia, determination of associations between biomarker profiles and clinical responses. Biomarker data were measured in pre-treatment biopsies and (when available) in archived tumor samples. Results pertaining to predictive biomarkers measured in pre-treatment biopsies are described herein.

The following study was performed to assess biomarkers to be used to predict response to ErbB3 inhibitor (MM-121) therapy.

Assays

Four types of assay (each set forth above) were used to assess the six primary biomarkers assessed in this study (EGFR, ErbB2, ErbB3, ErbB4, HRG and BTC):
1. Fluorescence-based quantitative immunohistochemistry (Fl-IHC)
2. Chromogenic quantitative immunohistochemistry (qIHC).
3. Chromogenic RNA-in situ hybridization (RNA-ISH).
4. Real-time quantitative polymerase chain reaction (RT-PCR).

Scoring Systems for Chromogenic Assays

For the two chromogenic assays (qIHC and RNA-ISH), two different overall scores were used for biomarker analyses:

Composite score=highest score x % tumor cells exhibiting highest score+second highest score x % tumor cells exhibiting second highest score.

Top-10 score=highest score in at least 10% of tumor cells.

A summary of the assays used in this study is provided in Table 10.

TABLE 10

| Primary Biomarker Assays | | | | |
|---|---|---|---|---|
| Biomarker | Fl-IHC (protein) | qIHC (protein) | RNA-ISH (RNA) | RT-PCR (RNA) |
| EGFR | C | | | C |
| ErbB2 | C | | | C |
| ErbB3 | C | D | D | C |
| ErbB4 | | D | | |
| HRG | C | | D | C |
| HRG-1β1 (HRG isotype) | | | | C |
| BTC | | | D | C |

C = Continuous variable|D = Discrete variable (pathologist-scored as 0, 1+, 2+, 3+ or 4+)

Biomarker Values

Figure 5A:
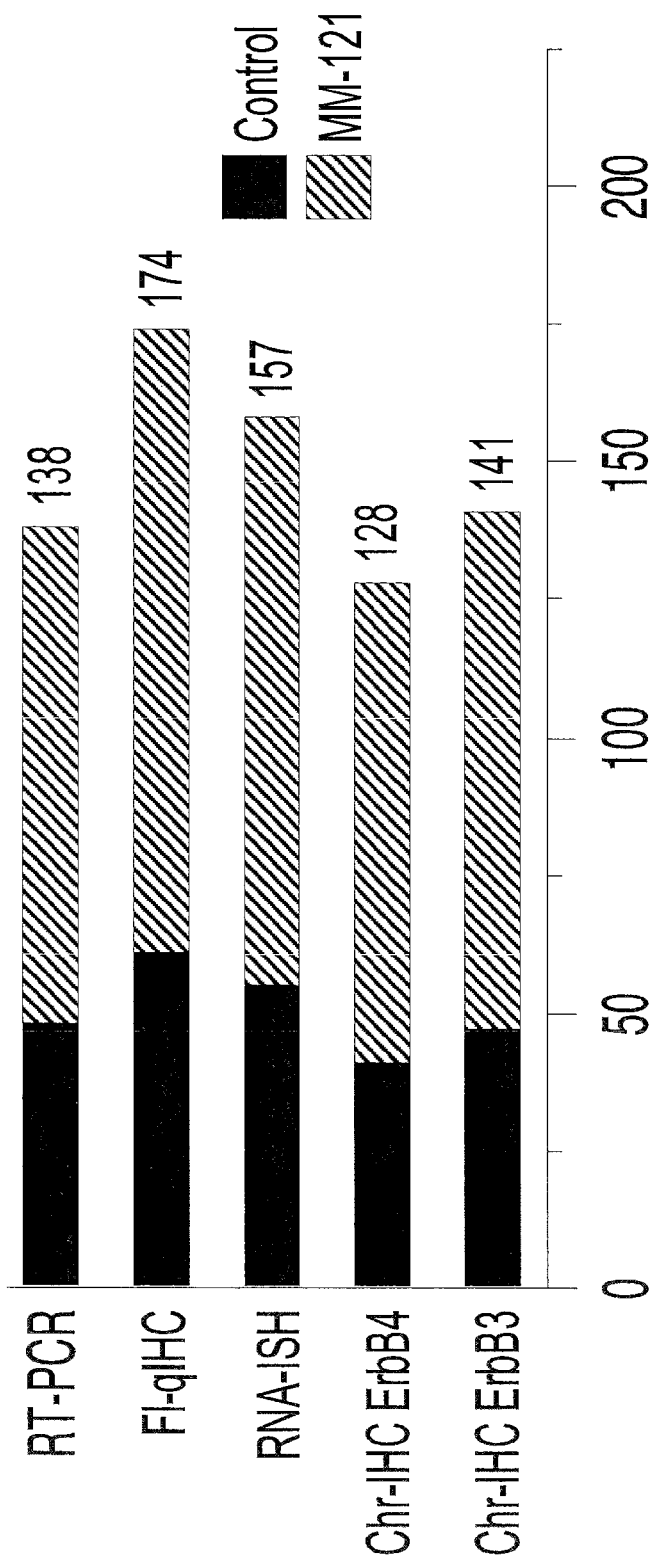
FIGS. 5A and 5B summarize biomarker analysis data from the clinical trial described in Example 5.

Biomarker analyses were performed on the 220 subjects in the safety population of this trial. The number of subjects with biomarker data for each type of assay is summarized in FIG. 5A. The number of subjects for whom serum biomarker data are available is provided for reference. The primary cause underlying missing data was insufficient tumor material in the biopsies.

Of the six biomarkers, EGFR was the least prevalent. It was at or below the limit of detection, either by RT-PCR or IHC, in >60% of the samples.

Univariate Analyses

In total, six primary biomarkers were measured using 15 assays. For the 5 chromogenic assays (qIHC and RNA-ISH), two different overall scores were used: composite score and top-10 score. Accordingly, 20 different variables were assessed at this stage. A Cox proportional hazard model was used to rank the biomarkers. This method determines if PFS varies with biomarker values differently in the treatment arm relative to the control arm. A P-value cutoff of 0.4 was used to determine which biomarkers would be prioritized for subsequent bivariate analyses. The results of these biomarker ranking experiments are provided in FIG. 5B.

Figure 5B:
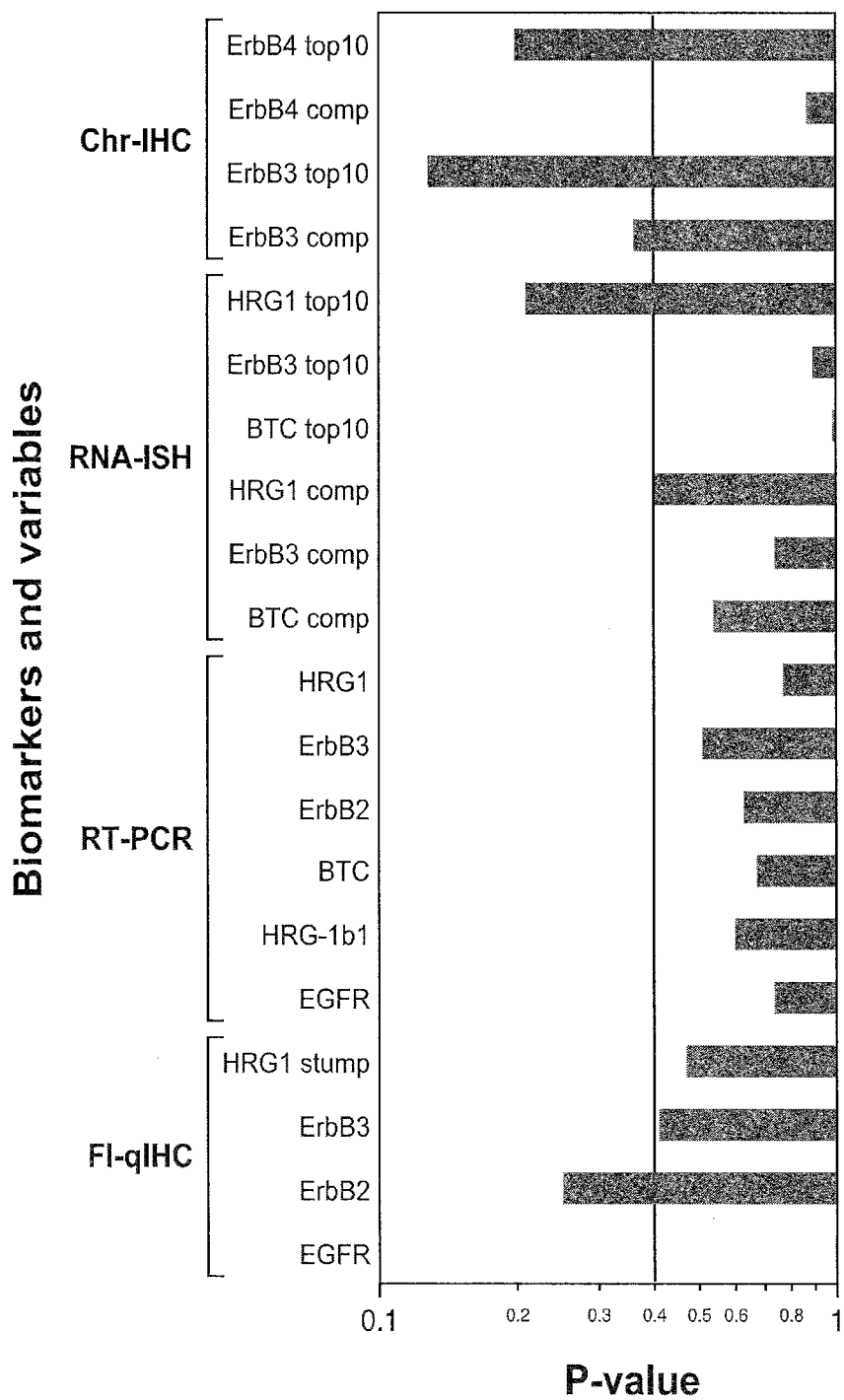

Overall, four biomarkers were prioritized for further analysis based on the data summarized in FIG. 5B: 1) ErbB2 qIHC, 2) HRG RNA-ISH (top-10), 3) ErbB3 qIHC (top-10), and 4) ErbB4 qIHC (top-10). For all of the pathologist-scored assays, the top-10 score correlated better with HR than the composite score. In addition, the imaging-based methods (IHC and ISH) provided better correlations than RT-PCR, which relies on homogenized tissue. One explanation for this observation is that imaging-based methods can account for variability in the tumor cell content of a specimen, whereas RT-PCR cannot.

Relationship Between ErbB2 Levels and HR

Figure 6A:
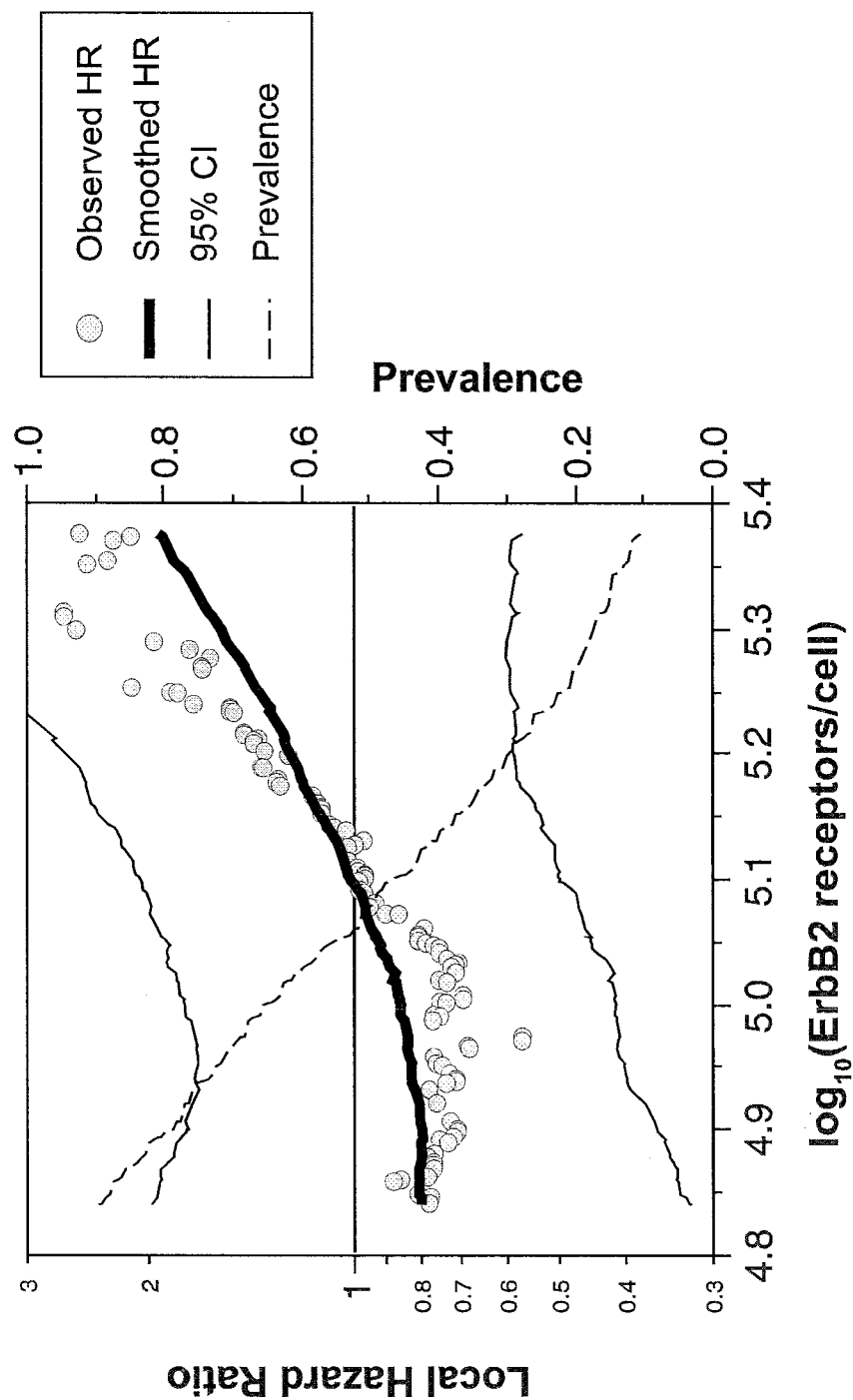
FIGS. 6A to 6D summarize hazard ratio (HR) data for the various biomarkers from the clinical trial described in Example 5. In these results, HR of less than one indicates that patients receiving the study treatment are surviving longer than patients receiving control treatment.

The relationship between ErbB2 levels and local hazard ratio (HR) is shown in FIG. 6A. This plot shows local HR (the HR within a defined window of ErbB2 levels), rather than cumulative HR (the HR for all patients either above or below a given ErbB2 level). As can be seen in FIG. 6A, local HR decreases (favors the treatment arm) as ErbB2 levels decrease. The level of ErbB2, as a single biomarker, at which the HR crosses 1 (no treatment effect) is approximately 5.1 on a $\log_{in}$ scale, which corresponds to about 126,000 receptors per cell. This is consistent with pre-clinical predictions from computational modeling and pre-clinical data showing that MM-121 loses potency when ErbB2 levels rise above about 100,000 to about 200,000 receptors per cell. Of the patients for which ErbB2 data are available (n=174), 53% fall below a threshold of 5.1. Coincidentally, this threshold corresponds to the approximate boundary defining the difference between a score of 1+ and a score of 2+ of the HercepTest® assay ("HCT"). Accordingly, HCT can be used as an alternative HER2 assay in this and other aspects of the disclosed methods, with HCT score of less than 2+ indicating a favorable HER2 level for treatment with an ErbB3 inhibitor such as MM-121.

The relationship between ErbB2 levels and HR was not observed at the interim analysis of this trial. At the time of the interim analysis, very few patients (n=37) had ErbB2 levels above 5.1. In the final dataset, more patients (n=81) were observed with a level above this value, providing increased resolution in the local HR scans.

Relationships between Biomarker Measurements and HRs for HRG, ErbB3, and ErbB4

Figure 6B:
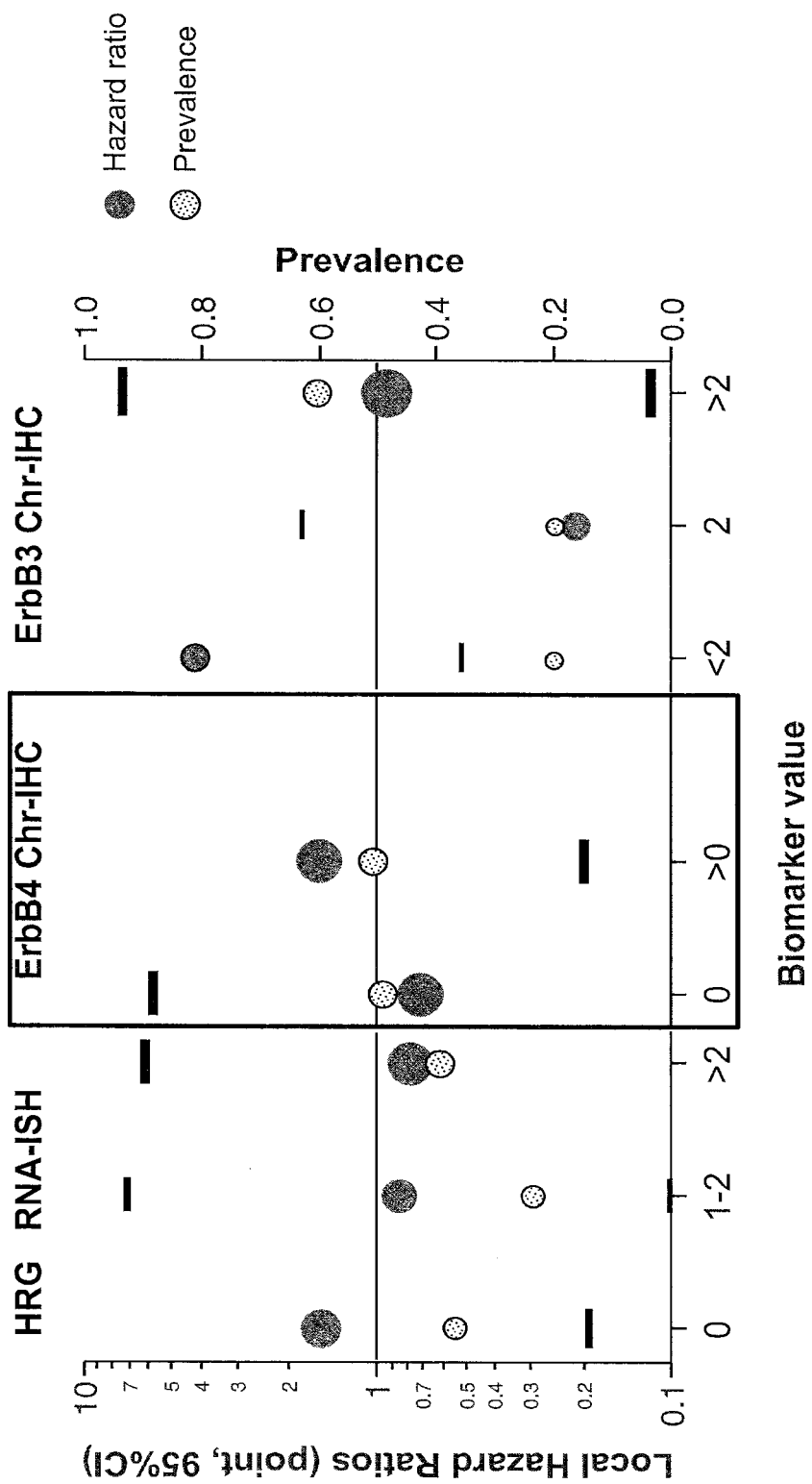
Figure 6C:
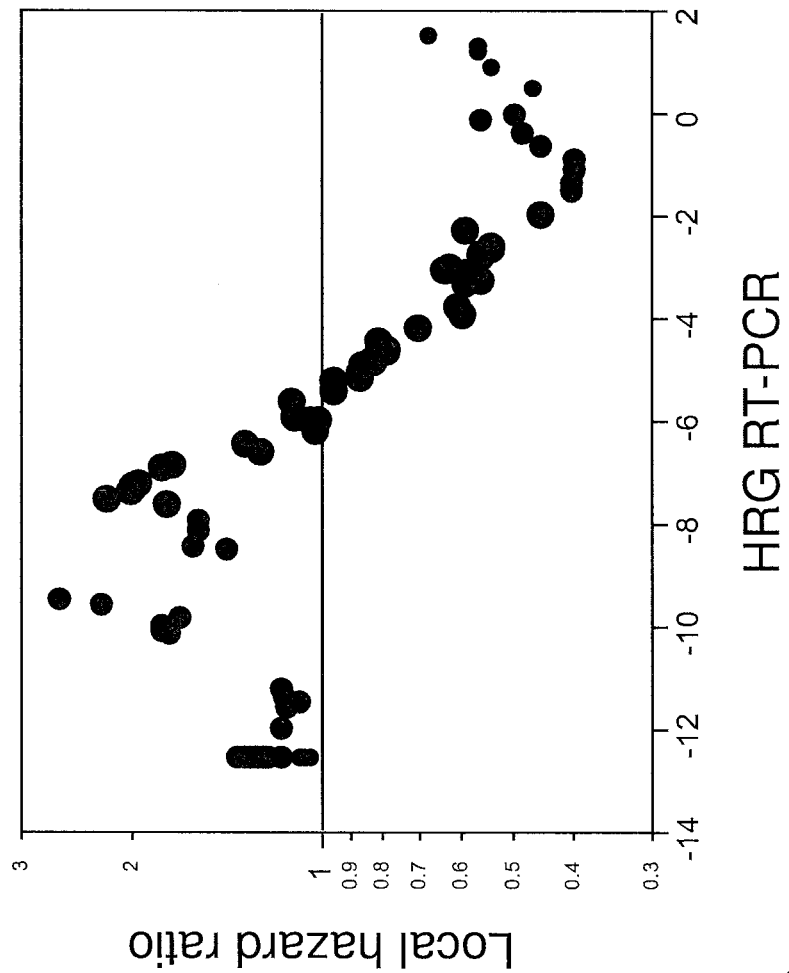
Figure 6D:
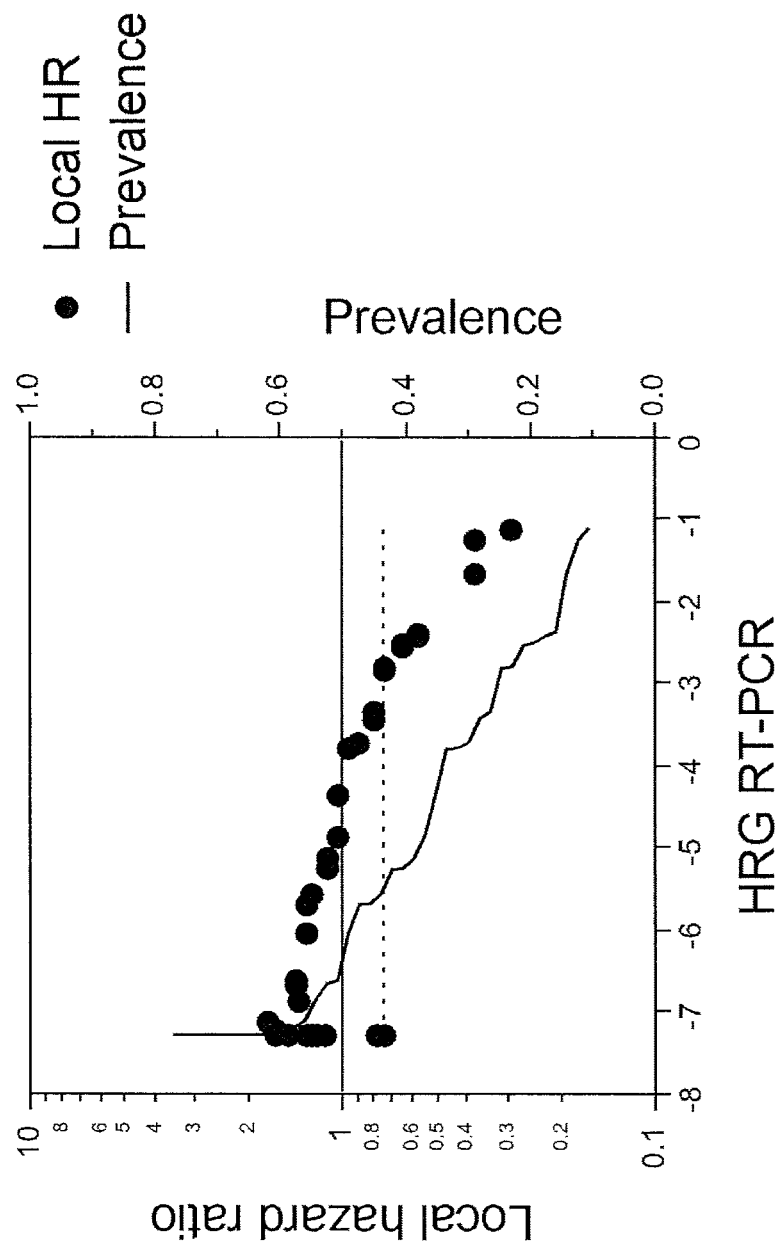

The relationships between biomarker measurements and local HRs for HRG, ErbB3, and ErbB4 (all pathologist-scored assays) are shown in FIG. 6B. The solid dots indicate local HRs, whereas the speckled dots show the percentage of patients with the given biomarker value. The different sizes of the various dots provide a heuristic for prevalence at each biomarker value that is redundant to the prevalence scale. Black lines represent the 95% CI of the HR estimates.

With regard to HRG, subjects with undetectable levels of HRG (score of 0) had a HR that favored control, whereas those with detectable levels of HRG (score of 1-2 or >2) had HRs that favored treatment. This is consistent with the concept underlying MM-121, which was designed to block HRG-driven ErbB3 signaling. The HR is similar for a score of 1-2 and a score of >2. The detection limit of the assay thus provides a natural cut-point for HRG of either HRG present or absent. Of the patients for which HRG data are available (n=157), 62% have detectable levels of HRG (score of 1 or higher).

With regard to ErbB4, subjects with undetectable levels of ErbB4 (score of 0) had a HR that favored treatment, whereas those with detectable levels of ErbB4 (score >0) had a HR that favored control. This is consistent with the pre-clinical prediction that high ErbB4 levels provide an alternative way for HRG to signal independently of ErbB3 and hence render cells less sensitive to MM-121. Of the patients for which ErbB4 data are available (n=128), 49% have undetectable levels of ErbB4 (score of 0).

Finally, with regard to ErbB3, the data show that low or undetectable levels of ErbB3 (score <2) favor the control, whereas medium to high levels of ErbB3 favor treatment. The result is complex, however, as medium levels of ErbB3 (score of 2) favor treatment to a greater extent than high levels of ErbB3 (score of 3 or 4). A similar result was observed using data from the fluorescence-based qIHC assay for ErbB3. Although the decrease in HR from low to medium levels of ErbB3 was observed at interim, the increase in HR from medium to high levels of ErbB3 was not observed. The observed increase in HR with high levels of ErbB3 in the final dataset occurs at levels above about 20,000 receptors per cell. At the time of the interim analysis, very few patients (n=34) had ErbB3 levels above this inflection point. In the final dataset, more patients (n=101) were observed with levels above this value, providing increased resolution in the local HR scans.

Conclusion of Univariate Analyses

Overall, low levels of ErbB2 (53% of patients), detectable levels of HRG (62%), medium to high levels of ErbB3 (80%), and undetectable levels of ErbB4 (49%) were all independently found to favor treatment over control. The results show that intermediate levels of ErbB3 favor treatment to a greater extent than high ErbB3 levels.

Bivariate Analyses (Models with Two Biomarkers)

Figure 7A:
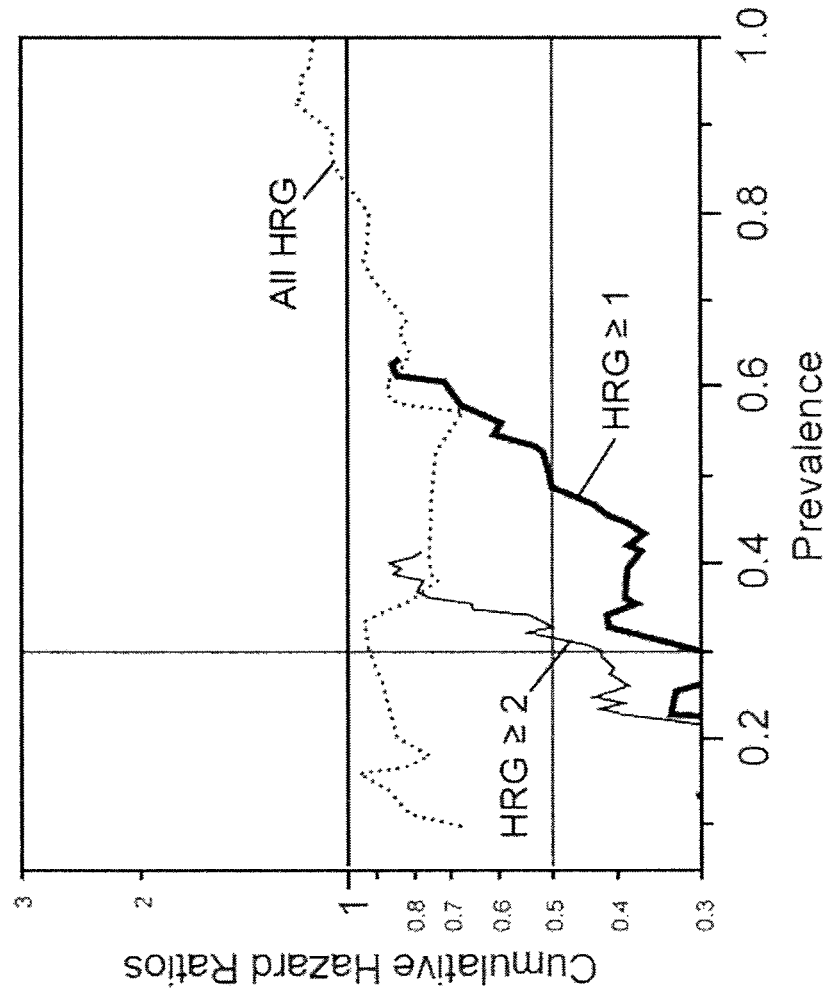
FIGS. 7A to 7G show hazard ratio (HR) analysis data from the clinical trial described in Example 5.
Figure 7B:
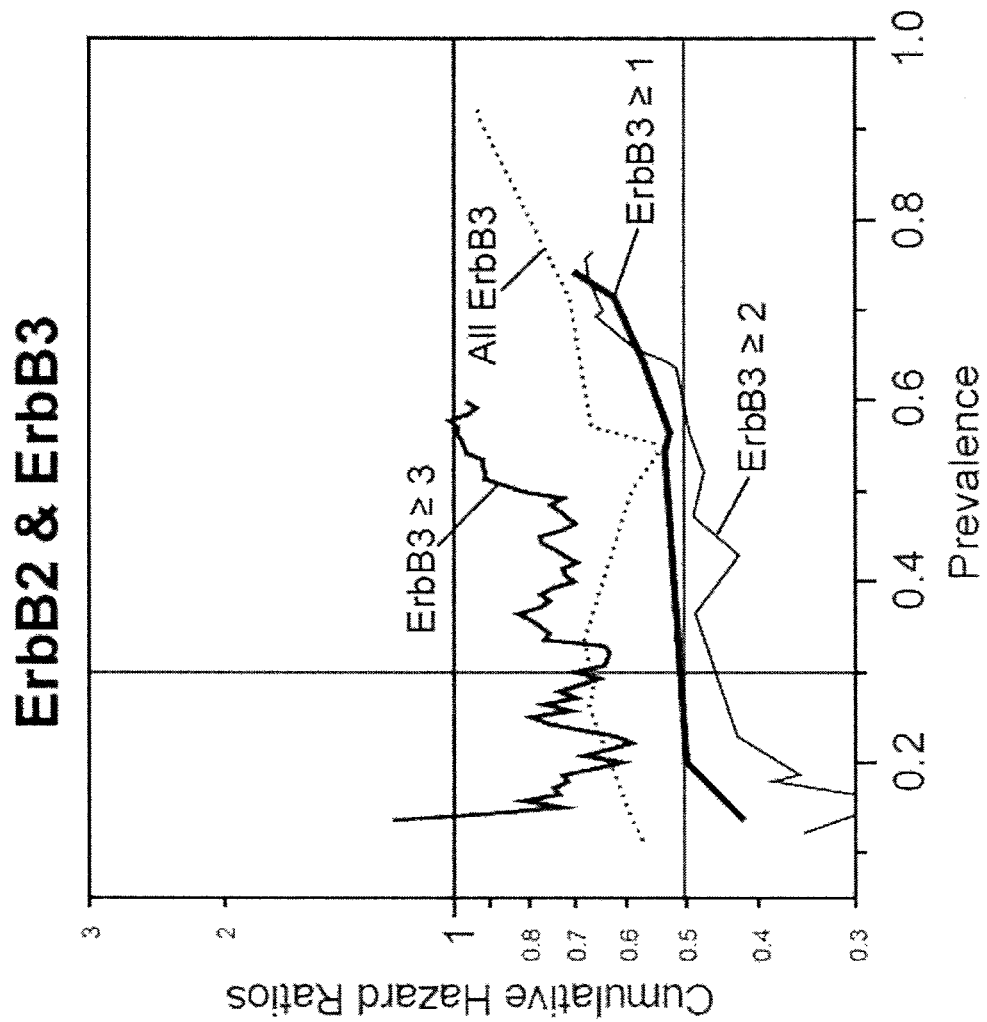
Figure 7C:
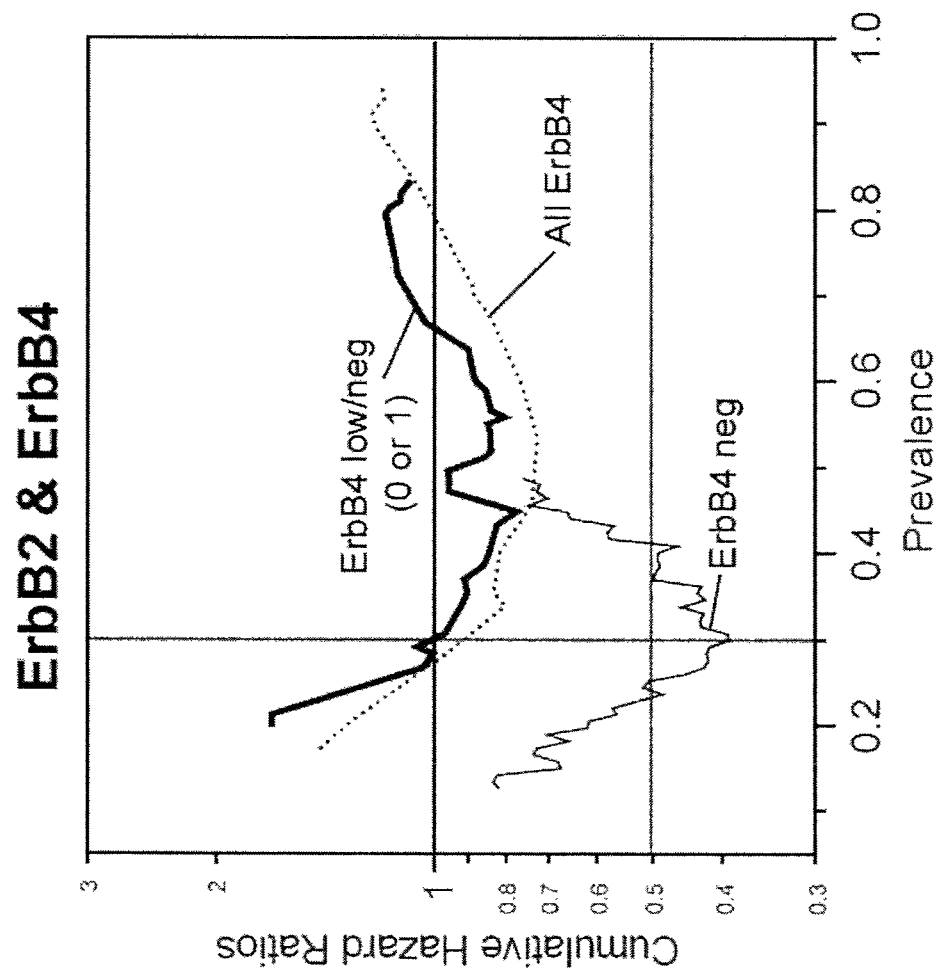
Figure 7D:
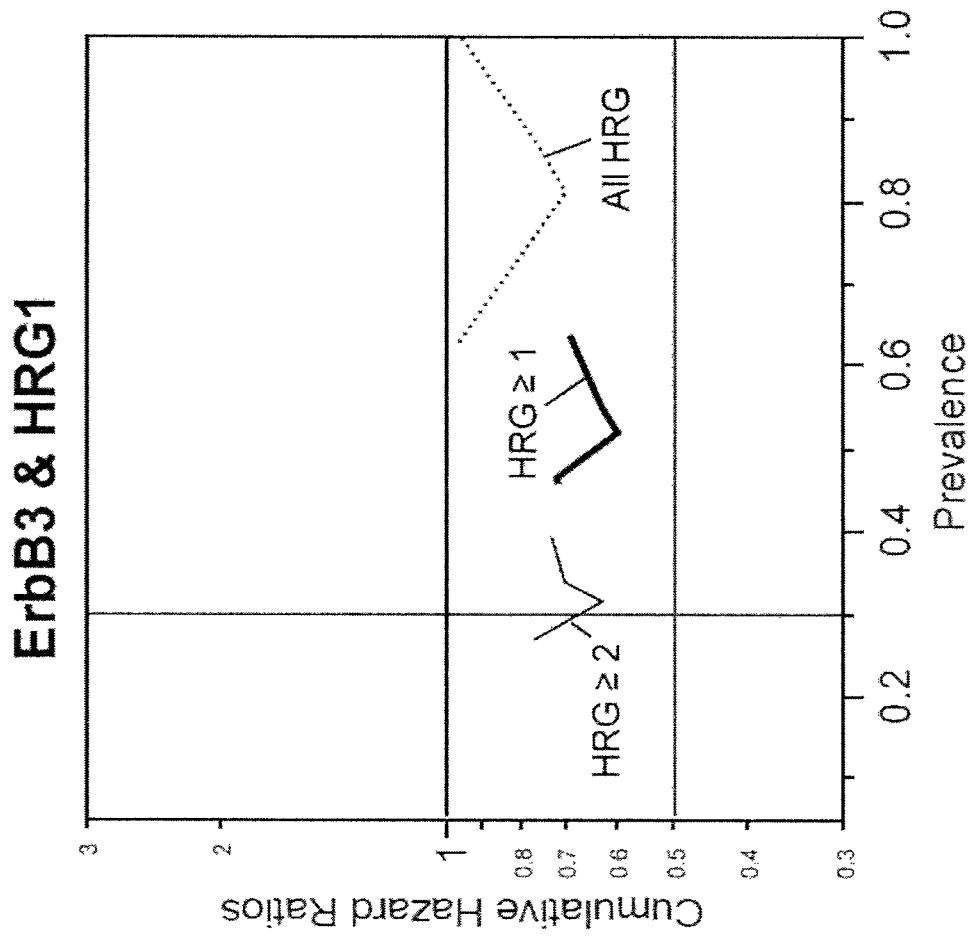
Figure 7E:
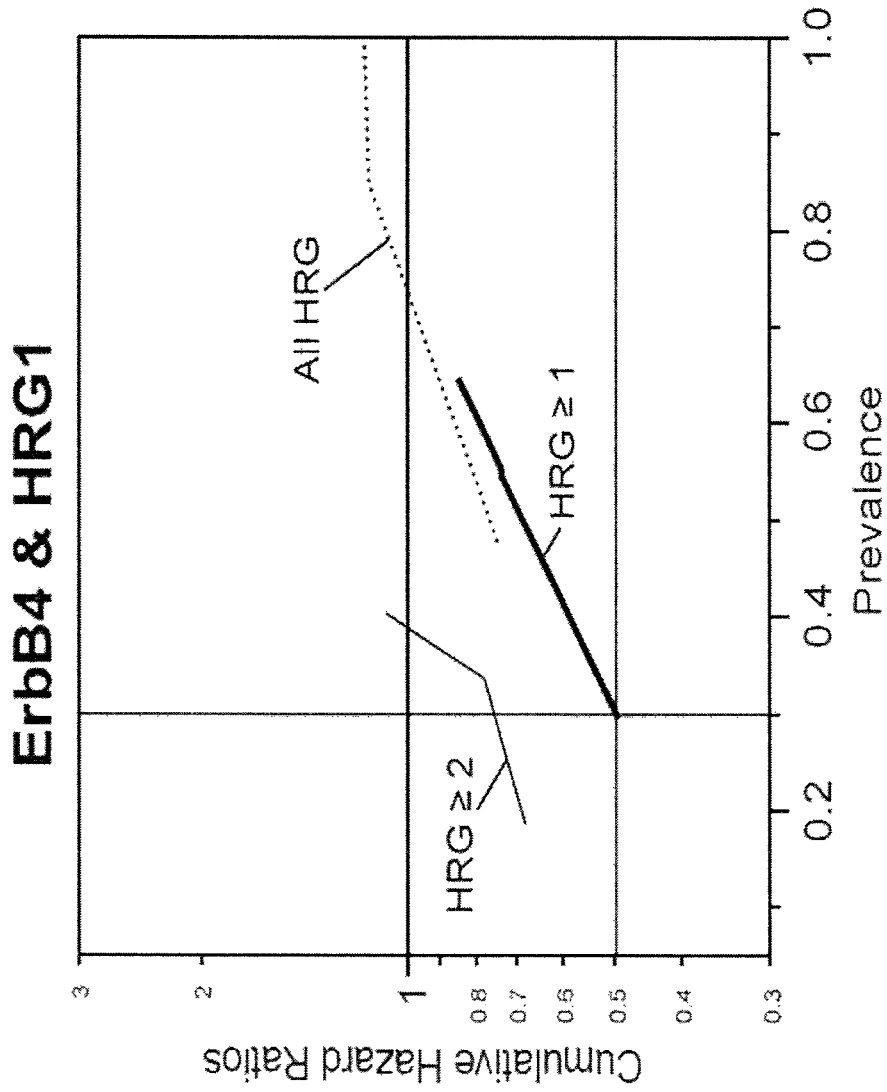
Figure 7F:
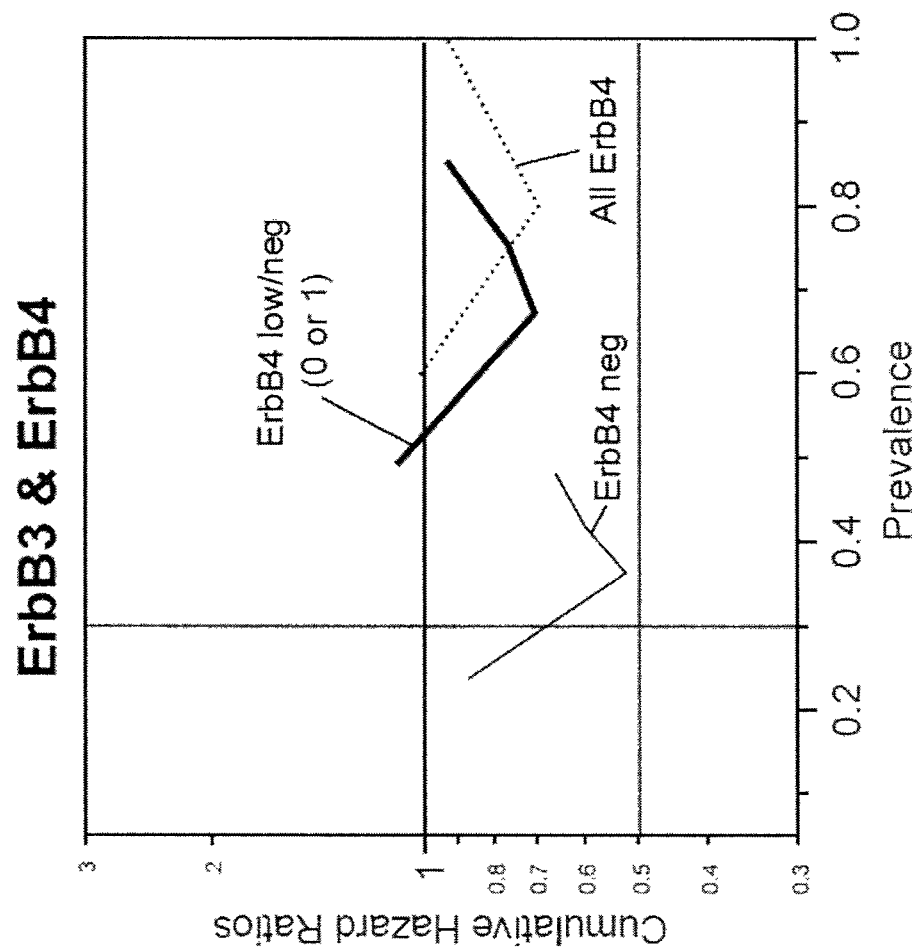

Pairwise interactions between biomarkers were evaluated as follows. In total, there are six two-biomarker models that can be constructed using four biomarkers: ErbB2&HRG, ErbB2&ErbB3, ErbB2&ErbB4, HRG&ErbB3, HRG&ErbB4, and ErbB3&ErbB4. To understand pairwise relationships between biomarkers, cumulative HR was plotted as a function of one biomarker and then repeated at different values of the other biomarker. The results of these calculations are shown in FIG. 7A.

Focusing on the ErbB2 and HRG model as an example (top-left plot), the cumulative HR scans were determined by selecting a subpopulation of patients based on their HRG status and then plotting cumulative HR across ErbB2 levels. The x-axes represent a scan of ErbB2 levels, showing the overall percentage of patients with ErbB2 levels below each value in the scan. The dashed lines represent patients with any score for HRG (i.e., all the patients with BM measurements). The right side of the plot shows all of these patients (HR≈1, prevalence=100%). Moving from right to left, the ErbB2 threshold above which patients are excluded progressively decreases. Thus, the midway point of this plot (Prevalence=50%) represents all the patients with ErbB2 levels below the median. The cumulative HR decreases as ErbB2 high patients are successively excluded. The thickest solid line on this plot shows the same procedure performed only on the patients with a HRG score of 1 or higher (i.e., detectable levels of HRG). The right end of this plot starts at a prevalence of 62% because 38% of patients had undetectable levels of HRG. Moving from right to left along the red line, the ErbB2 threshold above which patients are excluded progressively decreases, as before. The thinnest solid line represents the same procedure, performed using subjects with a HRG score ≥2 (41% of subjects). The starting point for this scan (right end of the thinnest solid line) is therefore at 41% prevalence. This plot shows that patients with detectable levels of HRG and low levels of ErbB2 derive meaningful clinical benefit from MM-121 (HR<0.5). The thinnest solid line (HRG score ≥2) is shifted to the left relative to the thickest solid line because fewer patients have a HRG score ≥2 than a HRG score ≥1. The thinnest solid line does not drop appreciably below the thickest solid line, showing that a detectable level of HRG is roughly equivalent to a high level of HRG in this context (i.e., here higher HRG scores do not predict greater benefit than lower, but detectable HRG levels).

The other five plots were prepared in a similar fashion to the ErbB2 and HRG plot. For the ErbB2 andErbB3 and ErbB2 and ErbB4 plots, cumulative HR was scanned on ErbB2 levels (as above). For the ErbB3 and HRG and ErbB3 and ErbB4 plots, cumulative HR was scanned on ErbB3 values. For the ErbB4 and HRG plot, cumulative HR was scanned on ErbB4 values.

Figure 7G:
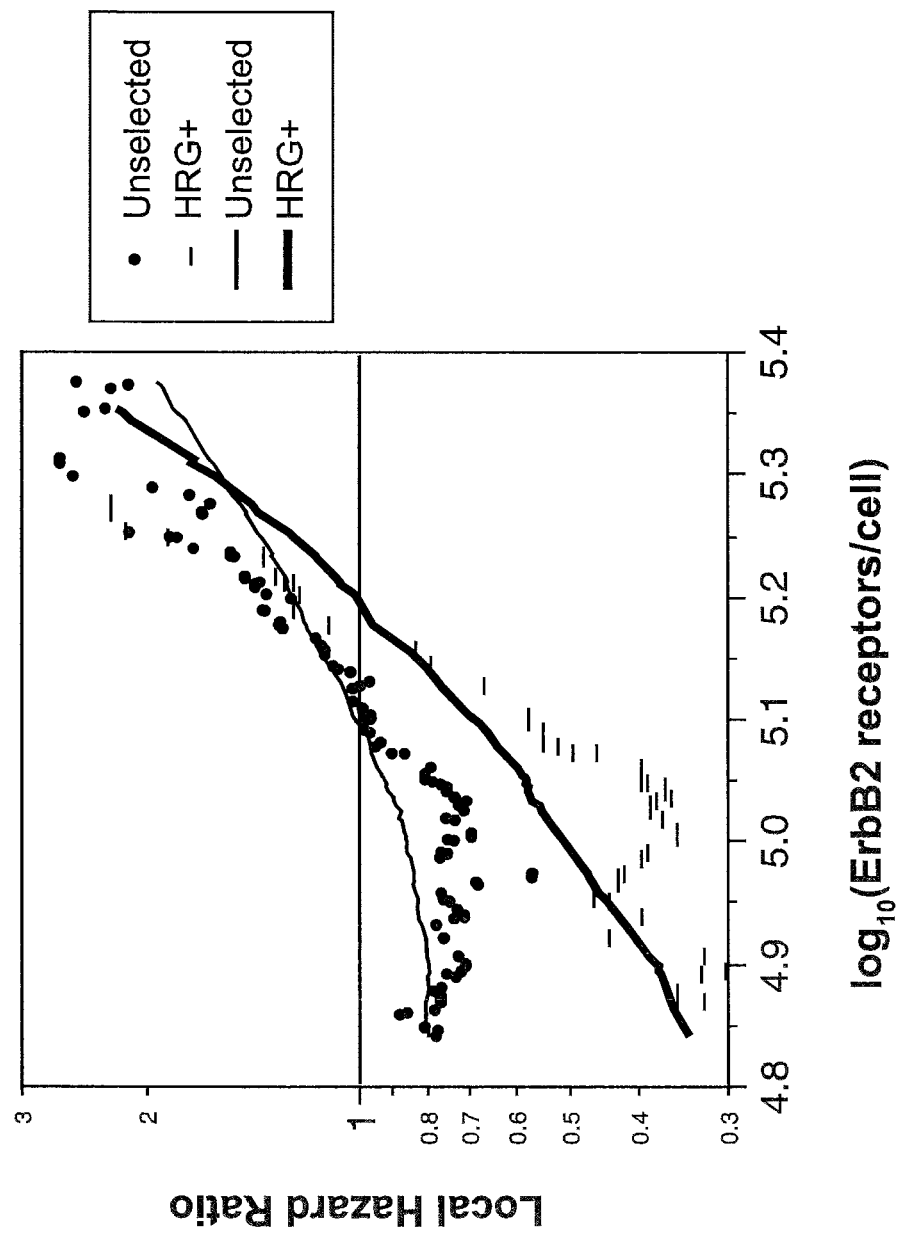

Overall, the strongest pairwise interaction (resulting in the most favorable balance between HR and prevalence) was observed for the interaction between ErbB2 and HRG. To explore this interaction further, local HR was plotted as a function of ErbB2 levels for all subjects and for HRG-positive subjects (score ≥1) (FIG. 7G). The dots and dashes are observed HRs, while the thin and heavy lines are smoothed renderings of these data accounting for noise in the ErbB2 measurements. Notably, the thick line is shifted down relative to the thin line at low levels of ErbB2, indicating that HRG status augments ErbB2 status in the identification of patients that derive benefit from MM-121. Based on this plot, a HRG score of ≥1 and an ErbB2 threshold of $\log_{10}$ 5.1 (corresponding to about 126,000 receptors per cell) were chosen for subsequent analyses.

Based on these two thresholds, a biomarker profile positive (BM+) subpopulation is defined for subsequent analyses as: (ErbB2 levels≤$\log_{10}$ 5.1) AND (HRG score ≥1) ("ErbB2 low" AND "HRG positive"). Accordingly, a biomarker profile negative (BM−) subpopulation is defined as (ErbB2 levels>$\log_{10}$ 5.1) OR (HRG score <1) This definition results in a BM+ prevalence of 34% in the clinical trial population.

Survival Characteristics of BM+ and BM− Subpopulations

Figure 8A:
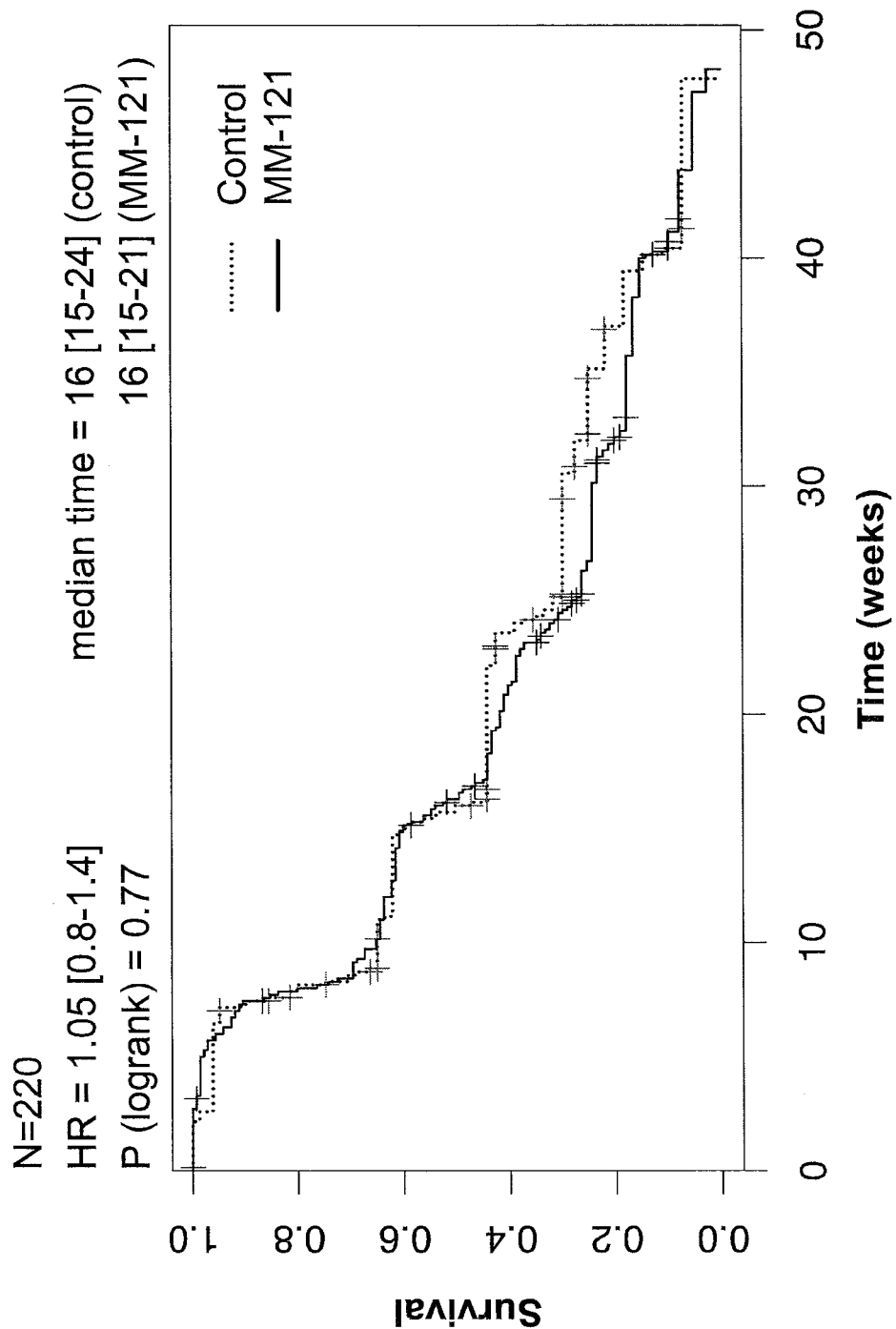

Progression-free survival: The Kaplan-Meier PFS plot for the overall safety population after 60 weeks is provided in FIG. 8A. In this and plots 8B and 8C, the treatment arm (paclitaxel+MM-121) is represented by a solid black line and the control arm (paclitaxel) is represented by a dashed line. In FIG. 8G (progression free survival at 10+ months) and FIG. 8H (overall survival at 10+ months), the treatment arm is represented by a blue line and the control arm is represented by a black line.

Figure 8B:
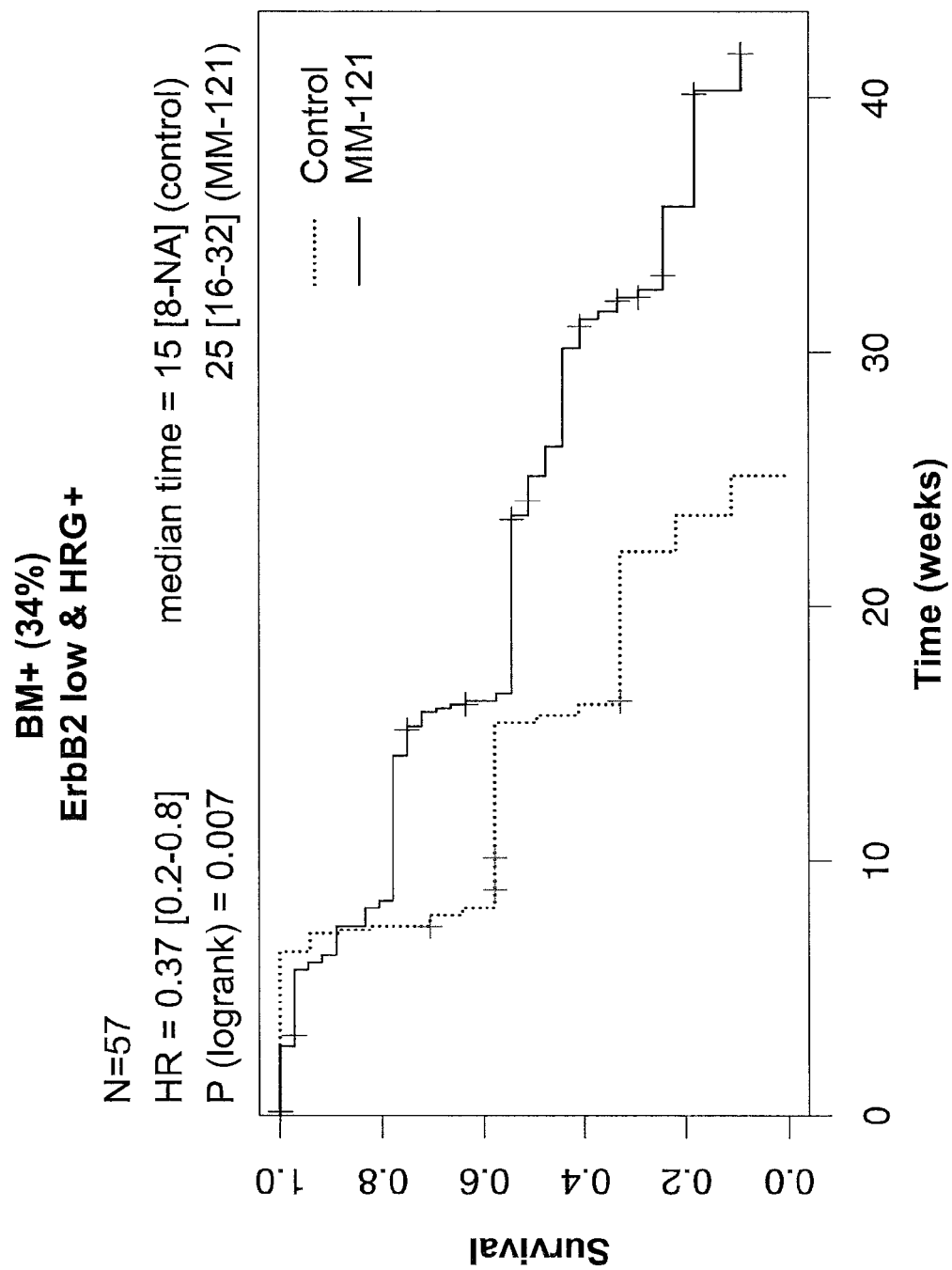
Figure 8C:
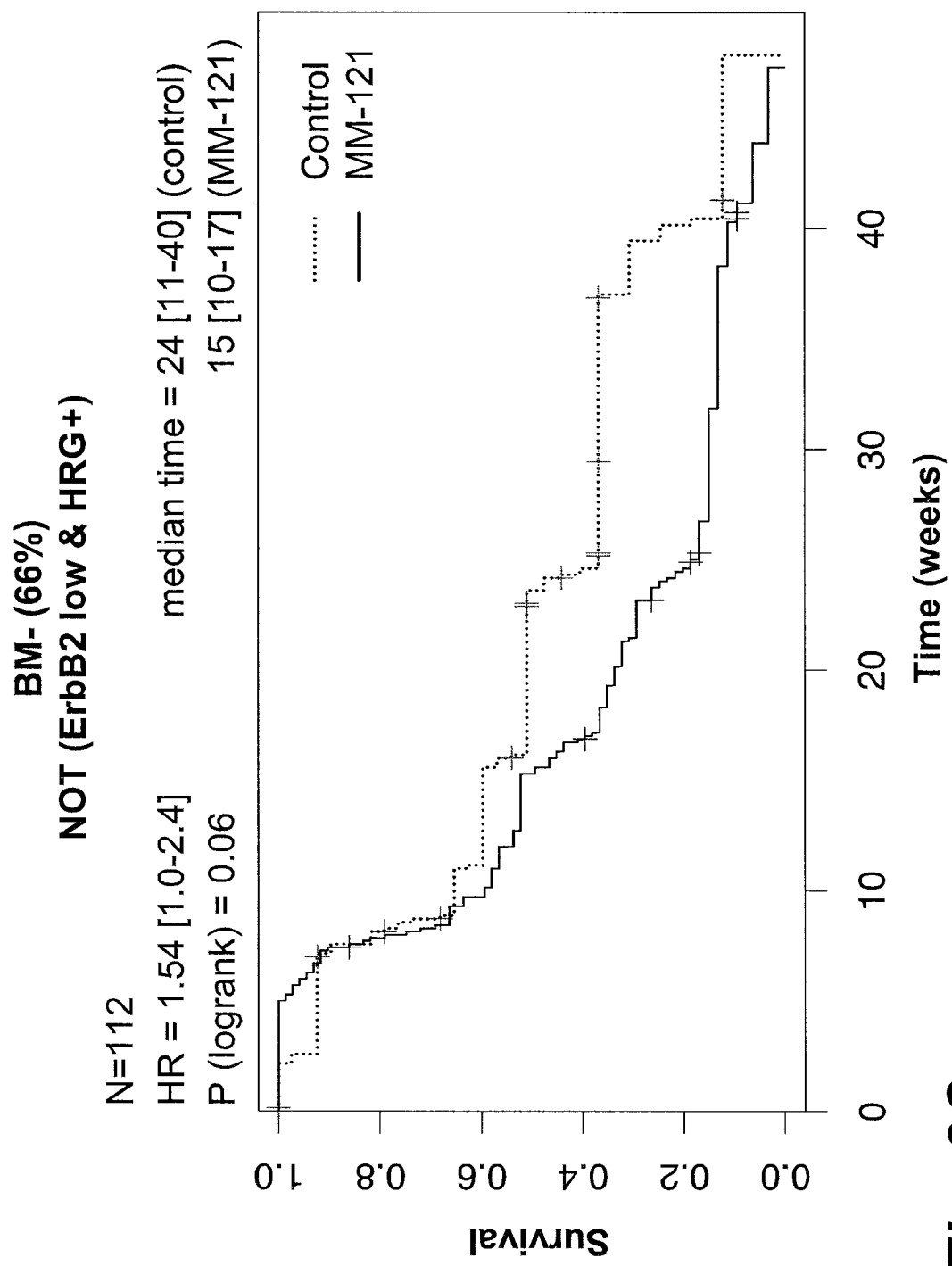
Figure 8D:
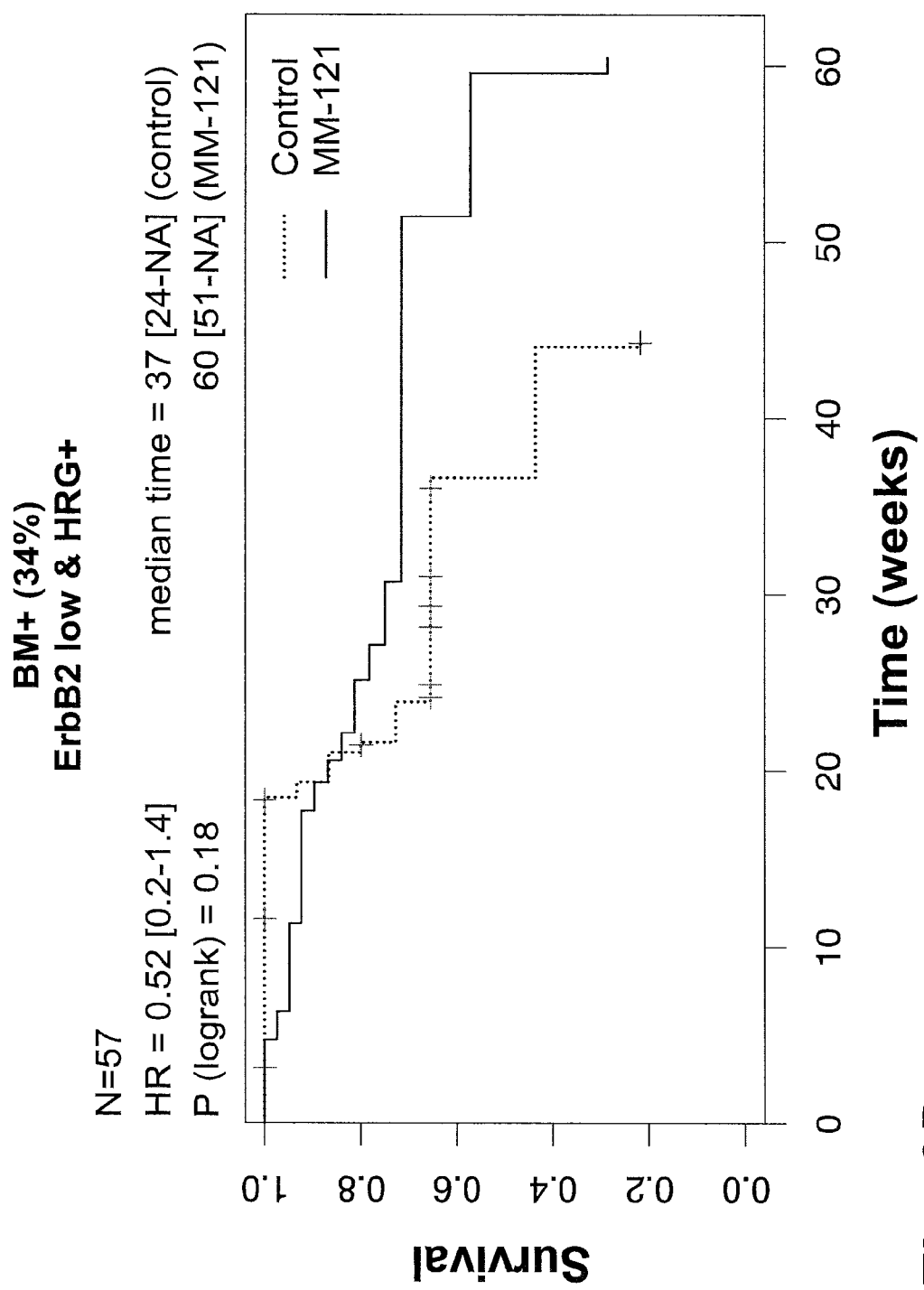
Figure 8E:
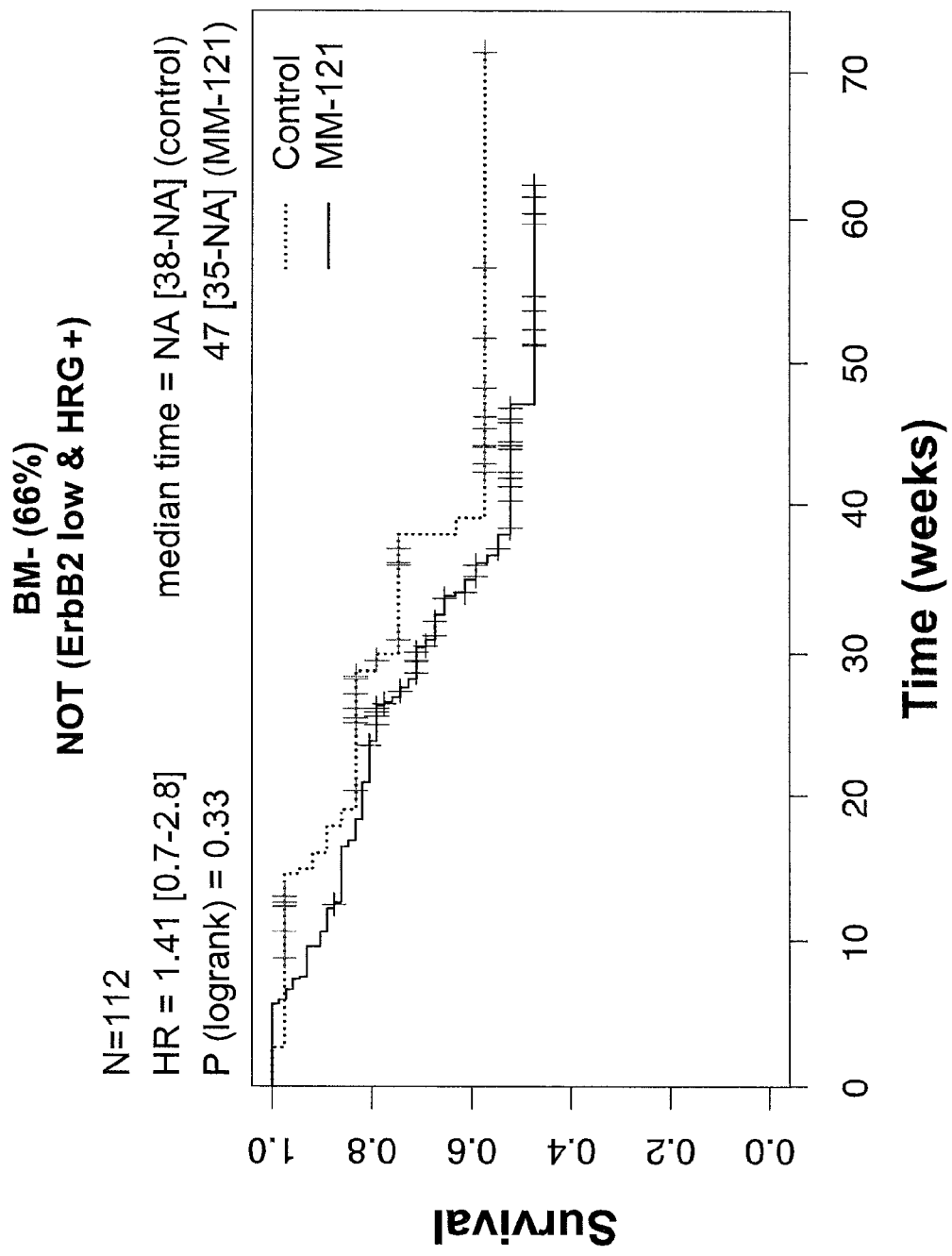

Kaplan-Meier PFS plots for the BM+ and BM− profile subpopulations are provided in FIGS. 8B and 8C for data collected at 60 weeks. The BM+ profile subpopulation had a 0.37 [95% CI 0.2-0.8] HR and the BM− subpopulation had a 1.54 [95% CI 1.0-2.4] HR. In comparing the control arms in these two populations, the BM+ profile subpopulation performs worse than the BM− profile subpopulation (i.e., BM+ profile is indicative of poor prognosis when treated only with paclitaxel). A Kaplan-Meier PFS plot for the BM+ and BM− profile subpopulations is provided in FIG. 8I.

No imbalances were observed between treatment and control arms in the BM+ profile population for a) number of lines of prior therapy, b) time to first metastatic event, histology, or c) age. A slight imbalance was observed in dichotomized age (>60 vs. ≤60) and stage of disease (stage IV vs. stage I, II, III).

Best Response Rates

Figure 8F:
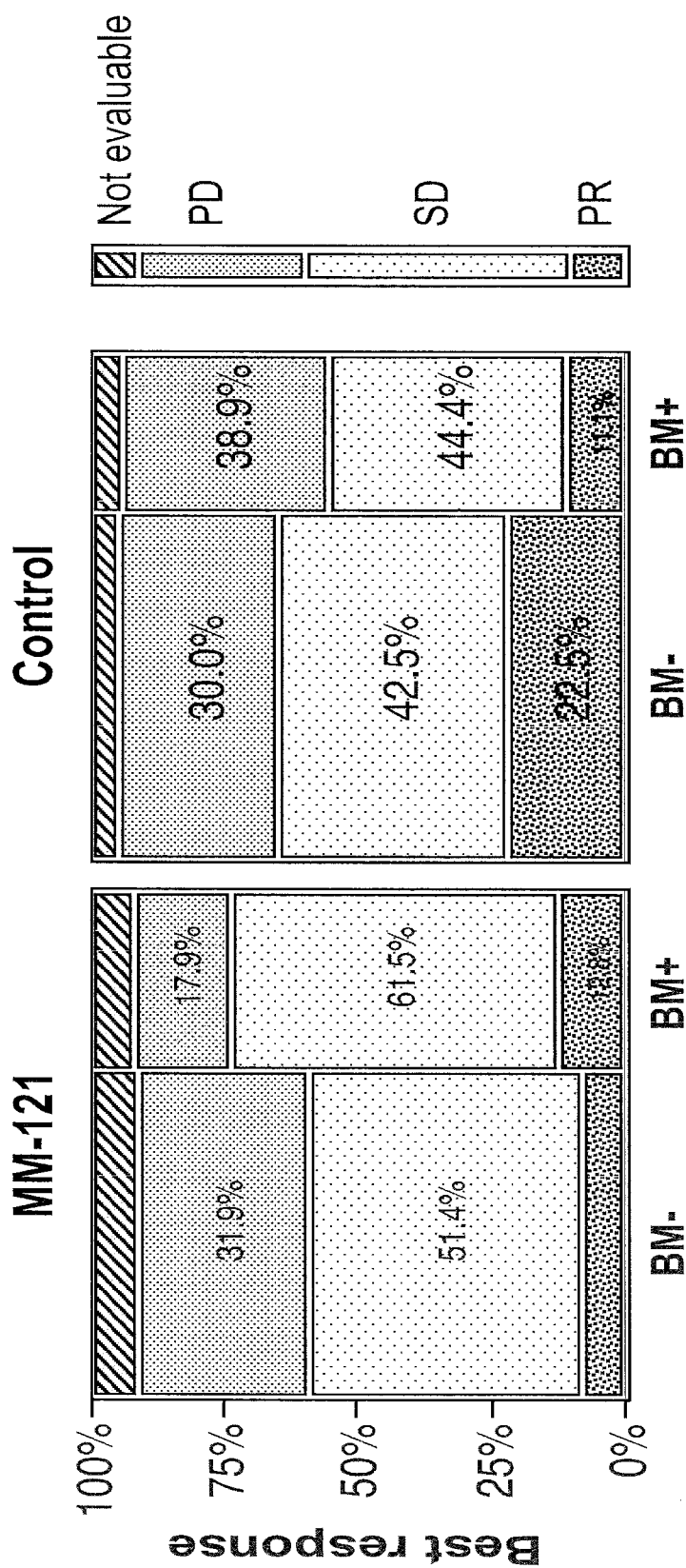
Figure 8G:
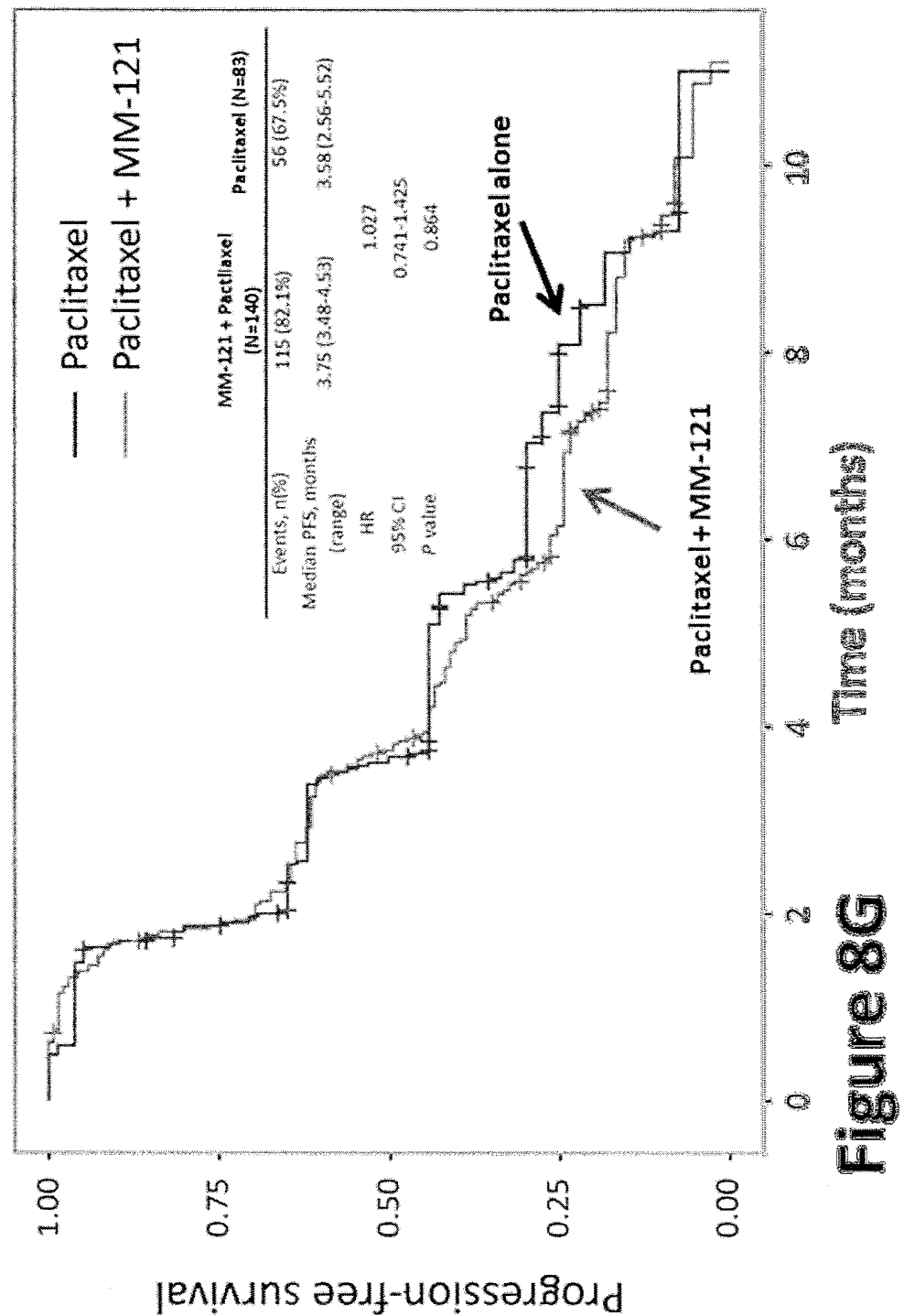
Figure 8H:
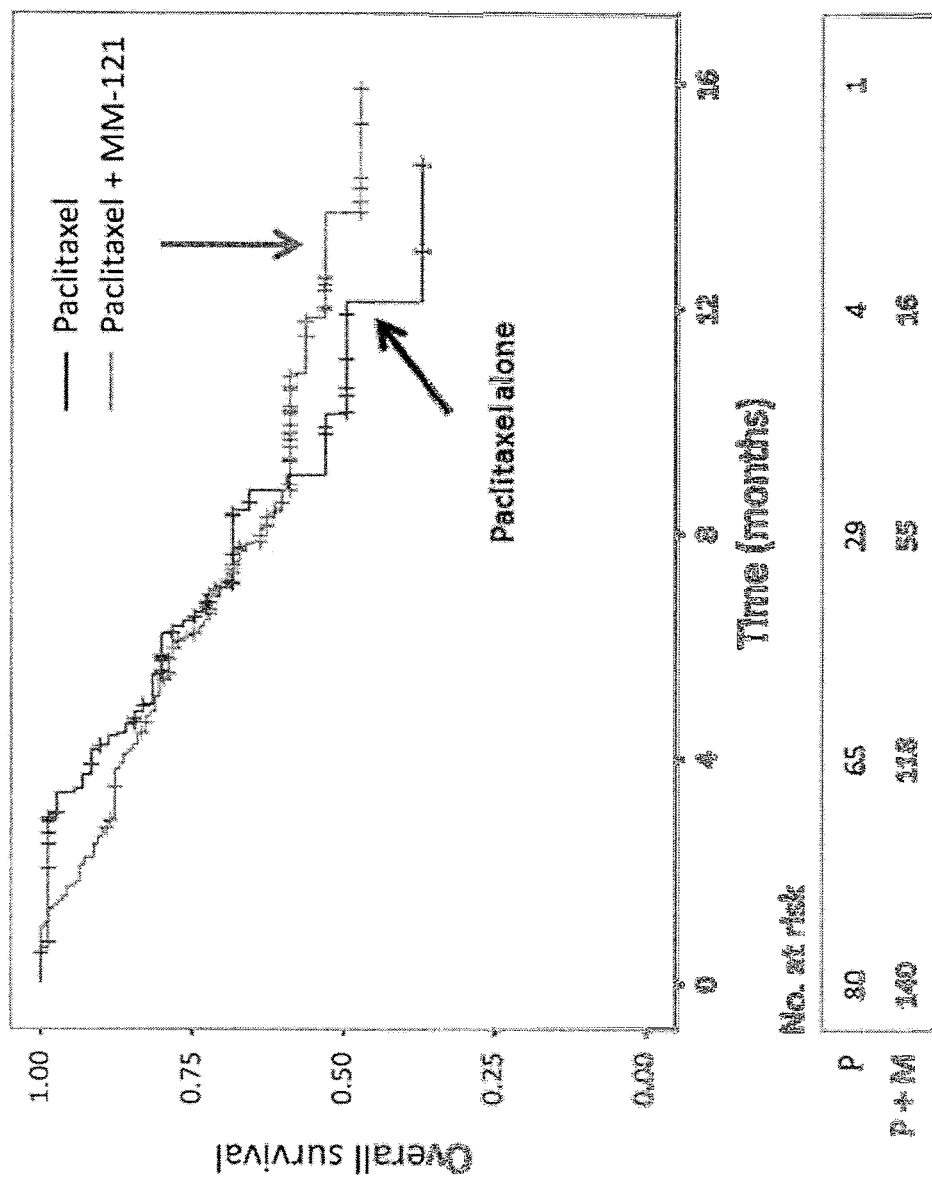
Figure 9A:
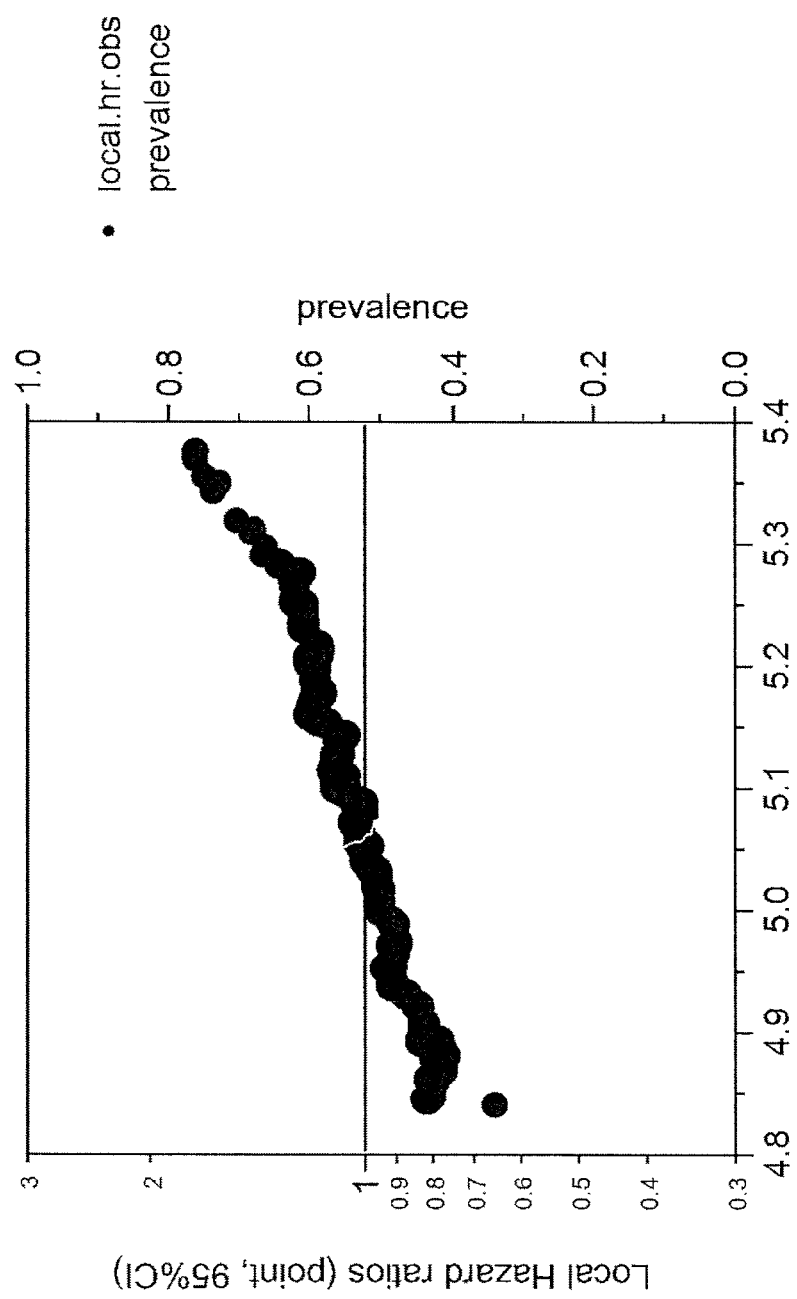
FIGS. 9A to 9D show calculated observed local HRs ("local.hr.obs" Y axis—left scale) from the clinical trial described in Example 6. These HRs are plotted as a series of often overlapping points or dots, with the diameter of each point indicating the 95% confidence interval for that data point, with HR values plotted against regressed HER2 receptors per cell from cytokeratin (CK) positive cells (X-axis, log 10 values shown). Prevalence for each HER2 amount is indicated by a plot line descending from left to right and read off the Y axis—right scale.
Figure 9B:
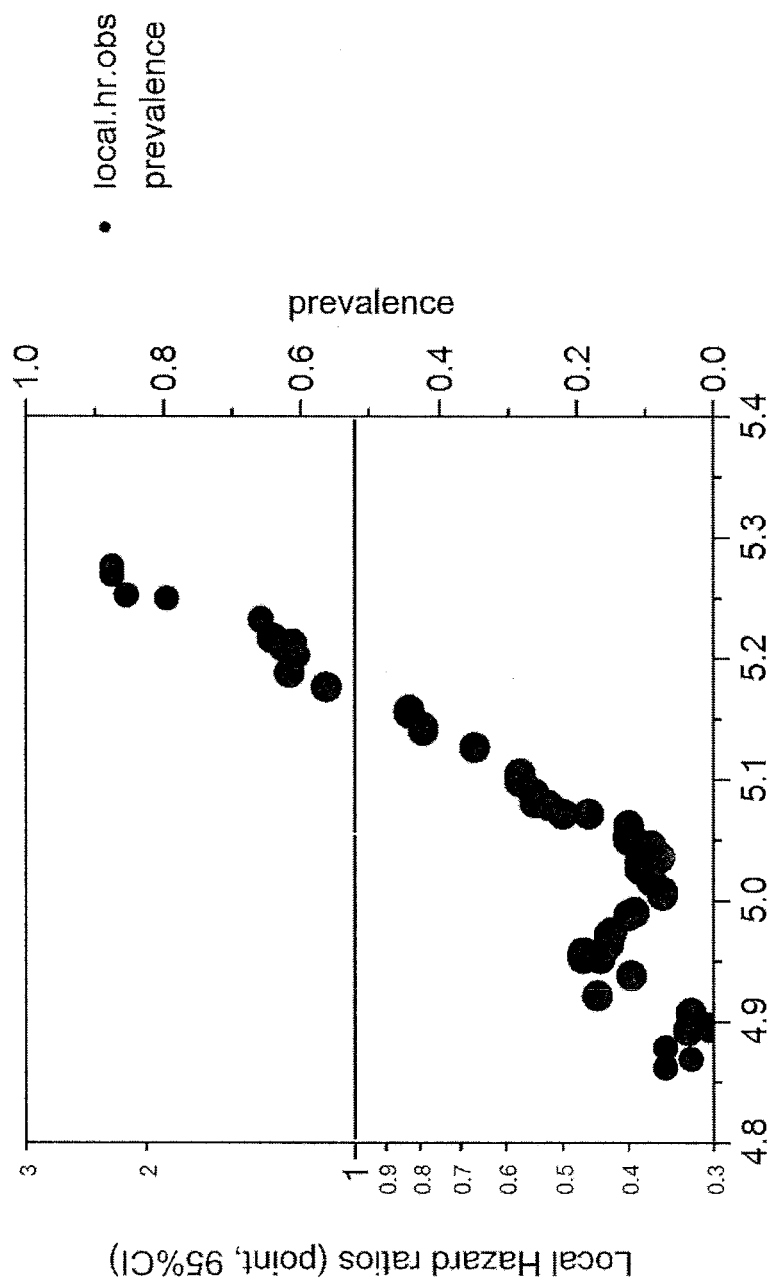
Figure 9C:
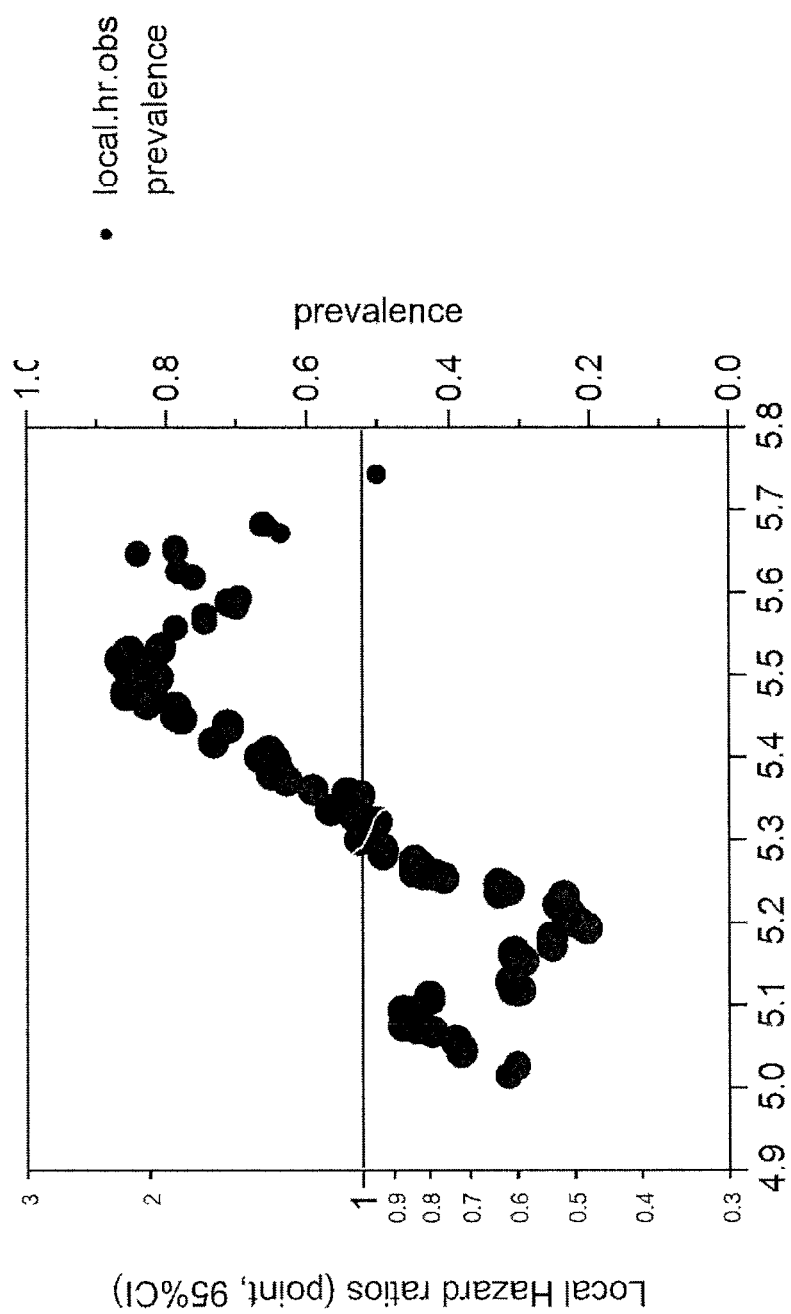
Figure 9D:
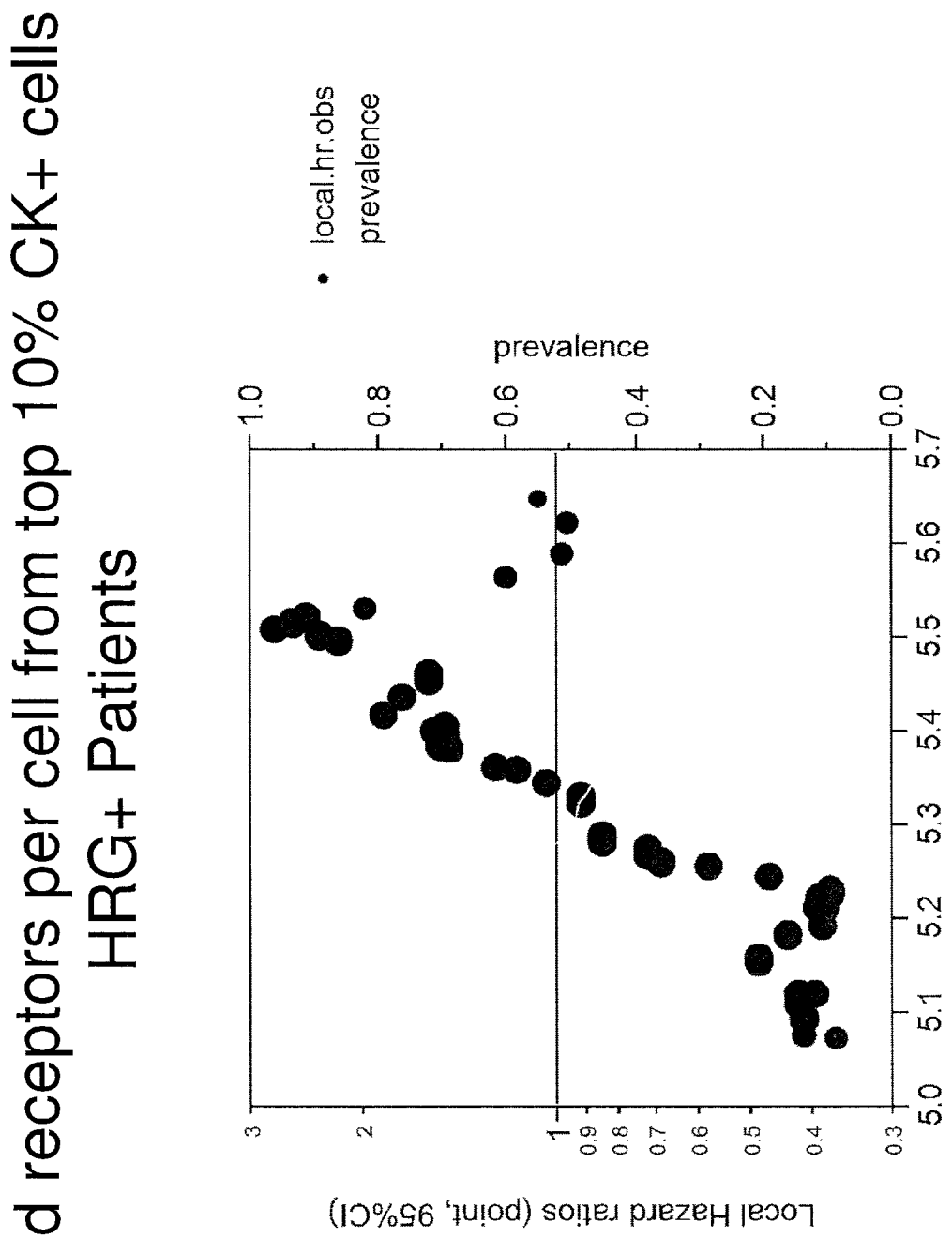

Best response rates for treatment and control arms are shown in FIG. 8F.

Although the numbers are low, the PR and SD rates are higher in the BM+ subpopulation than in the BM− subpopulation on the treatment arm. This contrasts with the control arm, where the PR rate is higher in the BM− subpopulation than in the BM+ subpopulation.

Consequence of ErbB3 and ErbB4 Status in the BM+ Subpopulation

To evaluate the potential significance of not including ErbB3 and ErbB4 measurements in the definition of a biomarker profile positive subpopulation (ErbB2 low and HRG positive), HRs were estimated for subgroups in the BM+ and BM− subpopulations as determined by ErbB3 or ErbB4 status. The results are provided in Table 11.

TABLE 11

HR estimates in subgroups of BM+ and BM− patients as defined by ErbB3 and ErbB4 status.

| BM + or − (HER2 low & HRG+) | Subgroup BM | Subgroup BM score | Prevalence in BM sub-population | N (MM-121) | N (ctrl) | HR (trt:ctrl) | HR (95% CI) |
|---|---|---|---|---|---|---|---|
| BM− | ErbB4 | 0 | 0.49 | 28 | 13 | 1.05 | 0.13-8.8 |
| BM− | ErbB4 | ≥1 | 0.51 | 27 | 15 | 2.20 | 0.27-18 |
| BM+ | ErbB4 | 0 | 0.48 | 14 | 6 | 0.13 | 0.02-1.1 |
| BM+ | ErbB4 | ≥1 | 0.52 | 16 | 6 | 0.65 | 0.08-5.5 |
| BM− | ErbB3 | <2 | 0.17 | 11 | 4 | NA | NA-NA |
| BM− | ErbB3 | ≥2 | 0.83 | 46 | 28 | 0.86 | 0.11-7.0 |
| BM+ | ErbB3 | <2 | 0.21 | 10 | 0 | NA | NA-NA |
| BM+ | ErbB3 | ≥2 | 0.79 | 24 | 13 | 0.33 | 0.04-2.7 |

(trt = treatment, ctrl = control)

The HR for the ErbB4 positive subgroup (score ≥1) within the BM+ subpopulation is 0.65 [0.08-5.5] in favor of the treatment arm. This subgroup represents 52% of the BM+ patients. Thus, there is no evidence that this subgroup is adversely affected by treatment. Conversely, for the subgroup of ErbB4 negative patients (score=0) in the BM− subpopulation, the estimated HR is 1.05 (0.13-8.8). There is therefore no evidence that these patients would receive benefit from MM-121, even though they are excluded from treatment by the definition of BM+(ErbB2 low & HRG positive). This subgroup constitutes 49% of the BM− subpopulation.

For the ErbB3 low/negative subgroup (score <2) in the BM+ subpopulation (21%), the HR is not calculable as there are no patients within this subgroup enrolled in the control arm. For the ErbB3 med/high subgroup (score ≥2) in the BM− subpopulation, the estimated HR is 0.86 (0.11-7.0). Thus, there is no evidence that these patients would receive substantial benefit from MM-121, even though they are excluded from treatment by the definition of BM+(ErbB2 low & HRG positive).

Summary of Results

Overall, four biomarkers were identified that favored treatment relative to control. These include low ErbB2 (less than 2+ as measured by qIHC, =about 126,000 ErbB2 receptors per cell, =HCT less than 2+) representing 53% of patients, HRG positive (1+ or higher as measured by RNA-ISH) representing 62% of patients, ErbB4 negative (less than 1+ as measured by IHC) representing 49% of patients, and ErbB3 medium to high (2+ or higher as measured by IHC) representing 80% of patients.

The interpretation of the ErbB3 results was found to be more complex than for the other biomarkers, and it was determined that ErbB3 negative/low (20%) favors control and ErbB3 medium/high (80%) favors treatment, but ErbB3 medium favors treatment more so than ErbB3 high.

No major imbalances in clinical covariates are observed in the BM+ subpopulation and there is no evidence suggesting that low ErbB3 status or high ErbB4 status places patients in the BM+ subpopulation at risk.

A two-biomarker model (ErbB2 low and HRG positive) identifies a subpopulation of patients that benefit from MM-121 (HR of 0.37 [95% CI of 0.2-0.8]; prevalence of 34%). The subpopulation of patients, defined by $\log_{10}$(ErbB2)<5.1 and HRG detectable, resulted in HR of 0.37 (95% CI of 0.2-0.8) with a prevalence of 34%.

The HR in the biomarker negative population (66%) was 1.54 (95% CI of 1.0-2.4)

The results of the study suggest that ligand-driven ErbB3 signaling mediates tumor cell survival and so renders tumors less responsive to chemotherapy (weekly paclitaxel). MM-121 is designed to block ligand-driven ErbB3 signaling and therefore may provide benefit to patients in which ErbB3 signaling is providing a mechanism of resistance to chemotherapy.

A biomarker profile of low ErbB2 (less than or equal to about 126,000 receptors per cell by chromogenic qIHC as disclosed herein, or below 2+ by HCT) and HRG positive (+1 or higher by chromogenic RNA-ISH) has been identified as an exemplary biomarker signature indicative of an increased likelihood of responsiveness to ErbB3 inhibitor therapy.

In summary, this study determined that HRG mRNA levels predicted response to MM-121, which was further enhanced in patients with low ErbB2 levels. BM+ patients were defined as having detectable HRG mRNA and low ErbB2 protein in pre-treatment biopsies, and while BM+ patients responded poorly to paclitaxel alone, these same patients benefited from the combination therapy of MM-121 and paclitaxel. Results from this study further implicate heregulin-driven ErbB3 signaling as a mechanism of resistance to standard-of-care therapies such as paclitaxel in advanced, platinum-resistant ovarian cancer.

Blockade of this pathway by MM-121 enhances sensitivity to paclitaxel in this molecularly-defined patient population. These data, together with findings from other MM-121 Phase 2 studies, establish the role for heregulin-dependent ErbB3 signaling as a critical survival pathway mediating resistance to anti-proliferative therapies across indications.

Example 6

Clinical Trial—Breast Cancer

A randomized, double-blind phase 2 trial of exemestane+/−MM-121 in postmenopausal women with locally advanced or metastatic estrogen receptor positive (ER+) and/or progesterone receptor positive (PR+), HER2 negative breast cancer was performed. 118/145 patients were randomized to receive treatment. Patients were randomized in a 1:1 fashion to receive MM-121 plus exemestane (M, n=59) or placebo plus exemestane (P, n=59). Of the 118 patients randomized, 118/118 (100%) were successfully randomized and included in the intent to treat (ITT) population. The safety population, 115/118 (97.5%) patients (56 (M), 59 (P)) is a subset of the ITT population that received at least one dose (including a partial dose) of study medication (MM-121/placebo or exemestane). This population is for safety analyses, as well as the primary population for all efficacy parameters.

An objective of the trial was to assess biomarker profiles as predictors of clinical responses to MM-121 and/or exemestane. Biomarker analyses were performed using the safety population (n=115). Analyses were performed on the five pre-specified primary biomarkers, all mechanistically linked to ErbB3 signaling, as measured in FFPE archived tissue blocks. Biomarkers were assessed based on local HR scans. Thresholds for defining biomarker profile positive populations were chosen based on these scans and on results obtained in the above-described ovarian cancer trial. A single two-variable model was assessed using HRG and ErbB2, based on the findings from the above-described ovarian cancer trial. HRs in the biomarker profile positive and negative populations were calculated using a Cox proportional hazard model that included biomarker groups by treatment and stratification factors as additive factors. Only patients with non-missing biomarkers were used in each calculation.

For these analyses, ErbB2 levels were determined using a fluorescence-based quantitative immunohistochemistry assay (as described above in Example 2) and HRG RNA was determined using RT-PCR (as described above in Example 4). Both assays were performed using FFPE archived tissue blocks. The RNA-ISH assay that was used in the ovarian cancer trial described above in Example 5 failed to provide usable data in this context, presumably because the assay is not robust to the degraded RNA found in old, archived tissue.

Effects of Single Biomarkers: Local HR Scans

Biomarker effects were assessed by preparing local HR scans for each biomarker independently. Scans for HRG RT-PCR and ErbB2 qIHC are shown in FIG. 9. Both HRG and ErbB2 presented in the same direction as observed in the ovarian cancer trial described above and are consistent with pre-clinical predictions. HRG mRNA was measured in archived tissue using RT-PCR rather than RNA-ISH (as used in the ovarian cancer trial). The positive control for the RNA-ISH assay failed in 17 of the 48 evaluable samples. Of the remaining 31 samples, the RNA-ISH positive control scores were generally lower than those observed in the ovarian pre-treatment biopsies.

Effects of Biomarkers: BM+ and BM− Subpopulations

Biomarker profile positive (BM+) and biomarker profile negative (BM−) subpopulations were defined by dichotomizing biomarker values for HRG and ErbB2. For HRG, a cut point of −5 (RT-PCR score) was chosen based on the local HR scan (value at which HR=1). For ErbB2, the cut point used in the analysis of the ovarian cancer trial was used: $\log_{10}(\text{ErbB2})=5.1$ corresponding to about 126,000 receptors per cell. HRs and prevalence of biomarker-defined subpopulations are provided in Table 12, below. Two separate analyses of ErbB2 levels are provided: (1) ErbB2 levels based on the qIHC assay; and (2) for patients where qIHC data are missing, but HCT results were available, ErbB2 levels were adapted from the reported HCT results, with a score of HCT 2+ being deemed equal to $\log_{10}(\text{ErbB2})=5.1$.

TABLE 12

HRs and prevalence of biomarker-defined subpopulations.

| Group | BM population | | | BM positive | | | | BM negative | | | |
|---|---|---|---|---|---|---|---|---|---|---|---|
| | N | HR | 95% CI | N | % | HR | 95% CI | N | % | HR | 95% CI |
| no selection | 115 | 0.75 | 0.48-1.15 | | | | | | | | |
| HRG >−5 | 57 | 0.68 | 0.38-1.23 | 21 | 37% | 0.35 | 0.13-0.94 | 36 | 63% | 0.99 | 0.47-2.08 |
| ErbB2 <5.1 (qIHC) | 72 | 1.16 | 0.67-2.01 | 53 | 74% | 0.84 | 0.44-1.61 | 19 | 26% | 3.00 | 1.01-8.93 |
| ErbB2 <5.1 (HCT) | 103 | 0.82 | 0.52-1.3 | 84 | 82% | 0.62 | 0.37-1.04 | 19 | 18% | 3.00 | 1.01-8.93 |
| ErbB2 <5.1 (qIHC) & HRG >−5 | 44 | 0.86 | 0.44-1.68 | 14 | 32% | 0.32 | 0.09-1.12 | 30 | 68% | 1.30 | 0.59-2.86 |
| ErbB2 <5.1 (HCT) & HRG >−5 | 55 | 0.66 | 0.36-1.2 | 17 | 31% | 0.32 | 0.1-1 | 38 | 69% | 0.89 | 0.44-1.79 |

Description of BM Population

The BM population (biomarker-assessed population) is a subset of the safety population and includes all patients with measured HRG levels and either measured ErbB2 qIHC levels or available HCT results as described above. A total of 55/115 patients (48%) were part of the BM population. The HR of the BM population was 0.66 [95% CI 0.36-1.20]. Of the 55 patients with ErbB2 and HRG data, 17 (31%) were BM+ and 38 (69%) were BM−. Relative to control arm, patients in the treatment arm of the BM+ group have a higher proportion of non-bone-only lesions, a higher proportion of last treatment in the adjuvant setting, a lower proportion of anti-estrogen as the most recent therapy, and a higher proportion of patients with ECOG=0. Using a Cox proportional hazard model that includes additive terms for treatment, biomarker groups, and these clinical covariates as a sensitivity analysis, the estimated HR in the BM+ group is 0.38 [95% CI 0.12-1.24].

Efficacy Analysis of the BM+ Subpopulation

Figure 10A:
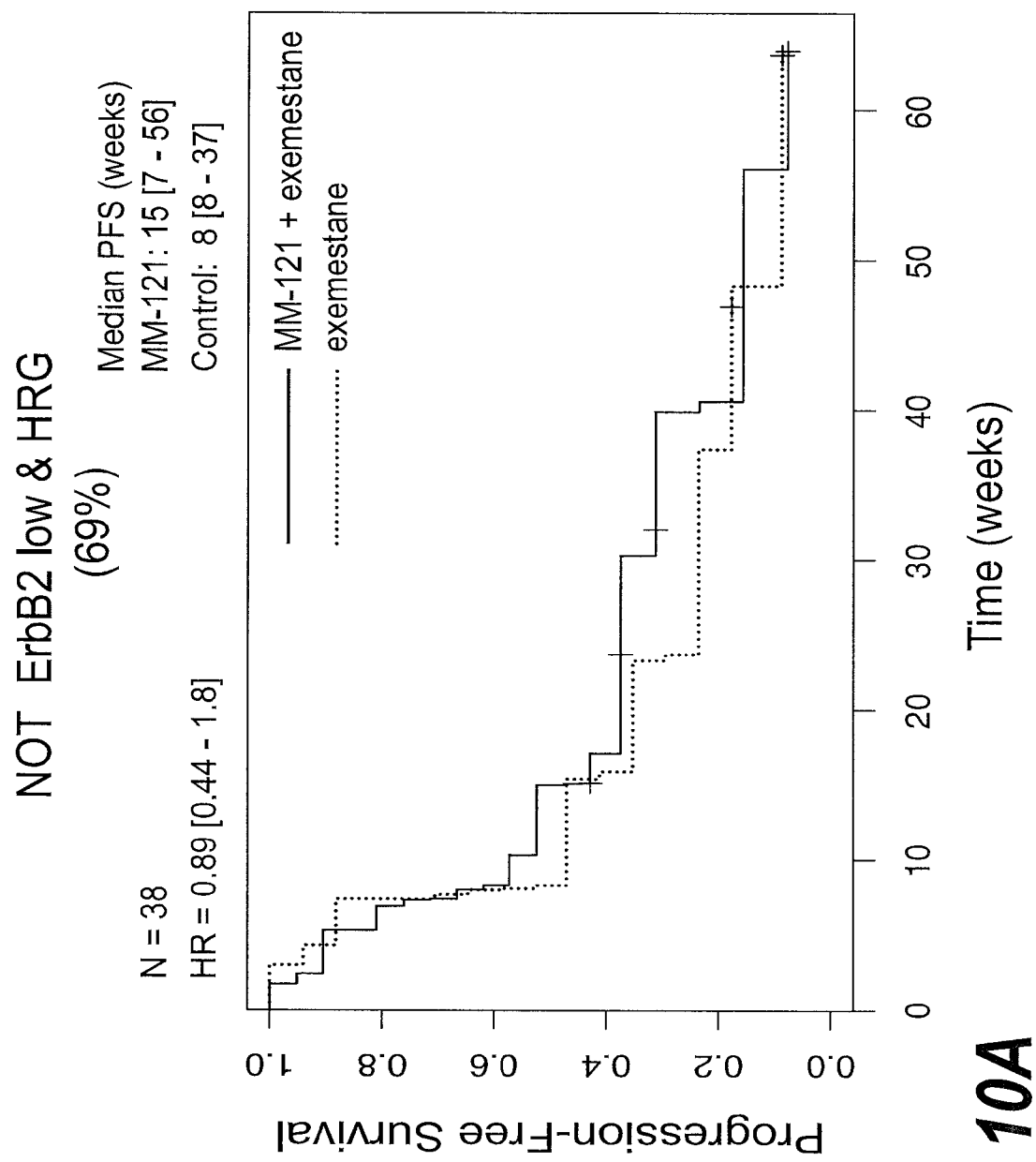
FIGS. 10A to 10E provide Kaplan Meier survival curves generated from data obtained from the breast cancer clinical trial described in Example 6.
Figure 10B:
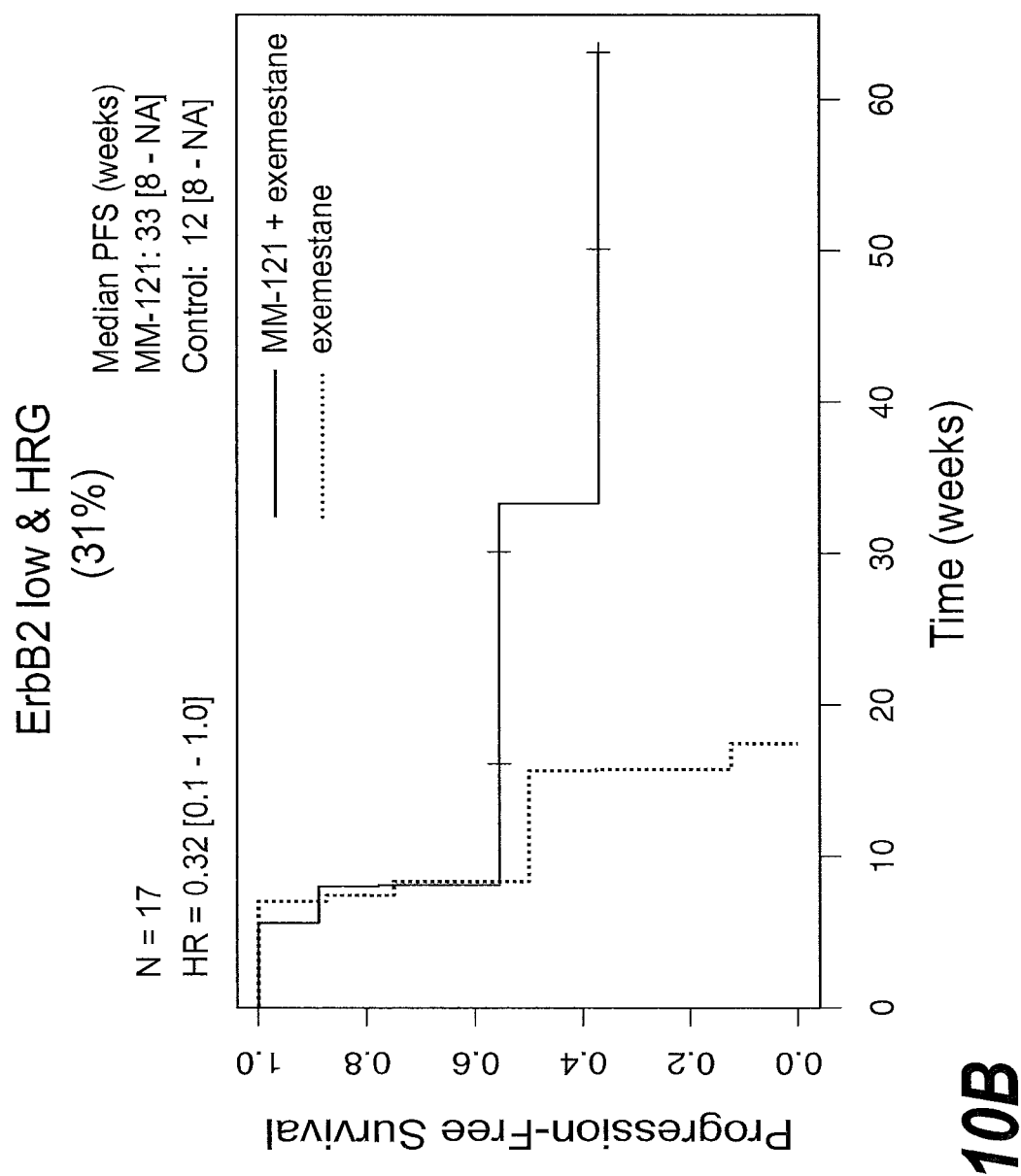
Figure 10C:
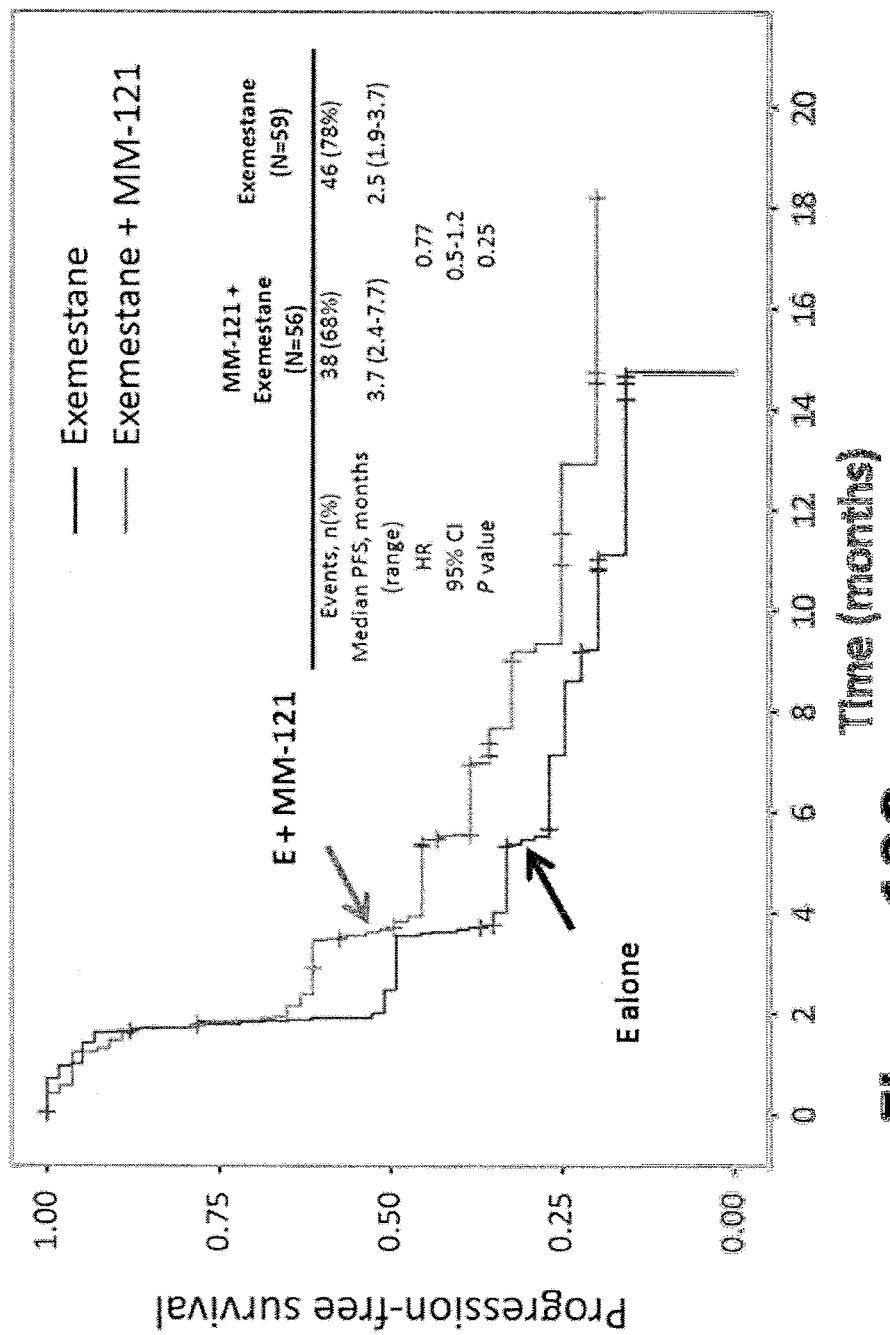
Figure 10D:
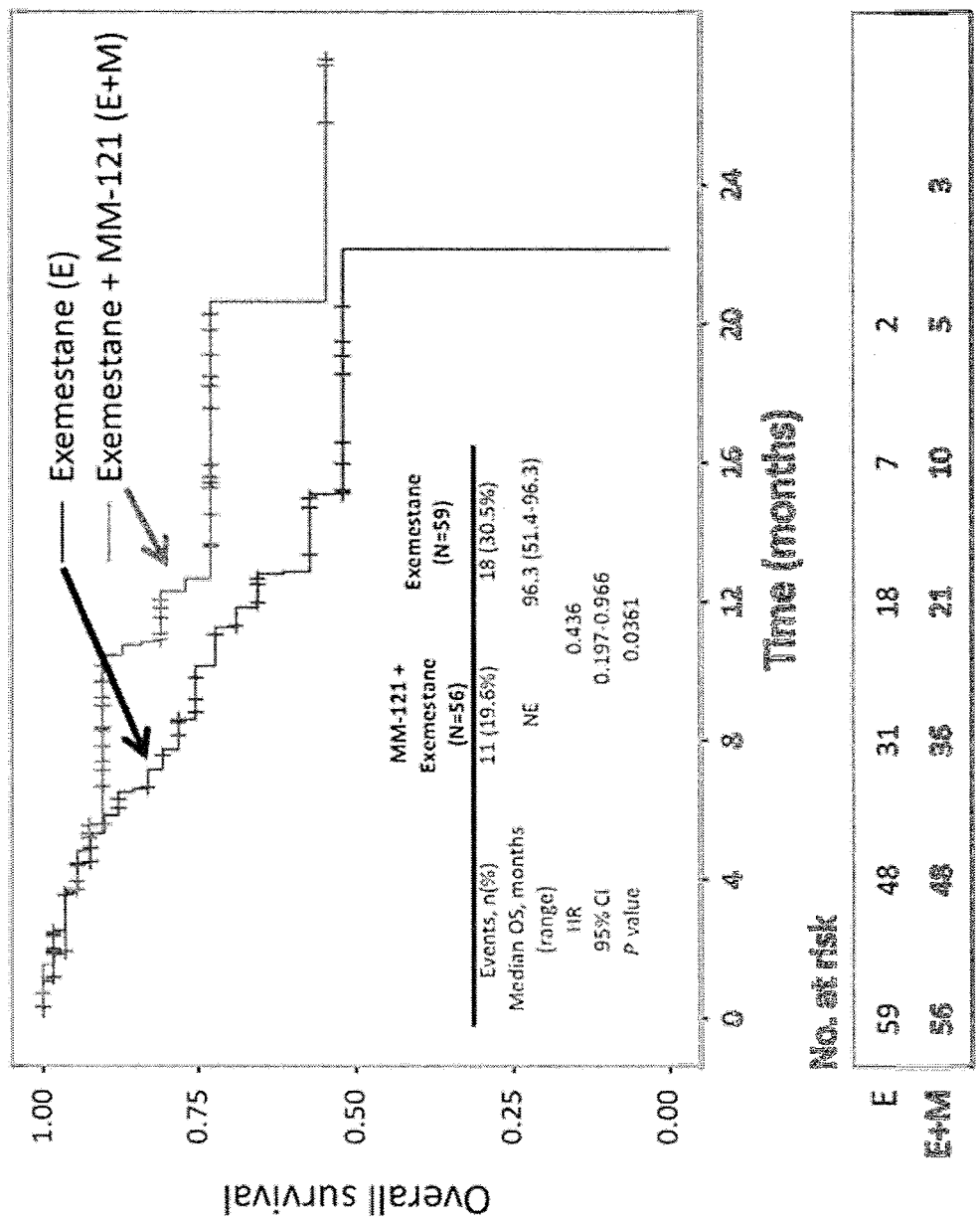
Figure 10E:
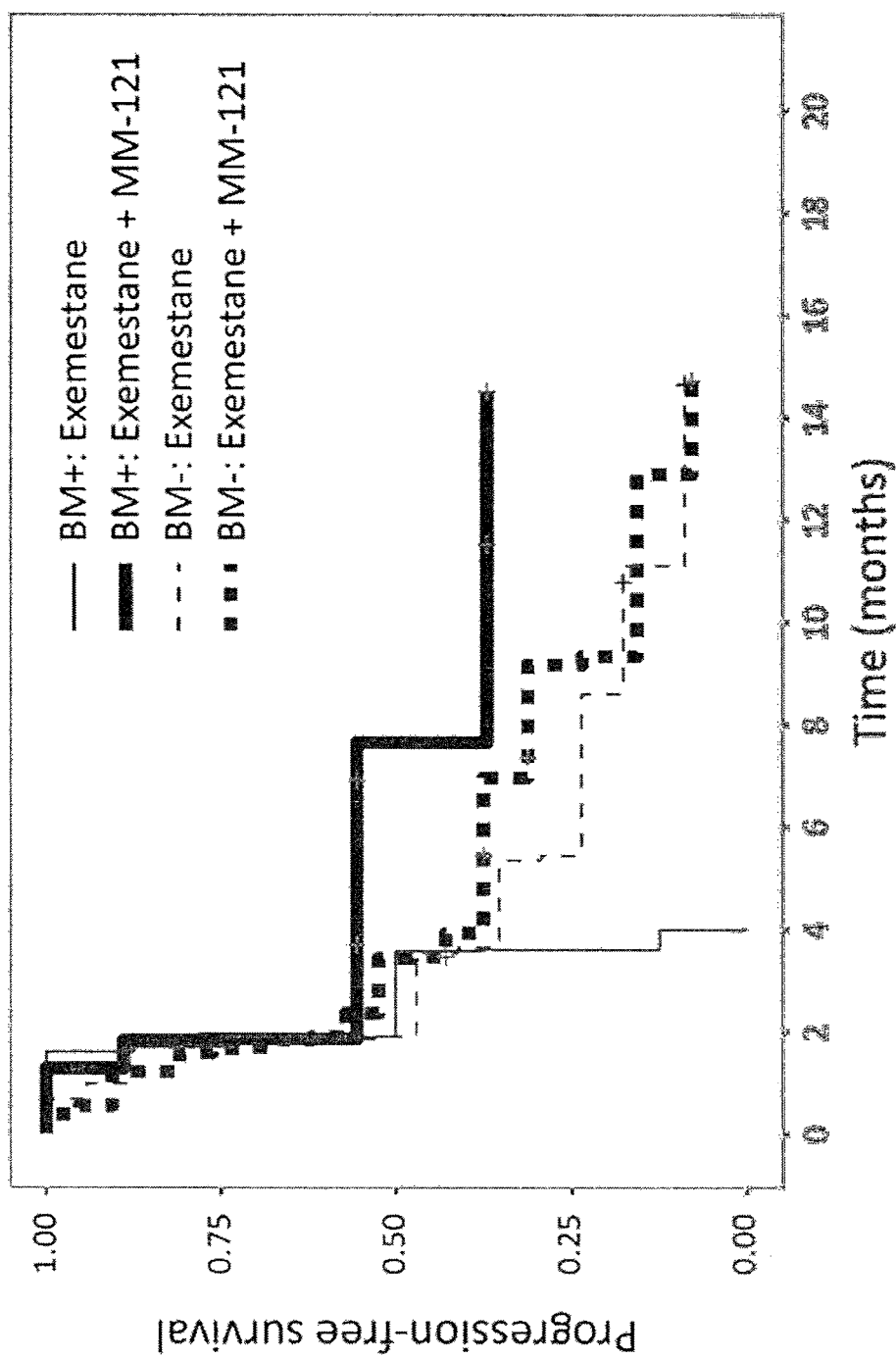

All efficacy analyses for the BM subgroups were performed using a Cox proportional hazard model that included both of the pre-specified strata as additive effects in combination with the treatment effect. The ErbB2 low & HRG high BM+ subpopulation was defined as patients with $\log_{10}$ (ErbB2)≤5.1 and HRG RT-PCR>−5. Kaplan-Meier PFS plots for the BM+ and BM− subpopulations are provided in FIG. 10 for data collected at about 60 weeks (10A-10B) and for data collected at about 18 months (10C-10E). For PFS at about 60 weeks the BM+ subpopulation HR was 0.32 [95% CI 0.10-1.00] (FIG. 10A) and the BM− subpopulation HR was 0.89 [95% CI 0.44-1.79] (FIG. 10B). PFS for the overall population in the study was calculated for data collected at end of study and shows that patients in the treatment arm had overall better outcomes than patients in the control arm (FIG. 10C). A similar result is seen for overall survival (FIG. 10D). Data for BM+ patients in the control arm (thin solid line), BM+ patients in the treatment arm (thick solid line), BM− patients in the control arm (thin dashed line), and BM− patients in the treatment arm (thick dashed line) are shown in FIG. 10E, and illustrate that BM+ patients do considerably worse on the standard of care therapy (exemestane alone) than do BM− patients.

Objective Response Rates

In BM+ patients the objective response rate was 11% (1/9) on the treatment arm (M+E) and 0% (0/8) on the control arm (E). In BM− patients the objective response rate was 4.8% (1/21) on the treatment arm (M+E) and 5.9% (1/17) on the control arm (E).

Conclusions

A BM+ subpopulation was identified using the same combination of two primary biomarkers as identified in the ovarian cancer trial described in the preceding Example (ErbB2 low & HRG positive/high), albeit with different cutoffs for HRG as necessitated by the differing outputs of the RNA-ISH and RT-PCR HRG transcript assays used in the two trials. In this trial, HRG carried the most predictive information, with ErbB2 levels serving as a potential modifier. HRG high (RT-PCR score ≥−5) and ErbB2 low ($\log_{10}$(ErbB2)≤5.1) favored treatment (N=17; HR=0.32 [0.10-1.00]; prevalence=31%), whereas HRG low and/or ErbB2 high favored control (N=38; HR=0.89 [0.44-1.79]). The median PFS in the BM+ population was 33 [8-NA] weeks (7.59 months) (M+E) and 12 weeks [8-NA] (2.76 months) (E). The prevalence of 31% likely represents a lower boundary for this population, as the assays were performed on archived tissue rather than biopsies obtained immediately prior to treatment (treatments between archived tissue collection and current start of treatment may increase the number of patients with high HRG). The median PFS in the BM+ population was 33 weeks (7.59 months) (MM-121+ exemestane) and 12 weeks (2.76 months) (exemestane control). The HR in the BM− population was 0.89 [95% CI 0.44-1.79].

Example 7

HRG-β1 Intracellular Domain ("Stump") Fluorescence Staining Assay

Introduction:

HRG is initially synthesized as a transmembrane protein. The extracellular domain of this protein is proteolytically cleaved to yield HRG, leaving behind a transmembrane domain still imbedded in the cell membrane, and intracellular domain within the cell cytoplasm. Measuring this remaining "stump" of the HRG precursor protein was done to determine if levels of the HRG stump could serve as a predictive biomarker in accordance with the disclosure herein. Results of this assay indicated that this was not the case, and that tumor levels of HRG stump measured by the following procedure are not predictive of responsiveness to ErbB3 inhibition.

TABLE 13

Materials Chart:

| Incubation Time/Step | Reagent (numbered per materials list below) | Dilution Factor |
|---|---|---|
| N/A | DI Water | N/A |
| N/A | 5 | 1:20 |
| 25 min | 6 | 1:100 |
| 10 min | 7 | RTU |
| 10 min | 8 | RTU |
| 60 min | 9 | RTU |
|  | 1 | 1:1500 |
|  | 2 | 1:50 |
| 30 min | 3 | 1:200 |
|  | 4 | RTU |
| 10 min | 10 | 1:50 |
| N/A | 11 | 1:5000 |
| N/A | 12 | N/A |
| N/A | 16 | N/A |

Materials List:
1. Anti-NRG-01 monoclonal antibody clone 60-10 (start conc.=1 mg/mL)
2. Anti-human-cytokeratin monoclonal antibody clone AE1/AE3 (Dako, catalog # M351501)
3. Alexa Fluor® 555 Goat Anti-Mouse IgG (H+L) (Invitrogen, catalog # A-21422)
4. EnVision+ System-HRP Labelled Polymer Anti-Rabbit (Dako, catalog # K4003)
5. Tris Buffered Saline and Tween 20 (20×; TBS-T) (Fisher Scientific, catalog # TA-999-TT)
6. PT Module Buffer 4, Tris-EDTA, pH 9 (Fisher Scientific, catalog # TA-250-PM4X)
7. Peroxidazed 1 (BioCare Medical, catalog # PX968 H, M)
8. Background Sniper (BioCare Medical, catalog # BS966 H, M)
9. Da Vinci Green Diluent (BioCare Medical, catalog # PD900 H, M)
10. Cyanine 5 Tyramide (Perkin Elmer, catalog # SAT705A)
11. Hoechst 33342 (Invitrogen, catalog # H3570)
12. ProLong Gold Antifade reagent (Invitrogen, catalog # P36934)
13. Flex 100 Alcohol Solution (Fisher Scientific, catalog #8101)
14. Flex 80 Alcohol Solution (Fisher Scientific, catalog #8301R)
15. Xylene (VWR, catalog #534056)
16. Glass coverslips (VWR No. 1)

Methods:
1. Deparaffinize/hydrate slides
   1.1. If necessary, use a razor blade to scrape paraffin wax off of the back of the slides. Scrape the wax off of the front around the tissue region if it is visible. If the tissue is not clearly visible under the wax, do not scrape any wax from the front.
   1.2. Incubate slides for 30-50 min at 65° C. in a metal slide rack (or equivalent) in the oven to melt wax covering tissues.
   1.3. Transfer slides to a Tissue-Tek® (or equivalent) slide rack Immerse slides in the following solutions with occasional gentle agitation:
   xylene, twice for 20-30 min each
   100% ethanol, twice for 2-5 minutes
   80% ethanol, twice for 2-5 minutes
   Distilled water for 2-5 minutes 1.4. Apply programmed Dako slide labels to the front frosted end of the slides and place them on the Dako slide rack(s).
2. Antigen retrieval (AR):
   2.1. Perform AR in the PT module using PT module buffer 4 (Tris EDTA at pH 9±0.05) using the following settings:
      Incubation time: 25 minutes
      Incubation temperature: 102° C.
      No-boil function: Enabled
   2.2. Once the program has run and the solution cooled down to 65° C. remove the slide rack(s) from the PT module and place in the Dako buffer wash basin(s) containing 1× TB S-T for 3-5 minutes.
3. Reagent Preparation: This should be done when slides are in the PT module.
   3.1. In DakoLink® program, select all slides to be stained from the "Pending" tab and click "Reagents" button at the bottom of the screen. This will generate a list and volumes needed per reagent (this assumes two 150 µL drop zones for a total of 300 µL per slide). Print this list.
   3.2. Select the appropriate number and size of Dako user fillable bottles.
   3.3. Scan the barcode of each bottle and plug the volume required of that particular reagent into the "usable quantity" box. This will then factor in the dead volume of that particular size bottle into your "Fill quantity" or total volume.
   3.4. Calculate the individual amounts of reagents needed for your assay.
      Endogenous peroxidase block (Peroxidazed® 1) and protein block (Background Sniper) are ready to use reagents and may be filled right away.
      Primary antibody will be a cocktail consisting of the target antibody, a compatible tumor mask and blocking diluent.
      Secondary antibody will be a cocktail of a molecular probe and the Dako EnVision+ secondary that corresponds to the target being detected.
4. Autostainer run preparation: Once all reagents are made and AR process is complete, place the reagent bottles into the Dako AutostainerLink48.
   4.1. Fill the 10 L buffer carboy with 1×TBS-T (add more if required)
   4.2. Fill the 10 L water carboy with DI water
   4.3. Remove all the rack(s) from the wash basin(s) and place on the autostainer.
   4.4. Click on the "Instruments" tab in the DakoLink® software and click "Start" button.
5. Automated staining: The following is the summary of the Dako AutostainerLink48 NRG IF staining protocol. Note: The autostainer selects each rinse reagent and also calculates each rinse time and volume, therefore rinse reagent is indicated as an alternative and the rinse incubation times and volumes are not indicated.

TABLE 14

| Category | Protocol | | |
|---|---|---|---|
| | Reagent (numbered per materials list above) | Incubation (min) | Volume (µL) |
| Rinse | 1 or 5 | — | — |
| Endogenous enzyme block | 7 | 10 | 150 |
| Rinse | 1 or 5 | — | — |
| Rinse | 1 or 5 | — | — |

TABLE 14-continued

| Category | Protocol | | |
|---|---|---|---|
| | Reagent (numbered per materials list above) | Incubation (min) | Volume (µL) |
| Protein Block | 8 | 10 | 150 |
| Rinse | 1 or 5 | — | — |
| Rinse | 1 or 5 | — | — |
| Primary antibody | 1 | 60 | 150 |
| Rinse | 1 or 5 | — | — |
| Rinse | 1 or 5 | — | — |
| Rinse | 1 or 5 | — | — |
| Secondary Reagent | 4 | 30 | 150 |
| Rinse | 1 or 5 | — | — |
| Rinse | 1 or 5 | — | — |
| Rinse | 1 or 5 | — | — |
| Substrate-chromogen | 10 | 10 | 150 |
| Rinse | 1 or 5 | — | — |
| Rinse | 1 or 5 | — | — |
| Rinse | 1 or 5 | — | — |
| Counterstain | 11 | 5 | 150 |
| Rinse | 1 or 5 | — | — |

6. Remove the ProLong Gold antifade reagent from freezer and allow to come to room temperature.
7. Once the staining is complete, transfers Dako slide racks(s) from the autostainer to the Dako wash basin(s) fill with 1×TBS-T.
8. Mount each slide with 55-75 µL of room temperature ProLong Gold® antifade reagent.
9. Allow mounting medium to cure in a dark, dry and well ventilated place on a level surface.

Example 8

Clinical Trial—Non-Small Cell Lung Cancer

A global, multi-center, open-label study was performed of MM-121 and erlotinib in patients having non-small cell lung cancer (NSCLC). A group participating in the study was comprised of 132 patients with wild-type epidermal growth factor receptor (EGFR) who progressed on ≥1 platinum-based standard of care therapy and were EGFR tyrosine kinase inhibitor (TKO-naïve. Patients were randomized 2:1 to receive daily erlotinib alone at 150 mg, or 20 mg/kg MM-121 every other week plus daily erlotinib at 100 mg (see, e.g., International Publication No. WO/2012/154587). Data were collected at 10+ months.

An objective of the trial was to assess biomarker profiles as predictors of clinical responses to the combination therapy compared to erlotinib alone. As ErbB3 signaling was expected to be active in only a subset of patients, pre-treatment biopsies were collected from all patients to evaluate a pre-specified set of biomarkers mechanistically linked to ErbB3 signaling: heregulin (HRG), betacellulin, EGFR, ErbB2, and ErbB3. (Other objectives of the trial were to compare the progression-free survival (PFS) between the combination therapy (MM-121+erlotinib) and erlotinib alone, as well as overall survival (OS) and safety data.)

Based on the findings in ovarian cancer (Example 5) and breast cancer (Example 6) that HRG mRNA is predictive of beneficial effects of MM-121, biomarker analyses focused on HRG mRNA. Therefore, in this Example, Biomarker positive (BM+) is used interchangeably with Heregulin positive (HRG+). BM+ patients were defined as having detectable HRG mRNA by RNA-ISH (RNA in situ hybridization) as described above in Example 1.

Figure 11:
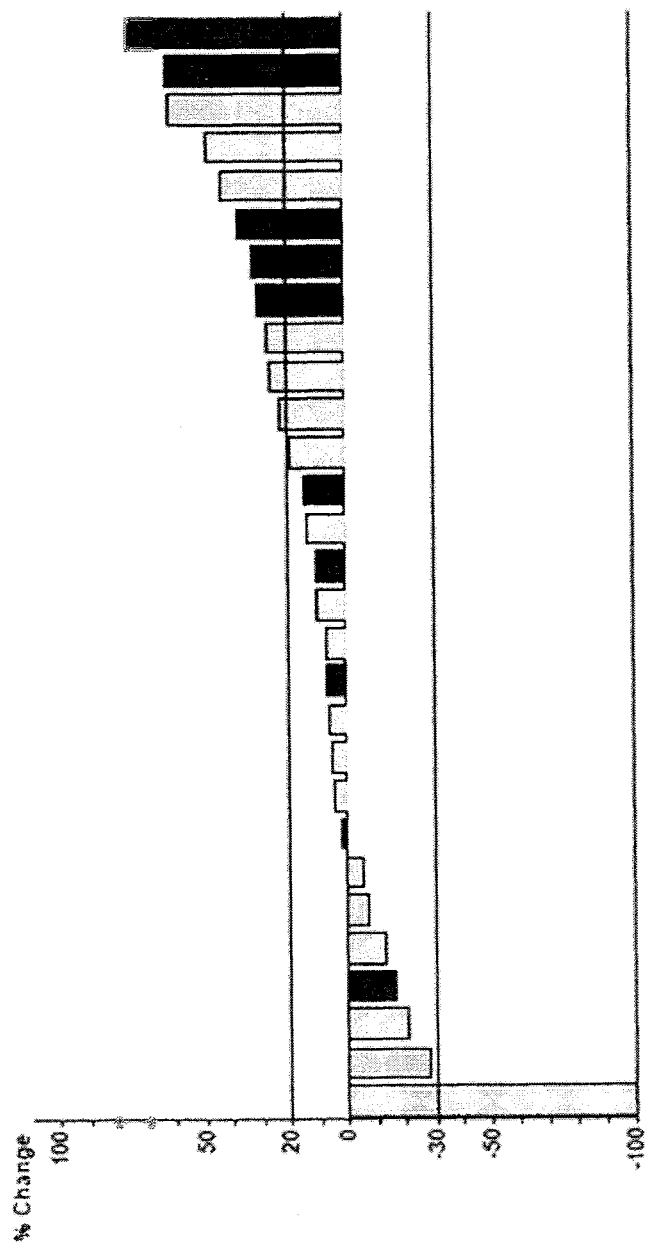
FIG. 11 is a graph showing data indicating the best overall response in the BM+ (heregulin+) study population from a Phase 2 trial of MM-121+erlotinib in EGFR-wild-type non-small cell lung cancer (NSCLC) patients. Patients were treated with erlotinib alone (N=30) or MM-121+erlotinib (n=70). Of the BM+ patients (in this case, heregulin+) treated with erlotinib alone, none had a complete response (CR) by the end of the study; 6.7% of patients had a partial response (PR), 36.7% had stable disease (SD), and 53.3% had progressive disease (PD). Of the patients treated with the combination therapy of MM-121+erlotinib, 1 patient (1.4%) had a CR, 4.3% had a PR, 30% had SD, and 33% had PD. Light bars indicate patients receiving combination therapy (N=19) and black bars indicate patients receiving erlotinib alone. Data are shown as % change in tumor volume.

Summary of Results:

As in the studies with ovarian cancer and breast cancer, it was found that HRG mRNA levels correlated with a beneficial effect of MM-121 treatment. HRG-positive patients (53.7%) were defined as having detectable levels of HRG mRNA by RNA-ISH in pretreatment biopsies. While HRG-positive patients responded poorly to erlotinib alone, most HRG-positive patients benefited from the addition of MM-121 to the erlotinib treatment. FIG. 11 is a graphical representation of the outcomes for individual BM+ patients on the study, with patients receiving erlotinib alone represented by black bars and patients receiving MM-121+ erlotinib represented by light bars. Of the 19 patients that received MM-121+erlotinib, only 6 had progressive disease (as shown by the horizontal line at 20% on the y-axis), in contrast to 5 out of the 10 patients that received erlotinib alone. Only 1 patient receiving erlotinib alone had a partial response, in contrast to 6 patients receiving combination therapy.

Figure 12A:
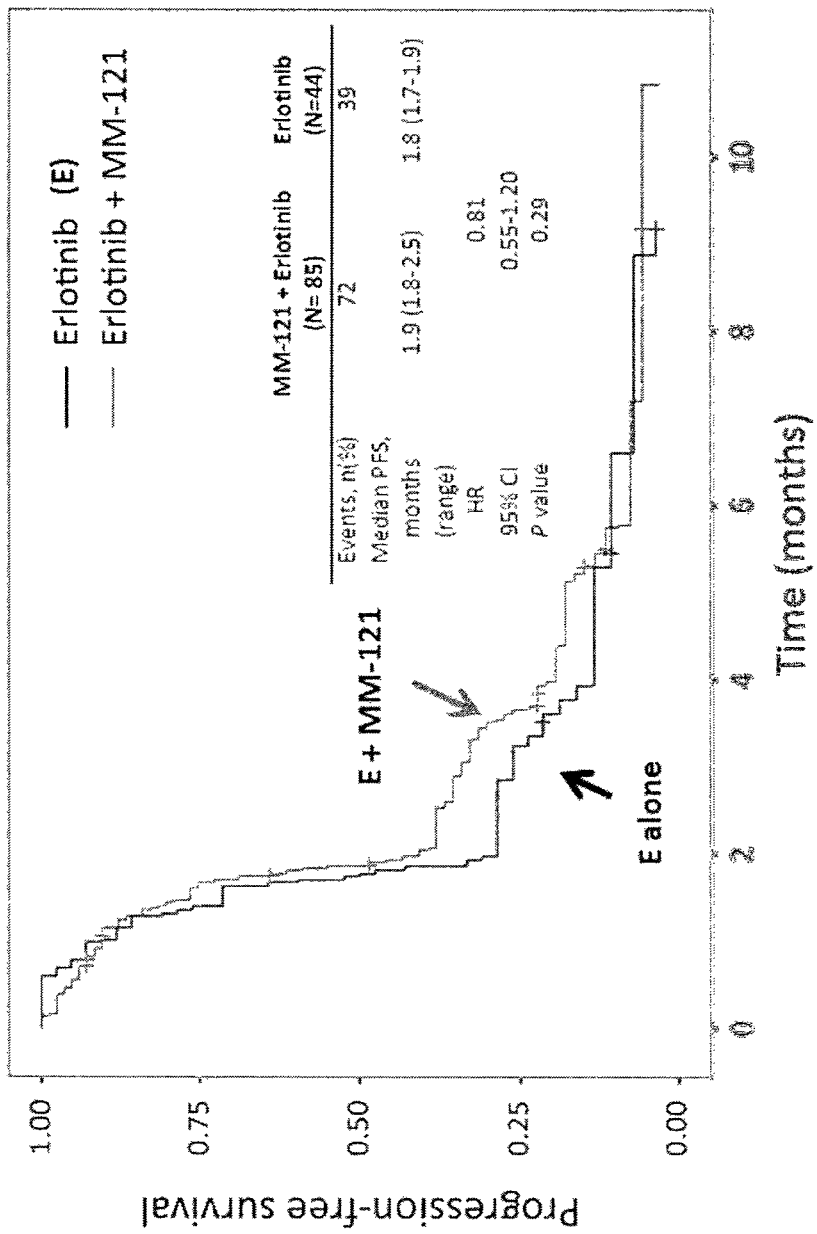
FIGS. 12A to 12C are graphs showing data resulting from a Phase 2 trial of MM-121+erlotinib in EGFR-wild-type non-small cell lung cancer (NSCLC) patients.
Figure 12B:
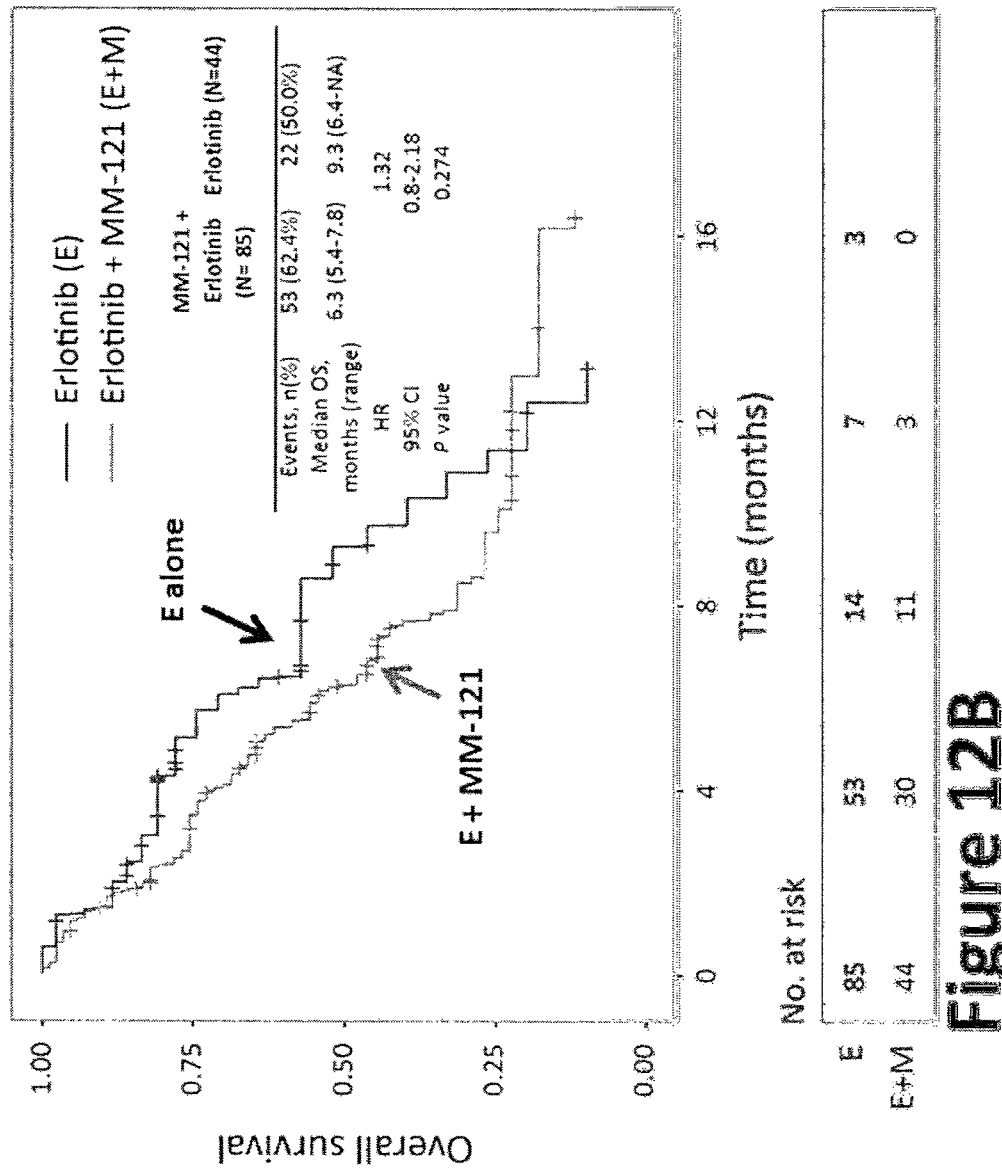
Figure 12C:
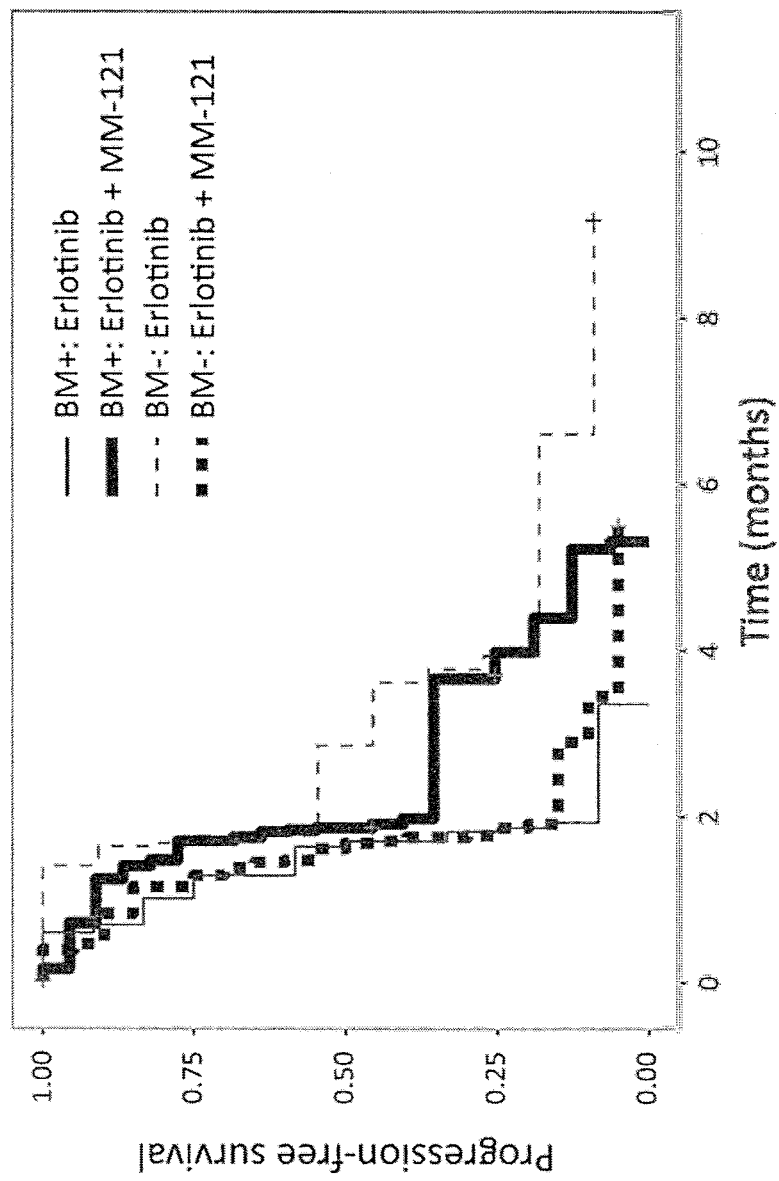
Figure 14A:
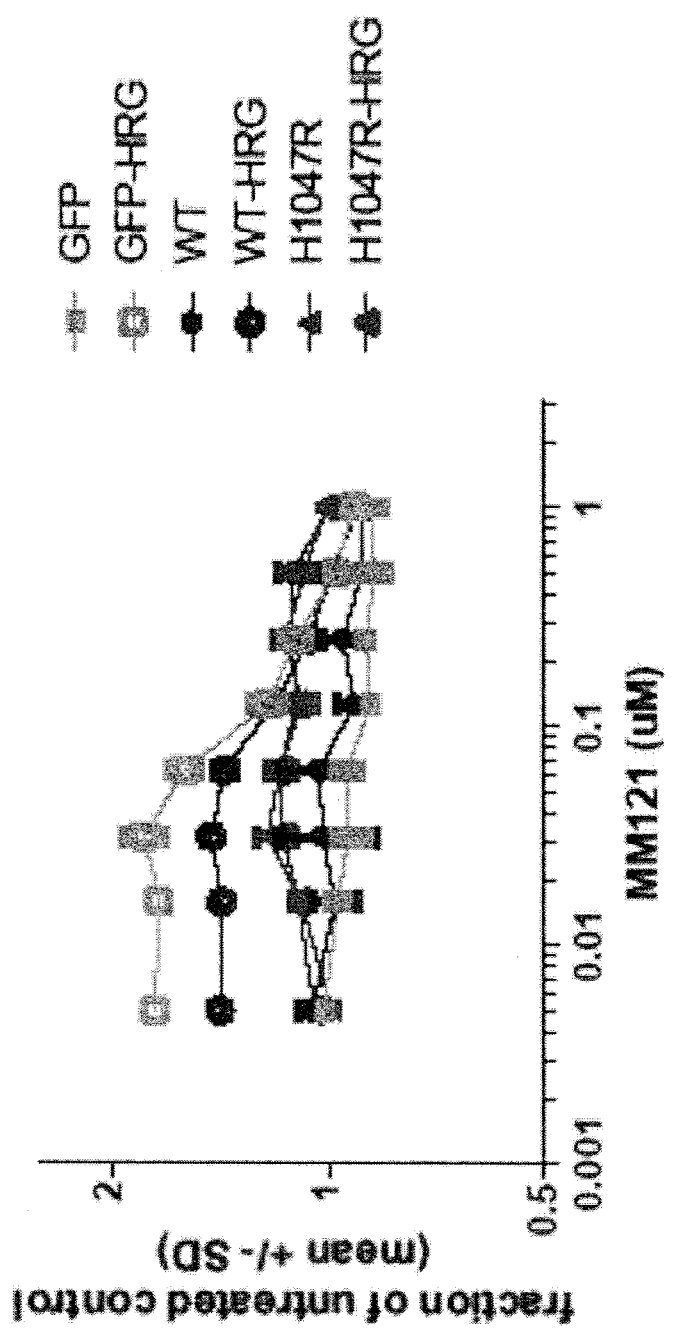
FIGS. 14A to 14D are graphs showing results from a titration of MM-121 treatment on spheroid cell cultures, both with and without exogenous heregulin. Each cell line, NCI-N87 cells (FIG. 14A), SKBR3 cells (FIG. 14B), OVCAR8 cells (FIG. 14C), and HCC1937 cells (FIG. 14D), were mock transduced (gray circles, either GFP or empty vector), transduced with wild-type PI3K (black squares), or transduced with PI3K containing the H1047R activating mutation (black triangles).
Figure 14B:
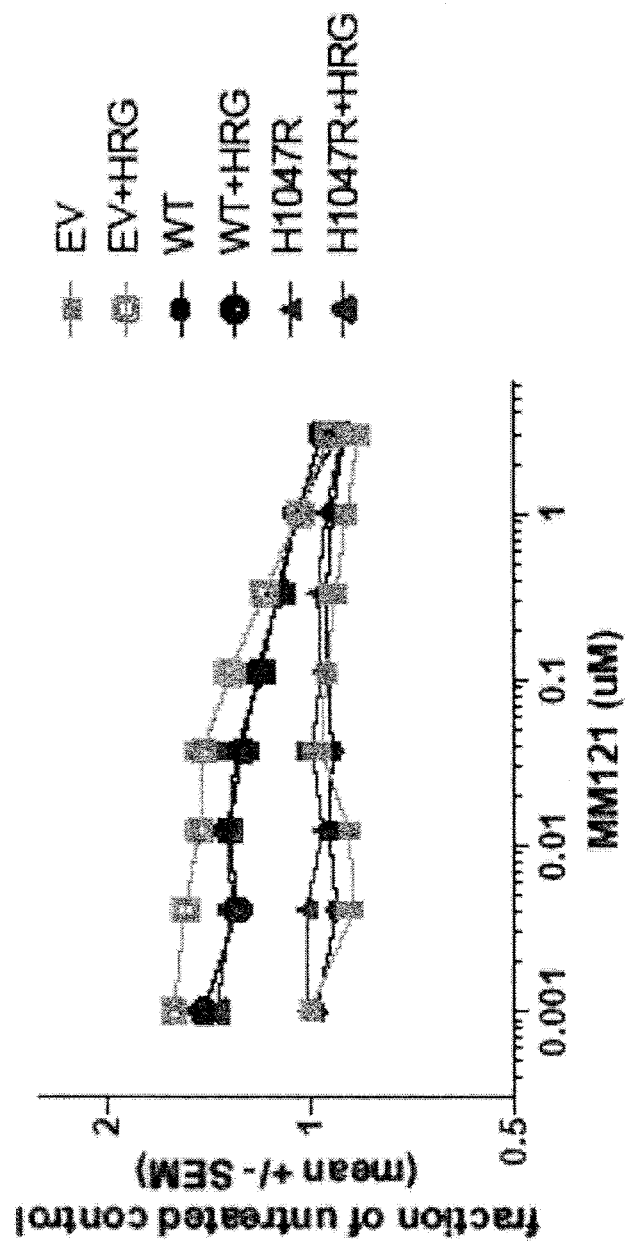
Figure 14C:
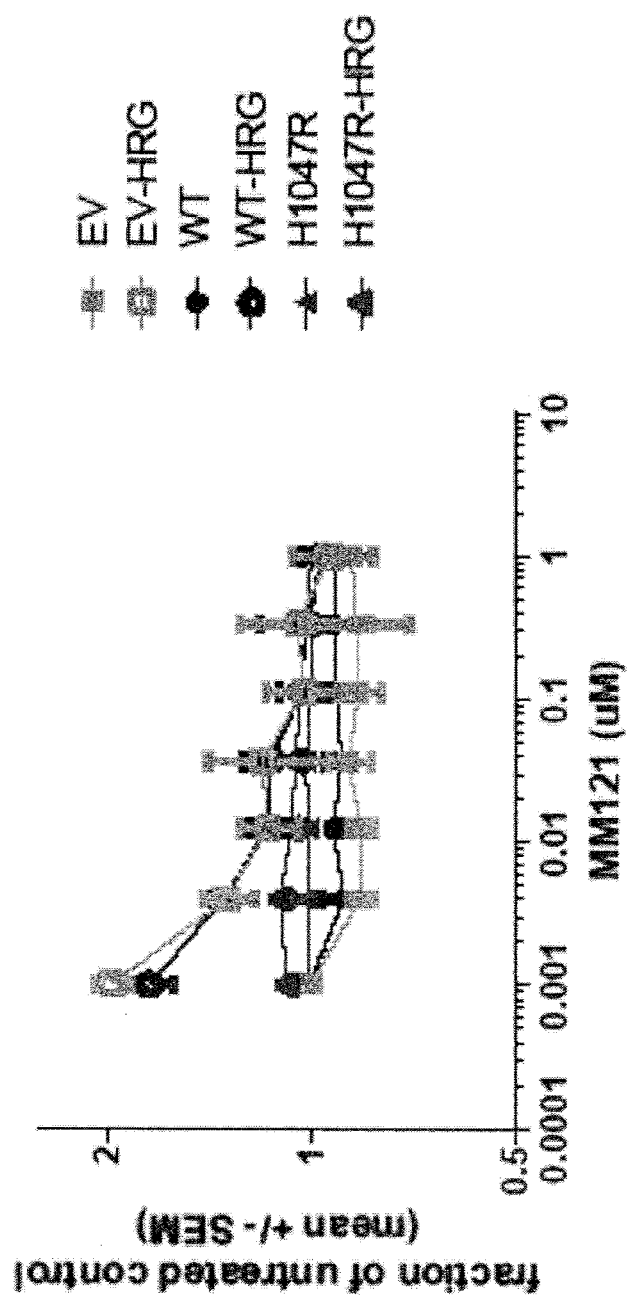
Figure 14D:
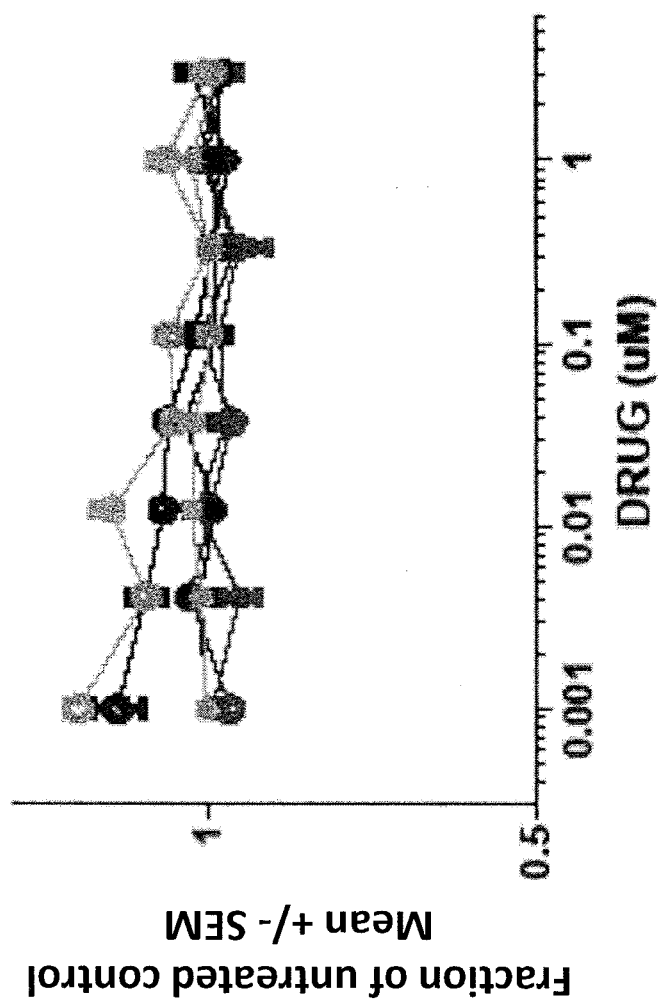

PFS for the overall population in the study was calculated for data collected at about 10 months and shows that patients in the treatment arm had overall better outcomes than patients in the control arm (FIG. 12A). A similar result is seen for overall survival (FIG. 12B). Data for BM+ patients in the control arm (thin solid line), BM+ patients in the treatment arm (thick solid line), BM− patients in the control arm (thin dashed line), and BM− patients in the treatment arm (thick dashed line) are shown in FIG. 12C, and illustrate that BM+ patients do considerably worse on the standard of care therapy (erlotinib alone) than do BM− patients. Results from this study further implicate heregulin-driven ErbB3 signaling as a mechanism of resistance to standard of care therapies, such as erlotinib, in EGFR wild-type NSCLC. As disclosed herein, blockade of this pathway by MM-121 confers sensitivity to erlotinib in this molecularly-defined patient population. As the impact of erlotinib treatment in EGFR wild-type NSCLC remains modest, however, future studies should not rely on erlotinib as backbone therapy. These data, together with findings from other MM-121 Phase 2 studies, establish the role for heregulin-dependent ErbB3 signaling as a critical survival pathway mediating resistance to anti-proliferative therapies across indications.

Example 9

In Vitro Analysis of PI3KCA Mutant Cells

N87, SKBR3, OVCAR8 cells and HCC1937 cancer cells were obtained from ATCC or NCI and maintained in culture per supplier's suggestions. For cell viability experiments, log phase growing cells were plated onto 96 well micro-honeycomb patterned, low adhesion culture plates (Scivax USA, Inc) or ultra-low attachment, round bottom plates (Corning). After 48 hours, heregulin-EGF domain (R&D Systems), and/or MM-121 (Merrimack Pharmaceuticals) was introduced to the cells. Cell viability assays were performed 4 days after treatment using the Cell Titer Glo® kit (Promega). For the measurement of growth rates, Cell Titer Glo® was performed on spheroids after 2, 5, and 7 days in culture, and normalized to control cells on the same plate.

NCI-N87 cells were transduced with either full-length PIK3CA-H1047R mutant or wild type (GeneCopoeia, Inc.) expressing lentiviruses that were also engineered to express PAC-PA-turboGFP (OriGene Technologies, Inc.). OVCAR8, HCC1937, and SKBR3 cells were transduced with PIK3CA-H1047R mutant or wild type retroviruses generated from a PIK3CA-IRES-tag2GFP vector (GeneWiz). PIK3CA-H1047R- or wild type expressing polyclonal cell lines were established after selecting for puromycin and FACS sorting for GFP-expressing cells. Control cell lines were engineered to express either GFP (NCI-N87) or empty vector (OVCAR8, HCC1937, and SKBR3) in the same manner as the PI3K expressing cells. Cells were maintained in puromycin-containing medium.

Results are shown in FIG. 14. Both wild-type and PI3K-activating mutant cells that were incubated with HRG had, in a four day growth assay, variable growth responses that were statistically indistinguishable from each other. Co-incubation of the cells with MM-121 blocked the HRG-stimulated growth, regardless of PI3K mutation. These results indicate that activating mutations in PI3K do not preclude HRG-stimulated growth, and do not prevent MM-121 activity.

Example 10

ErbB3 Expression is Reduced in HRG Non-Responsive PI3K-H1047R Cells

N87, SKBR3, OVCAR8 cells and HCC1937 cancer cells were grown as described in Example 9. To measure mRNA levels by quantitative reverse-transcriptase PCR (RT-PCR), RNA was extracted from spheroids using the RNAEasy® kit (Qiagen). ErbB3, actin, and GAPDH RNA levels were measured using the Taqman® assay (Applied Biosystems) on a ViiA 7 Real Time PCR System. For signaling experiments, log phase growing cells were plated onto 24 well micro-honeycomb patterned culture plates (Scivax USA, Inc) for 6 days, incubated with heregulin, then lysed in RIPA buffer (Sigma-Aldrich) supplemented with protease and phosphatase inhibitors (Roche) and 1% SDS (Sigma-Aldrich). All antibodies used in western blots were obtained from Cell Signaling Technologies, with the exception of the total ErbB3 antibody (AbCam). Protein levels were measured via quantitative western blot and levels were normalized to actin.

Figure 15A:
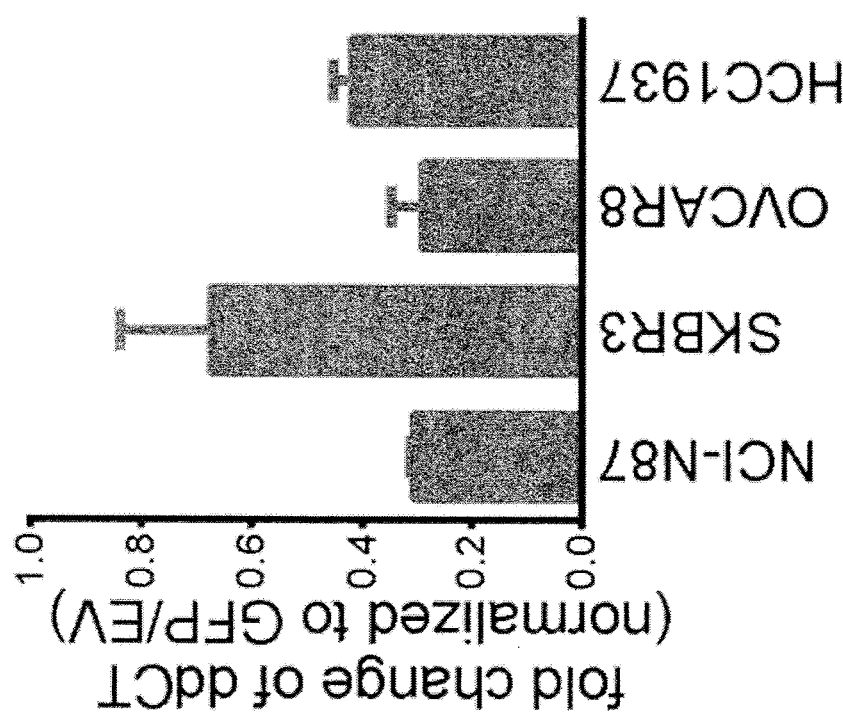
FIGS. 15A to 15D are graphs showing analysis of ErbB3 expression in HRG-stimulated OVCAR8 cells, as measured by quantitative RT-PCR (FIG. 15A, RNA expressed as fold change of ddCT normalized to GFP/EV) and western blot (FIG. 15B, ratio of ErbB3 to actin normalized to N87-GFP).
Figure 15B:
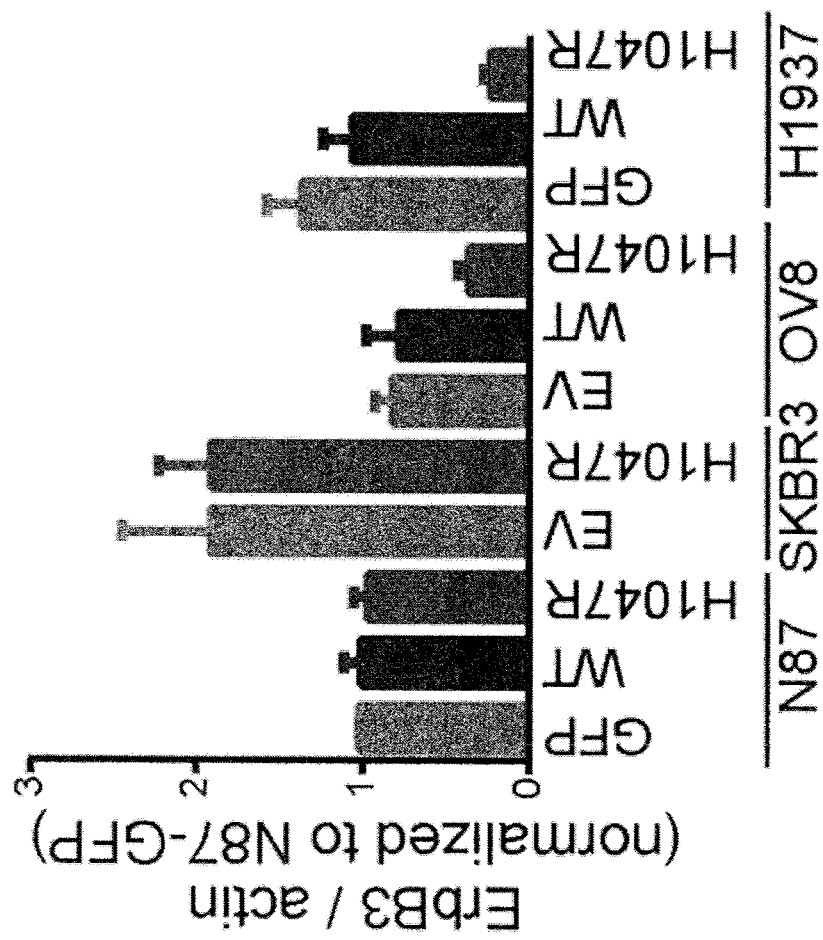

The heregulin receptor ErbB3 is negatively regulated by the FOXO feedback loop, in both cells that express endogenous PI3K and the engineered cells described in Example 9. In the PI3K-H1047R mutant expressing cells, there was a dramatic increase in phospho-FoxO in each of the cell lines, but an even more dramatic increase in those cell lines that didn't respond well to heregulin. The levels of phospho-FoxO correlated with levels of ErbB3 mRNA, as measured by real-time quantitative PCR in PI3K-H1047R NCI-N87, OVCAR8, and HCC1937 cells. The cells expressing mutant PI3K had reduced levels of ErbB3 transcript as compared to control cells (FIG. 15A). In addition, there was a consistent reduction in ErbB3 protein levels in OVCAR8 and HCC1937 PI3K-H1047R cells, in comparison to control ErbB3 levels (FIG. 15B). There was no reduction in ErbB3 protein levels in SKBR3 and NCI-N87 cells.

Figure 15C:
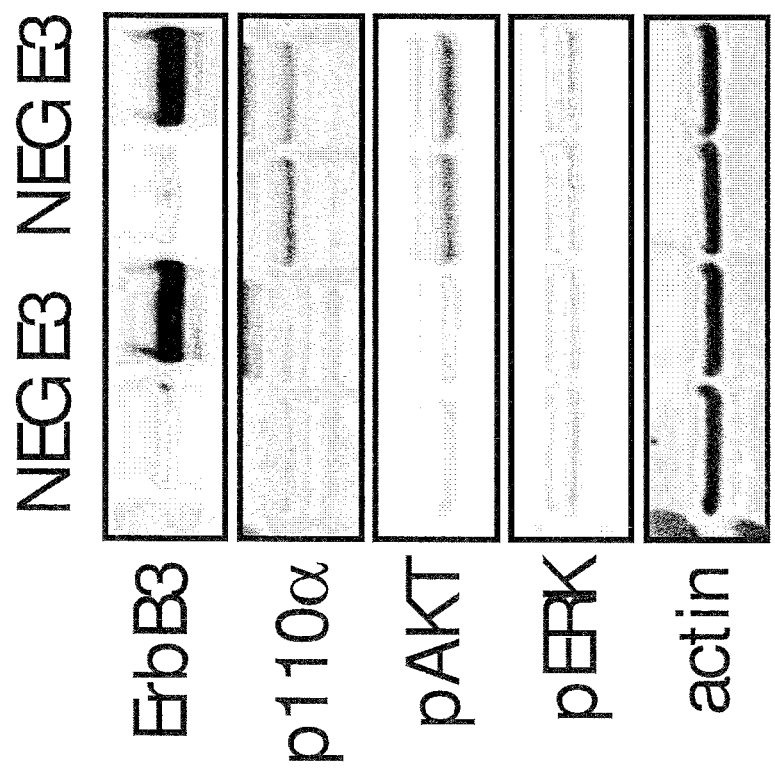
Figure 15D:
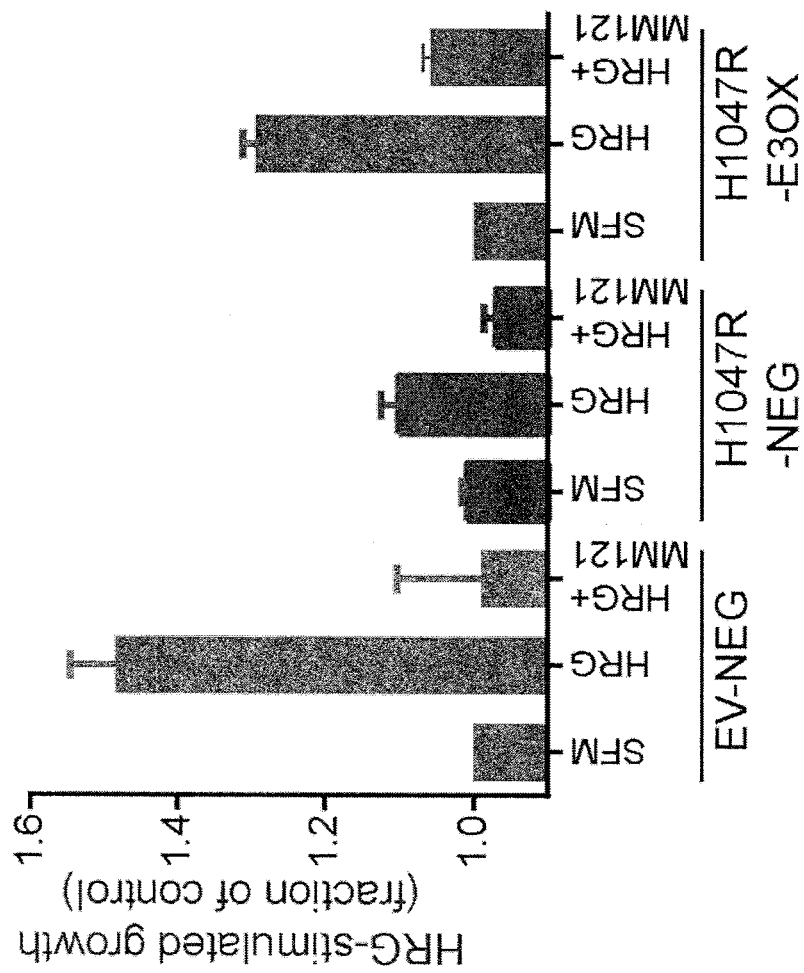

To determine whether ErbB3 levels were the limiting factor in signaling in PI3K mutant cells, rather than a downstream blockage of pAKT production, ErbB3 was re-expressed in PI3K-H1047R cells (FIG. 15C). Lysates from engineered OVCAR8 cells (control (EV) and PI3K-H1047R, expressing empty vector (NEG) or ErbB3 (E3)). p110, pAKT, and pERK levels were unchanged with added ErbB3. As shown in FIG. 15D, control cells (empty vector, EV) were stimulated by HRG but PI3K-H1047R cells were stimulated to a much lesser extent. Re-expression of ErbB3 partially rescued the HRG-stimulated growth, demonstrating that the level of ErbB3 is a limiting factor in signaling. Importantly, as shown in the figure, MM-121 abrogates the heregulin stimulated growth in these mutant cells.

Taken together, these results show that activating mutations in PI3K do not preclude potential benefit from ErbB3-directed therapy, but that patients with HRG-positive, PI3K-mutant cancer will benefit from testing of ErbB3 levels to ensure a minimum threshold of +2 is met so that patients will benefit from MM-121 and other ErbB3-directed therapies.

SUMMARY OF SEQUENCE LISTING

MM-121 $V_H$ amino acid sequence (SEQ ID NO: 1)
EVQLLESGGGLVQPGGSLRLSCAASGFTFSHYVMAWVRQAPGKGLEWVSSISSSGG
WTLYADSVKGRFTISRDNSKNTLYLQMNSLRAEDTAVYYCTRGLKMATIFDYWGQ
GTLVTVSS MM-121 $V_L$ amino acid sequence (SEQ ID NO: 2)
QSALTQPASVSGSPGQSITISCTGTSSDVGSYNVVSWYQQHPGKAPKLIIYEVSQRPSG
VSNRFSGSKSGNTASLTISGLQTEDEADYYCCSYAGSSIFVIFGGGTKVTVL

MM-121 $V_H$ CDR1 (SEQ ID NO: 3)
HYVMA

MM-121 $V_H$ CDR2 (SEQ ID NO: 4)
SISSSGGWTLYADSVKG

MM-121 $V_H$ CDR3 (SEQ ID NO: 5)
GLKMATIFDY

MM-121 $V_L$ CDR1 (SEQ ID NO: 6)
TGTSSDVGSYNVVS

MM-121 $V_L$ CDR2 (SEQ ID NO: 7)
EVSQRPS

MM-121 $V_L$ CDR3 (SEQ ID NO: 8)
CSYAGSSIFVI

Ab # 3 $V_H$ amino acid sequence (SEQ ID NO: 9)
EVQLLESGGGLVQPGGSLRLSCAASGFTFSAYNMRWVRQAPGKGLEWVSVIYPSGG
ATRYADSVKGRFTISRDNSKNTLYLQMNSLRAEDTAVYYCARGYYYYGMDVWGQ
GTLVTVSS Ab # 3 $V_L$ amino acid sequence (SEQ ID NO: 10)
QSVLTQPPSASGTPGQRVTISCSGSDSNIGRNYIYWYQQFPGTAPKLLIYRNNQRPSG
VPDRISGSKSGTSASLAISGLRSEDEAEYHCGTWDDSLSGPVFGGGTKLTVL Ab # 3 $V_H$ CDR1 (SEQ ID NO: 11)
AYNMR Ab # 3 $V_H$ CDR2 (SEQ ID NO: 12)
VIYPSGGATRYADSVKG Ab # 3 $V_H$ CDR3 (SEQ ID NO: 13)
GYYYYGMDV Ab # 3 $V_L$ CDR1 (SEQ ID NO: 14)
SGSDSNIGRNYIY Ab # 3 $V_L$ CDR2 (SEQ ID NO: 15)
RNNQRPS Ab # 3 $V_L$ CDR3 (SEQ ID NO: 16)
GTWDDSLSGPV Ab # 14 $V_H$ amino acid sequence (SEQ ID NO: 17)
EVQLLESGGGLVQPGGSLRLSCAASGFTFSAYGMGWVRQAPGKGLEWVSYISPSGG
HTKYADSVKGRFTISRDNSKNTLYLQMNSLRAEDTAVYYCAKVLETGLLVDAFDIW
GQGTMVTVSS Ab # 14 $V_L$ amino acid sequence (SEQ ID NO: 18)
QYELTQPPSVSVYPGQTASITCSGDQLGSKFVSWYQQRPGQSPVLVMYKDKRRPSEI
PERFSGSNSGNTATLTISGTQAIDEADYYCQAWDSSTYVFGTGTKVTVL Ab # 14 $V_H$ CDR1 (SEQ ID NO: 19)
AYGMG Ab # 14 $V_H$ CDR2 (SEQ ID NO: 20)
YISPSGGHTKYADSVKG Ab # 14 $V_H$ CDR3 (SEQ ID NO: 21)
VLETGLLVDAFDI Ab # 14 VI, CDR1 (SEQ ID NO: 22)
SGDQLGSKFVS Ab # 14 $V_L$ CDR2 (SEQ ID NO: 23)
YKDKRRPS

SUMMARY OF SEQUENCE LISTING

Ab # 14 $V_L$ CDR3 (SEQ ID NO: 24)
QAWDSSTYV

Ab # 17 $V_H$ amino acid sequence (SEQ ID NO: 25)
EVQLLESGGGLVQPGGSLRLSCAASGFTFSWYGMGWVRQAPGKGLEWVSYISPSGG
ITVYADSVKGRFTISRDNSKNTLYLQMNSLRAEDTAVYYCARLNYYYGLDVWGQG
TTVTVSS Ab # 17 $V_L$ amino acid sequence (SEQ ID NO: 26)
QDIQMTQSPSSLSASVGDRITITCQASQDIGDSLNWYQQKPGKAPRLLIYDASNLETG
VPPRFSGSGSGTDFTFTFRSLQPEDIATYFCQQSANAPFTFGPGTKVDIK Ab # 17 $V_H$ CDR1 (SEQ ID NO: 27)
WYGMG Ab # 17 $V_H$ CDR2 (SEQ ID NO: 28)
YISPSGGITVYADSVKG Ab # 17 $V_H$ CDR3 (SEQ ID NO: 29)
LNYYYGLDV Ab # 17 $V_L$ CDR1 (SEQ ID NO: 30)
QASQDIGDSLN Ab # 17 VI, CDR2 (SEQ ID NO: 31)
DASNLET Ab # 17 $V_L$ CDR3 (SEQ ID NO: 32)
QQSANAPFT Ab # 19 $V_H$ amino acid sequence (SEQ ID NO: 33)
EVQLLESGGGLVQPGGSLRLSCAASGFTFSRYGMWWVRQAPGKGLEWVSYIGSSGG
PTYYVDSVKGRFTISRDNSKNTLYLQMNSLRAEDTAVYYCAGGRGTPYYFDSWGQ
GTLVTVSS Ab # 19 $V_L$ amino acid sequence (SEQ ID NO: 34)
QYELTQPASVSGSPGQSITISCTGTSSDIGRWNIVSWYQQHPGKAPKLMIYDVSNRPS
GVSNRF
SGSKSGNTASLTISGLQAEDEADYYCSSYTSSSTWVFGGGTKLTVL Ab # 19 $V_H$ CDR1 (SEQ ID NO: 35)
RYGMW Ab # 19 $V_H$ CDR2 (SEQ ID NO: 36)
YIGSSGGPTYYVDSVKG Ab # 19 $V_H$ CDR3 (SEQ ID NO: 37)
GRGTPYYFDS Ab # 19 $V_L$ CDR1 (SEQ ID NO: 38
TGTSSDIGRWNIVS Ab # 19 $V_L$ CDR2 (SEQ ID NO: 39)
DVSNRPS Ab # 19 $V_L$ CDR3 (SEQ ID NO: 40)
SSYTSSSTWV ErbB3 (SEQ ID NO: 41)
SEVGNSQAVCPGTLNGLSVTGDAENQYQTLYKLYERCEVVMGNLEIVLTGHNADLS
FLQWIREVTGYVLVAMNEFSTLPLPNLRVVRGTQVYDGKFAIFVMLNYNTNSSHAL
RQLRLTQLTEILSGGVYIEKNDKLCHMDTIDWRDIVRDRDAEIVVKDNGRSCPPCHE
VCKGRCWGPGSEDCQTLTKTICAPQCNGHCFGPNPNQCCHDECAGGCSGPQDTDCF
ACRHFNDSGACVPRCPQPLVYNKLTFQLEPNPHTKYQYGGVCVASCPHNFVVDQTS
CVRACPPDKMEVDKNGLKMCEPCGGLCPKACEGTGSGSRFQTVDSSNIDGFVNCTK
ILGNLDFLITGLNGDPWHKIPALDPEKLNVFRTVREITGYLNIQSWPPHMHNFSVFSN
LTTIGGRSLYNRGFSLLIMKNLNVTSLGFRSLKEISAGRIYISANRQLCYHHSLNWTK
VLRGPTEERLDIKHNRPRRDCVAEGKVCDPLCSSGGCWGPGPGQCLSCRNYSRGGV
CVTHCNFLNGEPREFAHEAECFSCHPECQPMEGTATCNGSGSDTCAQCAHFRDGPH
CVSSCPHGVLGAKGPIYKYPDVQNECRPCHENCTQGCKGPELQDCLGQTLVLIGKTH
LTMALTVIAGLVVIFMMLGGTFLYWRGRRIQNKRAMRRYLERGESIEPLDPSEKANK
VLARIFKETELRKLKVLGSGVFGTVHKGVWIPEGESIKIPVCIKVIEDKSGRQSFQAVT
DHMLAIGSLDHAHIVRLLGLCPGSSLQLVTQYLPLGSLLDHVRQHRGALGPQLLLNW
GVQIAKGMYYLEEHGMVHRNLAARNVLLKSPSQVQVADFGVADLLPPDDKQLLYS
EAKTPIKWMALESIHFGKYTHQSDVWSYGVTVWELMTFGAEPYAGLRLAEVPDLLE -continued

SUMMARY OF SEQUENCE LISTING

KGERLAQPQICTIDVYMVMVKCWMIDENIRPTFKELANEFTRMARDPPRYLVIKRES
GPGIAPGPEPHGLTNKKLEEVELEPELDLDLDLEAEEDNLATTTLGSALSLPVGTLNR
PRGSQSLLSPSSGYMPMNQGNLGESCQESAVSGSSERCPRPVSLHPMPRGCLASESSE
GHVTGSEAELQEKVSMCRSRSRSRSPRPRGDSAYHSQRHSLLTPVTPLSPPGLEEEDV
NGYVMPDTHLKGTPSSREGTLSSVGLSSVLGTEEEDEDEEYEYMNRRRRHSPPHPPR
PSSLEELGYEYMDVGSDLSASLGSTQSCPLHPVPIMPTAGTTPDEDYEYMNRQRDGG
GPGGDYAAMGACPASEQGYEEMRAFQGPGHQAPHVHYARLKTLRSLEATDSAFDN
PDYWHSRLFPKANAQRT

HRG cDNA (SEQ ID NO: 42)
(GenBank accession number NM-013956)

```
    1 gaggccaggg gagggtgcga aggaggcgcc tgcctccaac ctgcgggcgg gaggtgggtg
   61 gctgcggggc aattgaaaaa gagccggcga ggagttcccc gaaacttgtt ggaactccgg
  121 gctcgcgcgg aggccaggag ctgagcggcg gcggctgccg gacgatggga gcgtgagcag
  181 gacggtgata acctctcccc gatcgggttg cgaggggcgcc gggcagaggc caggacgcga
  241 gccgcagcg gtgggaccca tcgacgactt cccggggcga caggagcagc cccgagagcc
  301 agggcgagcg cccgttccag gtggccggac cgcccgcgc gtccgcgccg cgctccctgc
  361 aggcaacggg agacgccccc gcgcagcgcg agcgcctcag cgcggccgct cgctctcccc
  421 ctcgagggac aaactttttcc caaacccgat ccgagccctt ggaccaaact cgcctgcgcc
  481 gagagccgtc cgcgtagagc gctccgtctc cggcgagatg tccgagcgca aagaaggcag
  541 aggcaaaggg aagggcaaga agaaggagcg aggctccggc aagaagccgg agtccgcggc
  601 gggcagccag agcccagcct tgcctcccg attgaaagag atgaaaagcc aggaatcggc
  661 tgcaggttcc aaactagtcc ttcggtgtga aaccagttct gaatactcct ctctcagatt
  721 caagtggttc aagaatggga atgaattgaa tcgaaaaaac aaaccacaaa atatcaagat
  781 acaaaaaaag ccagggaagt cagaacttcg cattaacaaa gcatcactgg ctgattctgg
  841 agagtatatg tgcaaagtga tcagcaaatt aggaaatgac agtgcctctg caatatcac
  901 catcgtgaa tcaaacgaga tcatcactgg tatgccagcc tcaactgaag gagcatatgt
  961 gtcttcagag tctcccatta gaatatcagt atccacagaa ggagcaaata cttcttcatc
 1021 tacatctaca tccaccactg ggacaagcca tcttgtaaaa tgtgcggaga aggagaaaac
 1081 tttctgtgtg aatggaggg agtgcttcat ggtgaaagac cttttcaaacc cctcgagata
 1141 cttgtgcaag tgcccaaatg agtttactgg tgatcgctgc caaaactacg taatggccag
 1201 cttctacaag catcttggga ttgaatttat ggaggcggag gagctgtacc agaagagagt
 1261 gctgaccata accggcatct gcatcgccct ccttgtggtc ggcatcatgt gtgtggtggc
 1321 ctactgcaaa accaagaaac agcggaaaaa gctgcatgac cgtcttcggc agagccttcg
 1381 gtctgaacga aacaatatga tgaacattgc caatgggcct caccatccta acccaccccc
 1441 cgagaatgtc cagctggtga atcaatacgt atctaaaaac gtcatctcca gtgagcatat
 1501 tgttgagaga gaagcagaga catcctttttc caccagtcac tatacttcca cagcccatca
 1561 ctccactact gtcacccaga ctcctagcca cagctggagc aacggacaca ctgaaagcat
 1621 cctttccgaa agccactctg taatcgtgat gtcatccgta gaaaacagta ggcacagcag
 1681 cccaactggg ggcccaagag gacgtcttaa tggcacagga ggccctcgtg aatgtaacag
 1741 cttcctcagg catgccagag aaaccctga ttcctaccga gactctcctc aagtcgaaag
 1801 gtatgtgtca gccatgacca ccccggctcg tatgtcacct gtagatttcc acacgccaag
 1861 ctccccccaaa tcgcccccctt cggaaatgtc tccaccgtg tccagcatga cggtgtccat
 1921 gccttccatg gcggtcagcc ccttcatgga agaagagaga cctctacttc tcgtgacacc
 1981 accaaggctg cgggagaaga agtttgacca tcaccctcag cagttcagct ccttccacca
 2041 caacccccgcg catgacagta acagcctccc tgctagcccc ttgaggatag tggaggatga
 2101 ggagtatgaa acgacccaag agtacgagcc agcccaagag cctgttaaga aactcgccaa
 2161 tagccggcgg gccaaaagaa ccaagcccaa tggccacatt gctaacagat tggaagtgga
 2221 cagcaacaca agctcccaga gcagtaactc agagagtgaa acagaagatg aaagagtagg
 2281 tgaagatacg cctttcctgg gcatacagaa ccccctggca gccagtcttg aggcaacacc
 2341 tgccttccgc ctggctgaca gcaggactaa cccagcaggc cgcttctcga cacaggaaga
 2401 aatccaggcc aggctgtcta gtgtaattgc taaccaagac cctattgctg tataaaacct
 2461 aaataaacac atagattcac ctgtaaaact ttattttata taataaagta ttccaccta
 2521 aattaaacaa tttattttat tttagcagtt ctgcaaatag aaaacaggaa aaaaacttttt
 2581 ataaattaaa tatatgtatg taaaatgtg ttatgtgcca tatgtagcaa ttttttacag
 2641 tatttcaaaa cgagaaagat atcaatggtg cctttatgtt atgttatgtc gagagcaagt
 2701 tttgtacagt tacagtgatt gcttttccac agtatttctg caaaacctct catagattca
 2761 gtttttgctg gcttcttgtg cattgcatta tgatgttgac tggatgtatg atttgcaaga
 2821 cttgcaactg tccctctgtt tgcttgtagt agcacccgat cagtatgtct tgtaatggca
 2881 catccatcca gatatgcctc tcttgtgtat gaagttttct ttgctttcag aatatgaaat
 2941 gagttgtgtc tactctgcca gccaaaggtt tgcctcattg ggctctgaga taatagtaga
 3001 tccaacagca tgctactatt aaatacagca agaaactgca ttaagtaatg ttaaatatta
 3061 ggaagaaagt aatactgtga tttaaaaaaa act
```

---

We claim:

1. A method of treating a human patient having lung cancer with a heregulin RNA in situ hybridization (RNA-ISH) score of 1+ or higher measured in a biological sample from the patient, the method comprising administering to the patient an effective amount of:
   1) a first agent that is an anti-ErbB3 antibody, wherein the anti-ErbB3 antibody comprises CDRH1, CDRH2, and CDRH3 sequences comprising the amino acid sequences set forth in SEQ ID NO: 3 (CDRH1), SEQ ID NO: 4 (CDRH2), and SEQ ID NO: 5 (CDRH3), respectively, and CDRL1, CDRL2, and CDRL3 sequences comprising the amino acid sequences set forth in SEQ ID NO: 6 (CDRL1), SEQ ID NO: 7 (CDRL2), and SEQ ID NO: 8 (CDRL3), respectively; and
   2) a second agent that is an anticancer agent, wherein said second anticancer agent is docetaxel or paclitaxel.

2. The method of claim 1, wherein the RNA-ISH uses one or more nucleic acid probes that specifically hybridize to RNAs that encode each of the heregulin isoforms α, β1, β1b, β1c, β1d, β2, β2b, β3, β3b, γ, γ2, γ3, ndf43, ndf43b, and GGF2.

3. The method of claim 2, wherein the one or more nucleic acid probes specifically hybridize to a nucleic acid comprising nucleotides 442-2977 of SEQ ID NO:42.

4. The method of claim 1, wherein the anti-ErbB3 antibody comprises $V_H$ and $V_L$ amino acid sequences set forth in SEQ ID NO:1 and SEQ ID NO:2, respectively.

5. The method of claim 1, wherein the sample is a microtome section of a biopsy.

6. The method of claim 5, wherein the biopsy is a formalin fixed and paraffin embedded biopsy.

7. The method of claim 1, wherein the sample was taken from the patient within 90 days prior to treating the patient.

8. The method of claim 1, wherein the treatment produces at least one therapeutic effect selected from the group consisting of reduction in size of a tumor, reduction in number of metastatic lesions over time, complete response, partial response, stable disease, or a pathologic complete response.

9. The method of claim 1, wherein the second anticancer agent is paclitaxel.

10. The method of claim 1, wherein the second anticancer agent is docetaxel.

11. The method of claim 1, wherein the lung cancer is NSCLC.

12. A method of treating a human patient having lung cancer comprising:
　1) selecting a human lung cancer patient having a heregulin RNA in situ hybridization (RNA-ISH) score of 1+ or higher measured in a biological sample from the patient, and
　2) administering to the patient (a) an effective amount of a first agent that is an anti-ErbB3 antibody, wherein the anti-ErbB3 antibody comprises CDRH1, CDRH2, and CDRH3 sequences comprising the amino acid sequences set forth in SEQ ID NO: 3 (CDRH1), SEQ ID NO: 4 (CDRH2), and SEQ ID NO: 5 (CDRH3), respectively, and CDRL1, CDRL2, and CDRL3 sequences comprising the amino acid sequences set forth in SEQ ID NO: 6 (CDRL1), SEQ ID NO: 7 (CDRL2), and SEQ ID NO: 8 (CDRL3), respectively; and (b) a second agent that is an anticancer agent, wherein said second anticancer a ent is docetaxel or aclitaxel.

13. The method of claim 12, wherein the anti-ErbB3 antibody comprises $V_H$ and $V_L$ amino acid sequences set forth in SEQ ID NO:1 and SEQ ID NO:2, respectively.

14. The method of claim 12, wherein the second anticancer agent a is paclitaxel.

15. The method of claim 12, wherein the second anticancer agent is docetaxel.

16. The method of claim 12, wherein the treatment produces at least one therapeutic effect selected from the group consisting of reduction in size of a tumor, reduction in number of metastatic lesions over time, complete response, partial response, stable disease, or a pathologic complete response.

17. The method of claim 12, wherein the lung cancer is NSCLC.

18. A method of treating a human patient having lung cancer comprising:
　1) selecting a human lung cancer patient having a heregulin RNA in situ hybridization (RNA-ISH) score of 1+ or higher measured in a biological sample from the patient, and
　2) administering to the patient (a) an effective amount of a first agent that is an anti-ErbB3 antibody, wherein the anti-ErbB3 antibody comprises $V_H$ and $V_L$ amino acid sequences set forth in SEQ ID NO: 1 and SEQ ID NO:2, respectively; and (b) a second agent that is an anticancer agent, wherein said second anticancer agent is docetaxel or paclitaxel.

19. The method of claim 18, wherein the second anticancer agent a is paclitaxel.

20. The method of claim 18, wherein the second anticancer agent is docetaxel.

21. The method of claim 18, wherein the treatment produces at least one therapeutic effect selected from the group consisting of reduction in size of a tumor, reduction in number of metastatic lesions over time, complete response, partial response, stable disease, or a pathologic complete response.

22. The method of claim 18, wherein the lung cancer is NSCLC.

23. The method of claim 12, wherein the RNA-ISH uses one or more nucleic acid probes, wherein the one or more nucleic acid probes specifically hybridize to a nucleic acid comprising nucleotides 442-2977 of SEQ ID NO:42.

24. The method of claim 18, wherein the RNA-ISH uses one or more nucleic acid probes, wherein the one or more nucleic acid probes specifically hybridize to a nucleic acid comprising nucleotides 442-2977 of SEQ ID NO:42.

* * * * *

UNITED STATES PATENT AND TRADEMARK OFFICE
CERTIFICATE OF CORRECTION

PATENT NO. : 9,688,761 B2  
APPLICATION NO. : 14/965301  
DATED : June 27, 2017  
INVENTOR(S) : Bambang Adiwijaya et al.

Page 1 of 1

It is certified that error appears in the above-identified patent and that said Letters Patent is hereby corrected as shown below:

In the Claims

At Column 95, Claim number 12, Line number 34, delete "a ent" and insert --agent--.

At Column 95, Claim number 12, Line number 35, delete "aclitaxel" and insert --paclitaxel--.

At Column 95, Claim number 14, Line number 40, delete "agent a is" and insert --agent is--.

At Column 96, Claim number 19, Line number 23, delete "agent a is" and insert --agent is--.

Signed and Sealed this  
Tenth Day of October, 2017

Joseph Matal  
*Performing the Functions and Duties of the*  
*Under Secretary of Commerce for Intellectual Property and*  
*Director of the United States Patent and Trademark Office*

SEQUENCE LISTING

<160> NUMBER OF SEQ ID NOS: 69

<210> SEQ ID NO 1
<211> LENGTH: 119
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser His Tyr
            20                  25                  30

Val Met Ala Trp Val Arg Gln Ala Pro Gly Lys Gly Leu Glu Trp Val
        35                  40                  45

Ser Ser Ile Ser Ser Gly Gly Trp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg Gly Leu Lys Met Ala Thr Ile Phe Asp Tyr Trp Gly Gln Gly
            100                 105                 110

Thr Leu Val Thr Val Ser Ser
        115

<210> SEQ ID NO 2
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Ser Tyr
            20                  25                  30

Asn Val Val Ser Trp Tyr Gln Gln His Pro Gly Lys Ala Pro Lys Leu
        35                  40                  45

Ile Ile Tyr Glu Val Ser Gln Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Thr Glu Asp Glu Ala Asp Tyr Tyr Cys Cys Ser Tyr Ala Gly Ser
                85                  90                  95

Ser Ile Phe Val Ile Phe Gly Gly Gly Thr Lys Val Thr Val Leu
            100                 105                 110

<210> SEQ ID NO 3
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

His Tyr Val Met Ala
1               5
```

```
<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Ser Ile Ser Ser Ser Gly Gly Trp Thr Leu Tyr Ala Asp Ser Val Lys
1               5                   10                  15
Gly

<210> SEQ ID NO 5
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Leu Lys Met Ala Thr Ile Phe Asp Tyr
1               5                   10

<210> SEQ ID NO 6
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Thr Gly Thr Ser Ser Asp Val Gly Ser Tyr Asn Val Val Ser
1               5                   10

<210> SEQ ID NO 7
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Glu Val Ser Gln Arg Pro Ser
1               5

<210> SEQ ID NO 8
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Cys Ser Tyr Ala Gly Ser Ser Ile Phe Val Ile
1               5                   10
```

```
<210> SEQ ID NO 9
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Asn Met Arg Trp Val Arg Gln Ala Pro Gly Lys Gly Leu Glu Trp Val
        35                  40                  45

Ser Val Ile Tyr Pro Ser Gly Ala Thr Arg Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Tyr Tyr Tyr Gly Met Asp Val Trp Gly Gln Gly Thr
            100                 105                 110

Leu Val Thr Val Ser Ser
        115

```
<210> SEQ ID NO 10
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10
```

Gln Ser Val Leu Thr Gln Pro Pro Ser Ala Ser Gly Thr Pro Gly Gln
1               5                   10                  15

Arg Val Thr Ile Ser Cys Ser Gly Ser Asp Ser Asn Ile Gly Arg Asn
            20                  25                  30

Tyr Ile Tyr Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Ile Ser
    50                  55                  60

Gly Ser Lys Ser Gly Thr Ser Ala Ser Leu Ala Ile Ser Gly Leu Arg
65                  70                  75                  80

Ser Glu Asp Glu Ala Glu Tyr His Cys Gly Thr Trp Asp Asp Ser Leu
                85                  90                  95

Ser Gly Pro Val Phe Gly Gly Gly Thr Lys Leu Thr Val Leu
            100                 105                 110

```
<210> SEQ ID NO 11
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 11

Ala Tyr Asn Met Arg
1               5

<210> SEQ ID NO 12
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Val Ile Tyr Pro Ser Gly Gly Ala Thr Arg Tyr Ala Asp Ser Val Lys
1               5                   10                  15

Gly

<210> SEQ ID NO 13
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gly Tyr Tyr Tyr Tyr Gly Met Asp Val
1               5

<210> SEQ ID NO 14
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ser Gly Ser Asp Ser Asn Ile Gly Arg Asn Tyr Ile Tyr
1               5                   10

<210> SEQ ID NO 15
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Arg Asn Asn Gln Arg Pro Ser
1               5

<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 16

Gly Thr Trp Asp Asp Ser Leu Ser Gly Pro Val
1               5                   10

<210> SEQ ID NO 17
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Gly Met Gly Trp Val Arg Gln Ala Pro Gly Lys Gly Leu Glu Trp Val
        35                  40                  45

Ser Tyr Ile Ser Pro Ser Gly Gly His Thr Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Leu Glu Thr Gly Leu Leu Val Asp Ala Phe Asp Ile Trp
            100                 105                 110

Gly Gln Gly Thr Met Val Thr Val Ser Ser
        115                 120

<210> SEQ ID NO 18
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Gln Tyr Glu Leu Thr Gln Pro Pro Ser Val Ser Val Tyr Pro Gly Gln
1               5                   10                  15

Thr Ala Ser Ile Thr Cys Ser Gly Asp Gln Leu Gly Ser Lys Phe Val
            20                  25                  30

Ser Trp Tyr Gln Gln Arg Pro Gly Gln Ser Pro Val Leu Val Met Tyr
        35                  40                  45

Lys Asp Lys Arg Arg Pro Ser Glu Ile Pro Glu Arg Phe Ser Gly Ser
    50                  55                  60

Asn Ser Gly Asn Thr Ala Thr Leu Thr Ile Ser Gly Thr Gln Ala Ile
65                  70                  75                  80

Asp Glu Ala Asp Tyr Tyr Cys Gln Ala Trp Asp Ser Ser Thr Tyr Val
                85                  90                  95

Phe Gly Thr Gly Thr Lys Val Thr Val Leu
            100                 105

<210> SEQ ID NO 19
<211> LENGTH: 5
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 19

Ala Tyr Gly Met Gly
1               5

<210> SEQ ID NO 20
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Tyr Ile Ser Pro Ser Gly Gly His Thr Lys Tyr Ala Asp Ser Val Lys
1               5                   10                  15

Gly

<210> SEQ ID NO 21
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Val Leu Glu Thr Gly Leu Leu Val Asp Ala Phe Asp Ile
1               5                   10

<210> SEQ ID NO 22
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ser Gly Asp Gln Leu Gly Ser Lys Phe Val Ser
1               5                   10

<210> SEQ ID NO 23
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Tyr Lys Asp Lys Arg Arg Pro Ser
1               5

<210> SEQ ID NO 24
<211> LENGTH: 9
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 24

Gln Ala Trp Asp Ser Ser Thr Tyr Val
1               5

<210> SEQ ID NO 25
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Trp Tyr
            20                  25                  30

Gly Met Gly Trp Val Arg Gln Ala Pro Gly Lys Gly Leu Glu Trp Val
        35                  40                  45

Ser Tyr Ile Ser Pro Ser Gly Gly Ile Thr Val Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Leu Asn Tyr Tyr Tyr Gly Leu Asp Val Trp Gly Gln Gly Thr
            100                 105                 110

Thr Val Thr Val Ser Ser
        115

<210> SEQ ID NO 26
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Gln Asp Ile Gln Met Thr Gln Ser Pro Ser Ser Leu Ser Ala Ser Val
1               5                   10                  15

Gly Asp Arg Ile Thr Ile Thr Cys Gln Ala Ser Gln Asp Ile Gly Asp
            20                  25                  30

Ser Leu Asn Trp Tyr Gln Gln Lys Pro Gly Lys Ala Pro Arg Leu Leu
        35                  40                  45

Ile Tyr Asp Ala Ser Asn Leu Glu Thr Gly Val Pro Pro Arg Phe Ser
    50                  55                  60

Gly Ser Gly Ser Gly Thr Asp Phe Thr Phe Thr Phe Arg Ser Leu Gln
65                  70                  75                  80

Pro Glu Asp Ile Ala Thr Tyr Phe Cys Gln Gln Ser Ala Asn Ala Pro
                85                  90                  95

Phe Thr Phe Gly Pro Gly Thr Lys Val Asp Ile Lys
            100                 105
```

```
<210> SEQ ID NO 27
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Trp Tyr Gly Met Gly
1               5

<210> SEQ ID NO 28
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Tyr Ile Ser Pro Ser Gly Gly Ile Thr Val Tyr Ala Asp Ser Val Lys
1               5                   10                  15

Gly

<210> SEQ ID NO 29
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Leu Asn Tyr Tyr Tyr Gly Leu Asp Val
1               5

<210> SEQ ID NO 30
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Gln Ala Ser Gln Asp Ile Gly Asp Ser Leu Asn
1               5                   10

<210> SEQ ID NO 31
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Asp Ala Ser Asn Leu Glu Thr
1               5
```

-continued

```
<210> SEQ ID NO 32
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gln Gln Ser Ala Asn Ala Pro Phe Thr
1               5

<210> SEQ ID NO 33
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Trp Trp Val Arg Gln Ala Pro Gly Lys Gly Leu Glu Trp Val
        35                  40                  45

Ser Tyr Ile Gly Ser Ser Gly Gly Pro Thr Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Gly Arg Gly Thr Pro Tyr Tyr Phe Asp Ser Trp Gly Gln Gly
            100                 105                 110

Thr Leu Val Thr Val Ser Ser
        115

<210> SEQ ID NO 34
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Gln Tyr Glu Leu Thr Gln Pro Ala Ser Val Ser Gly Ser Pro Gly Gln
1               5                   10                  15

Ser Ile Thr Ile Ser Cys Thr Gly Thr Ser Ser Asp Ile Gly Arg Trp
            20                  25                  30

Asn Ile Val Ser Trp Tyr Gln Gln His Pro Gly Lys Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80
```

Gln Ala Glu Asp Glu Ala Asp Tyr Tyr Cys Ser Ser Tyr Thr Ser Ser
            85                  90                  95

Ser Thr Trp Val Phe Gly Gly Gly Thr Lys Leu Thr Val Leu
            100                 105                 110

<210> SEQ ID NO 35
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Arg Tyr Gly Met Trp
1               5

<210> SEQ ID NO 36
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Tyr Ile Gly Ser Ser Gly Gly Pro Thr Tyr Tyr Val Asp Ser Val Lys
1               5                   10                  15
Gly

<210> SEQ ID NO 37
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Gly Arg Gly Thr Pro Tyr Tyr Phe Asp Ser
1               5                   10

<210> SEQ ID NO 38
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Thr Gly Thr Ser Ser Asp Ile Gly Arg Trp Asn Ile Val Ser
1               5                   10

<210> SEQ ID NO 39
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

```
<400> SEQUENCE: 39

Asp Val Ser Asn Arg Pro Ser
1               5

<210> SEQ ID NO 40
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Ser Ser Tyr Thr Ser Ser Ser Thr Trp Val
1               5                   10

<210> SEQ ID NO 41
<211> LENGTH: 1323
<212> TYPE: PRT
<213> ORGANISM: Homo sapiens

<400> SEQUENCE: 41

Ser Glu Val Gly Asn Ser Gln Ala Val Cys Pro Gly Thr Leu Asn Gly
1               5                   10                  15

Leu Ser Val Thr Gly Asp Ala Glu Asn Gln Tyr Gln Thr Leu Tyr Lys
            20                  25                  30

Leu Tyr Glu Arg Cys Glu Val Val Met Gly Asn Leu Glu Ile Val Leu
        35                  40                  45

Thr Gly His Asn Ala Asp Leu Ser Phe Leu Gln Trp Ile Arg Glu Val
    50                  55                  60

Thr Gly Tyr Val Leu Val Ala Met Asn Glu Phe Ser Thr Leu Pro Leu
65                  70                  75                  80

Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
        115                 120                 125

Tyr Ile Glu Lys Asn Asp Lys Leu Cys His Met Asp Thr Ile Asp Trp
    130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
        195                 200                 205

His Asp Glu Cys Ala Gly Gly Cys Ser Gly Pro Gln Asp Thr Asp Cys
    210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
            260                 265                 270
```

```
His Asn Phe Val Val Asp Gln Thr Ser Cys Val Arg Ala Cys Pro Pro
            275                 280                 285

Asp Lys Met Glu Val Asp Lys Asn Gly Leu Lys Met Cys Glu Pro Cys
290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
                325                 330                 335

Lys Ile Leu Gly Asn Leu Asp Phe Leu Ile Thr Gly Leu Asn Gly Asp
            340                 345                 350

Pro Trp His Lys Ile Pro Ala Leu Asp Pro Glu Lys Leu Asn Val Phe
        355                 360                 365

Arg Thr Val Arg Glu Ile Thr Gly Tyr Leu Asn Ile Gln Ser Trp Pro
370                 375                 380

Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
                405                 410                 415

Leu Asn Val Thr Ser Leu Gly Phe Arg Ser Leu Lys Glu Ile Ser Ala
            420                 425                 430

Gly Arg Ile Tyr Ile Ser Ala Asn Arg Gln Leu Cys Tyr His His Ser
        435                 440                 445

Leu Asn Trp Thr Lys Val Leu Arg Gly Pro Thr Glu Glu Arg Leu Asp
450                 455                 460

Ile Lys His Asn Arg Pro Arg Arg Asp Cys Val Ala Glu Gly Lys Val
465                 470                 475                 480

Cys Asp Pro Leu Cys Ser Ser Gly Gly Cys Trp Gly Pro Gly Pro Gly
                485                 490                 495

Gln Cys Leu Ser Cys Arg Asn Tyr Ser Arg Gly Gly Val Cys Val Thr
            500                 505                 510

His Cys Asn Phe Leu Asn Gly Glu Pro Arg Glu Phe Ala His Glu Ala
        515                 520                 525

Glu Cys Phe Ser Cys His Pro Glu Cys Gln Pro Met Glu Gly Thr Ala
530                 535                 540

Thr Cys Asn Gly Ser Gly Ser Asp Thr Cys Ala Gln Cys Ala His Phe
545                 550                 555                 560

Arg Asp Gly Pro His Cys Val Ser Ser Cys Pro His Gly Val Leu Gly
                565                 570                 575

Ala Lys Gly Pro Ile Tyr Lys Tyr Pro Asp Val Gln Asn Glu Cys Arg
            580                 585                 590

Pro Cys His Glu Asn Cys Thr Gln Gly Cys Lys Gly Pro Glu Leu Gln
        595                 600                 605

Asp Cys Leu Gly Gln Thr Leu Val Leu Ile Gly Lys Thr His Leu Thr
610                 615                 620

Met Ala Leu Thr Val Ile Ala Gly Leu Val Val Ile Phe Met Met Leu
625                 630                 635                 640

Gly Gly Thr Phe Leu Tyr Trp Arg Gly Arg Ile Gln Asn Lys Arg
                645                 650                 655

Ala Met Arg Arg Tyr Leu Glu Arg Gly Glu Ser Ile Glu Pro Leu Asp
            660                 665                 670

Pro Ser Glu Lys Ala Asn Lys Val Leu Ala Arg Ile Phe Lys Glu Thr
        675                 680                 685
```

-continued

Glu Leu Arg Lys Leu Lys Val Leu Gly Ser Gly Val Phe Gly Thr Val
690                 695                 700
His Lys Gly Val Trp Ile Pro Glu Gly Glu Ser Ile Lys Ile Pro Val
705                 710                 715                 720
Cys Ile Lys Val Ile Glu Asp Lys Ser Gly Arg Gln Ser Phe Gln Ala
                725                 730                 735
Val Thr Asp His Met Leu Ala Ile Gly Ser Leu Asp His Ala His Ile
                740                 745                 750
Val Arg Leu Leu Gly Leu Cys Pro Gly Ser Ser Leu Gln Leu Val Thr
            755                 760                 765
Gln Tyr Leu Pro Leu Gly Ser Leu Leu Asp His Val Arg Gln His Arg
770                 775                 780
Gly Ala Leu Gly Pro Gln Leu Leu Leu Asn Trp Gly Val Gln Ile Ala
785                 790                 795                 800
Lys Gly Met Tyr Tyr Leu Glu Glu His Gly Met Val His Arg Asn Leu
                805                 810                 815
Ala Ala Arg Asn Val Leu Leu Lys Ser Pro Ser Gln Val Gln Val Ala
                820                 825                 830
Asp Phe Gly Val Ala Asp Leu Leu Pro Pro Asp Asp Lys Gln Leu Leu
            835                 840                 845
Tyr Ser Glu Ala Lys Thr Pro Ile Lys Trp Met Ala Leu Glu Ser Ile
850                 855                 860
His Phe Gly Lys Tyr Thr His Gln Ser Asp Val Trp Ser Tyr Gly Val
865                 870                 875                 880
Thr Val Trp Glu Leu Met Thr Phe Gly Ala Glu Pro Tyr Ala Gly Leu
                885                 890                 895
Arg Leu Ala Glu Val Pro Asp Leu Leu Glu Lys Gly Glu Arg Leu Ala
                900                 905                 910
Gln Pro Gln Ile Cys Thr Ile Asp Val Tyr Met Val Met Val Lys Cys
            915                 920                 925
Trp Met Ile Asp Glu Asn Ile Arg Pro Thr Phe Lys Glu Leu Ala Asn
930                 935                 940
Glu Phe Thr Arg Met Ala Arg Asp Pro Pro Arg Tyr Leu Val Ile Lys
945                 950                 955                 960
Arg Glu Ser Gly Pro Gly Ile Ala Pro Gly Pro Glu Pro His Gly Leu
                965                 970                 975
Thr Asn Lys Lys Leu Glu Glu Val Glu Leu Pro Glu Leu Asp Leu
                980                 985                 990
Asp Leu Asp Leu Glu Ala Glu Glu Asp Asn Leu Ala Thr Thr Thr Leu
            995                 1000                1005
Gly Ser Ala Leu Ser Leu Pro Val Gly Thr Leu Asn Arg Pro Arg
    1010                1015                1020
Gly Ser Gln Ser Leu Leu Ser Pro Ser Ser Gly Tyr Met Pro Met
    1025                1030                1035
Asn Gln Gly Asn Leu Gly Glu Ser Cys Gln Glu Ser Ala Val Ser
    1040                1045                1050
Gly Ser Ser Glu Arg Cys Pro Arg Pro Val Ser Leu His Pro Met
    1055                1060                1065
Pro Arg Gly Cys Leu Ala Ser Glu Ser Ser Glu Gly His Val Thr
    1070                1075                1080
Gly Ser Glu Ala Glu Leu Gln Glu Lys Val Ser Met Cys Arg Ser
    1085                1090                1095

| | | | | | | | | | | | |
|---|---|---|---|---|---|---|---|---|---|---|---|
| Arg | Ser | Arg | Ser | Arg | Ser | Pro | Arg | Pro | Arg | Gly | Asp | Ser | Ala | Tyr |
| | 1100 | | | | 1105 | | | | 1110 | | |
| His | Ser | Gln | Arg | His | Ser | Leu | Leu | Thr | Pro | Val | Thr | Pro | Leu | Ser |
| | 1115 | | | | 1120 | | | | 1125 | | |
| Pro | Pro | Gly | Leu | Glu | Glu | Glu | Asp | Val | Asn | Gly | Tyr | Val | Met | Pro |
| | 1130 | | | | 1135 | | | | 1140 | | |
| Asp | Thr | His | Leu | Lys | Gly | Thr | Pro | Ser | Ser | Arg | Glu | Gly | Thr | Leu |
| | 1145 | | | | 1150 | | | | 1155 | | |
| Ser | Ser | Val | Gly | Leu | Ser | Ser | Val | Leu | Gly | Thr | Glu | Glu | Glu | Asp |
| | 1160 | | | | 1165 | | | | 1170 | | |
| Glu | Asp | Glu | Glu | Tyr | Glu | Tyr | Met | Asn | Arg | Arg | Arg | Arg | His | Ser |
| | 1175 | | | | 1180 | | | | 1185 | | |
| Pro | Pro | His | Pro | Pro | Arg | Pro | Ser | Ser | Leu | Glu | Glu | Leu | Gly | Tyr |
| | 1190 | | | | 1195 | | | | 1200 | | |
| Glu | Tyr | Met | Asp | Val | Gly | Ser | Asp | Leu | Ser | Ala | Ser | Leu | Gly | Ser |
| | 1205 | | | | 1210 | | | | 1215 | | |
| Thr | Gln | Ser | Cys | Pro | Leu | His | Pro | Val | Pro | Ile | Met | Pro | Thr | Ala |
| | 1220 | | | | 1225 | | | | 1230 | | |
| Gly | Thr | Thr | Pro | Asp | Glu | Asp | Tyr | Glu | Tyr | Met | Asn | Arg | Gln | Arg |
| | 1235 | | | | 1240 | | | | 1245 | | |
| Asp | Gly | Gly | Pro | Gly | Gly | Asp | Tyr | Ala | Ala | Met | Gly | Ala | Cys |
| | 1250 | | | | 1255 | | | | 1260 | | |
| Pro | Ala | Ser | Glu | Gln | Gly | Tyr | Glu | Glu | Met | Arg | Ala | Phe | Gln | Gly |
| | 1265 | | | | 1270 | | | | 1275 | | |
| Pro | Gly | His | Gln | Ala | Pro | His | Val | His | Tyr | Ala | Arg | Leu | Lys | Thr |
| | 1280 | | | | 1285 | | | | 1290 | | |
| Leu | Arg | Ser | Leu | Glu | Ala | Thr | Asp | Ser | Ala | Phe | Asp | Asn | Pro | Asp |
| | 1295 | | | | 1300 | | | | 1305 | | |
| Tyr | Trp | His | Ser | Arg | Leu | Phe | Pro | Lys | Ala | Asn | Ala | Gln | Arg | Thr |
| | 1310 | | | | 1315 | | | | 1320 | | |

<210> SEQ ID NO 42
<211> LENGTH: 3093
<212> TYPE: DNA
<213> ORGANISM: Homo sapiens

<400> SEQUENCE: 42

| | | | | | |
|---|---|---|---|---|---|
| gaggccaggg | gagggtgcga | aggaggcgcc | tgcctccaac | ctgcgggcgg | gaggtgggtg | 60 |
| gctgcgggc | aattgaaaaa | gagccggcga | ggagttcccc | gaaacttgtt | ggaactccgg | 120 |
| gctcgcgcgg | aggccaggag | ctgagcggcg | gcggctgccg | gacgatggga | gcgtgagcag | 180 |
| gacggtgata | acctctcccc | gatcgggttg | cgagggcgcc | gggcagaggc | caggacgcga | 240 |
| gccgccagcg | gtgggaccca | tcgacgactt | cccggggcga | caggagcagc | ccgagagcc | 300 |
| agggcgagcg | cccgttccag | gtggccggac | cgcccgccgc | gtccgcgccg | cgctccctgc | 360 |
| aggcaacggg | agacgccccc | gcgcagcgcg | agcgcctcag | cgcggccgct | cgctctcccc | 420 |
| ctcgagggac | aaactttttcc | caaacccgat | ccgagccctt | ggaccaaaact | cgcctgcgcc | 480 |
| gagagccgtc | cgcgtagagc | gctccgtctc | cggcgagatg | tccgagcgca | agaaggcag | 540 |
| aggcaaaggg | aagggcaaga | agaaggagcg | aggctccggc | aagaagccgg | agtccgcggc | 600 |
| gggcagccag | agcccagcct | tgcctccccg | attgaaagag | atgaaaagcc | aggaatcggc | 660 |
| tgcaggttcc | aaactagtcc | ttcggtgtga | aaccagttct | gaatactcct | ctctcagatt | 720 |
| caagtggttc | aagaatggga | atgaattgaa | tcgaaaaaac | aaaccacaaa | atatcaagat | 780 |

```
acaaaaaaag ccagggaagt cagaacttcg cattaacaaa gcatcactgg ctgattctgg      840
agagtatatg tgcaaagtga tcagcaaatt aggaaatgac agtgcctctg ccaatatcac      900
catcgtggaa tcaaacgaga tcatcactgg tatgccagcc tcaactgaag gagcatatgt      960
gtcttcagag tctcccatta gaatatcagt atccacagaa ggagcaaata cttcttcatc     1020
tacatctaca tccaccactg ggacaagcca tcttgtaaaa tgtgcggaga aggagaaaac     1080
tttctgtgtg aatggagggg agtgcttcat ggtgaaagac ctttcaaacc cctcgagata     1140
cttgtgcaag tgcccaaatg agtttactgg tgatcgctgc caaaactacg taatggccag     1200
cttctacaag catcttggga ttgaatttat ggaggcggag gagctgtacc agaagagagt     1260
gctgaccata accggcatct gcatcgccct ccttgtggtc ggcatcatgt gtgtggtggc     1320
ctactgcaaa accaagaaac agcggaaaaa gctgcatgac cgtcttcggc agagccttcg     1380
gtctgaacga aacaatatga tgaacattgc caatgggcct caccatccta cccacccccc     1440
cgagaatgtc cagctggtga atcaatacgt atctaaaaac gtcatctcca gtgagcatat     1500
tgttgagaga gaagcagaga catccttttc caccagtcac tatacttcca cagcccatca     1560
ctccactact gtcacccaga ctcctagcca cagctggagc aacggacaca ctgaaagcat     1620 ccttttccgaa agccactctg taatcgtgat gtcatccgta gaaaacagta ggcacagcag     1680
cccaactggg ggcccaagag gacgtcttaa tggcacagga ggccctcgtg aatgtaacag     1740
cttcctcagg catgccagag aaaccccctga ttcctaccga gactctcctc atagtgaaag     1800
gtatgtgtca gccatgacca ccccggctcg tatgtcacct gtagatttcc acacgccaag     1860
ctcccccaaa tcgccccctt cggaaatgtc tccaccgtg tccagcatga cggtgtccat     1920
gccttccatg gcggtcagcc ccttcatgga agaagagaga cctctacttc tcgtgacacc     1980
accaaggctg cgggagaaga gtttgacca tcaccctcag cagttcagct ccttccacca     2040
caaccccgcg catgacagta acagcctccc tgctagcccc ttgaggatag tggaggatga     2100
ggagtatgaa acgacccaag agtacgagcc agcccaagag cctgttaaga aactcgccaa     2160
tagccggcgg gccaaaagaa ccaagcccaa tggccacatt gctaacagat tggaagtgga     2220
cagcaacaca agctcccaga gcagtaactc agagagtgaa acagaagatg aaagagtagg     2280
tgaagatacg ccttttcctgg gcatacagaa ccccctggca gccagtcttg aggcaacacc     2340
tgccttccgc ctggctgaca gcaggactaa cccagcaggc cgcttctcga cacaggaaga     2400
aatccaggcc aggctgtcta gtgtaattgc taaccaagac cctattgctg tataaaacct     2460
aaataaacac atagattcac ctgtaaaact ttatttata taataaagta ttccaccta     2520 aattaaacaa tttattttat tttagcagtt ctgcaaatag aaaacaggaa aaaactttt     2580 ataaattaaa tatatgtatg taaaaatgtg ttatgtgcca tatgtagcaa ttttttacag     2640
tatttcaaaa cgagaaagat atcaatggtg cctttatgtt atgttatgtc gagagcaagt     2700
tttgtacagt tacagtgatt gcttttccac agtatttctg caaaacctct catagattca     2760 gttttttgctg gcttcttgtg cattgcatta tgatgttgac tggatgtatg atttgcaaga     2820
cttgcaactg tccctctgtt tgcttgtagt agcacccgat cagtatgtct tgtaatggca     2880
catccatcca gatatgcctc tcttgtgtat gaagttttct ttgctttcag aatatgaaat     2940
gagttgtgtc tactctgcca gccaaaggtt tgcctcattg ggctctgaga taatagtaga     3000
tccaacagca tgctactatt aaatacagca agaaactgca ttaagtaatg ttaaatatta     3060
ggaagaaagt aatactgtga tttaaaaaaa act                                  3093
```

<210> SEQ ID NO 43
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
ctatgtgcag aggaattatg atctttc                                27

<210> SEQ ID NO 44
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
gctaaggcat aggaattttc gtag                                   24

<210> SEQ ID NO 45
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 45
tgcaggtttt ccaaaggaat tcgctc                                 26

<210> SEQ ID NO 46
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
ggaaacctgg aactcaccta c                                      21

<210> SEQ ID NO 47
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
cctgcctcac ttggttgtga                                        20

<210> SEQ ID NO 48
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

```
<400> SEQUENCE: 48
accaatgcca gcctgtcctt cc                                                22

<210> SEQ ID NO 49
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
gcaactctca ggcagtgtg                                                    19

<210> SEQ ID NO 50
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
tggtattggt tctcagcatc g                                                 21

<210> SEQ ID NO 51
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 51
cggtcacact caggccattc aga                                               23

<210> SEQ ID NO 52
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
cttgtaaaat gtgcggagaa gga                                               23

<210> SEQ ID NO 53
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
atctcgaggg gtttgaaagg tct                                               23

<210> SEQ ID NO 54
<211> LENGTH: 26
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic probe"

<400> SEQUENCE: 54
tgtgaatgga ggggagtgct tcatgg                                          26

<210> SEQ ID NO 55
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
gtgcaagtgc ccaaatgagt ttac                                            24

<210> SEQ ID NO 56
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
ctccataaat tcaatcccaa gatgc                                           25

<210> SEQ ID NO 57
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 57
tggccattac gtagttttgg cagcga                                          26

<210> SEQ ID NO 58
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
tgggaattcc accagaagtc                                                 20

<210> SEQ ID NO 59
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 59
gcctttccgc tttgattgt                                                  19
```

<210> SEQ ID NO 60
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic probe"

<400> SEQUENCE: 60
actgtgcagc taccaccaca ccaatc                                    26

<210> SEQ ID NO 61
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 61
ggaattttgc cgatttcatg actg                                      24

<210> SEQ ID NO 62
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 62
gtctctgccg agtgaagatc                                           20

<210> SEQ ID NO 63
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic probe"

<400> SEQUENCE: 63
caccgacgag agtgctgggg                                           20

<210> SEQ ID NO 64
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 64
tgactttgtc acagcccaag ata                                       23

<210> SEQ ID NO 65
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

```
<400> SEQUENCE: 65
aatccaaatg cggcatcttc                                                  20

<210> SEQ ID NO 66
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 66
tgatgctgct tacatgtctc gatccca                                          27

<210> SEQ ID NO 67
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 67
ccttggtcag gcagtataat cc                                               22

<210> SEQ ID NO 68
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 68
tctggcttat atccaacact tcg                                              23

<210> SEQ ID NO 69
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 69
aagcttgctg gtgaaaagga ccc                                              23
```